(12) United States Patent
Corkey et al.

(10) Patent No.: US 9,371,329 B2
(45) Date of Patent: Jun. 21, 2016

(54) FUSED HETEROCYCLIC COMPOUNDS AS ION CHANNEL MODULATORS

(71) Applicants: Britton Corkey, San Francisco, CA (US); Elfatih Elzein, Fremont, CA (US); Robert Jiang, Cupertino, CA (US); Rao Kalla, Sunnyvale, CA (US); Tetsuya Kobayashi, Sunnyvale, CA (US); Dmitry Koltun, Foster City, CA (US); Xiaofen Li, Mountain View, CA (US); Gregory Notte, San Mateo, CA (US); Eric Parkhill, San Francisco, CA (US); Thao Perry, San Jose, CA (US); Jeff Zablocki, Los Altos, CA (US)

(72) Inventors: Britton Corkey, San Francisco, CA (US); Elfatih Elzein, Fremont, CA (US); Robert Jiang, Cupertino, CA (US); Rao Kalla, Sunnyvale, CA (US); Tetsuya Kobayashi, Sunnyvale, CA (US); Dmitry Koltun, Foster City, CA (US); Xiaofen Li, Mountain View, CA (US); Gregory Notte, San Mateo, CA (US); Eric Parkhill, San Francisco, CA (US); Thao Perry, San Jose, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/274,422

(22) Filed: May 9, 2014

(65) Prior Publication Data

US 2014/0303158 A1    Oct. 9, 2014

Related U.S. Application Data

(62) Division of application No. 12/843,702, filed on Jul. 26, 2010, now Pat. No. 8,952,034.

(60) Provisional application No. 61/360,037, filed on Jun. 30, 2010, provisional application No. 61/228,864, filed on Jul. 27, 2009.

(51) Int. Cl.
  C07D 487/04    (2006.01)
  C07D 471/04    (2006.01)

(52) U.S. Cl.
  CPC ............ *C07D 487/04* (2013.01); *C07D 471/04* (2013.01)

(58) Field of Classification Search
  CPC ........................... C07D 487/04; C07D 471/04
  USPC .......................................... 544/236; 514/248
  See application file for complete search history.

(56) References Cited

U.S. PATENT DOCUMENTS

| | | | |
|---|---|---|---|
| 3,483,193 A * | 12/1969 | Gall | ...................... C07D 487/04 544/224 |
| 4,230,705 A | 10/1980 | Allen, Jr. et al. | |
| 4,242,515 A | 12/1980 | Trust et al. | |
| 4,244,953 A | 1/1981 | Trust et al. | |
| 4,326,525 A | 4/1982 | Swanson et al. | |
| 4,654,343 A | 3/1987 | Albright et al. | |
| 4,746,655 A | 5/1988 | Cale, Jr. | |
| 4,812,565 A | 3/1989 | Cale, Jr. | |
| 4,902,514 A | 2/1990 | Barclay et al. | |
| 4,992,445 A | 2/1991 | Lawter et al. | |
| 5,001,139 A | 3/1991 | Lawter et al. | |
| 5,023,252 A | 6/1991 | Hseih | |
| 5,565,449 A | 10/1996 | Blackburn et al. | |
| 5,616,345 A | 4/1997 | Geoghegan et al. | |
| 5,939,412 A | 8/1999 | Bondinell et al. | |
| 6,011,150 A | 1/2000 | Iwasaki et al. | |
| 6,579,875 B1 | 6/2003 | Carling et al. | |
| 6,908,917 B2 | 6/2005 | Ortwine | |
| 6,998,408 B2 | 2/2006 | Pinto | |
| 7,005,523 B2 | 2/2006 | Dombroski et al. | |
| 7,157,490 B2 | 1/2007 | Colandrea et al. | |
| 7,306,631 B2 | 12/2007 | Glenn, Jr. et al. | |
| 7,456,187 B2 | 11/2008 | Ford et al. | |
| 7,572,807 B2 | 8/2009 | Li et al. | |
| 7,579,348 B2 | 8/2009 | Wang et al. | |
| 7,790,741 B2 | 9/2010 | Calderwood et al. | |
| 8,212,041 B2 | 7/2012 | Albrecht et al. | |
| 8,389,500 B2 | 3/2013 | Abelman et al. | |
| 8,586,732 B2 | 11/2013 | Corkey et al. | |
| 2004/0063580 A1 | 4/2004 | Kuragano et al. | |
| 2004/0204404 A1 | 10/2004 | Zelle et al. | |
| 2005/0239767 A1 | 10/2005 | Chan et al. | |
| 2007/0066584 A1 | 3/2007 | Yao et al. | |

(Continued)

FOREIGN PATENT DOCUMENTS

| | | |
|---|---|---|
| CA | 2068255 | 11/1992 |
| DE | 4010488 | 10/1991 |

(Continued)

OTHER PUBLICATIONS

Vippagunta et al. (2001).*

(Continued)

*Primary Examiner* — Paul V Ward
(74) *Attorney, Agent, or Firm* — Francis O. Ginah

(57) ABSTRACT

The present invention relates to compounds that are sodium channel inhibitors and to their use in the treatment of various disease states, including cardiovascular diseases and diabetes. In particular embodiments, the structure of the compounds is given by Formula I:

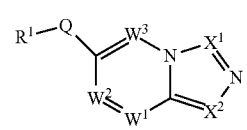

wherein $W^1$, $W^2$, $W^3$, $R^1$, Q, $X^1$, $X^2$ and $X^3$ are as described herein, to methods for the preparation and use of the compounds and to pharmaceutical compositions containing the same.

2 Claims, No Drawings

(56) References Cited

U.S. PATENT DOCUMENTS

| | | |
|---|---|---|
| 2007/0142376 A1 | 6/2007 | Fleenor et al. |
| 2009/0012095 A1 | 1/2009 | Zelle et al. |
| 2009/0069300 A1 | 3/2009 | Zhou et al. |
| 2009/0203707 A1 | 8/2009 | Rajamani et al. |
| 2009/0221555 A1 | 9/2009 | Ahmed et al. |
| 2009/0253689 A1 | 10/2009 | Baeschlin et al. |
| 2010/0056536 A1 | 3/2010 | Antzelevitch et al. |
| 2010/0099676 A1 | 4/2010 | Endoh et al. |
| 2010/0113461 A1 | 5/2010 | Koltun et al. |
| 2010/0144715 A1 | 6/2010 | Hoyt et al. |
| 2010/0240635 A1 | 9/2010 | Cordi et al. |
| 2011/0021521 A1 | 1/2011 | Corkey |
| 2011/0076292 A1 | 3/2011 | Blaquiere et al. |
| 2011/0183990 A1 | 7/2011 | Antzelevitch et al. |
| 2012/0010192 A1 | 1/2012 | Kobayashi et al. |
| 2012/0289493 A1 | 11/2012 | Corkey et al. |
| 2013/0005706 A1 | 1/2013 | Corkey et al. |
| 2013/0012492 A1 | 1/2013 | Corkey et al. |
| 2013/0184255 A1 | 7/2013 | Elzein et al. |
| 2014/0135317 A1 | 5/2014 | Corkey et al. |

FOREIGN PATENT DOCUMENTS

| | | |
|---|---|---|
| DE | 10317526 | 11/2004 |
| EP | 0017438 | 3/1983 |
| EP | 0464572 | 1/1992 |
| EP | 0477789 | 4/1992 |
| EP | 0540334 | 5/1993 |
| EP | 0597423 | 5/1994 |
| EP | 0635488 | 1/1995 |
| EP | 1182195 | 2/2002 |
| EP | 1333031 | 8/2003 |
| EP | 1354602 | 10/2003 |
| EP | 1803748 | 6/2010 |
| JP | 04209692 | 7/1992 |
| JP | 06107647 | 4/1994 |
| JP | 09157262 | 6/1997 |
| JP | 11100394 | 4/1999 |
| JP | 2003277384 | 10/2003 |
| JP | 2003321461 | 11/2003 |
| JP | 2006063064 | 3/2006 |
| TW | WO 2007/061677 | 5/2007 |
| WO | WO 93/00095 | 1/1993 |
| WO | WO 93/08174 | 4/1993 |
| WO | WO 94/13272 | 6/1994 |
| WO | WO 94/13292 | 6/1994 |
| WO | WO 97/03975 | 2/1997 |
| WO | WO 2007/061696 | 5/1997 |
| WO | WO 98/11890 | 3/1998 |
| WO | WO 98/47885 | 10/1998 |
| WO | WO 99/13038 | 3/1999 |
| WO | WO 99/41246 | 8/1999 |
| WO | WO 99/42456 | 8/1999 |
| WO | WO-99/65904 A1 | 12/1999 |
| WO | WO 00/23451 | 4/2000 |
| WO | WO 01/16110 | 3/2001 |
| WO | WO 01/16263 | 3/2001 |
| WO | WO 01/16274 | 3/2001 |
| WO | WO 01/16275 | 3/2001 |
| WO | WO 01/16276 | 3/2001 |
| WO | WO 01/16277 | 3/2001 |
| WO | WO 01/16278 | 3/2001 |
| WO | WO 01/87883 | 11/2001 |
| WO | WO 02/18377 | 3/2002 |
| WO | WO 02/38562 | 5/2002 |
| WO | WO 02/010135 | 7/2002 |
| WO | WO 02/072579 | 9/2002 |
| WO | WO 02/096873 | 12/2002 |
| WO | WO 03/024941 | 3/2003 |
| WO | WO 03/075858 | 9/2003 |
| WO | WO 2004/020440 | 3/2004 |
| WO | WO 2004/026292 | 4/2004 |
| WO | WO 2004/037192 | 5/2004 |
| WO | WO 2004/043940 | 5/2004 |
| WO | WO 2004/062616 | 7/2004 |
| WO | WO 2004/083190 | 9/2004 |
| WO | WO 2004/094371 | 11/2004 |
| WO | WO 2004/096767 | 11/2004 |
| WO | WO 2005/002520 | 1/2005 |
| WO | WO 2005/014558 | 2/2005 |
| WO | WO 2005/060967 | 7/2005 |
| WO | WO 2005/097052 | 10/2005 |
| WO | WO 2006/002470 | 1/2006 |
| WO | WO 2006/011669 | 2/2006 |
| WO | WO 2006/020959 | 2/2006 |
| WO | WO 2006/021544 | 3/2006 |
| WO | WO 2006/023750 | 3/2006 |
| WO | WO 2006/031676 | 3/2006 |
| WO | WO 2006/048727 | 5/2006 |
| WO | WO 2006/091897 | 8/2006 |
| WO | WO 2006/095014 | 9/2006 |
| WO | WO 2006/113864 | 10/2006 |
| WO | WO 2006/125119 | 11/2006 |
| WO | WO 2006/125972 | 11/2006 |
| WO | WO 2006/138549 | 12/2006 |
| WO | WO 2006/138657 | 12/2006 |
| WO | WO 2006/138695 | 12/2006 |
| WO | WO 2007/004028 | 1/2007 |
| WO | WO 2007/023750 | 3/2007 |
| WO | WO 2007/038209 | 4/2007 |
| WO | WO 2007/047604 | 4/2007 |
| WO | WO 2007/058583 | 5/2007 |
| WO | WO 2007/069986 | 6/2007 |
| WO | WO 2007/070866 | 6/2007 |
| WO | WO 2007/113226 | 10/2007 |
| WO | WO 2007/146284 | 12/2007 |
| WO | WO 2008/005338 | 1/2008 |
| WO | WO 2008/005457 | 1/2008 |
| WO | WO 2008/006540 | 1/2008 |
| WO | WO 2008/007661 | 1/2008 |
| WO | WO 2008/055068 | 5/2008 |
| WO | WO 2008/079570 | 7/2008 |
| WO | WO 2008/080012 | 7/2008 |
| WO | WO 2008/094909 | 8/2008 |
| WO | WO 2008/108445 | 9/2008 |
| WO | WO 2008/117061 | 10/2008 |
| WO | WO 2008/118141 | 10/2008 |
| WO | WO 2008/134553 | 11/2008 |
| WO | WO 2008/144483 | 11/2008 |
| WO | WO 2009/005675 | 1/2009 |
| WO | WO 2009/026444 | 2/2009 |
| WO | WO 2009/045753 | 4/2009 |
| WO | WO 2009/085980 | 7/2009 |
| WO | WO 2009/089027 | 7/2009 |
| WO | WO 2009/091374 | 7/2009 |
| WO | WO 2009/137462 | 11/2009 |
| WO | WO 2009/137499 | 11/2009 |
| WO | WO 2009/141026 | 11/2009 |
| WO | WO 2009/153589 | 12/2009 |
| WO | WO 2010/006292 | 1/2010 |
| WO | WO 2010/018686 | 2/2010 |
| WO | WO 2010/022001 | 2/2010 |
| WO | WO 2010/077680 | 7/2010 |
| WO | WO 2010/077686 | 7/2010 |
| WO | WO 2010/111534 | 9/2010 |
| WO | WO 2010/118208 | 10/2010 |
| WO | WO 2011/036280 | 3/2011 |
| WO | WO 2011/075607 | 6/2011 |
| WO | WO 2011/084733 | 7/2011 |
| WO | WO 2012/019071 | 2/2012 |
| WO | WO 2012/019076 | 2/2012 |
| WO | WO 2012/037105 | 3/2012 |
| WO | WO 2012/050918 | 4/2012 |
| WO | WO 2012/071509 | 5/2012 |
| WO | WO 2013/006485 | 1/2013 |
| WO | WO 2013/112932 | 8/2013 |

OTHER PUBLICATIONS

U.S. Appl. No. 14/217,011, filed Mar. 17, 2014, Kobayashi, et al.
U.S. Appl. No. 14/345,893, filed Sep. 20, 2012, Belardinelli, et al.

(56) References Cited

OTHER PUBLICATIONS

Belardinelli et al., "A Novel, Potent, and Selective Inhibitor of Cardiac Late Sodium Current Suppresses Experimental Arrhythmias," J. Pharm. Exp. Ther., 344(1), pp. 23-32, 2013.
Benson et al., "SUMO modification regulates inactivation of the voltage-gtes potassium channel Kv1.5" Proc. Nat. Acad. Sci., 104(6), pp. 1805-1810, 2007.
Burashnikov et al., "Role of late sodium channel current block in the management of atrial fibrillation," Cardiovascular Drugs and Therapy / Sponsored by the International Society of Cardiovascular Pharmacotherapy, 27(1), pp. 79-89, 2013.
Clare et al, Drug Discovery Today 2000, vol. 5, No. 11, 506-520.
Database WPI, Week 198132, Thomson Scientific, London, abstract, 1981, XP-002690413, JP56075428.
Database WPI, Week 199346, Thomson Scientific, London, abstract, 1993, XP-002690414, JP5271069.
Dermer et al., Bio/Technology, 1994, 12:30.
Freshney et al., Culture of Animal Cells, A Manual of Basic Technique, Alan R. Liss, Inc., 1983, New York, pp. 1-6.
Hale et al., Journal of Molecular and Cellular Cardiology, vol. 44 (2008), pp. 954-967.
International Search Report and Written Opinion for PCT/US2012/056419, dated Jan. 30, 2013.
International Search Report with Written Opinion for PCT/US2013/023291, dated Mar. 13, 2013.
Krafte et al., Current Opinion in Pharmacology 2008, 8:50-56.
Kumar et al., "New and emerging antiarrhythmic drugs for atrial fibrillation: what may become available to the clinician in the near future", Curr. Treat. Options Cardiovasc. Med., pp. 11(55), 2009.
Nagashima et al., "Dual effects of disopyramide to the glycemic control in patients with diabetes mellitus", Diabetes, American Diabetes Association, vol. 53, No. Suppl. 2, 2004.
Office Action, U.S. Appl. No. 13/174,587, mailed on May 14, 2013.
Office Action, U.S. Appl. No. 13/466,995, dated Jun. 9, 2014.
Office Action, U.S. Appl. No. 13/538,307, mailed on Apr. 24, 2014.
Office Action, U.S. Appl. No. 13/538,847, dated May 3, 2013.
Rush et al., Molecular Interventions 2007, vol. 4, issue 7, 192-195.
Toussaint et al., "Late sodium current as a promising antiarrhythmic drug target for treatment of atrial fibrilolation?" Naunyn-Schmiedeberg's Archives of Pharmacology, 383(1), p. 61, 20117 77th Annual Meeting on German-Society-For Experimental-And-Clinical-Pharmacology-And Toxicology; Frankfurt, Germany; Mar. 30-Apr. 2, 2011.
Toyofuku et al. JP 06001779, Jan. 11, 1995; CA 122;10048, 1995. Abstract provided.
Wu, et al., "Late Sodium Current Contributes to the Reverse Rate-Dependent Effect of I-KR Inhibition on Ventricular Repolarization", Circulation, 123(16), pp. 1713-1720, 2011.
Barsky et al., "Hypoglycemic Cyclic Amidines", J. Med. Chem., vol. 14, No. 1, 1971, pp. 40-44.
Chiu et al., "Cycloaddition of Alpha-Chloroformylarylhydrazines with Pyridines Afford 2-Aryl-2H-[1,2,4] triazolo[4,3-a] pyridine-3-ones", Journal of the Chinese Chemical Society, Chinese Electronic Periodical Services, China, vol. 48, 2001, pp. 1135-1142.
Chuohan et al., "Domino Ring-Opening/Carboxamidation Reactions of N-Tosyl Aziridines and 2-Halophenols/Pyridinol: Efficient Synthesis of 1,4-Benzo- and Pyrido-oxazepinones" Organic Letters, vol. 12, No. 1, pp. 192-195, 2010.
Cleator et al., "Synthesis of Novel Benzoxathiazepine-1,1-dioxides by Means of a One-pot Multicomponent Reaction", Tetrahedron Letters, 51, pp. 1079-1082, 2010.
Elzein et al., "Novel 1,3-dipropyl-8-(1-heteroarylmethyl-1 $H$-pyrazol-4-yl)-xanthine derivatives as high affinity and selective $A_{2B}$ adenosine receptor antagonists," *Bioorganic & Medicinal Chemistry Letters*, 16:302-306 2006.
Foster, "Deuterium Isotope Effects in Studies of Drug Metabolism", Trends Pharmacol. Sci., 5(12):524-527, 1984.
Ila Sircar: "Synthesis of 1,2,4-triazolo[4,3-b]pyridazines and related compounds" Journal of Heterocyclic Chemistry 22(1):1045-1048 (1985). ISSN: 0022-152X.
International Search Report and Written Opinion for PCT/US2011/042700, dated Aug. 17, 2011.
International Search Report and Written Opinion for PCT/US2012/036976, dated Jul. 2, 2012.
International Search Report and Written Opinion for PCT/US2012/045021, dated Oct. 9, 2012.
International Search Report and Written Opinion for PCT/US2012/045086, dated Sep. 19, 2012.
International Search Report with Written Opinion for PCT/US2010/043264, dated Sep. 28, 2010.
Ning et al., "Ranolazine Increases Beta-Cell Survival and Improves Glucose Homeostasis in Low-Dose Streptozotocin-induced Diabetes in Mice", J. Pharmacol. Exp. Ther., 337(1), 50-58, 2011.
Rudolph et al., "Quinazolinone Derivatives as Orally Available Ghrelin Receptor Anagonists for the Treatment of Diabetes and Obesity", Journal of Medicinal Chemistry, vol. 50, No. 21, 2007, pp. 5202-5216.
Shin et al., "New Synthesis of Highly Potential Efficient Bluish-Green Electroluminescent Materials Based on 1,3,4-Oxadiazole Triazolopyridinone Carbazole Derivatives for Single-Layer Devices", Heteroatom Chemistry, Wiley Periodicals, Inc., vol. 17, No. 2, 2006, pp. 160-166.
Shin et al., "Synthesis and Characterization of New Bluish-Green Electroluminescent Materials Based on 1,3,4-Oxadiazole Triazolopyridinone Hybrids", Heteroatom Chemistry, Wiley Periodicals, Inc., vol. 10, No. 3, 2007, pp. 212-219.
Vippagunta et al., "Crystalline solids", Advanced Drug Delivery Reviews 48, pp. 3-26, (2001).
Yang, et al., "Synthesis of Dibenzo[b,f][1,4]oxazepin-11(10H)-ones via Intramolecular Cyclocarbonylation Reactions Using pfl2/Cytop 292 as the Catalytic System", Journal of Organic Chemistry, 75(18), 2010, pp. 6297-6299.
Zaza et al., "Pathophysiology and Pharmacology of the Cardiac "Late Sodium Current"," *Pharmacology and Therapeutics*, 119, pp. 326-339, 2008.
Search Report dated Dec. 28, 2015 for Taiwan Application No. 104112388.

* cited by examiner

FUSED HETEROCYCLIC COMPOUNDS AS ION CHANNEL MODULATORS

CROSS-REFERENCE TO RELATED APPLICATIONS

This application claims priority to U.S. Provisional Patent Application Ser. No. 61/228,864, filed Jul. 27, 2009 and U.S. Provisional Patent Application Ser. No. 61/360,037, Jun. 30, 2010, the entireties of each of which is incorporated herein by reference.

FIELD OF THE INVENTION

The present invention relates to novel compounds and to their use in the treatment of various disease states, including cardiovascular diseases and diabetes. The invention also relates to methods for their preparation, and to pharmaceutical compositions containing such compounds.

BACKGROUND

The late sodium current (INaL) is a sustained component of the fast Na+ current of cardiac myocytes and neurons. Many common neurological and cardiac conditions are associated with abnormal (INaL) enhancement, which contributes to the pathogenisis of both electrical and contactile dysfunction in mammals. See, for example, Pathophysiology and Pharmacology of the Cardiac "Late Sodium Current", Pharmacology and Therapeutics 119 (2008) 326-339. Accordingly, pharmaceutical compounds that selectively inhibit (INaL) in mammals are useful in treating such disease states.

One example of a selective inhibitor of (INaL) is RANEXA®, a compound approved by the FDA for the treatment of chronic stable angina pectoris. RANEXA® has also been shown to be useful for the treatment of a variety of cardiovascular diseases, including ischemia, reperfusion injury, arrhythmia and unstable angina, and also for the treatment of diabetes. It would be desirable to provide novel compounds that selectively inhibit (INaL) in mammals and that have the same selectivity over peak INa inhibition as RANEXA®.

SUMMARY OF THE INVENTION

Accordingly, in typical embodiments the present invention provides novel compounds that function as late sodium channel blockers. In typical embodiments the invention provides compounds of Formula I:

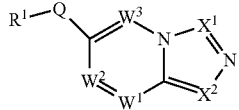

I wherein:
$R^1$ is aryl or heteroaryl,
wherein said aryl or heteroaryl are optionally substituted with one, two, or three substituents independently selected from the group consisting of hydroxyl, halo, —$NO_2$, CN, —$SF_5$, —$Si(CH_3)_3$, —O—$CF_3$, —O—$R^{20}$—C(O)—$R^{20}$, C(O)OH, —N($R^{20}$)($R^{22}$), —C(O)—N($R^{20}$)($R^{22}$), —N($R^{20}$)—C(O)—$R^{22}$, —N($R^{20}$)—S(=O)$_2$—$R^{26}$, —S(=O)$_2$—$R^{20}$, —S(=O)$_2$—N($R^{20}$)($R^{22}$), $C_1$-$C_3$ alkoxy, $C_{1-4}$ alkyl, $C_{2-4}$ alkenyl, $C_{2-4}$ alkynyl, cycloalkyl, heteroaryl, and heterocyclyl;
wherein said alkoxy, alkyl, alkenyl, alkynyl, heteroaryl, cycloalkyl, or heterocyclyl are optionally substituted with one, two, or three substituents independently selected from hydroxyl, halo, —$NO_2$, —O—$CF_3$, —O—$CF_2$, phenyl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, $W^1$ is N or $CR^2$ wherein $R^2$ is independently selected from the group consisting of hydrogen, optionally substituted alkyl, amino, optionally substituted alkoxy, —$CF_3$, —O—$CF_3$, —CN, and —N($R^{20}$)C(O)—$R^{22}$;

$W^2$ is N or $CR^3$ wherein $R^3$ is independently selected from the group consisting of hydrogen, optionally substituted alkyl, —$CF_3$, -halo, and —O—$R^{24}$;

$W^3$ is N or $CR^4$ wherein $R^4$ is independently selected from the group consisting of hydrogen, hydroxyl, halo, $C_{1-4}$ alkyl, $C_1$-$C_3$ alkoxy, —$R^{25}$—N($R^{20}$)($R^{22}$), —$R^{25}$—O—$R^{20}$, —$R^{25}$—C(O)—O—$R^{20}$, —$R^{25}$—C(O)—N($R^{20}$)($R^{22}$), —$R^{25}$—C(O)—O—N($R^{20}$)($R^{22}$), —$R^{25}$—N($R^{20}$)—C(O)—$R^{22}$, and —$R^{25}$—O—C(O)—N($R^{20}$)($R^{22}$),
wherein said alkyl are optionally substituted with one, two, or three substituents independently selected from hydroxyl, halo, Q is selected from a covalent bond or $C_{2-4}$ alkynylene;
$X^1$ is N or $CR^a$ wherein
$R^a$ is hydrogen, $C_{1-15}$ alkyl, $C_{1-4}$ alkoxy, —C(O)—O—$R^{26}$, —C(O)—N($R^{26}$)($R^{28}$), —N($R^{20}$)—S(=O)$_2$—$R^{20}$, cycloalkyl, aryl, heteroaryl, heterocyclyl,
wherein said alkyl is optionally substituted with one, two, or three substituents independently selected from hydroxyl, halo, —$NO_2$, —O—$CF_3$, —O—$CHF_2$, cycloalkyl, —CN, and $C_{1-4}$ alkoxy; and
said alkoxy, cycloalkyl, aryl, heterocyclyl, or heteroaryl are optionally substituted with one, two, or three substituents independently selected from hydroxyl, halo, —$NO_2$, —O—$CF_3$, —O—$CHF_2$, phenyl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and O—$R^{20}$; or
$R^a$ is —Y—Z—$R^{25}$—$R^{23}$—$R^{20}$, wherein,
Y is a covalent bond or selected from $C_1$-$C_3$ alkylene optionally substituted with one or two $C_1$-$C_3$ alkyl or fluoro groups;
Z is $C_{2-4}$ alkynylene, —O—, —S—, —R", —$NR^{5'}$—C(O)—, —NR"—C(O)—$NR^{5'}$—, or —C(O)—$NR^3$, wherein each R" and $R^{5'}$ is independently hydrogen or $C_{1-6}$ lower alkyl; and
further wherein said alkyl are optionally substituted with one, two, or three substituents independently selected from hydroxyl, halo, —$NO_2$, —O—$CF_3$, —O—$CF_2$, phenyl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, $X^2$ is N or $CR^b$;
$R^b$ is selected from the group consisting of hydrogen, substituted alkyl, —$CF_3$, —O—$CF_3$, —O—$R^{20}$, —S—$R^{20}$, —N($R^{20}$)($R^{22}$), —N($R^{20}$)—C(O)—$R^{22}$, —$CF_2$—$R^{20}$, —$CF_2$—C(O)—O—$R^{20}$, —$CF_2$—C(O)—N($R^{20}$)—S(=O)$_2$—$R^{26}$, —$CF_2$-tetrazolyl, —C(O)—N($R^{20}$)—S(=O)$_2$—$R^{26}$, —N($R^{20}$)—C(O)—N($R^{20}$)($R^{22}$), —C(O)—$R^{20}$, —C(O)—O—$R^{20}$, —C(O)—N(R$^{20}$)(R$^{22}$), and —N(R$^{20}$)—S(=O)$_2$—R$^{26}$, R$^{25}$-optionally substituted heteroaryl, —R$^{25}$-optionally substituted aryl;

R$^{20}$ and R$^{22}$ are in each instance independently selected from the group consisting of hydrogen, C$_1$-C$_{15}$ alkyl, C$_2$-C$_{15}$ alkenyl, C$_2$-C$_{15}$ alkynyl, cycloalkyl, heterocyclyl, aryl, and heteroaryl,
  wherein the alkyl, alkenyl, alkynyl, heterocyclyl, aryl, and heteroaryl are optionally substituted with one, two, or three substituents independently selected from hydroxyl, halo, alkyl, mono- or dialkylamino, alkyl or aryl or heteroaryl amide, —NO$_2$, —SO$_2$R$^{26}$, —CN, C$_{1-3}$ alkoxy, —CF$_3$, —OCF$_3$, aryl, cycloalkyl, and heteroaryl; or;

when R$^{20}$ and R$^{22}$ are attached to a common nitrogen atom R$^{20}$ and R$^{22}$ may join to form a heterocyclic ring which is then optionally substituted with one, two, or three substituents independently selected from hydroxyl, halo, alkyl, mono- or dialkylamino, alkyl or aryl or heteroaryl amide, —NO$_2$, —SO$_2$R$^{26}$, —CN, C$_{1-3}$ alkoxy, —CF$_3$, and —OCF$_3$, aryl, cycloalkyl;

R$^{23}$ is a covalent bond or is selected from the group consisting of cycloalkylene, heterocyclylene, arylene, and heteroarylene,
  wherein the cycloalkylene, heterocyclylene, arylene, and heteroarylene are optionally substituted with one to three substituents independently selected from hydroxyl, halo, alkyl, mono- or dialkylamino, alkyl or aryl or heteroaryl amide, —NO$_2$, —SO$_2$R$^{26}$, —CN, C$_{1-3}$ alkoxy, —CF$_3$, —OCF$_3$, aryl, cycloalkyl, and heteroaryl;

R$^{24}$ is in each instance independently selected from alkyl or aryl either of which may be optionally substituted with 1, 2, or 3 groups independently selected from hydroxyl, —OCF$_3$, halo, C$_1$-C$_3$ alkoxy, —O—R$^{20}$, or alkyl optionally substituted with halo, —NO$_2$, —CF$_3$, —O—CF$_3$, —N(R$^{20}$)(R$^{22}$), —C(O)—R$^{20}$, —C(O)—O—R$^{20}$, —C(O)—N(R$^{20}$)(R$^{22}$), CN, or —O—R$^{20}$;

R$^{25}$ is in each instance independently a covalent bond or selected from C$_1$-C$_3$ alkylene optionally substituted with one or two C$_1$-C$_3$ alkyl groups; and R$^{26}$ and R$^{28}$ are in each instance independently selected from hydrogen, alkyl, or cycloalkyl, wherein the alkyl, phenyl and cycloalkyl may be further substituted with from 1 to 3 substituents independently selected from hydroxyl, halo, C$_{1-4}$ alkoxy, —CF$_3$, and —OCF$_3$;

or a pharmaceutically acceptable salt, ester, prodrug, or solvate thereof, with the provisos that
a. when X$^1$ is CR$^a$, R$^a$ is —Y—Z—R$^{25}$—R$^{23}$—R$^{20}$, Y is not a covalent bond and Z is —O—, —S—, —SO$_2$—, C(O)—NR$^3$, NR$^{5'}$—C(O)—, or NR"—, then R$^{25}$ cannot be a bond;
b. when X$^1$ is CR$^a$, R$^a$ is —Y—Z—R$^{25}$—R$^{23}$—R$^{20}$, Y is covalent bond and Z is —O—, —S—, —SO$_2$—, or NR"—, then R$^{25}$ is a covalent bond and R$^{23}$ is not cycloalkylene;
c. when Z is —NR$^{5'}$—C(O)—, then Y is not a covalent bond;
d. R$^{23}$ and R$^{25}$ cannot both be covalent bonds;
e. when X$^1$ is CR$^a$, Q is a bond, R$^1$ is heteroaryl and, W$^1$, W$^2$, and W$^3$ are all CH, then the R$^1$ heteroaryl may not be further substituted with phenyl;
f. when W$^1$, W$^2$, and W$^3$ are not N, R$^2$ is substituted alkyl, X$^1$ is CR$^a$, and X$^2$ is N, then R$^a$ is not alkyl, cycloalkyl, or heterocyclyl; and
g. when Q is a covalent bond, R$^1$ is phenyl, W$^1$, W$^2$, and W$^3$ are CH, X$^1$ is CR$^a$, and X$^2$ is N, then R$^a$ is not C$_{1-3}$ unsubstituted alkyl;
h. when Q is a covalent bond, W$^1$ and W$^2$ are CH, W$^3$ is NH, X$^1$ is CR$^a$, and X$^2$ is N, then R$^1$ is not heteroaryl substituted with aryl.

Some embodiments provide a method of using the compounds of Formula I in the treatment of a disease or condition in a mammal that is amenable to treatment by a late sodium channel blocker. The compounds of the invention and their therapeutically acceptable salts, esters, tautomeric forms are potentially of use as medicaments for the treatment of certain diseases, such as, cardiovascular diseases such as atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, cerebral ischemia, stroke, renal ischemia, and ischemia associated with organ transplant, reperfusion injury, myocardial infarction, acute coronary syndrome, peripheral arterial disease, and intermittent claudication. Such diseases may also include diabetes, and conditions related to diabetes, e.g. diabetic peripheral neuropathy. Such diseases may also include conditions affecting the neuromuscular system resulting in epilepsy, pain, seizures, or paralysis.

In certain embodiments the invention provides pharmaceutical formulations comprising a therapeutically effective amount of a compound of the invention (e.g. a compound of Formula I and at least one pharmaceutically acceptable excipient.

At present, the preferred compounds for use in the invention include, but are not limited to:

7-methyl-6-(4-(trifluoromethoxy)phenyl)-3-(trifluoromethyl)[1,2,4]triazolo[4,3-a]pyridine;
6-(3-(trifluoromethoxy)phenyl)-3-(trifluoromethyl)-[1,2,4]triazolo[4,3-a]pyridine;
3-(trifluoromethyl)-6-[4-(trifluoromethyl)phenyl][1,2,4]triazolo[4,3-a]pyridine;
6-(2,4-dichlorophenyl)-3-(trifluoromethyl)[1,2,4]triazolo[4,3-a]pyridine;
6-[4-(trifluoromethoxy)phenyl]-3-(trifluoromethyl)imidazo[1,5-a]pyridine;
6-[4-(difluoromethoxy)phenyl]-3-(trifluoromethyl)[1,2,4]triazolo[4,3-a]pyridine;
6-(4-phenoxyphenyl)-3-(trifluoromethyl)imidazo[1,5-a]pyridine;
6-[4-(trifluoromethoxy)phenyl]-3-(trifluoromethyl)[1,2,4]triazolo[4,3-b]pyridazine;
6-(3-phenoxyphenyl)-3-(trifluoromethyl)[1,2,4]triazolo[4,3-a]pyridine;
6-[4-chloro-3-(trifluoromethyl)phenyl]-3-(trifluoromethyl)[1,2,4]triazolo[4,3-a]pyridine;
6-(4-phenoxyphenyl)-3-(trifluoromethyl)[1,2,4]triazolo[4,3-b]pyridazine;
3-(difluoromethyl)-6-[4-(trifluoromethoxy)phenyl][1,2,4]triazolo[4,3-b]pyridazine;
3-(difluoromethyl)-6-(4-phenoxyphenyl)[1,2,4]triazolo[4,3-b]pyridazine;
6-(4-chloro-3-fluorophenyl)-3-(trifluoromethyl)[1,2,4]triazolo[4,3-a]pyridine;
6-[4-(trifluoromethoxy)phenyl]-3-(trifluoromethyl)[1,2,4]triazolo[4,3-a]pyrazine;
6-(4-phenoxyphenyl)-3-(trifluoromethyl)[1,2,4]triazolo[4,3-a]pyrazine;
7-methyl-6-[3-(trifluoromethoxy)phenyl]-3-(trifluoromethyl)[1,2,4]triazolo[4,3-a]pyridine;

3-(difluoromethyl)-6-(4-phenoxyphenyl)[1,2,4]triazolo[4,3-a]pyrazine;
{6-[4-(trifluoromethoxy)phenyl][1,2,4]triazolo[4,3-a]pyridin-3-yl}acetic acid;
3-(difluoromethyl)-6-[4-(trifluoromethoxy)phenyl][1,2,4]triazolo[4,3-a]pyridine;
3-phenyl-6-[4-(trifluoromethoxy)phenyl][1,2,4]triazolo[4,3-a]pyridine;
6-(4-phenoxyphenyl)[1,2,4]triazolo[4,3-b]pyridazine;
3-(difluoromethyl)-6-[4-(trifluoromethoxy)phenyl][1,2,4]triazolo[4,3-a]pyrazine;
6-(4-tert-butylphenyl)-3-(trifluoromethyl)[1,2,4]triazolo[4,3-a]pyridine;
6-[4-(trifluoromethoxy)phenyl][1,2,4]triazolo[4,3-b]pyridazine;
6-[2-methyl-4-(trifluoromethoxy)phenyl]-3-(trifluoromethyl)[1,2,4]triazolo[4,3-b]pyridazine;
3-(trifluoromethyl)-6-[4-(trimethylsilyl)phenyl][1,2,4]triazolo[4,3-a]pyridine;
6-[4-(2,2,2-trifluoroethoxy)phenyl]-3-(trifluoromethyl)imidazo[1,5-a]pyridine;
6-(4-methoxyphenyl)-3-(trifluoromethyl)[1,2,4]triazolo[4,3-a]pyridine;
6-(4-methoxyphenyl)-3-(trifluoromethyl)imidazo[1,5-a]pyridine;
6-(4-phenoxyphenyl)-3-(2,2,2-trifluoroethyl)[1,2,4]triazolo[4,3-b]pyridazine;
6-(4-phenoxyphenyl)-3-(propan-2-yl)[1,2,4]triazolo[4,3-b]pyridazine;
6-[2-methyl-4-(trifluoromethoxy)phenyl]-3-(propan-2-yl)[1,2,4]triazolo[4,3-b]pyridazine;
1-phenyl-6-[4-(trifluoromethoxy)phenyl]-3-(trifluoromethyl)imidazo[1,5-a]pyridine;
3-tert-butyl-6-(4-phenoxyphenyl)[1,2,4]triazolo[4,3-b]pyridazine;
3-tert-butyl-6-[4-(2,2,2-trifluoroethoxy)phenyl][1,2,4]triazolo[4,3-b]pyridazine;
6-[4-(2,2,2-trifluoroethoxy)phenyl]-3-(trifluoromethyl)[1,2,4]triazolo[4,3-a]pyridine;
3-ethyl-6-(4-phenoxyphenyl)[1,2,4]triazolo[4,3-b]pyridazine;
3-cyclopropyl-6-(4-phenoxyphenyl)[1,2,4]triazolo[4,3-b]pyridazine;
4-[6-(4-phenoxyphenyl)[1,2,4]triazolo[4,3-b]pyridazin-3-yl]benzonitrile;
4-{6-[2-methyl-4-(trifluoromethoxy)phenyl][1,2,4]triazolo[4,3-b]pyridazin-3-yl}benzonitrile;
4-{6-[4-(trifluoromethoxy)phenyl][1,2,4]triazolo[4,3-b]pyridazin-3-yl}benzonitrile;
3-(1-methyl-1H-pyrazol-4-yl)-6-(4-phenoxyphenyl)[1,2,4]triazolo[4,3-b]pyridazine;
4-[6-(4-methoxyphenyl)[1,2,4]triazolo[4,3-b]pyridazin-3-yl]benzonitrile;
3-[6-(4-methoxyphenyl)[1,2,4]triazolo[4,3-b]pyridazin-3-yl]benzonitrile;
methyl 4-[3-(trifluoromethyl)[1,2,4]triazolo[4,3-a]pyridin-6-yl]benzoate;
3-[4-(methylsulfonyl)phenyl]-6-(4-phenoxyphenyl)[1,2,4]triazolo[4,3-b]pyridazine;
2-{4-[3-(trifluoromethyl)[1,2,4]triazolo[4,3-a]pyridin-6-yl]phenyl}propan-2-ol;
3-{6-[6-(morpholin-4-yl)pyridin-3-yl][1,2,4]triazolo[4,3-b]pyridazin-3-yl}benzonitrile;
6-(4-phenoxyphenyl)-3-[4-(2H-tetrazol-5-yl)phenyl][1,2,4]triazolo[4,3-b]pyridazine;
3-[6-(4-fluorophenyl)[1,2,4]triazolo[4,3-b]pyridazin-3-yl]benzonitrile;
3-phenyl-6-[4-(trifluoromethoxy)phenyl][1,2,4]triazolo[4,3-a]pyridin-8-amine;
4-[3-(trifluoromethyl)[1,2,4]triazolo[4,3-a]pyridin-6-yl]benzonitrile;
6-[2-(1H-tetrazol-5-yl)phenyl]-3-(trifluoromethyl)[1,2,4]triazolo[4,3-a]pyridine;
3,6-bis[4-(trifluoromethoxy)phenyl][1,2,4]triazolo[4,3-a]pyridine;
3-(propan-2-yl)-6-[4-(trifluoromethoxy)phenyl][1,2,4]triazolo[4,3-a]pyridine;
6-(biphenyl-4-yl)-3-(trifluoromethyl)[1,2,4]triazolo[4,3-a]pyridine;
methyl (2E)-3-{6-[4-(trifluoromethoxy)phenyl]-3-(trifluoromethyl)imidazo[1,5-a]pyridin-1-yl}prop-2-enoate;
6-(1-methyl-1H-indazol-5-yl)-3-(trifluoromethyl)[1,2,4]triazolo[4,3-a]pyridine;
2-[6-(4-phenoxyphenyl)[1,2,4]triazolo[4,3-b]pyridazin-3-yl]propan-2-ol;
6-[4-(1H-1,2,4-triazol-1-yl)phenyl]-3-(trifluoromethyl)[1,2,4]triazolo[4,3-a]pyridine;
methyl 6-[4-(trifluoromethoxy)phenyl][1,2,4]triazolo[4,3-a]pyridine-3-carboxylate;
N-methyl-6-[4-(trifluoromethoxy)phenyl][1,2,4]triazolo[4,3-a]pyridine-3-carboxamide;
6-[4-(4-fluorophenoxy)phenyl]-3-(trifluoromethyl)[1,2,4]triazolo[4,3-a]pyridine;
6-[4-(4-chlorophenoxy)phenyl]-3-(trifluoromethyl)[1,2,4]triazolo[4,3-a]pyridine;
2-methyl-2-{4-[3-(trifluoromethyl)[1,2,4]triazolo[4,3-a]pyridin-6-yl]phenyl}propanenitrile;
6-[3-methyl-4-(trifluoromethoxy)phenyl]-3-(trifluoromethyl)[1,2,4]triazolo[4,3-a]pyridine;
6-[4-(propan-2-ylsulfonyl)phenyl]-3-(trifluoromethyl)[1,2,4]triazolo[4,3-a]pyridine;
3-methyl-6-[4-(trifluoromethoxy)phenyl][1,2,4]triazolo[4,3-a]pyridin-8-amine;
3-methyl-6-[2-methyl-4-(trifluoromethoxy)phenyl][1,2,4]triazolo[4,3-a]pyridin-8-amine;
6-[4-(5-methyl-1,3,4-oxadiazol-2-yl)phenyl]-3-(trifluoromethyl)[1,2,4]triazolo[4,3-a]pyridine;
6-[3-(morpholin-4-ylmethyl)-4-(trifluoromethoxy)phenyl]-3-(trifluoromethyl)[1,2,4]triazolo[4,3-a]pyridine;
4-{6-[4-(trifluoromethoxy)phenyl][1,2,4]triazolo[4,3-a]pyridin-3-yl}benzenesulfonamide;
3-(1,1-difluoro-2-methoxyethyl)-6-[4-(trifluoromethoxy)phenyl][1,2,4]triazolo[4,3-a]pyridine;
N-(4-{6-[4-(trifluoromethoxy)phenyl][1,2,4]triazolo[4,3-a]pyridin-3-yl}phenyl)methanesulfonamide;
N-{3-methyl-6-[2-methyl-4-(trifluoromethoxy)phenyl][1,2,4]triazolo[4,3-a]pyridin-8-yl}acetamide;
6-(4-ethoxyphenyl)-3-(trifluoromethyl)[1,2,4]triazolo[4,3-a]pyridine;
6-(4-tert-butoxyphenyl)-3-(trifluoromethyl)[1,2,4]triazolo[4,3-a]pyridine;
4-{6-[4-(trifluoromethoxy)phenyl][1,2,4]triazolo[4,3-a]pyridin-3-yl}benzamide;
diethyl 3,3'-[1,2,4]triazolo[4,3-a]pyridine-3,6-diyldibenzoate;
6-{3-[(4-methylpiperazin-1-yl)methyl]-4-(trifluoromethoxy)phenyl}-3-(trifluoromethyl)[1,2,4]triazolo[4,3-a]pyridine;
3-(1-methyl-1H-pyrazol-4-yl)-6-[4-(trifluoromethoxy)phenyl][1,2,4]triazolo[4,3-a]pyridine;
N,N-dimethyl-1-{2-(trifluoromethoxy)-5-[3-(trifluoromethyl)[1,2,4]triazolo[4,3-a]pyridin-6-yl]phenyl}methanamine;

2-({2-(trifluoromethoxy)-5-[3-(trifluoromethyl)[1,2,4]triazolo[4,3-a]pyridin-6-yl]benzyl}amino)ethanol;
N-{3-methyl-6-[4-(trifluoromethoxy)phenyl][1,2,4]triazolo[4,3-a]pyridin-8-yl}propanamide;
ethyl 4-{6-[4-(trifluoromethoxy)phenyl][1,2,4]triazolo[4,3-a]pyridin-3-yl}benzoate;
ethyl 3-{6-[4-(trifluoromethoxy)phenyl][1,2,4]triazolo[4,3-a]pyridin-3-yl}benzoate;
6-(6-cyclopropylpyridin-3-yl)-3-(trifluoromethyl)[1,2,4]triazolo[4,3-a]pyridine;
6-(2-cyclopropylpyrimidin-5-yl)-3-(trifluoromethyl)[1,2,4]triazolo[4,3-a]pyridine;
6-(4-cyclopropylphenyl)-3-(trifluoromethyl)[1,2,4]triazolo[4,3-a]pyridine;
3-(trifluoromethyl)-6-[6-(trifluoromethyl)pyridin-3-yl][1,2,4]triazolo[4,3-a]pyridine;
6-[6-(2,2,2-trifluoroethoxy)pyridin-3-yl]-3-(trifluoromethyl)[1,2,4]triazolo[4,3-a]pyridine;
N-(2-{6-[4-(trifluoromethoxy)phenyl][1,2,4]triazolo[4,3-a]pyridin-3-yl}phenyl)methanesulfonamide;
6-[4-(pyrazin-2-yloxy)phenyl]-3-(trifluoromethyl)[1,2,4]triazolo[4,3-a]pyridine;
N-({6-[4-(trifluoromethoxy)phenyl][1,2,4]triazolo[4,3-a]pyridin-3-yl}methyl)methanesulfonamide;
6-(5-cyclopropyl-1,3,4-thiadiazol-2-yl)-3-(trifluoromethyl)[1,2,4]triazolo[4,3-a]pyridine;
6-(4-phenoxyphenyl)tetrazolo[1,5-a]pyridine;
6-[4-(trifluoromethoxy)phenyl]tetrazolo[1,5-a]pyridine;
N-methyl-3-{6-[4-(trifluoromethoxy)phenyl][1,2,4]triazolo[4,3-a]pyridin-3-yl}benzamide;
6-[4-(pyridin-3-yloxy)phenyl]-3-(trifluoromethyl)[1,2,4]triazolo[4,3-a]pyridine;
6-[6-(methylsulfanyl)pyridin-3-yl]-3-(trifluoromethyl)imidazo[1,5-a]pyridine;
6-[4-(cyclopropyloxy)phenyl]-3-(trifluoromethyl)[1,2,4]triazolo[4,3-a]pyridine;
8-methyl-6-[4-(trifluoromethoxy)phenyl]-3-(trifluoromethyl)[1,2,4]triazolo[4,3-a]pyridine;
7-methoxy-6-[4-(trifluoromethoxy)phenyl]-3-(trifluoromethyl)[1,2,4]triazolo[4,3-a]pyridine;
6-[2-methoxy-4-(trifluoromethyl)phenyl]-3-(trifluoromethyl)[1,2,4]triazolo[4,3-a]pyridine;
6-(naphthalen-2-yl)-3-(trifluoromethyl)[1,2,4]triazolo[4,3-a]pyridine;
3-(trifluoromethyl)-6-(3,4,5-trimethoxyphenyl)[1,2,4]triazolo[4,3-a]pyridine;
8-(trifluoromethoxy)-5-[3-(trifluoromethyl)[1,2,4]triazolo[4,3-a]pyridin-6-yl]quinoline;
6-(3,5-difluoro-4-phenoxyphenyl)-3-(trifluoromethyl)[1,2,4]triazolo[4,3-a]pyridine;
6-[4-(4-fluoro-2-nitrophenoxy)phenyl]-3-(trifluoromethyl)[1,2,4]triazolo[4,3-a]pyridine;
2,2-difluoro-2-[6-(4-phenoxyphenyl)[1,2,4]triazolo[4,3-a]pyridin-3-yl]ethanol;
6-[4-(2-fluorophenoxy)phenyl]-3-(trifluoromethyl)[1,2,4]triazolo[4,3-a]pyridine;
6-[4-(pyridin-4-yloxy)phenyl]-3-(trifluoromethyl)[1,2,4]triazolo[4,3-a]pyridine;
N-phenyl-4-[3-(trifluoromethyl)[1,2,4]triazolo[4,3-a]pyridin-6-yl]aniline;
N-(2,2,2-trifluoroethyl)-4-[3-(trifluoromethyl)[1,2,4]triazolo[4,3-a]pyridin-6-yl]aniline;
N-[5-(trifluoromethyl)pyridin-2-yl]-2-{3-[4-(trifluoromethoxy)phenyl][1,2,4]triazolo[4,3-a]pyridin-6-yl}phenyl]acetamide;
6-[4-(trifluoromethoxy)phenyl]-3-(trifluoromethyl)imidazo[1,5-a]pyridine-1-carbonitrile;
3,6-bis[4-(trifluoromethoxy)phenyl][1,2,4]triazolo[4,3-b]pyridazine;
6-[4-(phenylsulfanyl)phenyl]-3-(trifluoromethyl)[1,2,4]triazolo[4,3-a]pyridine;
6-(naphthalen-1-yl)-3-(trifluoromethyl)[1,2,4]triazolo[4,3-a]pyridine;
3-(trifluoromethyl)-6-[6-(trifluoromethyl)pyridazin-3-yl][1,2,4]triazolo[4,3-a]pyridine;
3-(trifluoromethyl)-6-[2-(trifluoromethyl)pyrimidin-5-yl][1,2,4]triazolo[4,3-a]pyridine;
4-[3-(trifluoromethyl)[1,2,4]triazolo[4,3-a]pyridin-6-yl]-N-(2,2,2-trifluoro-1-phenylethyl)aniline;
6-[2-bromo-4-(trifluoromethoxy)phenyl]-3-(trifluoromethyl)[1,2,4]triazolo[4,3-a]pyridine;
{6-[4-(trifluoromethoxy)phenyl]-3-(trifluoromethyl)imidazo[1,5-a]pyridin-1-yl}methanol;
3-(difluoromethyl)-8-methoxy-6-[4-(trifluoromethoxy)phenyl][1,2,4]triazolo[4,3-a]pyridine;
3-[(benzyloxy)methyl]-6-[4-(trifluoromethoxy)phenyl][1,2,4]triazolo[4,3-a]pyridine;
3-[(cyclopropylmethoxy)methyl]-6-[4-(trifluoromethoxy)phenyl][1,2,4]triazolo[4,3-a]pyridine;
3-[(2,2,2-trifluoroethoxy)methyl]-6-[4-(trifluoromethoxy)phenyl][1,2,4]triazolo[4,3-a]pyridine;
{6-[4-(trifluoromethoxy)phenyl][1,2,4]triazolo[4,3-a]pyridin-3-yl}methanol;
6-[2-(2-methoxypyrimidin-5-yl)-4-(trifluoromethoxy)phenyl]-3-(trifluoromethyl)[1,2]triazolo[4,3-a]pyridine;
6-[2-(pyridin-3-yl)-4-(trifluoromethoxy)phenyl]-3-(trifluoromethyl)[1,2,4]triazolo[4,3-a]pyridine;
1-methyl-6-[4-(trifluoromethoxy)phenyl]-3-(trifluoromethyl)imidazo[1,5-a]pyridine;
2-(trifluoromethoxy)-5-[3-(trifluoromethyl)[1,2,4]triazolo[4,3-a]pyridin-6-yl]aniline;
1-{4-[3-(trifluoromethyl)[1,2,4]triazolo[4,3-a]pyridin-6-yl]phenyl}cyclopentanecarbonitrile;
3-(1,1-difluoro-2-methoxyethyl)-6-(4-phenoxyphenyl)[1,2,4]triazolo[4,3-a]pyridine;
6-[4-(4-chlorophenoxy)phenyl]-3-(1,1-difluoro-2-methoxyethyl)[1,2,4]triazolo[4,3-a]pyridine;
3-(1,1-difluoro-2-methoxyethyl)-6-[4-(4-fluorophenoxy)phenyl][1,2,4]triazolo[4,3-a]pyridine;
3-[1,1-difluoro-2-(pyridin-3-ylmethoxy)ethyl]-6-[4-(trifluoromethoxy)phenyl][1,2,4]triazolo[4,3-a]pyridine;
3-[difluoro(methoxy)methyl]-6-[4-(trifluoromethoxy)phenyl][1,2,4]triazolo[4,3-a]pyridine;
3-[difluoro(2-methoxyethoxy)methyl]-6-[4-(trifluoromethoxy)phenyl][1,2,4]triazolo[4,3-a]pyridine;
3-{difluoro[(3-methyloxetan-3-yl)methoxy]methyl}-6-[4-(trifluoromethoxy)phenyl][1,2,4]triazolo[4,3-a]pyridine;
3-phenoxy-6-[4-(trifluoromethoxy)phenyl][1,2,4]triazolo[4,3-a]pyridine;
3-(1,1-difluoro-2-methoxyethyl)-6-[6-(2,2,2-trifluoromethoxy)pyridin-3-yl][1,2,4]triazolo[4,3-a]pyridine;
6-[2-fluoro-4-(trifluoromethoxy)phenyl]-3-(trifluoromethyl)[1,2,4]triazolo[4,3-a]pyridine;
6-[3-fluoro-4-(trifluoromethoxy)phenyl]-3-(trifluoromethyl)[1,2,4]triazolo[4,3-a]pyridine;
3-{difluoro[(5-methyl-1,2,4-oxadiazol-3-yl)methoxy]methyl}-6-[4-(trifluoromethoxy)phenyl][1,2,4]triazolo[4,3-a]pyridine;
3-[(benzyloxy)(difluoro)methyl]-6-[4-(trifluoromethoxy)phenyl][1,2,4]triazolo[4,3-a]pyridine;
3-[difluoro(pyridin-4-ylmethoxy)methyl]-6-[4-(trifluoromethoxy)phenyl][1,2,4]triazolo[4,3-a]pyridine;

2-(2,2-difluoro-2-{6-[4-(trifluoromethoxy)phenyl][1,2,4]triazolo[4,3-a]pyridin-3-yl}ethoxy)-N,N-dimethylethanamine;

6-[4-(cyclopropylmethoxy)phenyl]-3-(trifluoromethyl)[1,2,4]triazolo[4,3-a]pyridine;

6-[2-methoxy-4-(trifluoromethoxy)phenyl]-3-(trifluoromethyl)[1,2,4]triazolo[4,3-a]pyridine;

6-[3-(1,3,4-oxadiazol-2-yl)-4-(trifluoromethoxy)phenyl]-3-(trifluoromethyl)[1,2,4]triazolo[4,3-a]pyridine;

1-(4-(3-(trifluoromethyl)-[1,2,4]triazolo[4,3-a]pyridin-6-yl)phenyl)ethanone;

2,2,2-trifluoro-1-{6-[4-(trifluoromethoxy)phenyl][1,2,4]triazolo[4,3-a]pyridin-3-yl}ethanol;

(2,2-difluoro-2-{6-[4-(trifluoromethoxy)phenyl][1,2,4]triazolo[4,3-a]pyridin-3-yl}ethoxy)acetonitrile;

2-(difluoro{6-[4-(trifluoromethoxy)phenyl][1,2,4]triazolo[4,3-a]pyridin-3-yl}methoxy)ethanol;

1-(difluoro{6-[4-(trifluoromethoxy)phenyl][1,2,4]triazolo[4,3-a]pyridin-3-yl}methoxy)propan-2-ol;

3-{6-[2-methyl-4-(trifluoromethoxy)phenyl][1,2,4]triazolo[4,3-b]pyridazin-3-yl}benzonitrile;

3-(2-chloro-1,1-difluoroethyl)-6-[4-(trifluoromethoxy)phenyl][1,2,4]triazolo[4,3-a]pyridine;

5-(trifluoromethoxy)-8-[3-(trifluoromethyl)[1,2,4]triazolo[4,3-a]pyridin-6-yl]quinoline;

6-[4-(2-methyl-1,3-dioxolan-2-yl)phenyl]-3-(trifluoromethyl)[1,2,4]triazolo[4,3-a]pyridine;

6-(phenylethynyl)-3-(trifluoromethyl)[1,2,4]triazolo[4,3-a]pyridine;

6-[3-chloro-4-(trifluoromethoxy)phenyl]-3-(trifluoromethyl)[1,2,4]triazolo[4,3-a]pyridine;

1,1-difluoro-1-{6-[4-(trifluoromethoxy)phenyl][1,2,4]triazolo[4,3-a]pyridin-3-yl}propan-2-ol;

1-cyclopropyl-2,2-difluoro-2-{6-[4-(trifluoromethoxy)phenyl][1,2,4]triazolo[4,3-a]pyridin-3-yl}ethanol;

ethyl (2,2-difluoro-2-{6-[4-(trifluoromethoxy)phenyl][1,2,4]triazolo[4,3-a]pyridin-3-yl}ethoxy)acetate;

N,N-dimethyl-6-[4-(trifluoromethoxy)phenyl][1,2,4]triazolo[4,3-a]pyridin-3-amine;

(2E)-3-{4-[3-(trifluoromethyl)[1,2,4]triazolo[4,3-a]pyridin-6-yl]phenyl}but-2-enenitrile;

3-(phenylsulfanyl)-6-[4-(trifluoromethoxy)phenyl][1,2,4]triazolo[4,3-a]pyridine;

3-(cyclopropylethynyl)-6-[4-(trifluoromethoxy)phenyl][1,2,4]triazolo[4,3-a]pyridine;

3-[1,1-difluoro-2-(pyridin-2-ylmethoxy)ethyl]-6-[4-(trifluoromethoxy)phenyl][1,2,4]triazolo[4,3-a]pyridine;

2-methyl-4-{6-[4-(trifluoromethoxy)phenyl][1,2,4]triazolo[4,3-a]pyridin-3-yl}but-3-yn-2-ol;

N-methyl-2-(trifluoromethoxy)-5-[3-(trifluoromethyl)[1,2,4]triazolo[4,3-a]pyridin-6-yl]benzamide;

N-(2,2-difluoro-2-{6-[4-(trifluoromethoxy)phenyl][1,2,4]triazolo[4,3-a]pyridin-3-yl}ethyl)methanesulfonamide;

1,1-difluoro-2-methyl-1-{6-[4-(trifluoromethoxy)phenyl][1,2,4]triazolo[4,3-a]pyridin-3-yl}propan-2-ol;

3-(trifluoromethyl)-6-{[4-(trifluoromethyl)phenyl]ethynyl}[1,2,4]triazolo[4,3-a]pyridine;

6-[2-(2-methoxyethoxy)-4-(trifluoromethoxy)phenyl]-3-(trifluoromethyl)[1,2,4]triazolo[4,3-a]pyridine;

6-[6-(2,2,2-trifluoro ethoxy)pyridin-3-yl]-3-(trifluoromethyl)imidazo[1,5-a]pyridine;

6-[6-(cyclopropyloxy)pyridin-3-yl]-3-(trifluoromethyl)[1,2,4]triazolo[4,3-a]pyridine;

{5-(trifluoromethoxy)-2-[3-(trifluoromethyl)[1,2,4]triazolo[4,3-a]pyridin-6-yl]phenoxy}acetonitrile;

6-[3-(3-methyl-1,2,4-oxadiazol-5-yl)-4-(trifluoromethoxy)phenyl]-3-(trifluoromethyl)[1,2,4]triazolo[4,3-a]pyridine;

6-(1,3-oxazol-2-yl)-3-(trifluoromethyl)imidazo[1,5-a]pyridine;

N-(2,2-difluoro-2-{6-[4-(trifluoromethoxy)phenyl][1,2,4]triazolo[4,3-a]pyridin-3-yl}ethyl)pyridine-2-carboxamide;

3-methoxy-6-[4-(trifluoromethoxy)phenyl][1,2,4]triazolo[4,3-a]pyridine;

3-(2,2,2-trifluoroethoxy)-6-[4-(trifluoromethoxy)phenyl][1,2,4]triazolo[4,3-a]pyridine;

6-[6-(2,2,2-trifluoroethoxy)pyridazin-3-yl]-3-(trifluoromethyl)[1,2,4]triazolo[4,3-a]pyridine;

3-(1,1-difluoro-2-methoxyethyl)-6-[3-methyl-4-(trifluoromethoxy)phenyl][1,2,4]triazolo[4,3-a]pyridine;

6-[4-(trifluoromethoxy)-3-(trifluoromethyl)phenyl]-3-(trifluoromethyl)[1,2,4]triazolo[4,3-a]pyridine;

3-{2-[(3,4-difluorobenzyl)oxy]-1,1-difluoroethyl}-6-[4-(trifluoromethoxy)phenyl][1,2,4]triazolo[4,3-a]pyridine;

6-(1,3-thiazol-2-yl)-3-(trifluoromethyl)imidazo[1,5-a]pyridine;

3-(1,1-difluoro-2-methoxyethyl)-6-(phenylethynyl)[1,2,4]triazolo[4,3-a]pyridine;

3-{difluoro[(5-methyl-1,2-oxazol-3-yl)methoxy]methyl}-6-[4-(trifluoromethoxy)phenyl][1,2,4]triazolo[4,3-a]pyridine;

6-phenyl-3-(trifluoromethyl)imidazo[1,5-a]pyridine;

1-{4-[3-(trifluoromethyl)[1,2,4]triazolo[4,3-a]pyridin-6-yl]phenyl}cyclopropanecarbonitrile;

2-[3-(trifluoromethyl)imidazo[1,5-a]pyridin-6-yl]-1,3-benzoxazole;

3-(difluoro{6-[4-(trifluoromethoxy)phenyl][1,2,4]triazolo[4,3-a]pyridin-3-yl}methyl)pentan-3-ol;

2,2-difluoro-2-(6-{[4-(trifluoromethyl)phenyl]ethynyl}[1,2,4]triazolo[4,3-a]pyridin-3-yl)ethanol;

6-[2,4-bis(trifluoromethyl)phenyl]-3-(trifluoromethyl)[1,2,4]triazolo[4,3-a]pyridine;

3-(1,1-difluoro-2-methoxyethyl)-6-[2-methyl-4-(trifluoromethoxy)phenyl][1,2,4]triazolo[4,3-a]pyridine;

6-(3,5-difluoro-4-phenoxyphenyl)-3-(propan-2-yl)[1,2,4]triazolo[4,3-b]pyridazine;

5-methyl-6-[4-(trifluoromethoxy)phenyl]-3-(trifluoromethyl)[1,2,4]triazolo[4,3-a]pyridine;

3-(propan-2-yl)-6-[6-(2,2,2-trifluoroethoxy)pyridin-3-yl][1,2,4]triazolo[4,3-b]pyridazine;

3-[difluoro(pyridin-3-ylmethoxy)methyl]-6-[4-(trifluoromethoxy)phenyl][1,2,4]triazolo[4,3-a]pyridine;

1-(2,2-difluoro-2-{6-[4-(trifluoromethoxy)phenyl][1,2,4]triazolo[4,3-a]pyridin-3-yl}ethoxy)-2-methylpropan-2-ol;

3-{[(5-cyclopropyl-1,2,4-oxadiazol-3-yl)methoxy](difluoro)methyl}-6-[4-(trifluoromethoxy)phenyl][1,2,4]triazolo[4,3-a]pyridine;

3-(difluoro{[5-(2-methylpropyl)-1,2,4-oxadiazol-3-yl]methoxy}methyl)-6-[4-(trifluoromethoxy)phenyl][1,2,4]triazolo[4,3-a]pyridine;

3-(difluoro{[5-(propan-2-yl)-1,2,4-oxadiazol-3-yl]methoxy}methyl)-6-[4-(trifluoromethoxy)phenyl][1,2,4]triazolo[4,3-a]pyridine;

6-[3-fluoro-4-(trifluoromethoxy)phenyl]-3-(trifluoromethyl)[1,2,4]triazolo[4,3-b]pyridazine;

6-(3,5-difluoro-4-phenoxyphenyl)-3-(trifluoromethyl)[1,2,4]triazolo[4,3-b]pyridazine;

3-[difluoro(pyridin-2-ylmethoxy)methyl]-6-[4-(trifluoromethoxy)phenyl][1,2,4]triazolo[4,3-a]pyridine;

4-[(difluoro{6-[4-(trifluoromethoxy)phenyl][1,2,4]triazolo[4,3-a]pyridin-3-yl}methoxy)methyl]quinoline;

2-[3-(trifluoromethyl)imidazo[1,5-a]pyridin-6-yl]-1,3-benzothiazole;

3-[(cyclopropylmethoxy)(difluoro)methyl]-6-[4-(trifluoromethoxy)phenyl][1,2,4]triazolo[4,3-a]pyridine;
3-{difluoro[(1-phenyl-1H-1,2,3-triazol-4-yl)methoxy]methyl}-6-[4-(trifluoromethoxy)phenyl][1,2,4]triazolo[4,3-a]pyridine;
3-[difluoro(pyridazin-3-ylmethoxy)methyl]-6-[4-(trifluoromethoxy)phenyl][1,2,4]triazolo[4,3-a]pyridine;
3-{difluoro[1-(4-fluorophenyl)ethoxy]methyl}-6-[4-(trifluoromethoxy)phenyl][1,2,4]triazolo[4,3-a]pyridine;
6-[4-(4-chlorophenoxy)phenyl]tetrazolo[1,5-a]pyridine;
6-[6-(2,2,2-trifluoroethoxy)pyridin-3-yl]tetrazolo[1,5-a]pyridine;
6-[4-(2-methoxypropan-2-yl)phenyl]-3-(trifluoromethyl)[1,2,4]triazolo[4,3-a]pyridine;
6-[6-(2,2,2-trifluoroethoxy)pyridin-3-yl]-3-(trifluoromethyl)[1,2,4]triazolo[4,3-b]pyridazine;
6-[2-ethoxy-4-(trifluoromethoxy)phenyl]-3-(trifluoromethyl)[1,2,4]triazolo[4,3-a]pyridine;
6-[2-(propan-2-yloxy)-4-(trifluoromethoxy)phenyl]-3-(trifluoromethyl)[1,2,4]triazolo[4,3-a]pyridine;
3-{difluoro[(1-methyl-5-phenyl-1H-pyrazol-3-yl)methoxy]methyl}-6-[4-(trifluoromethoxy)phenyl][1,2,4]triazolo[4,3-a]pyridine;
3-{[(2,2-difluoro-1,3-benzodioxol-5-yl)methoxy](difluoro)methyl}-6-[4-(trifluoromethoxy)phenyl][1,2,4]triazolo[4,3-a]pyridine;
6-[4-(trifluoromethoxy)phenyl]-3-({[4-(trifluoromethyl)benzyl]oxy}methyl)[1,2,4]triazolo[4,3-a]pyridine;
3-{[(4-fluorobenzyl)oxy]methyl}-6-[4-(trifluoromethoxy)phenyl][1,2,4]triazolo[4,3-a]pyridine;
3-{[(2,5-dimethyl-1,3-oxazol-4-yl)methoxy](difluoro)methyl}-6-[4-(trifluoromethoxy)phenyl][1,2,4]triazolo[4,3-a]pyridine;
3-{difluoro[(5-methyl-2-phenyl-1,3-oxazol-4-yl)methoxy]methyl}-6-[4-(trifluoromethoxy)phenyl][1,2,4]triazolo[4,3-a]pyridine;
3-{difluoro[1-(pyridin-2-yl)ethoxy]methyl}-6-[4-(trifluoromethoxy)phenyl][1,2,4]triazolo[4,3-a]pyridine;
3-{[1-(4-chlorophenyl)ethoxy](difluoro)methyl}-6-[4-(trifluoromethoxy)phenyl][1,2,4]triazolo[4,3-a]pyridine;
3-(1,1-difluoro-2-methoxyethyl)-6-[3-fluoro-4-(trifluoromethoxy)phenyl][1,2,4]triazolo[4,3-a]pyridine;
3-(1,1-difluoro-2-methoxyethyl)-6-(3,5-difluoro-4-phenoxyphenyl)[1,2,4]triazolo[4,3-a]pyridine;
3-(1,1-difluoro-2-methoxyethyl)-6-{[4-(trifluoromethyl)phenyl]ethynyl}[1,2,4]triazolo[4,3-a]pyridine;
3-(2-{[3-(4-chlorophenyl)-1,2-oxazol-5-yl]methoxy}-1,1-difluoroethyl)-6-[4-(trifluoromethoxy)phenyl][1,2,4]triazolo[4,3-a]pyridine;
6-[4-(4-chlorophenoxy)phenyl]-3-(trifluoromethyl)[1,2,4]triazolo[4,3-b]pyridazine;
3-(difluoromethyl)-6-[6-(2,2,2-trifluoroethoxy)pyridin-3-yl][1,2,4]triazolo[4,3-b]pyridazine;
3-{[(2-fluorobenzyl)oxy]methyl}-6-[4-(trifluoromethoxy)phenyl][1,2,4]triazolo[4,3-a]pyridine;
6-[4-(trifluoromethoxy)phenyl]-3-({[2-(trifluoromethyl)benzyl]oxy}methyl)[1,2,4]triazolo[4,3-a]pyridine;
3-{[(2,4-difluorobenzyl)oxy]methyl}-6-[4-(trifluoromethoxy)phenyl][1,2,4]triazolo[4,3-a]pyridine;
3-{[(4-chlorobenzyl)oxy]methyl}-6-[4-(trifluoromethoxy)phenyl][1,2,4]triazolo[4,3-a]pyridine;
3-({[4-(trifluoromethoxy)benzyl]oxy}methyl)-6-[4-(trifluoromethoxy)phenyl][1,2,4]triazolo[4,3-a]pyridine;
N-(2,2-difluoro-2-{6-[4-(trifluoromethoxy)phenyl][1,2,4]triazolo[4,3-a]pyridin-3-yl}ethyl)benzamide;
3-[(pyridin-2-ylmethoxy)methyl]-6-[4-(trifluoromethoxy)phenyl][1,2,4]triazolo[4,3-a]pyridine;
3-[difluoro(pyrimidin-2-ylmethoxy)methyl]-6-[4-(trifluoromethoxy)phenyl][1,2,4]triazolo[4,3-a]pyridine;
3-[(1-phenylethoxy)methyl]-6-[4-(trifluoromethoxy)phenyl][1,2,4]triazolo[4,3-a]pyridine;
3-{[1-(2,4-dichlorophenyl)ethoxy](difluoro)methyl}-6-[4-(trifluoromethoxy)phenyl][1,2,4]triazolo[4,3-a]pyridine;
1-[(difluoro{6-[4-(trifluoromethoxy)phenyl][1,2,4]triazolo[4,3-a]pyridin-3-yl}methoxy)methyl]cyclobutanol;
3-{1-[difluoro(pyridin-3-yl)methoxy]ethyl}-6-[4-(trifluoromethoxy)phenyl][1,2,4]triazolo[4,3-a]pyridine;
3-{[(2,4-dichlorobenzyl)oxy]methyl}-6-[4-(trifluoromethoxy)phenyl][1,2,4]triazolo[4,3-a]pyridine;
3-{[(2,4-dimethylbenzyl)oxy]methyl}-6-[4-(trifluoromethoxy)phenyl][1,2,4]triazolo[4,3-a]pyridine;
3-{[(5-methylpyridin-2-yl)methoxy]methyl}-6-[4-(trifluoromethoxy)phenyl][1,2,4]triazolo[4,3-a]pyridine;
3-(difluoromethyl)-6-[3-fluoro-4-(trifluoromethoxy)phenyl][1,2,4]triazolo[4,3-b]pyridazine;
4-{4-[3-(trifluoromethyl)[1,2,4]triazolo[4,3-a]pyridin-6-yl]phenyl}tetrahydro-2H-pyran-4-carbonitrile;
3-[1-(pyridin-2-ylmethoxy)ethyl]-6-[4-(trifluoromethoxy)phenyl][1,2,4]triazolo[4,3-a]pyridine;
tert-butyl (2S)-2-[(difluoro{6-[4-(trifluoromethoxy)phenyl][1,2,4]triazolo[4,3-a]pyridin-3-yl}methoxy)methyl]pyrrolidine-1-carboxylate;
3-{[difluoro(pyridin-3-yl)methoxy]methyl}-6-[4-(trifluoromethoxy)phenyl][1,2,4]triazolo[4,3-a]pyridine;
6-[4-(trifluoromethoxy)phenyl]-3-[3-(trifluoromethyl)phenoxy][1,2,4]triazolo[4,3-a]pyridine;
3-{[(5-cyclobutyl-1,2,4-oxadiazol-3-yl)methoxy](difluoro)methyl}-6-[4-(trifluoromethoxy)phenyl][1,2,4]triazolo[4,3-a]pyridine;
3-(4,4-difluoropiperidin-1-yl)-6-[4-(trifluoromethoxy)phenyl][1,2,4]triazolo[4,3-a]pyridine;
3-[(difluoro{6-[4-(trifluoromethoxy)phenyl][1,2,4]triazolo[4,3-a]pyridin-3-yl}methoxy)methyl]benzonitrile;
3-(difluoro{3-[(2-methoxyphenyl)sulfanyl]-2-methylpropoxy}methyl)-6-[4-(trifluoromethoxy)phenyl][1,2,4]triazolo[4,3-a]pyridine;
3-[difluoro(1-{3-[4-(trifluoromethyl)phenyl]-1,2-oxazol-5-yl}ethoxy)methyl]-6-[4-(trifluoromethoxy)phenyl][1,2,4]triazolo[4,3-a]pyridine;
1-(2,2-difluoro-2-{6-[4-(trifluoromethoxy)phenyl][1,2,4]triazolo[4,3-a]pyridin-3-yl}ethyl)-3-phenylurea;
3-(difluoro{2-[4-(4-methoxyphenyl)piperazin-1-yl]ethoxy}methyl)-6-[4-(trifluoromethoxy)phenyl][1,2,4]triazolo[4,3-a]pyridine;
6-[4-(trifluoromethoxy)phenyl][1,2,4]triazolo[4,3-a]pyridine-3-carboxamide;
3-{[(3-cyclopropyl-1-methyl-1H-pyrazol-5-yl)methoxy](difluoro)methyl}-6-[4-(trifluoromethoxy)phenyl][1,2,4]triazolo[4,3-a]pyridine;
1-(2-chlorophenoxy)-3-(2,2-difluoro-2-{6-[4-(trifluoromethoxy)phenyl][1,2,4]triazolo[4,3-a]pyridin-3-yl}ethoxy)propan-2-ol;
8-methyl-6-[4-(trifluoromethoxy)phenyl]tetrazolo[1,5-a]pyridine;
5-methyl-6-[4-(trifluoromethoxy)phenyl]tetrazolo[1,5-a]pyridine;
6-[4-(4-chlorophenoxy)phenyl]tetrazolo[1,5-b]pyridazine;
6-{4-[difluoro(pyridin-3-yl)methoxy]phenyl}-3-(trifluoromethyl)[1,2,4]triazolo[4,3-a]pyridine;
6-{4-[difluoro(phenyl)methoxy]phenyl}-3-(trifluoromethyl)[1,2,4]triazolo[4,3-a]pyridine;
3-(2-methylphenoxy)-6-[4-(trifluoromethoxy)phenyl][1,2,4]triazolo[4,3-a]pyridine;

1-(2,2-difluoro-2-{6-[4-(trifluoromethoxy)phenyl][1,2,4]
triazolo[4,3-a]pyridin-3-yl}ethoxy)-3-(2,5-dimethylphenoxy)propan-2-ol;
3-[(cyclopropylmethoxy)(difluoro)methyl]-6-[6-(trifluoromethyl)pyridin-3-yl][1,2,4]triazolo[4,3-a]pyridine;
5-chloro-2-({4-[3-(trifluoromethyl)[1,2,4]triazolo[4,3-a]pyridin-6-yl]phenyl}amino)benzonitrile;
5-(methoxymethyl)-6-[4-(trifluoromethoxy)phenyl]-3-(trifluoromethyl)[1,2,4]triazolo[4,3-a]pyridine;
N-methyl-N-phenyl-4-[3-(trifluoromethyl)[1,2,4]triazolo[4,3-a]pyridin-6-yl]aniline;
({6-[4-(trifluoromethoxy)phenyl]-3-(trifluoromethyl)[1,2,4]triazolo[4,3-a]pyridin-5-yl}methoxy)acetonitrile;
4-(difluoro{4-[3-(trifluoromethyl)[1,2,4]triazolo[4,3-a]pyridin-6-yl]phenoxy}methyl)benzonitrile;
5-[(difluoro{6-[4-(trifluoromethoxy)phenyl][1,2,4]triazolo[4,3-a]pyridin-3-yl}methoxy)methyl]quinoline;
3-[1-(difluoro{6-[4-(trifluoromethoxy)phenyl][1,2,4]triazolo[4,3-a]pyridin-3-yl}methoxy)ethyl]quinoline;
4-chloro-N-{4-[3-(trifluoromethyl)[1,2,4]triazolo[4,3-a]pyridin-6-yl]phenyl}aniline;
4-fluoro-N-{4-[3-(trifluoromethyl)[1,2,4]triazolo[4,3-a]pyridin-6-yl]phenyl}aniline;
3-{[2-(2,6-dimethylphenoxy)ethoxy](difluoro)methyl}-6-[4-(trifluoromethoxy)phenyl][1,2,4]triazolo[4,3-a]pyridine;
6-[4-(pentafluoro-lambda~6~-sulfanyl)phenyl]-3-(trifluoromethyl)[1,2,4]triazolo[4,3-a]pyridine;
3-{difluoro[(1-phenyl-1H-pyrazol-4-yl)methoxy]methyl}-6-[4-(trifluoromethoxy)phenyl][1,2,4]triazolo[4,3-a]pyridine;
3-[difluoro({2-[4-(trifluoromethyl)phenyl]-1,3-oxazol-4-yl}methoxy)methyl]-6-[4-(trifluoromethoxy)phenyl][1,2,4]triazolo[4,3-a]pyridine;
4-[(difluoro{6-[4-(trifluoromethoxy)phenyl][1,2,4]triazolo[4,3-a]pyridin-3-yl}methoxy)methyl]-2-methylquinoline;
4-[(difluoro{6-[4-(trifluoromethoxy)phenyl][1,2,4]triazolo[4,3-a]pyridin-3-yl}methoxy)methyl]-2-(trifluoromethyl)quinoline;
6-[(difluoro{6-[4-(trifluoromethoxy)phenyl][1,2,4]triazolo[4,3-a]pyridin-3-yl}methoxy)methyl]quinoxaline;
6-(2-chloro-4-nitrophenyl)-3-(trifluoromethyl)[1,2,4]triazolo[4,3-a]pyridine;
3-[(but-2-yn-1-yloxy)(difluoro)methyl]-6-[4-(trifluoromethoxy)phenyl][1,2,4]triazolo[4,3-a]pyridine;
3-{[(2,2-difluorocyclopropyl)methoxy](difluoro)methyl}-6-[4-(trifluoromethoxy)phenyl][1,2,4]triazolo[4,3-a]pyridine;
3-{difluoro[(3-phenylprop-2-yn-1-yl)oxy]methyl}-6-[4-(trifluoromethoxy)phenyl][1,2,4]triazolo[4,3-a]pyridine;
3-{difluoro[(1-methyl-1H-benzimidazol-2-yl)methoxy]methyl}-6-[4-(trifluoromethoxy)phenyl][1,2,4]triazolo[4,3-a]pyridine;
3-{[(1-benzyl-1H-1,2,3-triazol-4-yl)methoxy](difluoro)methyl}-6-[4-(trifluoromethoxy)phenyl][1,2,4]triazolo[4,3-a]pyridine;
3-{difluoro[(5-phenyl-1,2-oxazol-3-yl)methoxy]methyl}-6-[4-(trifluoromethoxy)phenyl][1,2,4]triazolo[4,3-a]pyridine;
3-{difluoro[(2-phenyl-1,3-oxazol-4-yl)methoxy]methyl}-6-[4-(trifluoromethoxy)phenyl][1,2,4]triazolo[4,3-a]pyridine;
3-{difluoro[(5-methyl-2-phenyl-2H-1,2,3-triazol-4-yl)methoxy]methyl}-6-[4-(trifluoromethoxy)phenyl][1,2,4]triazolo[4,3-a]pyridine;
3-{difluoro[(1-methyl-1H-pyrazol-3-yl)methoxy]methyl}-6-[4-(trifluoromethoxy)phenyl][1,2,4]triazolo[4,3-a]pyridine;
3-[{[1-(4-chlorophenyl)-5-methyl-1H-pyrazol-3-yl]methoxy}(difluoro)methyl]-6-[4-(trifluoromethoxy)phenyl][1,2,4]triazolo[4,3-a]pyridine;
3-[(3,3-diphenylpropoxy)(difluoro)methyl]-6-[4-(trifluoromethoxy)phenyl][1,2,4]triazolo[4,3-a]pyridine;
3-phenoxy-6-{[4-trifluoromethyl)phenyl]ethynyl}[1,2,4]triazolo[4,3-a]pyridine;
3-(difluoro{[3-(pyrimidin-2-yl)benzyl]oxy}methyl)-6-[4-(trifluoromethoxy)phenyl][1,2,4]triazolo[4,3-a]pyridine;
3-(difluoro{[3-(pyridin-3-yl)benzyl]oxy}methyl)-6-[4-(trifluoromethoxy)phenyl][1,2,4]triazolo[4,3-a]pyridine;
3-{difluoro[(1-methyl-1H-indazol-3-yl)methoxy]methyl}-6-[4-(trifluoromethoxy)phenyl][1,2,4]triazolo[4,3-a]pyridine;
3-[chloro(difluoro)methyl]-6-[4-(trifluoromethoxy)phenyl][1,2,4]triazolo[4,3-a]pyridine;
3-(1,1-difluoro-2-methoxyethyl)-6-{[4-(trifluoromethoxy)phenyl]ethynyl}[1,2,4]triazolo[4,3-a]pyridine;
3-(1,1-difluoro-2-methoxyethyl)-6-[(4-fluorophenyl)ethynyl][1,2,4]triazolo[4,3-a]pyridine;
3-(difluoro{[2-(1H-1,2,4-triazol-1-yl)benzyl]oxy}methyl)-6-[4-(trifluoromethoxy)phenyl][1,2,4]triazolo[4,3-a]pyridine;
3-(difluoro{[2-(2-methyl-1H-imidazol-1-yl)benzyl]oxy}methyl)-6-[4-(trifluoromethoxy)phenyl][1,2,4]triazolo[4,3-a]pyridine;
3-(difluoro{[2-phenyl-5-(trifluoromethyl)-1,3-oxazol-4-yl]methoxy}methyl)-6-[4-(trifluoromethoxy)phenyl][1,2,4]triazolo[4,3-a]pyridine;
3-(difluoro{[1-phenyl-3-(trifluoromethyl)-1H-pyrazol-4-yl]methoxy}methyl)-6-[4-(trifluoromethoxy)phenyl][1,2,4]triazolo[4,3-a]pyridine;
3-(difluoro{[6-(1H-pyrazol-1-yl)pyridin-3-yl]methoxy}methyl)-6-[4-(trifluoromethoxy)phenyl][1,2,4]triazolo[4,3-a]pyridine;
6-cyclopropyl-2'-[(difluoro{6-[4-(trifluoromethoxy)phenyl][1,2,4]triazolo[4,3-a]pyridin-3-yl}methoxy)methyl]-3,4'-bipyridine;
3-[{[3-(4-cyclopropyl-1H-imidazol-1-yl)benzyl]oxy}(difluoro)methyl]-6-[4-(trifluoromethoxy)phenyl][1,2,4]triazolo[4,3-a]pyridine;
3-(difluoro{[5-(4-fluorophenyl)-1,2-oxazol-3-yl]methoxy}methyl)-6-[4-(trifluoromethoxy)phenyl][1,2,4]triazolo[4,3-a]pyridine;
3-{difluoro[(5-phenyl-1,2-oxazol-3-yl)methoxy]methyl}-6-[6-(trifluoromethyl)pyridin-3-yl][1,2,4]triazolo[4,3-a]pyridine;
3-(difluoro{[2-(piperidin-1-yl)pyridin-4-yl]methoxy}methyl)-6-[4-(trifluoromethoxy)phenyl][1,2,4]triazolo[4,3-a]pyridine;
3-{[(2,2-dimethyl-2,3-dihydro-1-benzofuran-7-yl)methoxy](difluoro)methyl}-6-[4-(trifluoromethoxy)phenyl][1,2,4]triazolo[4,3-a]pyridine;
3-{[2-(2,6-difluorophenyl)ethoxy](difluoro)methyl}-6-[4-(trifluoromethoxy)phenyl][1,2,4]triazolo[4,3-a]pyridine;
3-{difluoro[(5-phenyl-1,2,4-oxadiazol-3-yl)methoxy]methyl}-6-[4-(trifluoromethoxy)phenyl][1,2,4]triazolo[4,3-a]pyridine;
3-{difluoro[(5-phenyl-1,2-oxazol-3-yl)methoxy]methyl}-6-[6-(2,2,2-trifluoroethoxy)pyridin-3-yl][1,2,4]triazolo[4,3-a]pyridine;
3-[{[2-(6-cyclopropylpyridin-3-yl)benzyl]oxy}(difluoro)methyl]-6-[4-(trifluoromethoxy)phenyl][1,2,4]triazolo[4,3-a]pyridine;

3-[{[5-(2-chlorophenyl)-1,2-oxazol-3-yl]methoxy}(difluoro)methyl]-6-[4-(trifluoromethoxy)phenyl][1,2,4]triazolo[4,3-a]pyridine;

3-(difluoro{[2-(pyridin-3-yl)benzyl]oxy}methyl)-6-[4-(trifluoromethoxy)phenyl][1,2,4]triazolo[4,3-a]pyridine; and 3-(difluoro{[2-(1H-pyrazol-1-yl)benzyl]oxy}methyl)-6-[4-(trifluoromethoxy)phenyl][1,2,4]triazolo[4,3-a]pyridine.

DETAILED DESCRIPTION OF THE INVENTION

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, (typically 1, 2, or 3 substituents) selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or 2) an alkyl group as defined above that is interrupted by 1-10 atoms (e.g. 1, 2, 3, 4, or 5 atoms) independently chosen from oxygen, sulfur and NRa—, where Ra is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or 3) an alkyl group as defined above that has both 1, 2, 3, 4 or 5 substituents as defined above and is also interrupted by 1-10 atoms (e.g. 1, 2, 3, 4, or 5 atoms) as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (typically 1, 2, or 3 substituents), as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, typically having from 1 to 20 carbon atoms (e.g. 1-10 carbon atoms, or 1, 2, 3, 4, 5 or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "lower alkylene" refers to a diradical of a branched or unbranched saturated hydrocarbon chain, typically having 1, 2, 3, 4, 5, or 6 carbon atoms.

The term "substituted alkylene" refers to:

(1) an alkylene group as defined above having 1, 2, 3, 4, or 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or (2) an alkylene group as defined above that is interrupted by 1-10 groups (e.g. 1, 2, 3, 4, or 5 groups) independently chosen from —O—, —S—, sulfonyl, —C(O)—, —C(O)O—, —C(O)N—, and —NRa—, where Ra is chosen from hydrogen, optionally substituted alkyl, cycloalkyl, cycloalkenyl, aryl, heteroaryl and heterocyclyl; or (3) an alkylene group as defined above that has both 1, 2, 3, 4 or 5 substituents as defined above and is also interrupted by 1-10 groups as defined above. Examples of substituted alkylenes are chloromethylene (—CH(Cl)—), aminoethylene (—$CH(NH_2)CH_2$—), methylaminoethylene (—$CH(NHMe)CH_2$—), 2-carboxypropylene isomers(—$CH_2CH(CO_2H)CH_2$—), ethoxyethyl (—$CH_2CH_2O$—$CH_2CH_2$—), ethylmethylaminoethyl (—$CH_2CH_2$—$N(CH_3)$—$CH_2CH_2$—), 1-ethoxy-2-(2-ethoxy-ethoxy)ethane (—$CH_2CH_2O$—$CH_2CH_2$—$OCH_2CH_2$—$OCH_2CH_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl as defined above. This term is exemplified by groups such as methoxy, ethoxy, n-propoxy, iso-propoxy, n-butoxy, iso-butoxy, t-butoxy, n-hexyloxy, and the like.

The term "alkylthio" refers to the group R—S—, where R is as defined for alkoxy.

The term "alkenyl" refers to a monoradical of a branched or unbranched unsaturated hydrocarbon group typically having from 2 to 20 carbon atoms (more typically from 2 to 10 carbon atoms, e.g. 2 to 6 carbon atoms) and having from 1 to 6 carbon-carbon double bonds, e.g. 1, 2, or 3 carbon-carbon double bonds. Typical alkenyl groups include ethenyl (or vinyl, i.e. —CH=CH$_2$), 1-propylene (or allyl, —CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and S(O)R, where R is alkyl, aryl, or heteroaryl and n is 0, 1 or 2.

The term "alkynyl" refers to a monoradical of an unsaturated hydrocarbon, typically having from 2 to 20 carbon atoms (more typically from 2 to 10 carbon atoms, e.g. 2 to 6 carbon atoms) and having from 1 to 6 carbon-carbon triple bonds e.g. 1, 2, or 3 carbon-carbon triple bonds. Typical alkynyl groups include ethynyl (—C≡CH), propargyl (or propynyl, —C≡CCH3), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and S(O)$_n$R, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, CF$_3$, amino, substituted amino, cyano, or —S(O)$_n$Ra, in which Ra is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl, fluorenyl, and anthryl). Typical aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl are as defined herein, and may be optionally further substituted by alkyl, alkenyl, alkynyl, alkoxy, halogen, $CF_3$, amino, substituted amino, cyano, or —$S(O)_nR$, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, $SO_2$-alkyl, $SO_2$-aryl and —$SO_2$-heteroaryl. The term "substituted cycloalkyl" also includes cycloalkyl groups wherein one or more of the annular carbon atoms of the cycloalkyl group is a carbonyl group (i.e. an oxygen atom is oxo to the ring). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a group comprising 1 to 15 carbon atoms and 1 to 4 heteroatoms selected from oxygen, nitrogen, and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, 1,2,3,4-tetrahydronaphthalene.

Unless otherwise constrained by the definition for the heteroaryl substituent, such heteroaryl groups can be optionally substituted with 1 to 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, acyloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group S-substituted alkyl.

The term "heteroarylthiol" refers to the group S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —$S(O)_2R$, in which R is alkyl, aryl, or heteroaryl. "Substituted sulfone" refers to a group —$S(O)_2R$, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

A compound of a given Formula (e.g. the "compound of Formula I") is intended to encompass the compounds of the invention as disclosed, and the pharmaceutically acceptable salts, pharmaceutically acceptable esters, hydrates, polymorphs, and prodrugs of such compounds. Additionally, the compounds of the invention may possess one or more asymmetric centers, and can be produced as a racemic mixture or as individual enantiomers or diastereoisomers. The number of stereoisomers present in any given compound of a given Formula depends upon the number of asymmetric centers present (there are 2n stereoisomers possible where n is the number of asymmetric centers). The individual stereoisomers may be obtained by resolving a racemic or non-racemic mixture of an intermediate at some appropriate stage of the synthesis, or by resolution of the compound by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable minor images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Calm Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients.

Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I).

The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention, any atom specifically designated as a deuterium (D) is meant to represent deuterium.

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of this invention are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Coronary diseases" or "cardiovascular diseases" refer to diseases of the cardiovasculature arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes, and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs, or calves when walking, climbing stairs, or exercising. The pain is called intermittent claudication. When listing the symptom intermittent claudication, it is intended to include both PAD and PVD Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia, and the ventricular tachycardias (VTs), including idiopathic ventricular tachycardia, ventricular fibrillation, pre-excitation syndrome, and Torsade de Pointes (TdP), Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

Nomenclature

Names of compounds of the present invention are provided using ACD/Name software for naming chemical compounds (Advanced Chemistry Development, Inc., Toronto). Other compounds or radicals may be named with common names, or systematic or non-systematic names. The naming and numbering of the compounds of the invention is illustrated with a representative compound of Formula I:

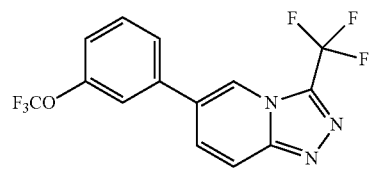 [SMILES: FC(F)(F)Oc1cccc(-c2ccc3nnc(C(F)(F)F)n3c2)c1]

which is named 6-(3-(trifluoromethoxy)phenyl)-3-(trifluoromethyl)-[1,2,4]triazolo[4,3-a]pyridine.

Compounds of Formula I

Accordingly, in typical embodiments the present invention provides compounds that function as sodium channel blockers. In typical embodiments the invention relates to compounds of Formula I:

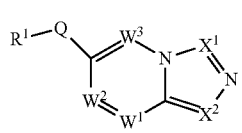

wherein:
$R^1$ is aryl or heteroaryl,
wherein said aryl or heteroaryl are optionally substituted with one, two, or three substituents independently selected from the group consisting of hydroxyl, halo, —$NO_2$, CN, —$SF_5$, —$Si(CH_3)_3$—O—$CF_3$, —O—$R^{20}$, —S—$R^{20}$, —C(O)—$R^{20}$, C(O)OH, —$N(R^{20})(R^{22})$, —C(O)—$N(R^{20})(R^{22})$, —$N(R^{20})$—C(O)—$R^{22}$, —$N(R^{20})$—S(=O)$_2$—$R^{26}$, —S(=O)$_2$—$R^{20}$, —S(=O)$_2$—$N(R^{20})(R^{22})$, $C_1$-$C_3$ alkoxy, $C_{1-4}$ alkyl, $C_{2-4}$ alkenyl, $C_{2-4}$ alkynyl, cycloalkyl, heteroaryl, and heterocyclyl;
wherein said alkoxy, alkyl, alkenyl, alkynyl, heteroaryl, cycloalkyl, or heterocyclyl are optionally substituted with one, two, or three substituents independently selected from hydroxyl, halo, —$NO_2$, —O—$CF_3$, —O—$CF_2$, phenyl, heterocyclyl, heteroaryl, cycloalkyl, —$N(R^{20})(R^{22})$, —C(O)—$R^{20}$, —C(O)—O—$R^{20}$, —C(O)—$N(R^{20})(R^{22})$, —CN, and —O—$R^{20}$,
$W^1$ is N or $CR^2$ wherein $R^2$ is independently selected from the group consisting of hydrogen, optionally substituted alkyl, amino, optionally substituted alkoxy, $CF_3$, $-O-CF_3$, $-CN$, and $-N(R^{20})C(O)-R^{22}$;

$W^2$ is N or $CR^3$ wherein $R^3$ is independently selected from the group consisting of hydrogen, optionally substituted alkyl, $-CF_3$, -halo, and $-O-R^{24}$;

$W^3$ is N or $CR^4$ wherein $R^4$ is independently selected from the group consisting of hydrogen, hydroxyl, halo, $C_{1-4}$ alkyl, $C_1$-$C_3$ alkoxy, $-R^{25}-N(R^{20})(R^{22})$, $-R^{25}-O-R^{20}$, $-R^{25}-C(O)-O-R^{20}$, $-R^{25}-C(O)-N(R^{20})(R^{22})$, $-R^{25}-C(O)-O-N(R^{20})(R^{22})$, $-R^{25}-N(R^{20})-C(O)-R^{22}$, and $-R^{25}-O-C(O)-N(R^{20})(R^{22})$, wherein said alkyl are optionally substituted with one, two, or three substituents independently selected from hydroxyl, halo, Q is selected from a covalent bond or $C_{2-4}$ alkynylene;

$X^1$ is N or $CR^a$ wherein
  $R^a$ is hydrogen, $C_{1-15}$ alkyl, $C_{1-4}$ alkoxy, $-C(O)-O-R^{26}$, $-C(O)-N(R^{26})(R^{28})$, $-N(R^{20})-S(=O)_2-R^{20}$, cycloalkyl, aryl, heteroaryl, heterocyclyl,
  wherein said alkyl is optionally substituted with one, two, or three substituents independently selected from hydroxyl, halo, $-NO_2$, $-O-CF_3$, cycloalkyl, $-CN$, and $C_{1-4}$ alkoxy; and
  said alkoxy, cycloalkyl, aryl, heterocyclyl, or heteroaryl are optionally substituted with one, two, or three substituents independently selected from hydroxyl, halo, $-NO_2$, $-O-CF_3$, $-O-CHF_2$, phenyl, heterocyclyl, heteroaryl, cycloalkyl, $-N(R^{20})(R^{22})$, $-C(O)-R^{20}$, $-C(O)-O-R^{20}$, $-C(O)-N(R^{20})(R^{22})$, $-CN$, and $O-R^{20}$; or
  $R^a$ is $-Y-Z-R^{25}-R^{23}-R^{20}$, wherein,
    Y is a covalent bond or selected from $C_1$-$C_3$ alkylene optionally substituted with one or two $C_1$-$C_3$ alkyl or fluoro groups;
    Z is $C_{2-4}$ alkynylene, $-O-$, $-S-$, $-NR''$, $-NR^{5'}-C(O)$, $-NR''-C(O)-NR^{5'}-$, or $-C(O)-NR^3$, wherein each R'' and $R^{5'}$ is independently hydrogen or $C_{1-6}$ lower alkyl; and
    further wherein said alkyl are optionally substituted with one, two, or three substituents independently selected from hydroxyl, halo, $-NO_2$, $-O-CF_3$, $-O-CF_2$, phenyl, heterocyclyl, heteroaryl, cycloalkyl, $-N(R^{20})(R^{22})$, $-C(O)-R^{20}$, $-C(O)-O-R^{20}$, $-C(O)-N(R^{20})(R^{22})$, $-CN$, and $O-R^{20}$, $X^2$ is N or $CR^b$;

$R^b$ is selected from the group consisting of hydrogen, substituted alkyl, $-CF_3$, $-O-CF_3$, $-O-R^{20}$, $-S-R^{20}$, $-N(R^{20})(R^{20})$, $-N(R^{20})-C(O)-R^{22}$, $-CF_2-R^{20}$, $-CF_2-C(O)-O-R^{20}$, $-CF_2-C(O)-N(R^{20})-S(=O)_2-R^{26}$, $-CF_2$ tetrazolyl, $-C(O)-N(R^{20})-S(=O)_2-R^{26}$, $-N(R^{20})-C(O)-N(R^{20})(R^{22})$, $-C(O)-R^{22}$, $-C(O)-O-R^{20}$, $-C(O)-N(R^{20})(R^{22})$, and $-N(R^{20})-S(=O)_2-R^{26}$, $-R^{25}$-optionally substituted heteroaryl, $R^{25}$-optionally substituted aryl;

$R^{20}$ and $R^{22}$ are in each instance independently selected from the group consisting of hydrogen, $C_1$-$C_{15}$ alkyl, $C_2$-$C_{15}$ alkenyl, $C_2$-$C_{15}$ alkynyl, cycloalkyl, heterocyclyl, aryl, and heteroaryl,
  wherein the alkyl, alkenyl, alkynyl, heterocyclyl, aryl, and heteroaryl are optionally substituted with one, two, or three substituents independently selected from hydroxyl, halo, alkyl, mono- or dialkylamino, alkyl or aryl or heteroaryl amide, $-NO_2$, $-SO_2R^{26}$, $-CN$, $C_{1-3}$ alkoxy, $-CF_3$, $-OCF_3$, aryl, cycloalkyl, and heteroaryl; or;

when $R^{20}$ and $R^{22}$ are attached to a common nitrogen atom $R^{20}$ and $R^{22}$ may join to form a heterocyclic ring which is then optionally substituted with one, two, or three substituents independently selected from hydroxyl, halo, alkyl, mono- or dialkylamino, alkyl or aryl or heteroaryl amide, $-NO_2$, $-SO_2R^{26}$, $-CN$, $C_{1-3}$ alkoxy, $-CF_3$, and $-OCF_3$, aryl, cycloalkyl;

$R^{23}$ is a covalent bond or is selected from the group consisting of cycloalkylene, heterocyclylene, arylene, and heteroarylene,
  wherein the cycloalkylene, heterocyclylene, arylene, and heteroarylene are optionally substituted with one to three substituents independently selected from hydroxyl, halo, alkyl, mono- or dialkylamino, alkyl or aryl or heteroaryl amide, $-NO_2$, $-SO_2R^{26}$, $-CN$, $C_{1-3}$ alkoxy, $-CF_3$, $-OCF_3$, aryl, cycloalkyl, and heteroaryl;

$R^{24}$ is in each instance independently selected from alkyl or aryl either of which may be optionally substituted with 1, 2, or 3 groups independently selected from hydroxyl, $-OCF_3$, halo, $C_1$-$C_3$ alkoxy, $-O-R^{20}$, or alkyl optionally substituted with halo, $-NO_2$, $-CF_3$, $-O-CF_3$, $-N(R^{20})(R^{22})$, $-C(O)-R^{20}$, $-C(O)-O-R^{20}$, $-C(O)-N(R^{20})(R^{22})$, $-CN$, or $-O-R^{20}$;

$R^{25}$ is in each instance independently a covalent bond or selected from $C_1$-$C_3$ alkylene optionally substituted with one or two $C_1$-$C_3$ alkyl groups; and $R^{26}$ and $R^{28}$ are in each instance independently selected from hydrogen, alkyl, phenyl or cycloalkyl, wherein the alkyl, phenyl and cycloalkyl may be further substituted with from 1 to 3 substituents independently selected from hydroxyl, halo, $C_1$ alkoxy, $-CF_3$, and $OCF_3$;

or a pharmaceutically acceptable salt, ester, prodrug, or solvate thereof, with the provisos that
a. when $X^1$ is $CR^a$, $R^a$ is $Y-Z-R^{25}-R^{23}-R^{20}$, Y is not a covalent bond and Z is $-O-$, $-S-$, $-SO_2-$, $C(O)NR^3-$, $-NR^{5'}-C(O)$, or $NR''-$, then $R^{25}$ cannot be a bond;
b. when $X^1$ is $CR^a$, $R^a$ is $Y-Z-R^{25}-R^{23}-R^{20}$, Y is covalent bond and Z is $-O-$, $-S-$, $-SO_2-$, or $NR''-$, then $R^{25}$ is a covalent bond and $R^{23}$ is not cycloalkylene;
c. when Z is $-NR^{5'}-C(O)-$, then Y is not a covalent bond;
d. $R^{23}$ and $R^{25}$ cannot both be covalent bonds;
e. when $X^1$ is $CR^a$, Q is a bond, $R^1$ is heteroaryl and, $W^1$, $W^2$, and $W^3$ are all CH, then the $R^1$ heteroaryl may not be further substituted with phenyl;
f. when $W^1$, $W^2$, and $W^3$ are not N, $R^2$ is substituted alkyl, $X^1$ is $CR^a$, and $X^2$ is N, then $R^a$ is not alkyl, cycloalkyl, or heterocyclyl;
g. when Q is a covalent bond, $R^1$ is phenyl, $W^1$, $W^2$, and $W^3$ are CH, $X^1$ is $CR^a$, and $X^2$ is N, then $R^a$ is not $C_{1-3}$ unsubstituted alkyl;
h. when Q is a covalent bond, $W^1$ and $W^2$ are CH, $W^3$ is NH, $X^1$ is $CR^a$, and $X^2$ is N, then $R^1$ is not heteroaryl substituted with aryl.

In one set of embodiments $W^1$ is $CR^2$, $W^2$ is $CR^3$, $W^3$ is $CR^4$, Q is a covalent bond and $R^1$ is substituted phenyl resulting in compounds having the struction of Formula II:

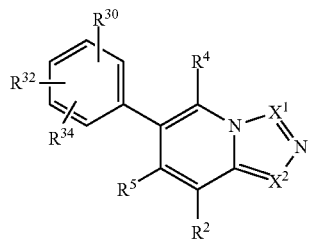

II wherein:
$R^{30}$, $R^{32}$, and $R^{34}$ are independently selected from the group consisting of hydrogen, hydroxyl, —$OCF_3$, halo, $C_1$-$C_3$ alkoxy, —O—$R^{20}$, or alkyl optionally substituted with halo, —$NO_2$, —$CF_3$, —O—$CF_3$, —$N(R^{20})(R^{22})$, —C(O)—$R^{20}$, —C(O)—O—$R^{20}$, —C(O)—$N(R^{20})(R^{22})$, —CN, or —O—$R^{20}$,
with the proviso that at least one of $R^{30}$, $R^{32}$, and $R^{34}$ is not hydrogen; and
$R^2$, $R^4$, $R^5$, $R^{20}$, $R^{22}$, $X^1$, $X^2$, and $X^3$ are as defined above.

In another set of embodiments, $W^1$ is $CR^2$, $W^2$ is $CR^3$, $W^3$ is $CR^4$, $X^2$ is nitrogen and $X^1$ is $CR^a$ resulting in compounds having the struction of Formula III:

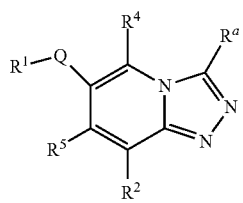

III wherein $R^1$, $R^2$, $R^4$, $R^5$, $R^a$, and Q are as defined above.
I
In yet another set of embodiments, $W^1$ is $CR^2$, $W^2$ is $CR^3$, $W^3$ is $CR^4$, Q is a covalent bond, $R^1$ is substituted phenyl $X^2$ and $X^3$ are both nitrogen and $X^1$ is $CR^a$ resulting in compounds having the struction of Formula IV:

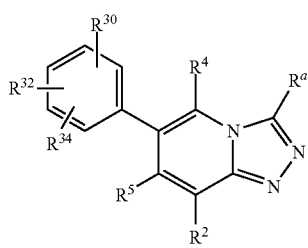

IV wherein $R^2$, $R^4$, $R^5$, $R^{20}$, $R^a$, $R^{22}$, $R^{30}$, $R^{32}$, and $R^{34}$ are as defined above.

Typical $R^1$ aryl and heteroaryl substituents are mono or bicyclic rings having 1 to 3 heteroatoms selected from O, N, and S. Exemplary $R^1$ moieties include, but are not limited to, the following:

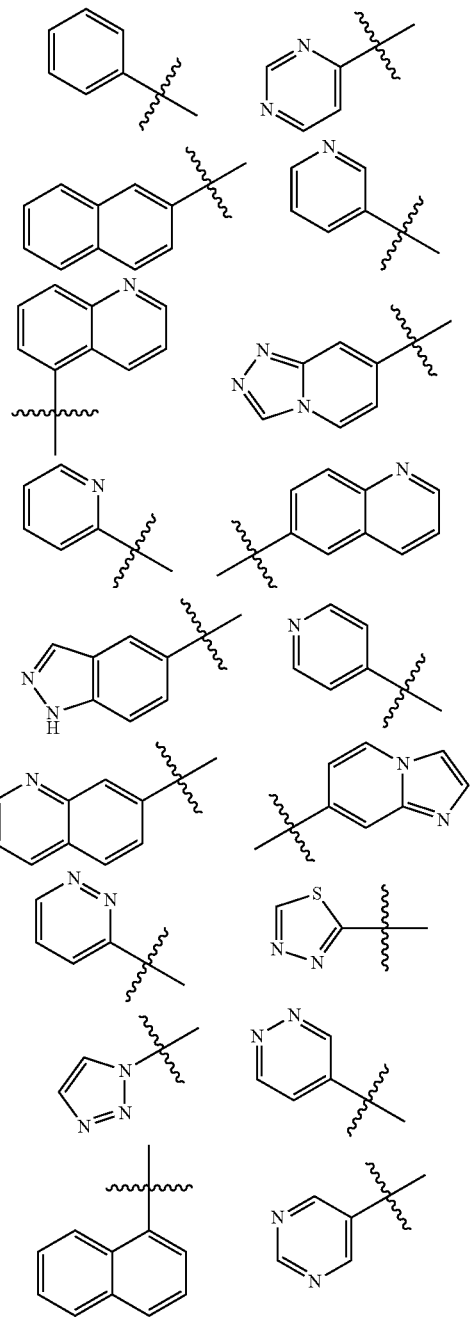

In many embodiments the $R^1$ moiety is further substituted with 1 to 3 substituents as defined above. For example, when $R^1$ is substituted aryl, such as substituted phenyl, common substituents such as $R^{30}$, $R^{32}$, and $R^{34}$. Common substituents on the $R^1$ ring structures include, but are not limited to hydrogen; methyl, ethyl, propyl, isopropyl, tert-butyl, halo; amino, alkylamino, such as methylamino, dialkylamino such as dimethylamino, aminoalkyl, alkaminoalkyl, dialkylaminoalkyl, aryloxy, such as phenoxy; halo substituted alkyl such as $CF_3$ and $CHF_2$; methoxy, ethoxy, propoxy, isopropoxy, tert-butoxy, methylthio, ethylthio, propylthio, and halo substituted alkyoxy, such as trifluoromethoxy and difluoromethoxy. Other typical substituents include, but are not limited to, the following:

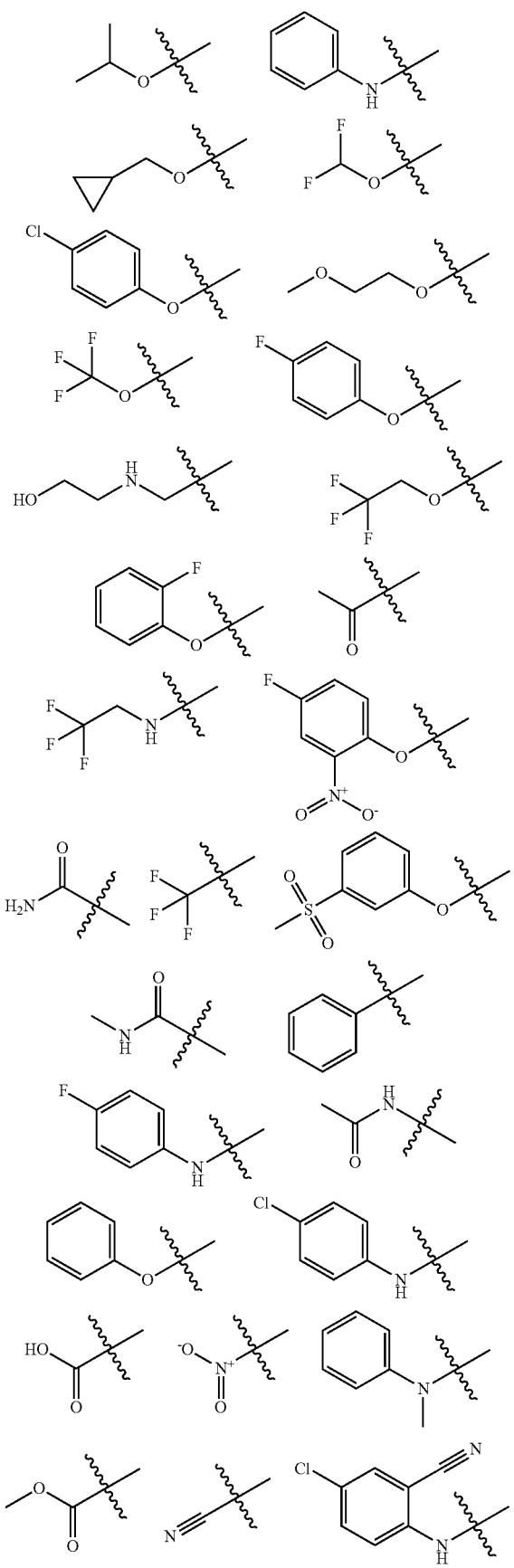
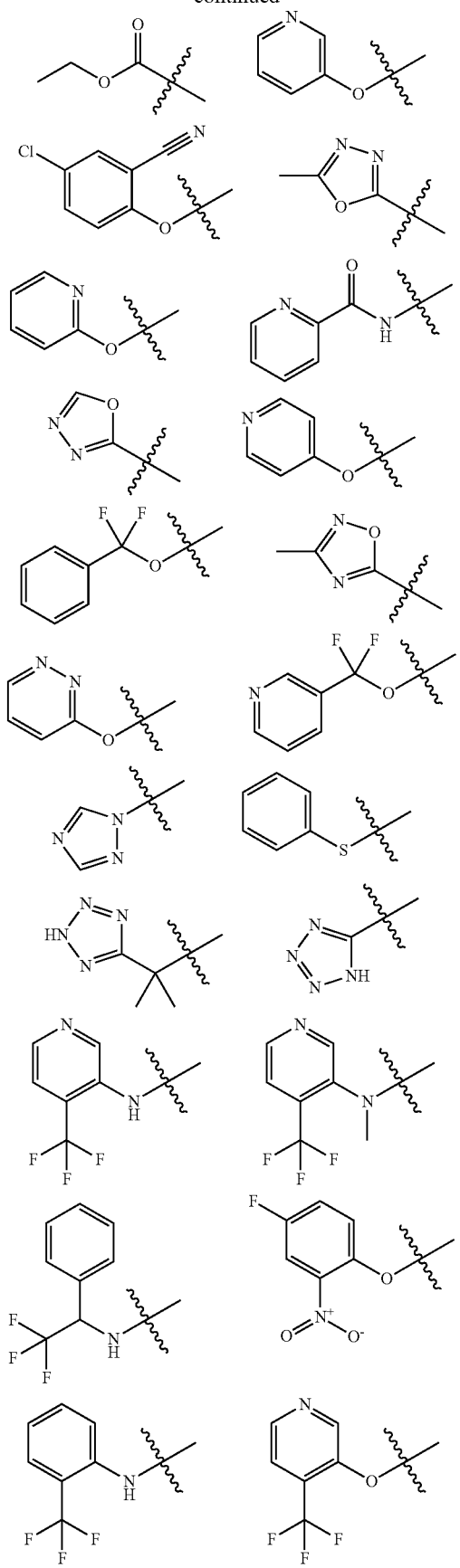

-continued

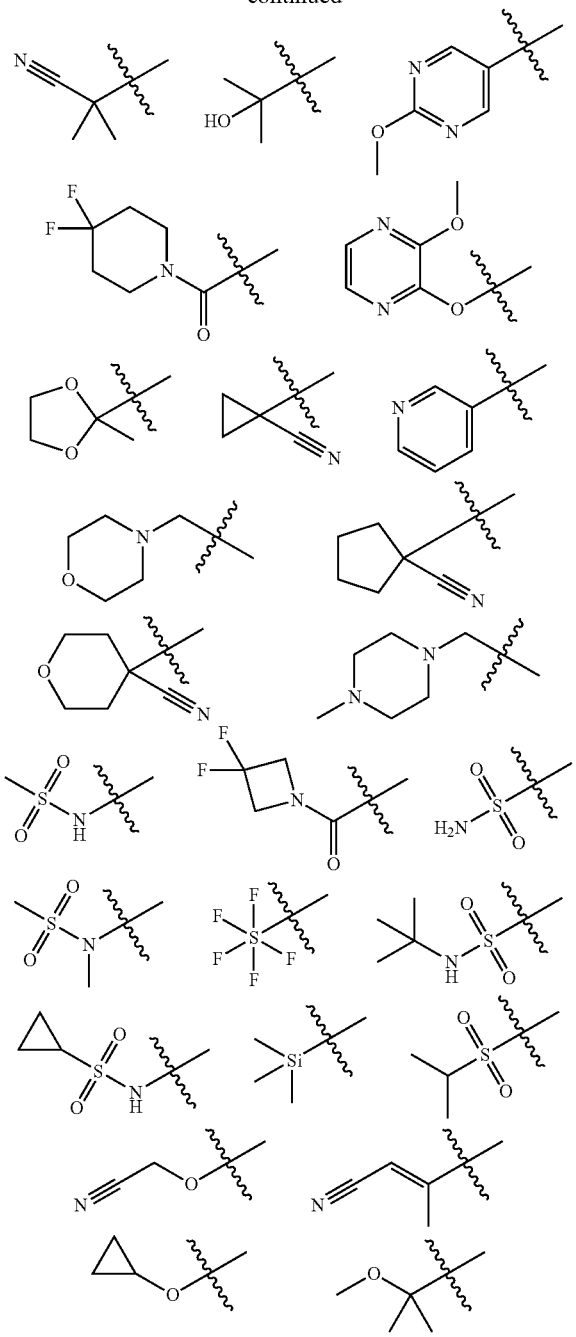

When W$^1$ is CR$^2$, common R$^2$ groups include, but are not limited to hydrogen, halo, methyl, methoxy, hydroxymethyl, CF$_3$, cyano, amino, acetamido, alkylamido, and cycloalkylcarboxamido.

When W$^2$ is CR$^3$, typical R$^3$ moieties include, but are not limited to hydrogen, methoxy, and methyl.

When W$^3$ is CR$^4$, common R$^4$ groups include, but are not limited to hydrogen, halo, methyl, methoxy, hydroxymethyl, (morpholine-4-carbonyloxy)methyl, (dimethylcarbamoyloxy)methyl, (cyanomethoxy)methyl, methoxymethyl, amino, dimethylamino, and cycloalkylcarboxamido.

When X$^1$ is CR$^a$ and/or X$^2$ is CR$^b$, common R$^a$ and R$^b$ moieties include but are not limited to hydrogen, methyl, amino, dimethylamino, —CF$_3$, —OCF$_3$, —OCH$_3$, —OCH$_2$COOH, NHCH$_2$CH$_3$, CONHCH$_3$, —CH$_2$CONH$_2$, —CH$_2$CONHCH$_3$, —CH$_2$CON(CH$_3$)$_2$, —CH$_2$CONH(CH$_2$)$_2$OH, —CH$_2$NHSO$_2$CH$_3$, —CH$_2$COOH, —COOCH$_2$CH$_3$, CH$_2$COOCH$_2$CH$_3$, —CH$_2$OH, —COOH, carboxyphenyl, methoxycarbonylphenyl. Very common R$^a$ and R$^b$ moieties are hydrogen, —CF$_3$, —OCF$_3$. Exemplary R$^a$ and R$^b$ moieties include, but are not limited to the following:

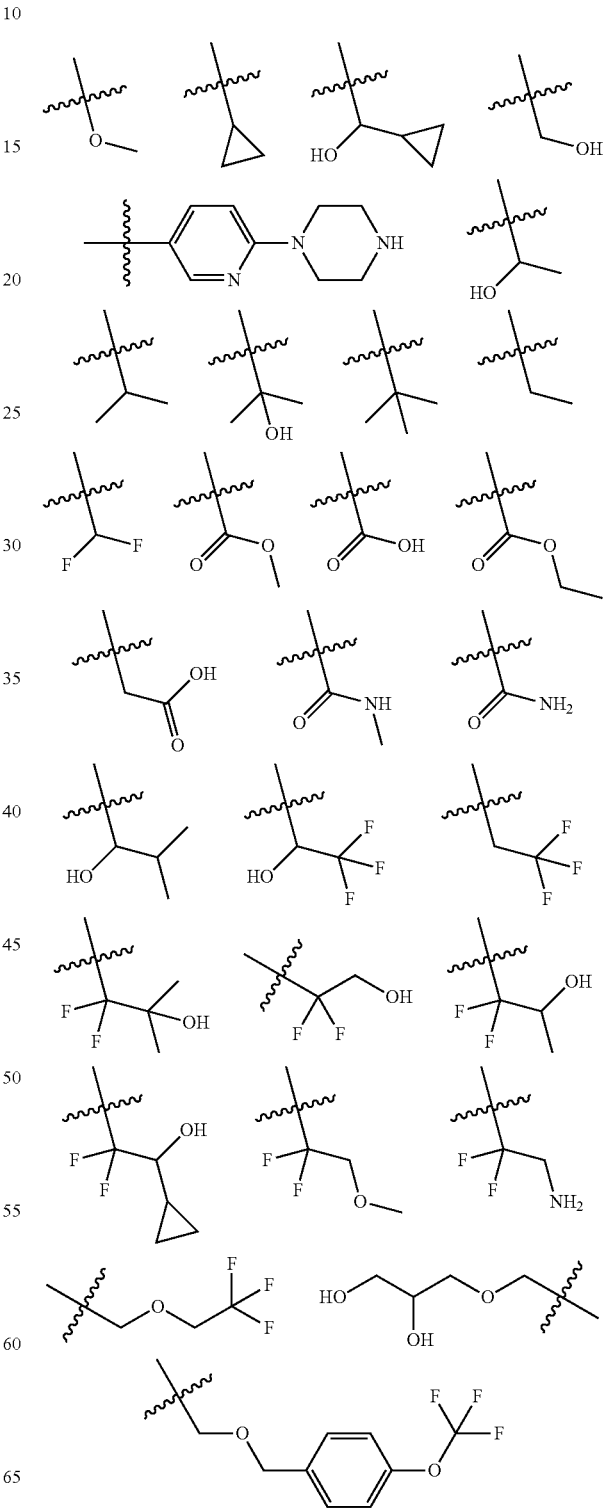

-continued
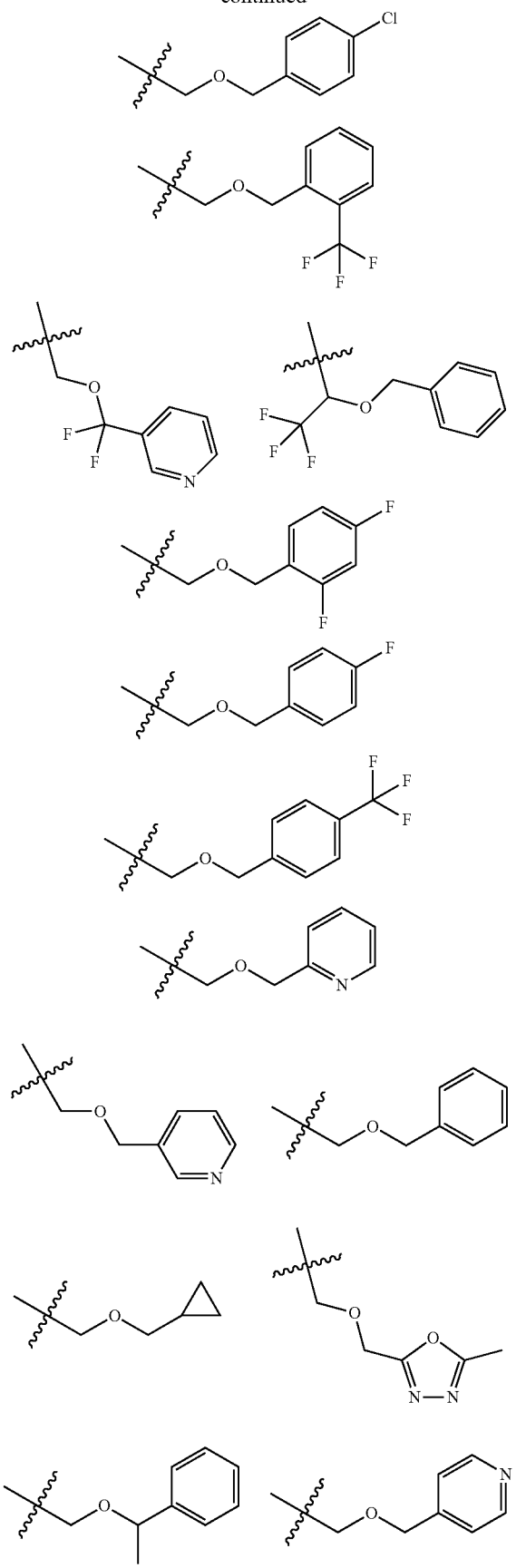
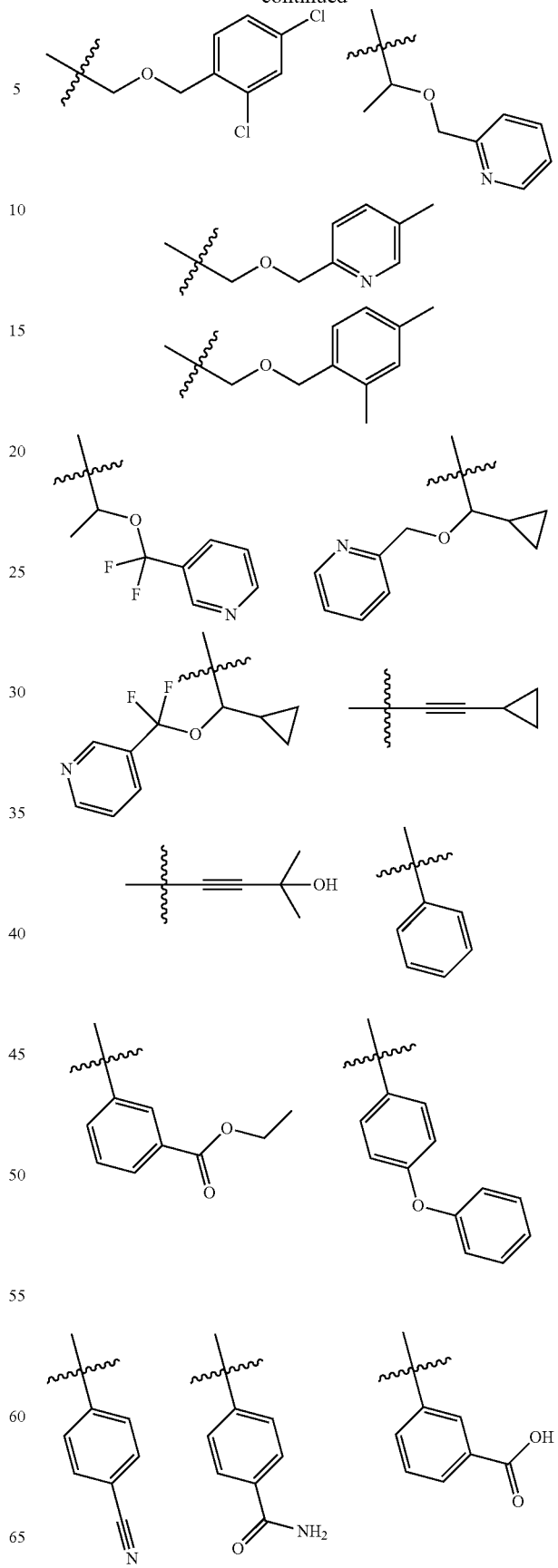

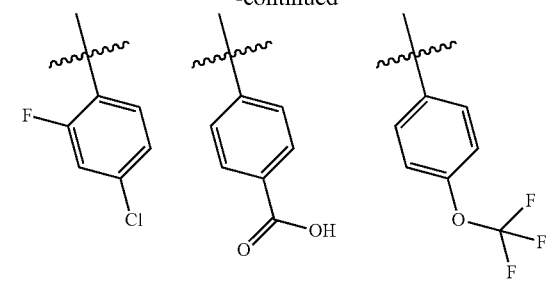
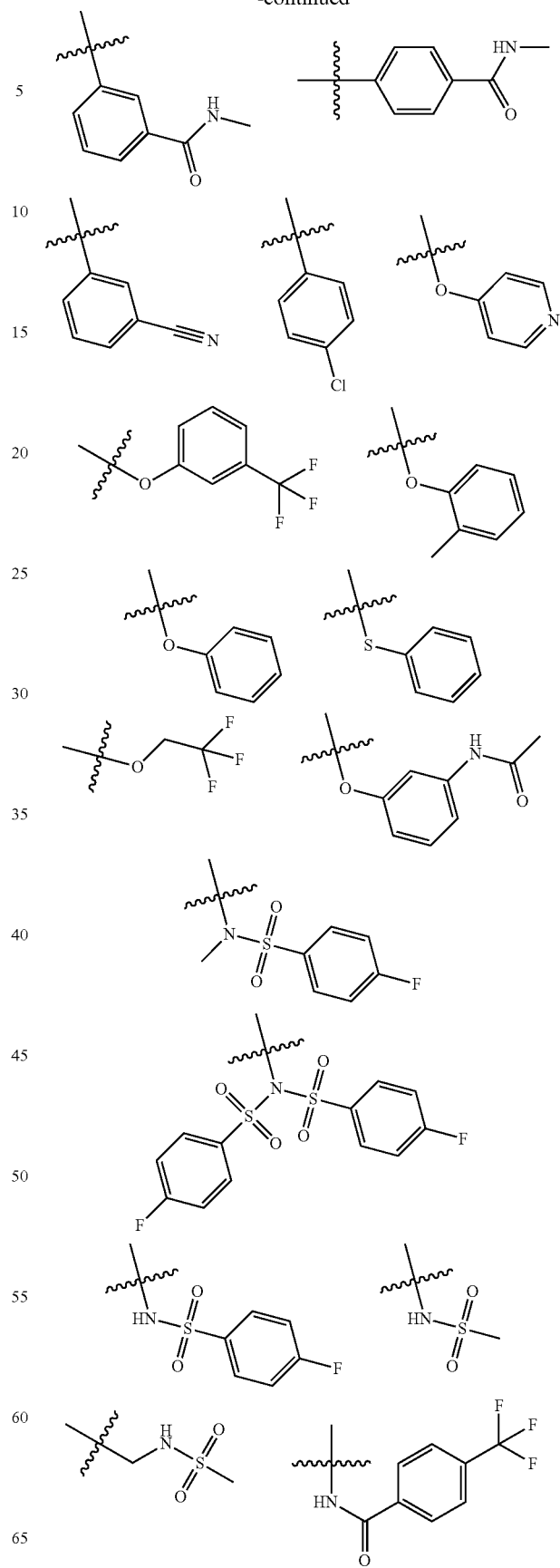

37
-continued
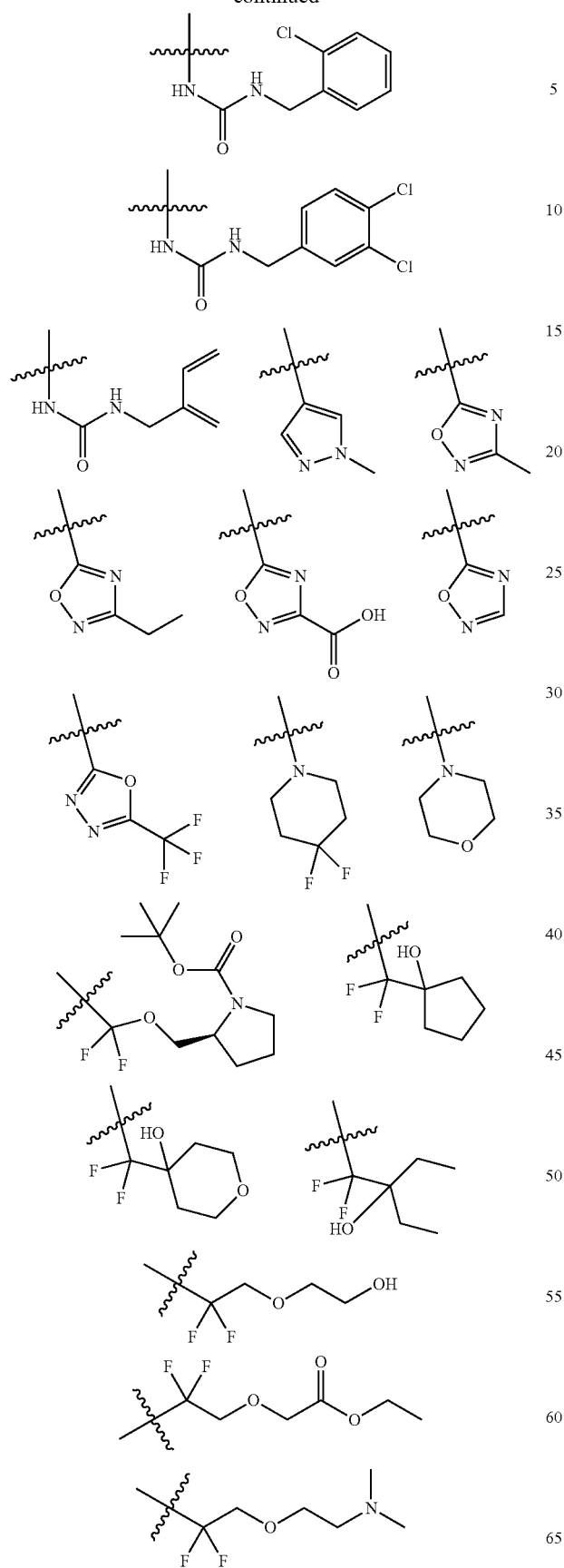
38
-continued
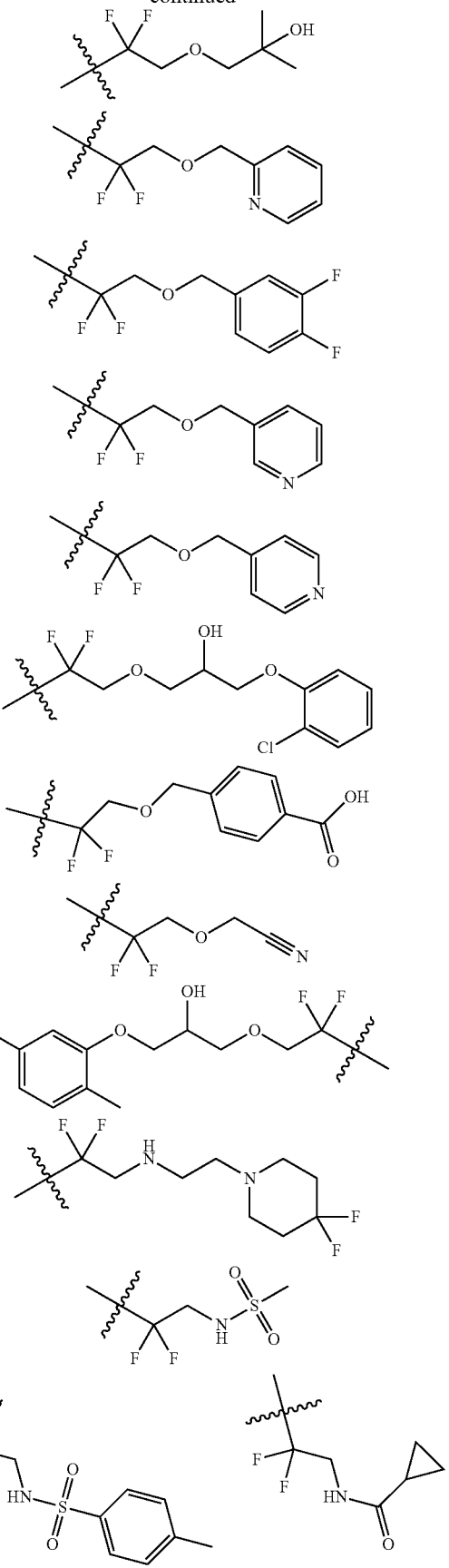

-continued
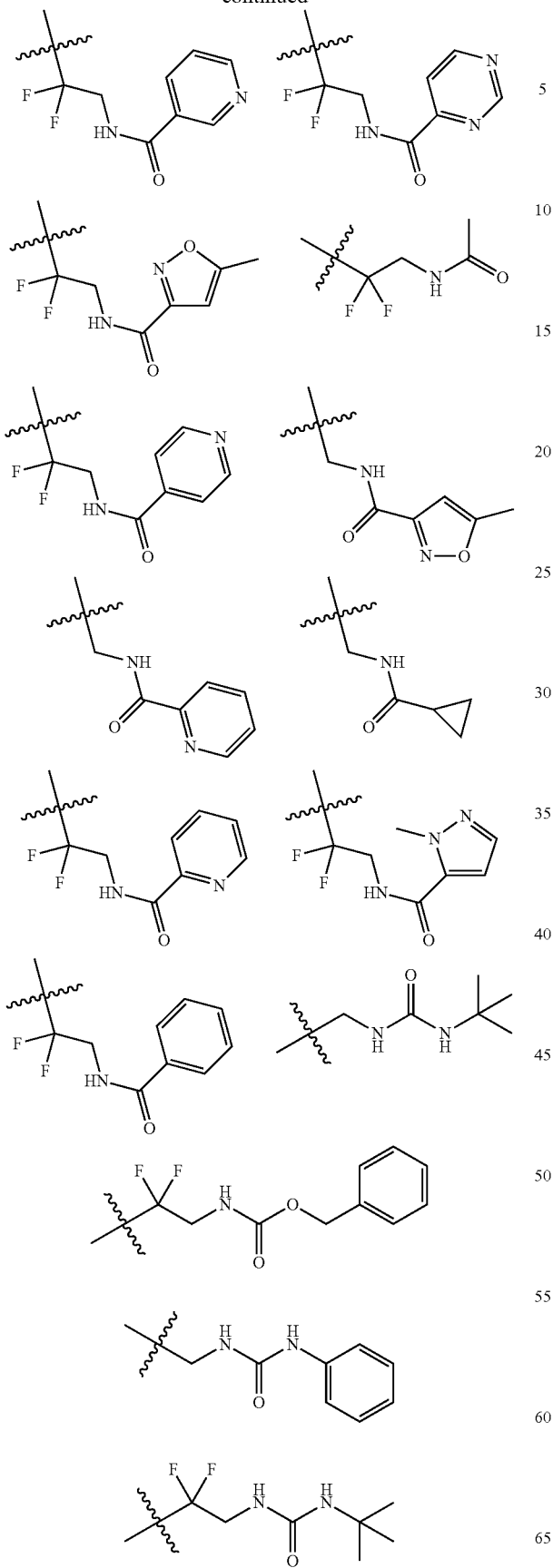
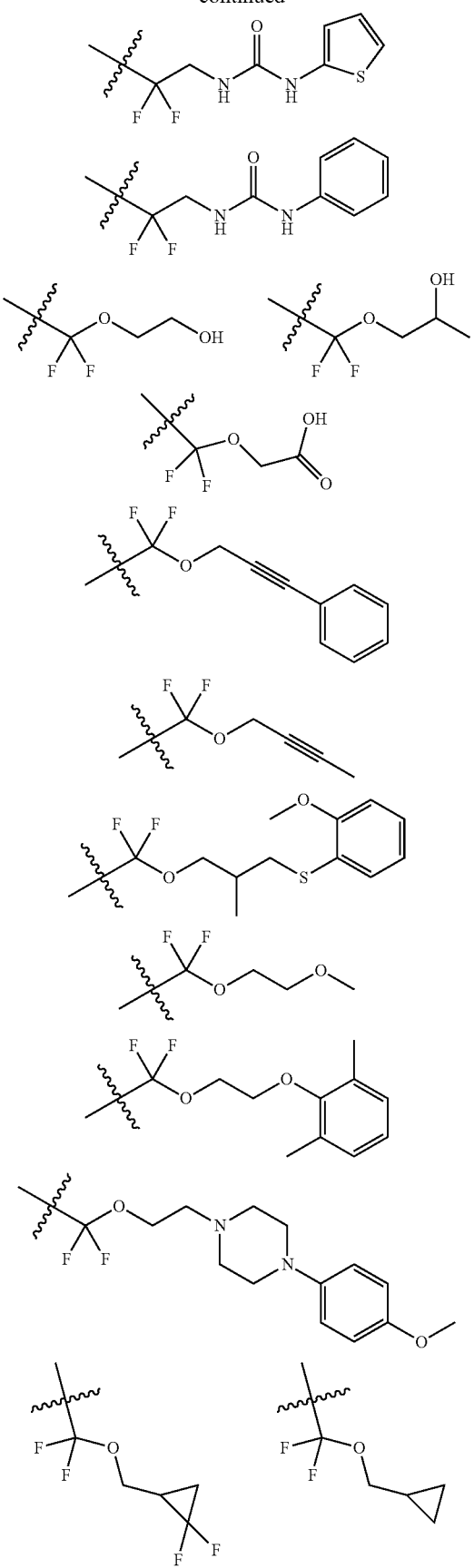

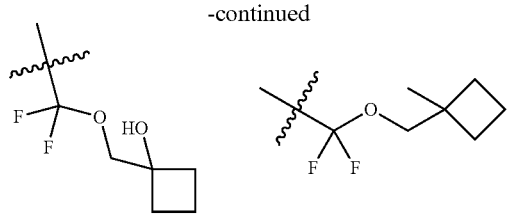
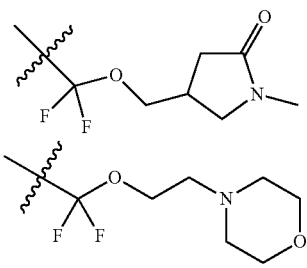
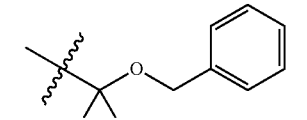
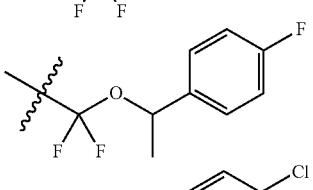
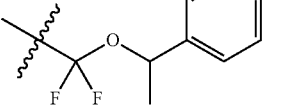
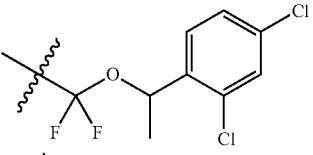
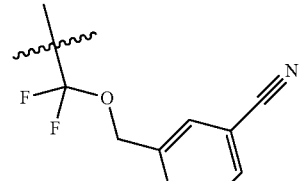
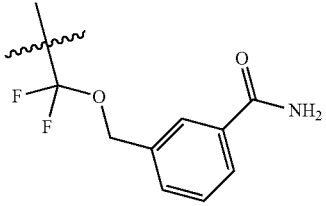
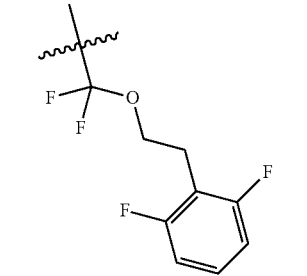
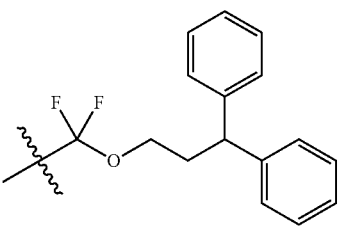
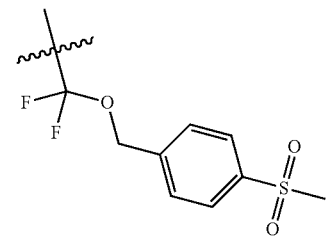
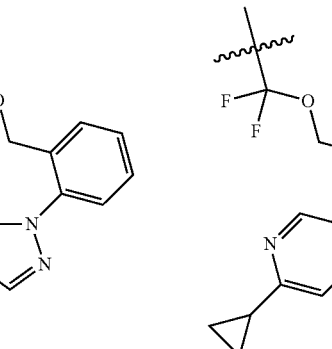
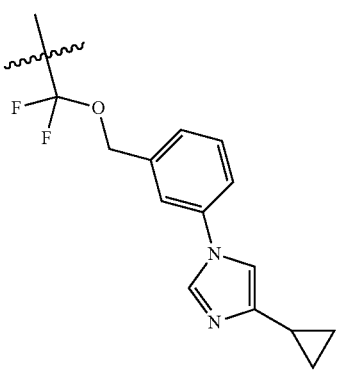
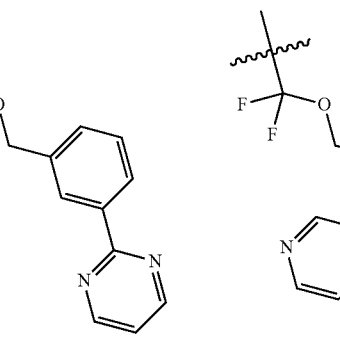

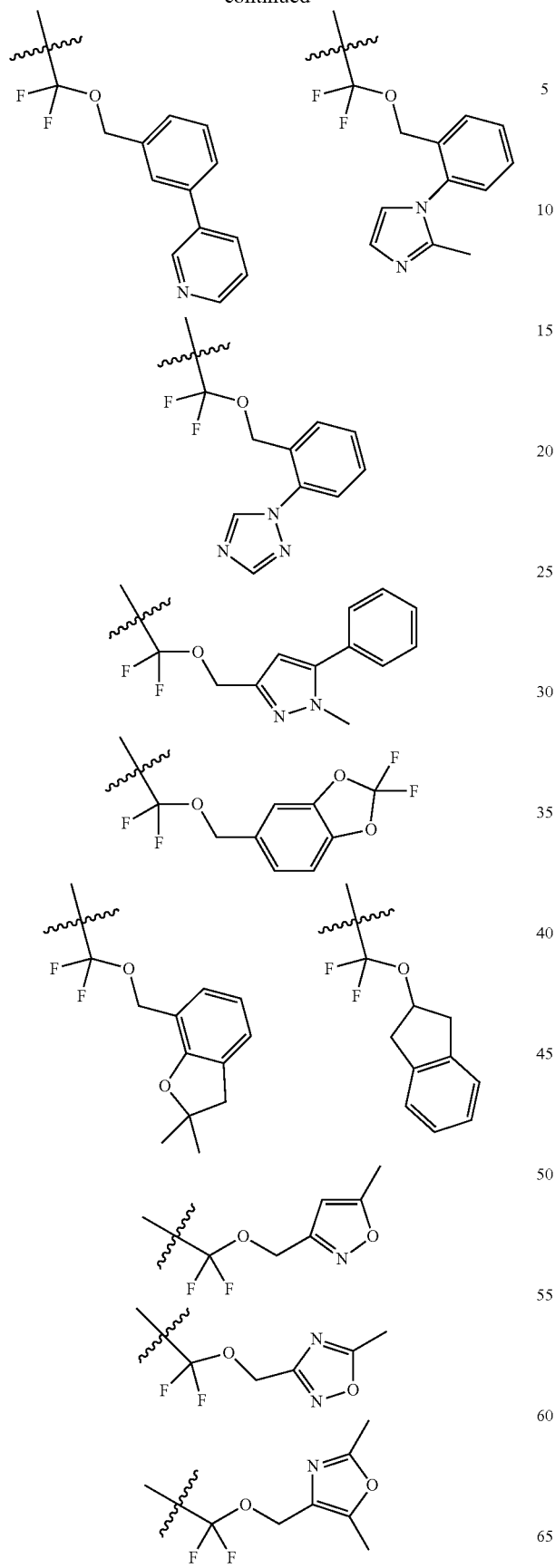
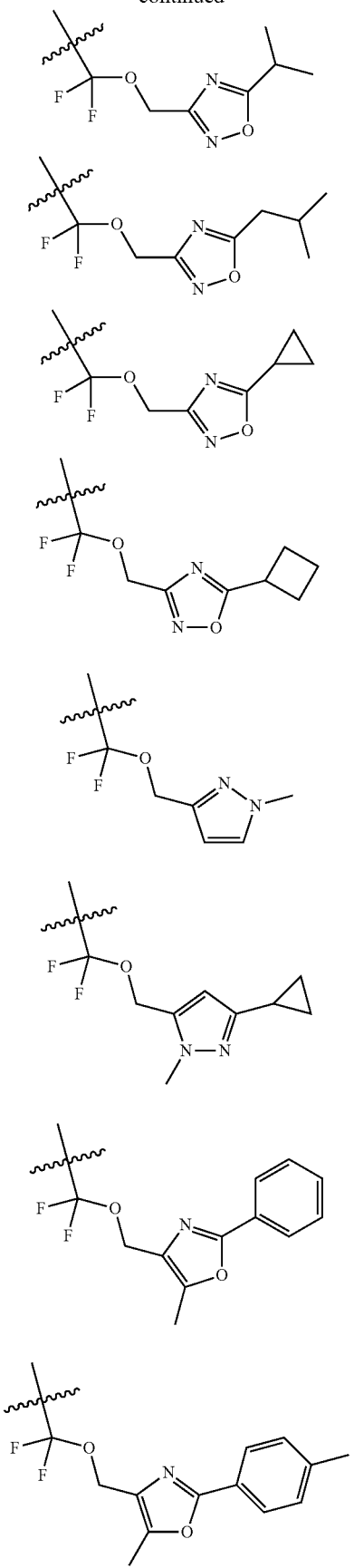

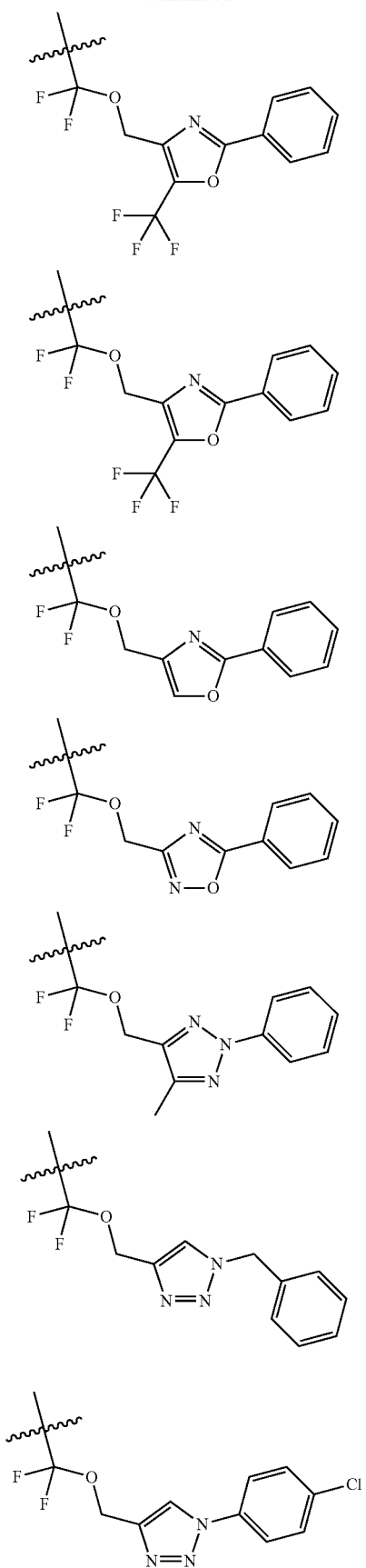
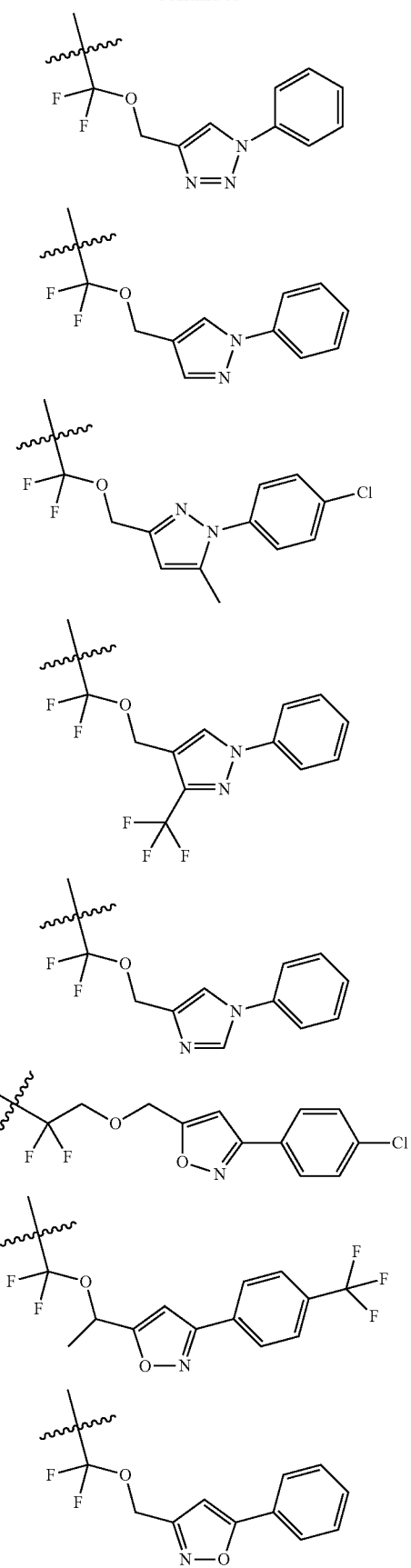

-continued

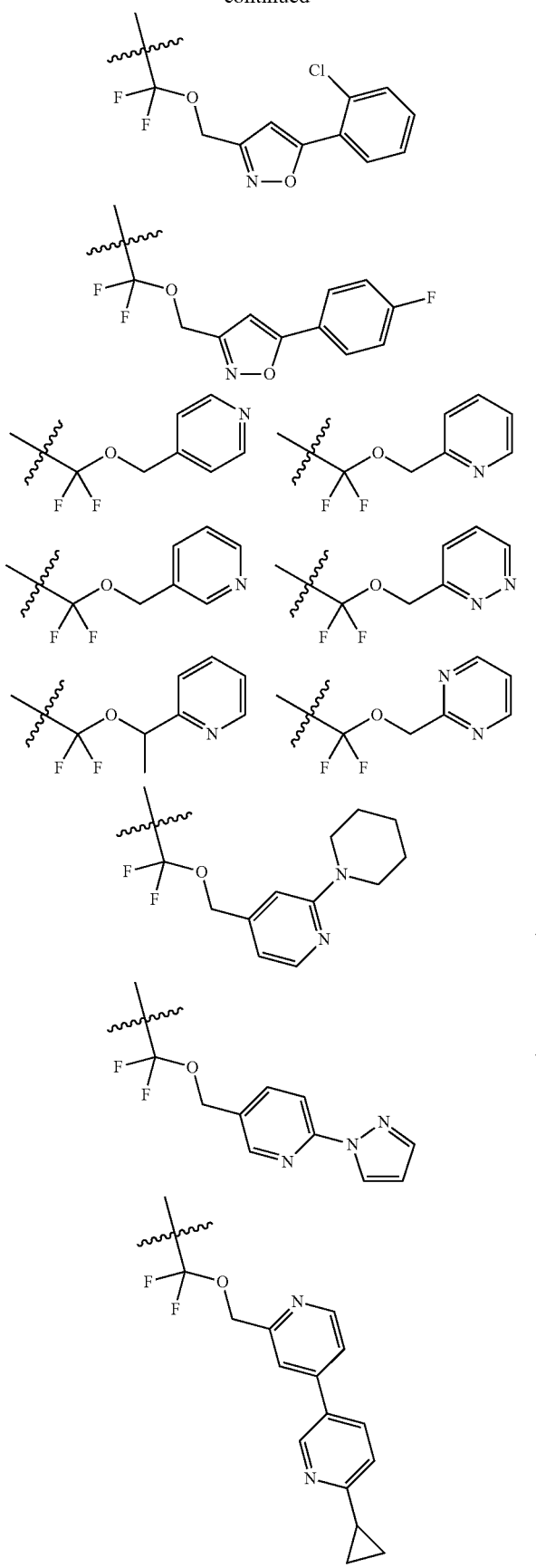

-continued

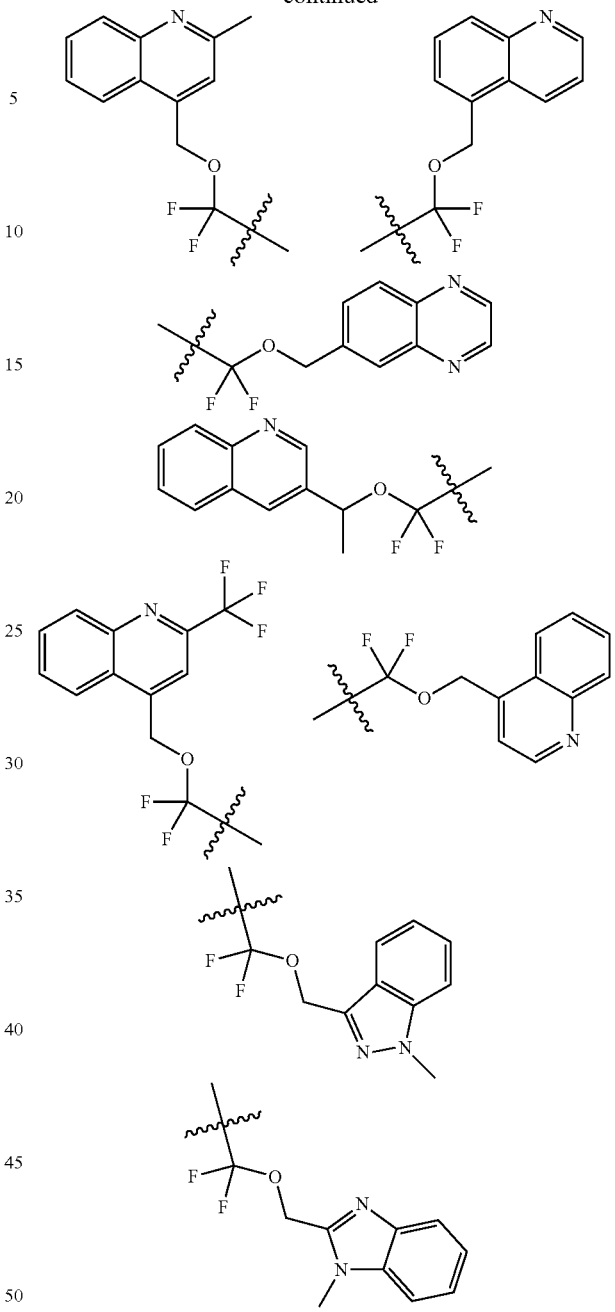

Further Embodiments

In typical embodiments, the compounds provided by the present invention are effective in the treatment of conditions known to respond to administration of late sodium channel blockers, including but not limited to cardiovascular diseases such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, and myocardial infarction. In some embodiments, compounds provided by the present invention which function as late sodium channel blockers may be used in the treatment of diseases affecting the neuromuscular system resulting in pain, itching, seizures, or paralysis, or in the treatment of diabetes or reduced insulin sensitivity, and disease states related to diabetes, such as diabetic peripheral neuropathy.

Certain compounds of the invention may also possess a sufficient activity in modulating neuronal sodium channels, i.e., $Na_v$ 1.1., 1.2, 1.7, and/or 1.8, and may have appropriate pharmacokinetic properties such that they may active with regard to the central and/or peripheral nervous system. Consequently, some compounds of the invention may also be of use in the treatment of epilepsy or pain or itching of a neuropathic origin.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a hydrate of an addition salt, a tautomeric form, a polymorph, an enantiomer, a mixture of enantiomers, a stereoisomer or mixture of stereoisomers (pure or as a racemic or non-racemic mixture) of a compound described herein, e.g. a compound of Formula (I); such as a compound of Formula (I) named herein.

Pharmaceutical Compositions and Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845, 770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992, 445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Combination Therapy

Patients being treated by administration of the late sodium channel blockers of the invention often exhibit diseases or conditions that benefit from treatment with other therapeutic agents. These diseases or conditions can be of the cardiovascular nature or can be related to pulmonary disorders, metabolic disorders, gastrointestinal disorders and the like. Additionally, some coronary patients being treated by administration of the late sodium channel blockers of the invention exhibit conditions that can benefit from treatment with therapeutic agents that are antibiotics, analgesics, and/or antidepressants and anti-anxiety agents.

Cardiovascular Agent Combination Therapy

Cardiovascular related diseases or conditions that can benefit from a combination treatment of the late sodium channel blockers of the invention with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the late sodium channel blockers of the invention with therapeutic agents suitable for treating cardiovascular related conditions allows enhancement in the standard of care therapy the patient is currently receiving.

Anti-anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (Inspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein IIb/IIIa inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest given the recently discovered synergistic effects of the late sodium channel blocker ranolazine and amioarone and dronedarone. See U.S. Patent Application Publication No. 20100056536 and U.S. Provisional Patent Application 61/288,739, the entirety of which is incorporated herein.

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot for illation. Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this invention, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient ranolazine in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Antibiotics, Analgesics, Antidepressants and Anti-Anxiety Agents Combination Therapy Patients presenting with an acute coronary disease event may exhibit conditions that benefit from administration of therapeutic agent or agents that are antibiotics, analgesics, antidepressant and anti-anxiety agents in combination with ranolazine.

Antibiotics

Antibiotics are therapeutic agents that kill, or stop the growth of, microorganisms, including both bacteria and fungi. Example of antibiotic agents include β-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the late sodium channel blockers of the invention to treat neuropathic pain via inhibition of the $Na_V$ 1.7 and 1.8 sodium channels, combination with analgesics are particularly envisioned. See U.S. Patent Application Publication 20090203707.

Antidepressant and Anti-anxiety Agents

Antidepressant and anti-anxiety agents include those agents used to treat anxiety disorders, depression, and those used as sedatives and tranquillers. Examples of antidepressant and anti-anxiety agents include benzodiazepines, such as diazepam, lorazepam, and midazolam; enzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban).

Accordingly, one aspect of the invention provides for a composition comprising the late sodium channel blockers of the invention and at least one therapeutic agent. In an alternative embodiment, the composition comprises the late sodium channel blockers of the invention and at least two therapeutic agents. In further alternative embodiments, the composition comprises the late sodium channel blockers of the invention and at least three therapeutic agents, the late sodium channel blockers of the invention and at least four therapeutic agents, or the late sodium channel blockers of the invention and at least five therapeutic agents.

The methods of combination therapy include co-administration of a single formulation containing the late sodium channel blockers of the invention and therapeutic agent or agents, essentially contemporaneous administration of more than one formulation comprising the late sodium channel blocker of the invention and therapeutic agent or agents, and consecutive administration of a late sodium channel blocker of the invention and therapeutic agent or agents, in any order, wherein preferably there is a time period where the late sodium channel blacker of the invention and therapeutic agent or agents simultaneously exert their therapeutic affect.

Synthesis of Example Compounds

The compounds of the invention may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula I, may be accomplished as described in the following examples. If available, reagents may be purchased commercially, e.g. from Sigma Aldrich or other chemical suppliers.

General Syntheses:

Typical embodiments of compounds in accordance with the present invention may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present invention, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula (I)

The compounds of Formula I are typically prepared by first providing the molecular core (1); which may be commercially obtained, for example 6-bromo-[1,2,4]triazolo[4,3-a]pyridine, 6-bromo-3-methyl-[1,2,4]triazolo[4,3-a]pyridine, 6-bromo-N-ethyl-[1,2,4]triazolo[4,3-a]pyridin-3-amine, and the like, or synthesized de novo, and then attaching the desired $R^1Q$ substituents using conditions known as Suzuki coupling. This is process is show below in Reaction Scheme I for a compound of Formula IA.

REACTION SCHEME I

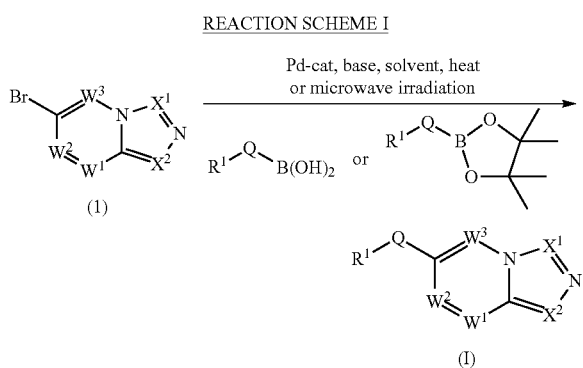

In general, a halogenated compound of formula (1), in this case a brominated compound, is reacted with an appropriately substituted boronic acid derivative of formula $R^1$-Q-B(OH)$_2$ in an inert solvent, for example aqueous N,N-dimethylformamide, in the presence of a mild base, for example sodium bicarbonate. The reaction is typically conducted in the presence of a metal catalyst with an appropriate ligand, for example dichlorobis(triphenylphosphine)palladium(II), at a temperature of about 120-170° C., for about 10 minutes to about 1 hour. When the reaction is substantially complete, the product of Formula I is isolated by conventional means.

It will be appreciated that various R substituents can be modified or added either before or after the addition of the $R^1$Q moiety. For example, in certain embodiments when $X^1$ is $CR^a$, the $R^a$ moiety may be coupled to the core before addition, of the $R^1$Q substituents. Also, in the case where the $R^a$ substituent contains a heteroaryl ring, the ring may be synthesized and cyclized before or after addition of the $R^1$Q portion.

It will also be appreciated that the addition of any substituent may result in the production of a number of isomeric products any or all of which may be isolated and purified using conventional techniques.

Optional Core Synthesis

When the compound of formula (1) is synthesized de novo, the various W and X components of the compounds are typically established by selecting the appropriate reactants for core synthesis. Additional modification to provide a desired $R^1$, $R^2$, $R^3$, $R^4$, $R^a$, or $R^b$, substituents may be subsequently carried out using conventional techniques.

Table 1 below illustrates methods for synthesizing typical compounds of formula (1).

TABLE 1

Formula (1) Core Compound Methods

| INTENDED FORMULA (1) STRUCTURE | REACTANTS | CONDITIONS |
|---|---|---|
| [Br-substituted tetrazolopyridine structure with $R^2$, $R^3$, $R^4$] | [pyridine with $R^1$, $R^2$, $R^3$, Cl] NaN$_3$, PTTS, DMF | Pyridine, sodium azide, and pyridine 4-methylbenzenesulfonate in anhydrous DMF is sealed in microwave reaction vial and subjected to irradiation at 160° C. for 30 min, cooled, and uncapped. Additional sodium azide and pyridine 4-methylbenzenesulfonate were added, capped, and subjected to irradiation at 200° C. for 30 min. After cooling, the mixture is concentrated in vacuo, diluted with DMF and MeOH, filtered, and subjected to preparative gradient HPLC. |
| [Br-substituted tetrazolopyridazine structure with $R^2$, $R^3$] | [pyridazine with $R^1$, $R^3$, $R^4$, Cl] NaN$_3$, PTTS, DMF | Pyridiazine, sodium azide, and pyridine 4-methylbenzenesulfonate in anhydrous DMF is sealed in microwave reaction vial and subjected to irradiation at 160° C. for 30 min, cooled, and uncapped. Additional sodium azide and pyridine 4-methylbenzenesulfonate were added, capped, and subjected to irradiation at 200° C. for 30 min. After cooling, the mixture is concentrated in vacuo, diluted with DMF and MeOH, filtered, and subjected to preparative gradient HPLC. |
| [Br-substituted triazolopyridine structure with $R^2$, $R^3$, $R^4$, $R^a$] | [Br-pyridine-NHNH$_2$] ($R^a$CCO)$_2$O | Anhydride is slowly added to hydrazinylpyridine and the reaction mixture was heated to reflux over 3 days, concentrated, and dried azeotropically with toluene and then purified with gradient chromatography. |

TABLE 1-continued

Formula (1) Core Compound Methods

| INTENDED FORMULA (1) STRUCTURE | REACTANTS | CONDITIONS |
|---|---|---|
| (triazolo-pyridine structure with $R^a$, $R^2$, $R^3$, $R^4$ and Br substituents) | 5-bromo-2-(aminomethyl)pyridine; $(R^aCCO)_2O$ | Dissolve pyridine in solvent such as $CH_2Cl_2$ at RT. Add base and anhydride at RT. Stir at RT for approximately 1 hour. Add $POCl_3$. Stir at RT for 12 to 24 hours, then at 160° C. for 0.5 to 2 hours at 180° C. for 4-6 hours. Quench in aqueous $NaHCO_3$ in ice bath then extract with EtOAc. Product may be collected by further washing and extraction and then purified using conventional techniques such as silica gel chromatography. |
| (triazolo-pyridazine structure with $R^a$, $R^2$, $R^3$ and Cl substituents) | 3-chloro-6-hydrazinylpyridazine; $(R^aCCO)_2O$ | Pyridazine or pyrazine and anhydride are placed in solvent such as toluene and heated from 100° C. to 120° C. for 1 to 4 hours. The reaction mixture is then concentrated and the product extracted by dissolution in $Cl_2CH_2$ followed by washing with $NaHCO_3$. |
| (triazolo-pyrazine structure with $R^a$, $R^2$, $R^4$ and Cl substituents) | 5-chloro-2-hydrazinylpyrazine; $(R^aCCO)_2O$ | |
| (triazolo-pyrimidine structure with $R^a$, $R^2$, $R^3$, $R^4$ and Br substituents) | 5-bromo-2-hydrazinylpyrimidine; $R^aCOOH$ | To a solution of hydrazinopyrimidine in solvent, e.g., dichloromethane, is added aldehyde followed by of acetic acid. The reaction mixture is stirred at room temperature for 1-4 hours after which is added iodobenzene diacetate. The resulting reaction mixture is stirred at RT for another 1-4 hours. The mixture is evaporated in vacuo and purified by preperative TLC. |

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula I where $W^1$, $W^2$, and $W^3$ are CH, $X^1$ is CH, and $X^2$ is N A. Preparation of a Compound of Formula I in which $R^1$ is 4-trifluoromethoxyphenyl, is a Covalent Bond, $W^1$, $W^2$, and $W^3$ are CH, $X^1$ is $CCF_1$, and $X^2$ is N

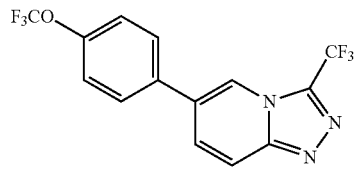 [SMILES: FC(F)(F)Oc1ccc(-c2ccc3nnc(C(F)(F)F)n3c2)cc1]

Step 1. Preparation of 6-bromo-3-(trifluoromethyl)-[1,2,4]triazolo[4,3-a]pyridine, a Compound of Formula (1)

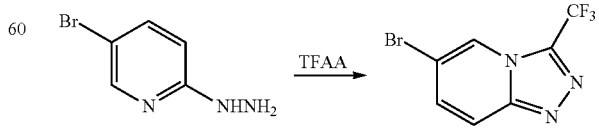

5-Bromo-2-hydrazinylpyridine (Frontier Scientific, Salt Lake City, Utah) (2.092 g) was placed in a 100 mL round-bottom flask equipped with reflux condenser. Trifluoroacetic anhydride was added (50 mL) was added slowly and the reaction mixture was heated to reflux over 3 days, concentrated, and dried azeotropically with toluene. Gradient chromatography (ethyl acetate/hexanes) afforded a tan solid.

$^1$H NMR (400 MHz, CDCl$_3$): δ 8.39 (br s, 1H); 7.83 (dd, J=9.8, 1.0 Hz, 1H); 7.54 (dd, J=9.8, 1.6 Hz, 1H).

Alternate Step 1. Preparation of 6-bromo-3-(trifluoromethyl)-[1,2,4]triazolo[4,3-a]pyridine, a Compound of Formula (1)

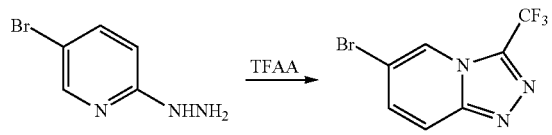 [SMILES: NNc1ccc(Br)cn1 ; "TFAA" ; FC(F)(F)c1nnc2ccc(Br)cn12]

To a suspension of the hydrazide (35.0 g, 0.186 mol) in butyronitrile at 0° C. in a sealable flask is added trifluoroacetic anhydride (79 mL, 0.558 mol) via syringe at such a rate that the internal temperature was maintained below 35° C. The flask is sealed and heated to 135° C. overnight. The reaction is cooled, and concentrated under reduced pressure. To the residue is added H$_2$O (100 ml) and the mixture is neutralized with NaHCO3 (aq). CH$_2$Cl$_2$ (200 ml) is added, the layers are separated, and the organic layer is washed with Brine (100 ml). The organics are dried over MgSO$_4$, filtered, and concentrated to a brown solid. The solids are suspended in a hexanes/ether mixture (2:1, 100 ml), sonicated until homogenous, and filtered. The solids are washed with cold hexanes/ether mixture (10:1, 2×50 ml) and dried to yield the product.

Alternate Step 1. Preparation of 6-bromo-3-(trifluoromethyl)-[1,2,4]triazolo[4,3-a]pyridine, a Compound of Formula (1)

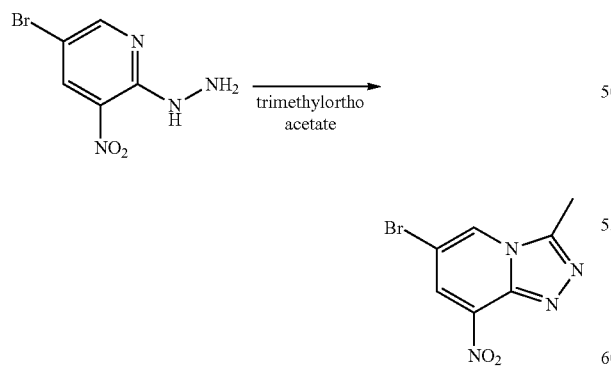

A suspension of 5-bromo-3-nitro-2-hydrazinopyridine (2.0 g, 8.58 mmol) in trimethylorthoacetate (20 mL) was heated at 80° C. for 20 h. After cooling, the solvent was distilled off, the residue was dissolved in ethyl acetate (200 mL), washed with water, brine, dried over sodium sulphate and concentrated to provide the product 6-bromo-3-methyl-8-nitro-[1,2,4]triazolo[4,3-a]pyridine.

Step 2. Preparation of 6-(4-(trifluoromethoxy)phenyl)-3-(trifluoromethyl)-[1,2,4]triazolo[4,3-a]pyridine

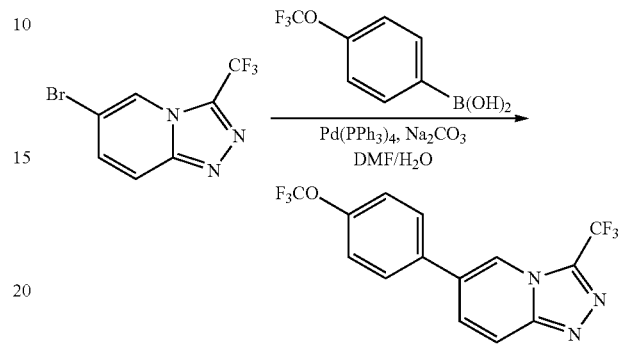

In a 100 mL round-bottom flask 6-bromo-3-(trifluoromethyl)[1,2,4]triazolo[4,3-a]pyridine (2.124 g), 4-trifluoromethoxyphenylboronic acid (2.466 g), and sodium carbonate (0.635 g) were suspended in a mixture of DMF (81 mL) and deionized water (9 mL) that was degassed with nitrogen. Tetrakis(triphenylphosphine)palladium (0.462 g) was added and the reaction mixture stirred at 90° C. overnight, concentrated, the residue dissolved in ethyl acetate, and washed with water (2x) and concentrated NaHCO$_3$. The combined organic phase dried over MgSO$_4$ and concentrated, then subjected to gradient chromatography (ethyl acetate/hexane) to produce dark grey solid. The solid was recrystallized from ethyl acetate/hexanes mixture to produce off-white material.

$^1$H NMR (400 MHz, CDCl$_3$): δ 8.32 (s, 1H); 8.03 (d, J=9.7 Hz, 1H); 7.69 (d, J=9.7, 1H); 7.62 (d, J=7.7 Hz, 2H); 7.41 (d, J=7.7, 2H).

$^{19}$F NMR (377 MHz, CDCl$_3$): δ −57.81 (s, 1F); −62.99 (s, 1F).

MS (ES+, m/z) 348.0 (base peak, M+H$^+$); 370.0 (M+Na$^+$); 717.0 (2M+Na$^+$).

Alternative Step 2. 6-(4-(trifluoromethoxy)phenyl)-[1,2,4]triazolo[4,3-a]pyridine

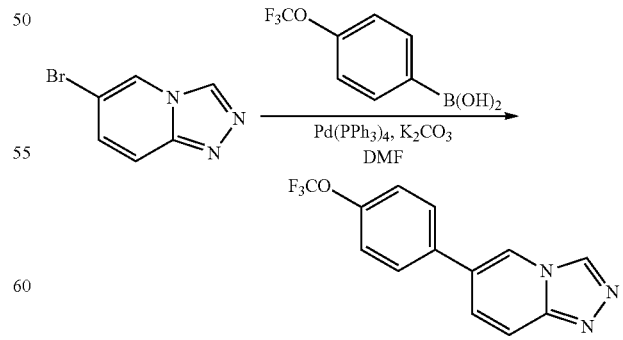

In a 5 mL vial 6-bromo-[1,2,4]triazolo[4,3-c]pyridine (93 mg), 4-trifluoromethoxyphenylboronic acid (115 mg), and potassium carbonate (187 mg) were suspended in DMF (2 mL) that was previously degassed with nitrogen. Tetrakis (triphenylphosphine)palladium (20 mg) was added and the reaction mixture was heated in a microwave reactor at 150° C. for 30 min, filtered, and concentrated. The residue was subjected to gradient chromatography (MeOH/dichloromethane) to produce white powder, 56.4 mg (43% yield).

¹H NMR (400 MHz, CDCl₃): δ 8.89 (s, 1H), 8.27 (br s, 1H); 7.89 (d, J=9.2 Hz, 1H); 7.59 (d, J=8.4, 2H); 7.52 (d, J=9.6 Hz, 1H); 7.36 (d, J=7.6, 2H).

MS (ES+, m/z) 280.0 (base peak, M+H⁺); 581.0 (2M+Na⁺).

Alternative Step 2. Preparation of 6-(4-cyclopropylphenyl)-3-(trifluoromethyl)-[1,2,4]triazolo[4,3-a]pyridine

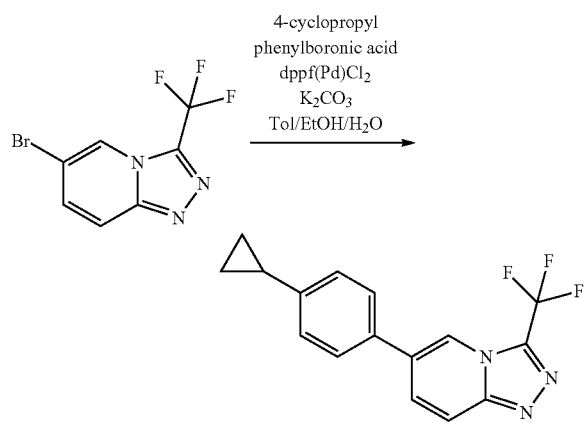

A suspension of 6-bromo-3-(trifluoromethyl)-[1,2,4]triazolo[4,3-a]pyridine (50 mg, 0.19 mmol), 4-cyclopropyl phenylboronic acid (34 mg, 0.21 mmol), dppf(Pd)Cl₂ (6.9 mg, 0.094 mmol), potassium carbonate (52 mg, 0.62 mmol) in degassed toluene (1 mL), degassed water (0.5 mL) and degassed ethanol (0.5 mL) was heated at 90° C. for 1 hour. The layers are separated, the organic layer was concentrated and the residue was purified by column chromatography to provide 6-(4-cyclopropylphenyl)-3-(trifluoromethyl)-[1,2,4]triazolo[4,3-a]pyridine as a white powder.

304.2 (M+1).

¹H NMR (DMSO) d 8.29 (s, 1H), 8.01 (d, J=9.6 Hz, 1H), 7.74 (dd, J=1.2, 9.6 Hz, 1H), 7.46 (d, J=8 Hz, 2H), 7.26 (s, 1H), 7.22 (d, J=8.4 Hz, 1H), 1.94-1.97 (m, 1H), 1.05-1.09 (m, 2H), 0.75-0.79 (m, 1H).

Optional Step 3. Preparation of N-methyl-3-(6-(4-(trifluoromethoxy)phenyl)-[1,2,4]triazolo[4,3-a]pyridin-3-yl)benzamide

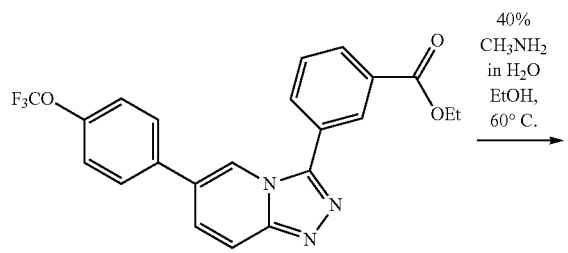

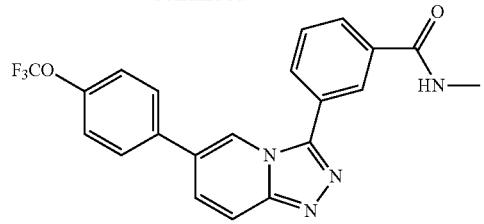

Ethyl 3-(6-(4-(trifluoromethoxy)phenyl)[1,2,4]triazolo[4,3-a]pyridin-3-yl)benzoate, prepared as described above was stirred in 40% CH₃NH₂ in H₂O (2.5 mL) and EtOH (1.5 mL) at 60° C. in a sealed tube overnight. The reaction mixture was concentrated and purified by HPLC followed by further purification with prep-TLC (5% MeOH/CH₂Cl₂) to afford N-methyl-3-(6-(4-(trifluoromethoxy)phenyl)-[1,2,4]triazolo[4,3-a]pyridin-3-yl)benzamide.

MS m/z 413.0 (M+H)

B. Preparation of Compounds of Formula I Varying R¹ and X¹

Similarly, following the procedure of Example 1A above, but optionally substituting other boronic acids or pinacolate esters for 4-trifluoromethoxyphenylboronic acid and/or substituting other compounds of formula (I), prepared using different formula (I) precursors either made as disclosed in the various Examples herein or commercially purchased and/or different anhydrides, the following compounds of Formula I were prepared:

3-methyl-6-[4-(trifluoromethoxy)phenyl][1,2,4]triazolo[4,3-a]pyridine;

N-ethyl-6-[4-(trifluoromethoxy)phenyl][1,2,4]triazolo[4,3-a]pyridin-3-amine;

6-(4-phenoxyphenyl)-3-(trifluoromethyl)[1,2,4]triazolo[4,3-a]pyridine;

3-methyl-6-(4-phenoxyphenyl)[1,2,4]triazolo[4,3-a]pyridine;

6-[2-methoxy-5-(trifluoromethyl)phenyl]-3-methyl[1,2,4]triazolo[4,3-a]pyridine;

N-ethyl-6-(4-phenoxyphenyl)[1,2,4]triazolo[4,3-a]pyridin-3-amine, 331.1 (base peak, M+H⁺); 683.3 (2M+Na⁺);

N-(4-{6-[4-(trifluoromethoxy)phenyl][1,2,4]triazolo[4,3-a]pyridin-3-yl}phenyl)methanesulfonamide MS m/z 449.0 (M+H)

4-{6-[4-(trifluoromethoxy)phenyl][1,2,4]triazolo[4,3-a]pyridin-3-yl}benzamide

MS m/z 399.0 (M+H)

diethyl 3,3'-[1,2,4]triazolo[4,3-a]pyridine-3,6-diyldibenzoate

MS m/z 416.1 (M+H)

ethyl 3-{6-[4-(trifluoromethoxy)phenyl][1,2,4]triazolo[4,3-a]pyridin-3-yl}benzoate MS m/z 428.0 (M+H)

N-(2-{6-[4-(trifluoromethoxy)phenyl][1,2,4]triazolo[4,3-a]pyridin-3-yl}phenyl)methanesulfonamide MS m/z 449.0 (M+H)

4-{6-[4-(trifluoromethoxy)phenyl][1,2,4]triazolo[4,3-a]pyridin-3-yl}benzenesulfonamide MS m/z 435.0 (M+H)

N-ethyl-6-(3-phenoxyphenyl)[1,2,4]triazolo[4,3-a]pyridin-3-amine, 331.1 (base peak, M+H⁺); 684.3 (2M+Na⁺);

7-methyl-6-[4-(trifluoromethoxy)phenyl]-3-(trifluoromethyl)[1,2,4]triazolo[4,3-a]pyridine;

6-[3-(trifluoromethoxy)phenyl]-3-(trifluoromethyl)[1,2,4]triazolo[4,3-a]pyridine;

3-(trifluoromethyl)-6-[4-(trifluoromethyl)phenyl][1,2,4]triazolo[4,3-a]pyridine;

6-(2,4-dichlorophenyl)-3-(trifluoromethyl)[1,2,4]triazolo[4,3-a]pyridine;

6-[4-(difluoromethoxy)phenyl]-3-(trifluoromethyl)[1,2,4]triazolo[4,3-a]pyridine;

6-(3-phenoxyphenyl)-3-(trifluoromethyl)[1,2,4]triazolo[4,3-a]pyridine;

6-[4-chloro-3-(trifluoromethyl)phenyl]-3-(trifluoromethyl)[1,2,4]triazolo[4,3-a]pyridine;

6-(4-chloro-3-fluorophenyl)-3-(trifluoromethyl)[1,2,4]triazolo[4,3-a]pyridine; and 6-[4-(trifluoromethoxy)phenyl][1,2,4]triazolo[1,5-a]pyridine;

6-(3-phenoxyphenyl)[1,2,4]triazolo[1,5-a]pyridine;

ethyl 4-{6-[4-(trifluoromethoxy)phenyl][1,2,4]triazolo[4,3-a]pyridin-3-yl}benzoate
$^1$H-NMR (DMSO-d6) δ 8.74 (s, 1H), 8.17 (s, 4H), 8.01 (dd, 1H), 7.91 (dd, 2H), 7.82 (dd, 1H), 7.49 (d, 2H), 4.36 (q, 2H), 1.35 (t, 3H);
MS m/z 428.0 (M+H)

3-phenyl-6-[4-(trifluoromethoxy)phenyl][1,2,4]triazolo[4,3-a]pyridine,
MS (ESI+) 356.14 (base peak, M+H$^+$);

3-(trifluoromethyl)-6-[4-(trifluoromethyl)phenyl][1,2,4]triazolo[4,3-a]pyridine
$^1$H NMR: 8.18 (s, 1H); 7.98 (d, 1H); 7.42 (d, 1H); 7.50 (d, 2H); 7.21 (s, 1H); 7.18 (d, 1H),
$^{19}$F NMR: −58.24 (s, 1F); −63.57 (s, 1F);

6-(4-phenoxyphenyl)-3-(trifluoromethyl)imidazo[1,5-a]pyridine,
MS (ESI+) 329.9 (base peak, M+H$^+$); 680.9 (2M+Na$^+$);

6-(2,4-dichlorophenyl)-3-(trifluoromethyl)[1,2,4]triazolo[4,3-a]pyridine,
MS (ESI+) 331.9 [base peak, M($^{35}$Cl$_2$)+H$^+$]; 333.9 [M($^{35}$Cl$^{37}$Cl)+H$^+$]; 335.9 [M($^{37}$Cl$_2$)+H$^+$]; 353.9; 686.8.

6-(3-(trifluoromethoxy)phenyl)-3-(trifluoromethyl)[1,2,4]triazolo[4,3-a]pyridine
MS (ESI+) 347.9 (base peak, M+H$^+$); 369.9 (M+Na$^+$); 716.9 (2M+Na$^+$);

7-methyl-6-(4-(trifluoromethoxy)phenyl)-3-(trifluoromethyl)-[1,2,4]triazolo[4,3-a]pyridine,
$^1$H NMR: 8.45 (s, 1H); 7.95 (s, 1H); 7.70 (d, 2H); 7.54 (d, 2H); 2.39 (d, 3H),
$^{19}$F NMR: −58.50 (s, 1F); −63.44 (s, 1F);

6-[4-(pentafluoro-lambda~6~-sulfanyl)phenyl]-3-(trifluoromethyl)[1,2,4]triazolo[4,3-a]pyridine
MS (ESI+) 389.9 (base peak, M+H$^+$).

1-(4-(3-(trifluoromethyl)[1,2,4]triazolo[4,3-a]pyridin-6-yl)phenyl)ethanone
MS (ESI+) 306.0 (base peak, M+H$^+$); 328.0 (M+Na$^+$); 633.1 (2M+Na$^+$).

6-(4-tert-butoxyphenyl)-3-(trifluoromethyl)[1,2,4]triazolo[4,3-a]pyridine
MS (ESI+) 336.0 (base peak, M+H$^+$); 693.1 (2M+Na$^+$).;

6-[4-(5-methyl-1,3,4-oxadiazol-2-yl)phenyl]-3-(trifluoromethyl)[1,2,4]triazolo[4,3-a]pyridine,
MS (ESI+) 346.0 (base peak, M+H$^+$); 368.0 (M+Na$^+$); 713.1 (2M+Na$^+$);

6-[4-(propan-2-ylsulfonyl)phenyl]-3-(trifluoromethyl)[1,2,4]triazolo[4,3-a]pyridine
MS (ESI+) 370.0 (base peak, M+H$^+$); 392.0 (M+Na$^+$); 761.0 (2M+Na$^+$);

6-[3-methyl-4-(trifluoromethoxy)phenyl]-3-(trifluoromethyl)[1,2,4]triazolo[4,3-a]pyridine,
MS (ESI+) 362.0 (base peak, M+H$^+$); 384.0 (M+Na$^+$); 745.1 (2M+Na$^+$);

2-methyl-2-{4-[3-(trifluoromethyl)[1,2,4]triazolo[4,3-a]pyridin-6-yl]phenyl}propanenitrile,
MS (ESI+) 331.0 (base peak, M+H$^+$); 353.0 (M+Na$^+$); 683.1 (2M+Na$^+$).;

6-(1-methyl-1H-indazol-5-yl)-3-(trifluoromethyl)[1,2,4]triazolo[4,3-a]pyridine,
MS (ESI+) 318.0 (base peak, M+H$^+$); 340.0 (M+Na$^+$); 657.1 (2M+Na$^+$);

6-(biphenyl-4-yl)-3-(trifluoromethyl)[1,2,4]triazolo[4,3-a]pyridine,
MS (ESI+) 340.1 (base peak, M+H$^+$); 701.1 (2M+Na$^+$).;

methyl 4-[3-(trifluoromethyl)[1,2,4]triazolo[4,3-a]pyridin-6-yl]benzoate;

3-(trifluoromethyl)-6-[4-(trimethylsilyl)phenyl][1,2,4]triazolo[4,3-a]pyridine,
MS (ESI+) 336.0 (base peak, M+H$^+$); 358.0 (M+Na$^+$); 693.1 (2M+Na$^+$);

6-(4-tert-butylphenyl)-3-(trifluoromethyl)[1,2,4]triazolo[4,3-a]pyridine,
MS (ESI+) 320.2 (base peak, M+H$^+$);

3-(difluoromethyl)-6-[4-(trifluoromethoxy)phenyl][1,2,4]triazolo[4,3-a]pyridine,
MS (ESI+) 330.2 (base peak, M+H$^+$);

6-(4-chloro-3-fluorophenyl)-3-(trifluoromethyl)[1,2,4]triazolo[4,3-a]pyridine,
MS (ESI+) 315.9 (base peak, M+H$^+$).;

6-[4-chloro-3-(trifluoromethyl)phenyl]-3-(trifluoromethyl)[1,2,4]triazolo[4,3-a]pyridine,
MS (ESI+) 365.9 (base peak, M+H$^+$);

6-(3-phenoxyphenyl)-3-(trifluoromethyl)[1,2,4]triazolo[4,3-a]pyridine,
MS (ESI+) 356.0 (base peak, M+H$^+$); 377.9 (M+Na$^+$); 733.0 (2M+Na$^+$);

7-methyl-6-[3-(trifluoromethoxy)phenyl]-3-(trifluoromethyl)[1,2,4]triazolo[4,3-a]pyridine,
MS (ESI+) 361.9 (base peak, M+H$^+$); 383.9 (M+Na$^+$); 744.9 (2M+Na$^+$).;

7-methoxy-6-[4-(trifluoromethoxy)phenyl]-3-(trifluoromethyl)[1,2,4]triazolo[4,3-a]pyridine,
MS (ESI+) 378.0 (base peak, M+H$^+$); 400.0 (M+Na$^+$); 777.1 (2M+Na$^+$);

6-(4-methoxyphenyl)-3-(trifluoromethyl)[1,2,4]triazolo[4,3-a]pyridine,
$^1$H NMR: 822 (s, 1H); 7.92 (d, 1H); 7.63 (d, 1H); 7.44 (d, 2H); 7.00 (d, 2H); 3.85 (s, 3H);

6-[4-(2,2,2-trifluoroethoxy)phenyl]-3-(trifluoromethyl)[1,2,4]triazolo[4,3-a]pyridine,
MS (ESI+) 362.0 (base peak, M+H$^+$); 384.0 (M+Na$^+$); 745.0 (2M+Na$^+$);

6-(2-methyl-4-(trifluoromethoxy)phenyl)-3-(trifluoromethyl)-[1,2,4]triazolo[4,3-a]pyridine,
MS (ESI+) 361.9 (base peak, M+H$^+$); 383.9 (M+Na$^+$);

2-methyl-6-(3-phenoxyphenyl)[1,2,4]triazolo[1,5-a]pyridine;

8-methyl-6-(4-phenoxyphenyl) [1,2,4]triazolo[1,5-a]pyridine;

5-methyl-6-[4-(trifluoromethyl)phenyl][1,2,4]triazolo[1,5-a]pyridine;

4-(3-(trifluoromethyl)[1,2,4]triazolo[4,3-a]pyridin-6-yl)phenol;

4-(3-(trifluoromethyl)[1,2,4]triazolo[4,3-a]pyridin-6-yl)aniline;

3-(propan-2-yl)-6-[4-(trifluoromethoxy)phenyl][1,2,4]triazolo[4,3-a]pyridine,
MS (ESI+) 322.0 (base peak, M+H$^+$);

6-(4-methoxyphenyl)-3-(trifluoromethyl)imidazo[1,5-a]pyridine,
LCMS (EI: 70 eV) 293 (M⁺+1);

6-(6-(2,2,2-trifluoroethoxy)pyridin-3-yl)-3-(trifluoromethyl)imidazo[1,5-a]pyridine,
LCMS (EI: 70 eV) 362 (M⁺+1);

6-phenyl-3-(trifluoromethyl)imidazo[1,5-a]pyridine,
LCMS (EI: 70 eV) 263 (M⁺+1);

6-(4-(2,2,2-trifluoroethoxy)phenyl)-3-(trifluoromethyl)imidazo[1,5-a]pyridine,
LCMS (EI: 70 eV) 293 (M⁺+1);

6-(6-(methylthio)pyridin-3-yl)-3-(trifluoromethyl)imidazo[1,5-a]pyridine,
LCMS (EI: 70 eV) 310 (M⁺+1);

3-(trifluoromethyl)-6-[6-(trifluoromethyl)pyridin-3-yl][1,2,4]triazolo[4,3-a]pyridine
MS (ESI+) 333.1 (M+1);

6-[6-(2,2,2-trifluoroethoxy)pyridin-3-yl]-3-(trifluoromethyl)[1,2,4]triazolo[4,3-a]pyridine,
MS (ESI+) 363.1 (M+1);

6-[2-methoxy-4-(trifluoromethyl)phenyl]-3-(trifluoromethyl)[1,2,4]triazolo[4,3-a]pyridine,
MS (ESI+) 362.1 (M+1);

8-(trifluoromethoxy)-5-[3-(trifluoromethyl)[1,2,4]triazolo[4,3-a]pyridin-6-yl]quinoline,
MS (ESI+) 399.1 (M+1);

N-phenyl-4-[3-(trifluoromethyl)[1,2,4]triazolo[4,3-a]pyridin-6-yl]aniline,
MS (ESI+) 355.3 (M+1);

6-[4-(phenylsulfanyl)phenyl]-3-(trifluoromethyl)[1,2,4]triazolo[4,3-a]pyridine,
MS (ESI+) 372.1 (M+1),
¹H NMR (CDCl₃) d 8.33 (s, 1H), 8.08-8.19 (m, 1H), 7.83 (d, J=6.8 Hz, 1H), 7.66-7.72 (m, 2H), 7.43-7.53 (m, 4H), 7.37-7.45 (m, 3H);

6-[4-(cyclopropylmethoxy)phenyl]-3-(trifluoromethyl)[1,2,4]triazolo[4,3-a]pyridine,
MS (ESI+) 334.2 (M+1); and 5-methyl-6-[4-(trifluoromethoxy)phenyl]-3-(trifluoromethyl)[1,2,4]triazolo[4,3-a]pyridine,
MS (ESI+) 362.2 (M+1),
¹H NMR (CDCl₃) d 7.87 (d, J=9.2 Hz, 1H), 7.32-7.42 (m, 5H), 2.68 (s, 3H).

C. Preparation of Compounds of Formula I Varying R¹, R², and R³

Similarly, following the procedure of Example 1A above, but optionally substituting other boronic acids or pinacolate esters for 4-trifluoromethoxyphenylboronic acid and/or substituting other compounds of formula (1), either commercially obtained or prepared using different formula (1) precursors or different anhydrides, other compounds of Formula I may be prepared.

EXAMPLE 2

Preparation of a Compound of Formula I wherein W¹ and W² are CH, W³ is N, and X¹ is CRᵃ, and X² is N A. Preparation of a Compound of Formula I in which R¹ is 4-trifluoromethoxyphenyl, Q is a Covalent Bond, W¹ and W² are CH, W³ is N, and X¹ is CCF₃, and X² is N

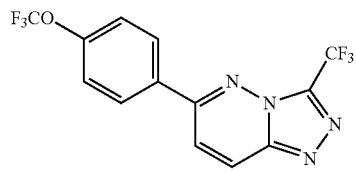 [SMILES: FC(F)(F)Oc1ccc(-c2ccc3nnc(C(F)(F)F)n3n2)cc1]

Step 1. Preparation of 6-chloro-3-(trifluoromethyl)[1,2,4]triazolo[4,3-b]pyridazine, a Compound of Formula (1)

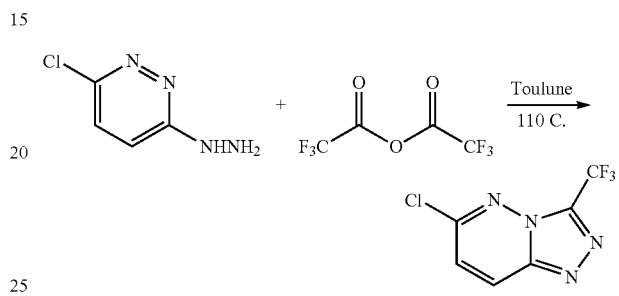

In a heavy-wall pressure tube, a suspension of 3-chloro-6-hydrazinopyridazine (6.90 mmole) and trifluoroacetic anhydride (7.59 mmole) in toluene (10 mL) was heated at 110 C for 2 hours. The reaction mixture was concentrated down. The residue was dissolved in dichloromethane and washed with saturated NaHCO₃. The organic extract was dried over Na₂SO₄ and evaporated in vacuo to afford the tan compound 6-chloro-3-(trifluoromethyl)-[1,2,4]triazolo[4,3-b]pyridazine.

Step 2. Preparation of 6-(4-(trifluoromethoxy)phenyl)-3-(trifluoromethyl)-[1,2,4]triazolo[4,3-b]pyridazine

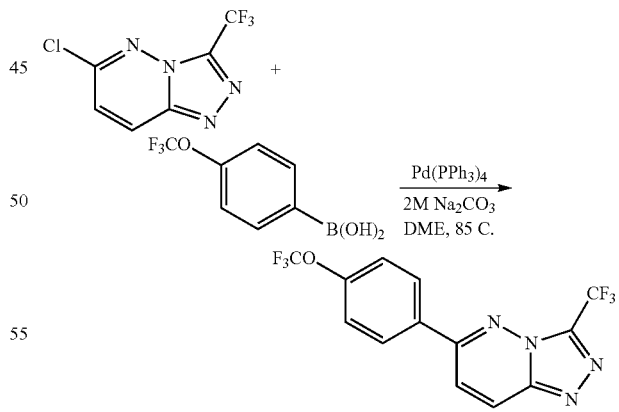

To a round bottom flask was added 6-chloro-3-(trifluoromethyl)[1,2,4]triazolo[4,3-b]pyridazine (0.982 mmole), 4-(trifluoromethoxy)phenylboronic acid (1.18 mmole), tetrakis(triphenylphosphine)palladium (0.0491 mmole), 2M Na₂CO₃ (2 mL), and 1,2-dimethoxyethane (3 mL). The resulting reaction mixture was heated at 85 C for 2 hours. The reaction mixture was diluted with ethyl acetate and filtered through celite. The filtrate was washed with water. The organic extract was dried over Na₂SO₄ and evaporated in vacuo. The crude residue was purified by preparative HPLC to yield 6-(4-(trifluoromethoxy)phenyl)-3-(trifluoromethyl)[1,2,4]triazolo[4,3-b]pyridazine.

¹H-NMR (DMSO) 7.65 (d, 2H, J=8.0 Hz), 8.25 (d, 1H, J=8.0 Hz), 8.26 (d, 2H, J=8.0 Hz), 8.74 (d, 1H, J=8.0 Hz), MS m/z 348.9 (M⁺).

Alternative Step 2. Preparation of 3-isopropyl-6-(2-methyl-4-(trifluoromethoxy)phenyl)-[1,2,4]triazolo[4,3-b]pyridazine

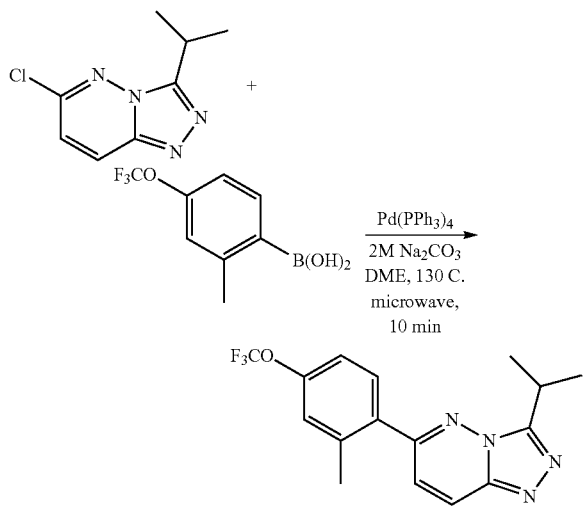

To a microwave reaction tube was added 6-chloro-3-isopropyl-[1,2,4]triazolo[4,3-b]pyridazine prepared as described in Step 1 above (1.28 mmole), 2-methyl-4-(trifluoromethoxy)phenylboronic acid (1.40 mmole), tetrakis(triphenylphosphine)palladium (0.064 mmole), 2M Na₂CO₃ (1 mL), and DMF (3 mL). The resulting reaction mixture was heated in the microwave at 130 C for 10 min. The reaction mixture was diluted with ethyl acetate and filtered through celite. The filtrate was washed with water. The organic extract was dried over Na₂SO₄ and evaporated in vacuo. The crude residue was purified by preparative HPLC to afford 3-isopropyl-6-(2-methyl-4-(trifluoromethoxy)phenyl)-[1,2,4]triazolo[4,3-b]pyridazine.

MS m/z 337 (M⁺).

¹H-NMR (DMSO) 8.375-8.408 (d, 1H), 7.667-7.695 (d, 1H), 7.525-7.557 (d, 1H), 7.405-7.441 (m, 2H), 3.460-3.645 (m, 1H), 1.420-1.444 (m, 6H).

B. Preparation of Compounds of Formula I varying R¹, X¹, and X²

Similarly, following the procedure of Example 4A above, but optionally substituting other boronic acids or pinacolate esters for 4-trifluoromethoxyphenylboronic acid and/or substituting other compounds of formula (1), either commercially obtained or prepared using conventional methods known in the art or disclosed herein, the following compounds of Formula 1 were prepared:

6-(4-phenoxyphenyl)-3-(trifluoromethyl)[1,2,4]triazolo[4,3-b]pyridazine;

3-(difluoromethyl)-6-[4-(trifluoromethoxy)phenyl][1,2,4]triazolo[4,3-b]pyridazine;

3-(difluoromethyl)-6-(4-phenoxyphenyl)[1,2,4]triazolo[4,3-b]pyridazine;

6-(4-phenoxyphenyl)[1,2,4]triazolo[4,3-b]pyridazine,
MS m/z 405.0 (M⁺);

6-[4-(trifluoromethoxy)phenyl][1,2,4]triazolo[4,3-b]pyridazine,
MS m/z 281.0 (M⁺);

3-(1-methyl-1H-pyrazol-4-yl)-6-(4-(trifluoromethoxy)phenyl)-[1,2,4]triazolo[4,3-a]pyridine,
MS m/z 360.1 (M⁺);

N[5-(trifluoromethoxy)-2-{3-[4-(trifluoromethoxy)phenyl][1,2,4]triazolo yl}phenyl]acetamide'
MS m/z 497.1 (M⁺):

3,6-bis[4-(trifluoromethoxy)phenyl][1,2,4]triazolo[4,3-b]pyridazine'
MS m/z 441.1 (M⁺);

6-[2-methyl-4-(trifluoromethoxy)phenyl]-3-(trifluoromethyl)[1,2,4]triazolo[4,3-b]pyridazine,
MS m/z 363 (M⁺),
¹H-NMR (DMSO) 8.671-8.703 (s, 1H), 7.847-7.880 (s, 1H), 7.691-7.719 (s, 1H), 7.400-7.459 (m, 2H), 2.442-2.494 (m, 3H);

6-(4-phenoxyphenyl)-3-(propan-2-yl)[1,2,4]triazolo[4,3-b]pyridazine,
MS m/z 331 (M⁺),
¹H-NMR (DMSO) 8.361-8.393 (d, 1H), 8.126-8.154 (d, 2H), 7.875-7.907 (d, 1H), 7.429-7.454 (t, 2H), 7.113-7.222 (m, 5H), 3.600-3.645 (m, 1H), 1.155-1.477 (m, 6H);

2-(trifluoromethoxy)-5-[3-(trifluoromethyl)[1,2,4]triazolo[4,3-a]pyridin-6-yl]aniline,
MS m/z 363.1 (M⁺);

6-(3,5-difluoro-4-phenoxyphenyl)-3-(propan-2-yl)[1,2,4]triazolo[4,3-b]pyridazine,
MS m/z 367.1 (M⁺);

3-(propan-2-yl)-6-[6-(2,2,2-trifluoroethoxy)pyridin-3-yl][1,2,4]triazolo[4,3-b]pyridazine,
MS m/z 338.1 (M⁺);

6-[3-fluoro-4-(trifluoromethoxy)phenyl]-3-(trifluoromethyl)[1,2,4]triazolo[4,3-b]pyridazine,
MS m/z 367.1 (M⁺),
¹H-NMR (DMSO) 8.749-8.782 (d, 1H), 8.248-8.281 (d, 2H), 8.072-8.100 (d, 1H), 7.800-7.825 (t, 1H);

6-(3,5-difluoro-4-phenoxyphenyl)-3-(trifluoromethyl)[1,2,4]triazolo[4,3-b]pyridazine,
MS m/z 393.1 (M⁺);

6-[4-(4-chlorophenoxy)phenyl]-3-(trifluoromethyl)[1,2,4]triazolo[4,3-b]pyridazine,
MS m/z 392.1 (M⁺);

3-(difluoromethyl)-6-[6-(2,2,2-trifluoroethoxy)pyridin-3-yl][1,2,4]triazolo[4,3-b]pyridazine,
MS m/z 346.1 (M⁺);

3-(difluoromethyl)-6-[3-fluoro-4-(trifluoromethoxy)phenyl][1,2,4]triazolo[4,3-b]pyridazine,
MS m/z 349.1 (M⁺);

3-tert-butyl-6-(4-phenoxyphenyl)[1,2,4]triazolo[4,3-b]pyridazine,
MS m/z 345.1 (M⁺);

3-tert-butyl-6-[4-(2,2,2-trifluoroethoxy)phenyl][1,2,4]triazolo[4,3-b]pyridazine,
MS m/z 351.1 (M⁺);

6-[6-(2,2,2-trifluoroethoxy)pyridin-3-yl]-3-(trifluoromethyl)[1,2,4]triazolo[4,3-b]pyridazine'
MS m/z 364.1 (M⁺).
¹H-NMR (DMSO) 8.992 (s, 1H), 8.703-8.734 (d, 1H), 8.483-8.514 (d, 1H), 8.256-8.288 (d, 1H), 7.245-7.273 (d, 1H), 5.105-5.135 (q, 2H);

3-ethyl-6-(4-phenoxyphenyl)[1,2,4]triazolo[4,3-b]pyridazine, and

MS m/z 317.1 (M+), $^1$H-NMR (DMSO) 8.358-8.390 (d, 1H), 8.127-8.155 (d, 2H), 7.871-7.903 (d, 1H), 7.426-7.479 (m, 2H), 7.110-7.245 (m, 5H), 3.138-3.163 (m, 2H), 1.392-1.442 (t, 3H).

C. Preparation of Compounds of Formula I Varying $R^1$, $X^1$, and $X^2$

Similarly, following the procedure of Example 4A above, but optionally substituting other boronic acids or pinacolate esters for 4-trifluoromethoxyphenylboronic acid and/or substituting other compounds of formula (1), either commercially obtained or prepared using different formula (1) precursors or different anhydrides, other compounds of Formula I may be prepared.

EXAMPLE 3

Preparation of a Compound of Formula I wherein $W^1$ and $W^2$ are CH, $W^3$ is N, and $X^1$ is $CR^a$, and $X^2$ is N

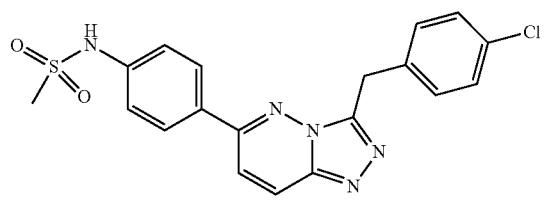 [SMILES: CS(=O)(=O)Nc1ccc(-c2ccc3nnc(Cc4ccc(Cl)cc4)n3n2)cc1]

A. Preparation of a Compound of Formula I in which $R^1$ is 4-methylsulfonylphenyl, Q is a Covalent Bond, $W^1$ and $W^2$ are CH, $W^3$ is N, and $X^1$ is $CR^a$, $R^a$ is 4-chlorobenzyl, and $X^2$ is N Step 1. Preparation of 6 N-(4-(6-chloropyridazin-3-yl)phenyl)methanesulfonamide, a Formula (1) Precursor Compound

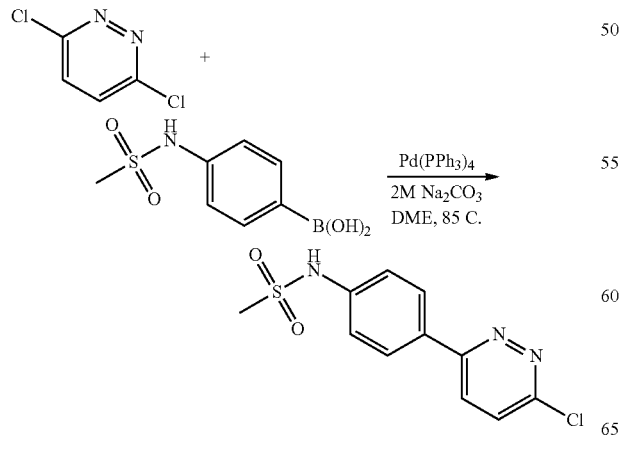

To a round bottom flask was added 3,6-dichloropyridazine (20.1 mmole), 4-(methylsulfonylamino)phenylboronic acid (20.1 mmole), tetrakis(triphenylphosphine)palladium (1.00 mmole), 2M Na2CO3 (30 mL), and 1,2-dimethoxyethane (120 mL). The resulting reaction mixture was heated at 85 C for 22 hours. The reaction mixture was diluted with ethyl acetate and filtered through celite. The filtrate was washed with water. The organic extract was dried over Na2SO4 and evaporated in vacuo. The crude residue was purified by biotage column chromatography eluting with 4:1 ethyl acetate to hexane mixture to afford N-(4-(6-chloropyridazin-3-yl)phenyl)methanesulfonamide.

Step 2. Preparation of N-(4-(6-hydrazinylpyridazin-3-yl)phenyl)methanesulfonamide

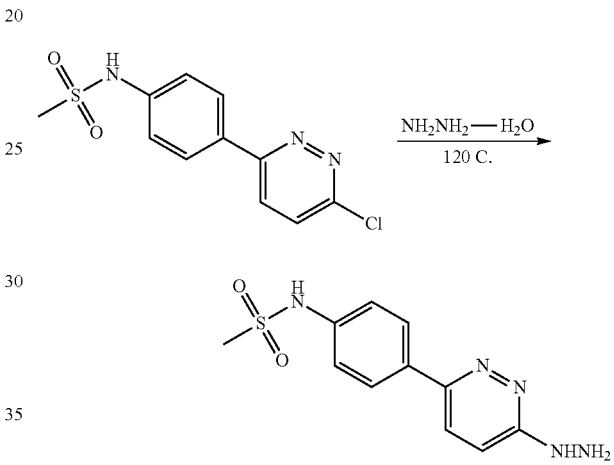

A suspension of N-(4-(6-chloropyridazin-3-yl)phenyl)methanesulfonamide (2.82 mmole) in hydrazine monohydrate (6 mL) was heated at 120 C for 1 hour and evaporated in vacuo. The residue was dissolved in dichloromethane, washed with water, dried over Na$_2$SO$_4$, and evaporated in vacuo to afford N-(4-(6-hydrazinylpyridazin-3-yl)phenyl)methanesulfonamide.

Step 3. Preparation of N-(4-(6-(2-(2-(4-chlorophenyl)acetyl)hydrazinyl)pyridazin-3-yl)phenyl)methanesulfonamide

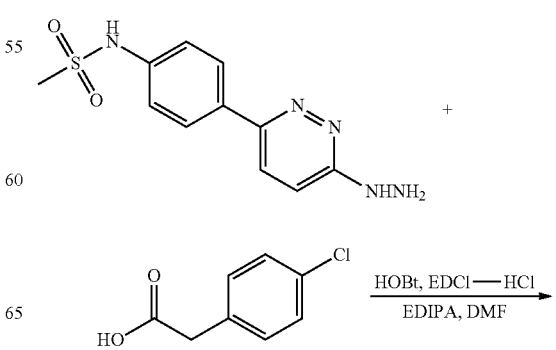

-continued

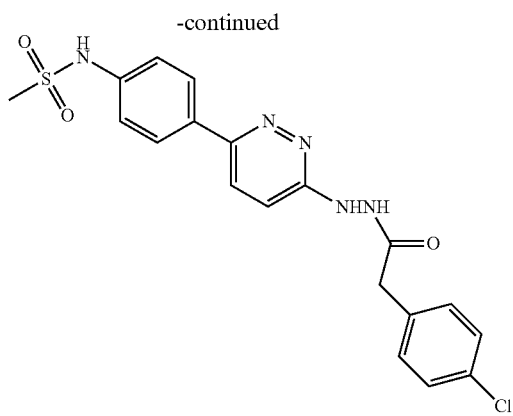

To a suspension of 2-(4-chlorophenyl)acetic acid (1.07 mmole), HOBT (1.07 mmole), and EDCI hydrochloride (1.61 mmole) in DMF (7 mL) were added N-(4-(6-hydrazinylpyridazin-3-yl)phenyl)methanesulfonamide (1.07 mmole) in 10 mL of DMF followed by diisopropylethylamine (3.77 mmole). The resulting mixture was stirred at room temperature for 22 hours and evaporated in vacuo. The desired product N-(4-(6-(2-(2-(4-chlorophenyl)acetyl)hydrazinyl)pyridazin-3-yl)phenyl)methanesulfonamide was precipitated out from water.

Step 4. Preparation of N-(4-(6-(2-(2-(4-chlorophenyl)acetyl)hydrazinyl)pyridazin-3-yl)phenyl)methanesulfonamide, a Compound of Formula I

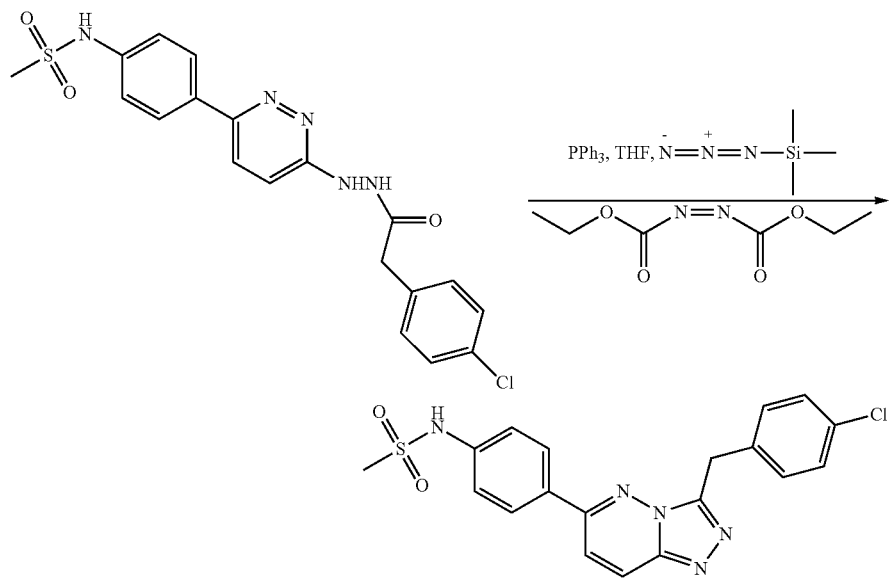

To a round bottom flask was added N-(4-(6-(2-(2-(4-chlorophenyl)acetyl)hydrazinyl)pyridazin-3-yl)phenyl)methanesulfonamide (0.928 mmole), triphenylphosphine (3.25 mmole), azidotrimethylsilane (3.25 mmole), diethyl azodicarboxylate (4.18 mmole), and THF (13 mL). The resulting mixture was stirred at room temperature for 22 hours. The reaction mixture was diluted with dichloromethane and washed with saturated $NaHCO_3$ and brine. The organic extract was dried over $Na_2SO_4$ and evaporated in vacuo. The crude product was washed with dichloromethane and methanol. The yellow solid was further purified by recrystallization with DMF and water to yield N-(4-(3-(4-chlorobenzyl)[1,2,4]triazolo[4,3-b]pyridazin-6-yl)phenyl)methanesulfonamide.

$^1$H-NMR (DMSO) 3.10 (s, 3H), 4.58 (s, 2H), 7.36-7.44 (m, 6H), 7.90-7.93 (d, 1H, J=12 Hz), 8.08-8.11 (d, 2H, J=12 Hz), 8.39-8.42 (d, 1H, J=12 Hz), 10.24 (s, 1H),

MS m/z 413.9 (M$^+$).

B. Preparation of a Compound of Formula I Varying R$^1$

Similarly, following the procedures of Example 3A above, but substituting other boronic acids or pinacolate esters for 4-(methylsulfonylamino)phenylboronic acid, the following compound of Formula I was prepared:

N-(4-{3-[4-(trifluoromethyl)benzyl][1,2,4]triazolo[4,3-b]pyridazin-6-yl}phenyl)methanesulfonamide; and 3-(difluoromethyl)-6-[4-(trifluoromethoxy)phenyl][1,2,4]triazolo[4,3-a]pyrazine, MS m/z 331 (M$^+$), $^1$H-NMR (DMSO) 9.683 (s, 1H), 9.227 (s, 1H), 8.236-8.265 (d, 2H), 8.013-7.669 (t, 1H).

C. Preparation of Compounds of Formula I Varying R$^1$ and R$^a$

Similarly, following the procedure of Example 3A above, but optionally substituting other boronic acids or pinacolate esters for 4-(methylsulfonylamino)phenylboronic acid and/or substituting other compounds CR$^a$ acid derivatives for diethyl azodicarboxylate, other compounds of Formula I may be prepared.

EXAMPLE 4

Preparation of a Compound of Formula I wherein W$^1$ and W$^2$ are CH, W$^3$ is N, and X$^1$ is CR$^a$, and X$^2$ is N A. Preparation of a Compound of Formula I in which R$^1$ is 4-trifluoromethoxyphenyl, Q is a covalent bond, W$^1$ and W$^2$ are CH, W$^3$ is N, and X$^1$ is CCH$_2$CF$_3$, and X$^2$ is N

75

Step 1. Preparation of 3,3,3-trifluoro-N-(6-(4-phenoxyphenyl)pyridazin-3-yl)propanehydrazide

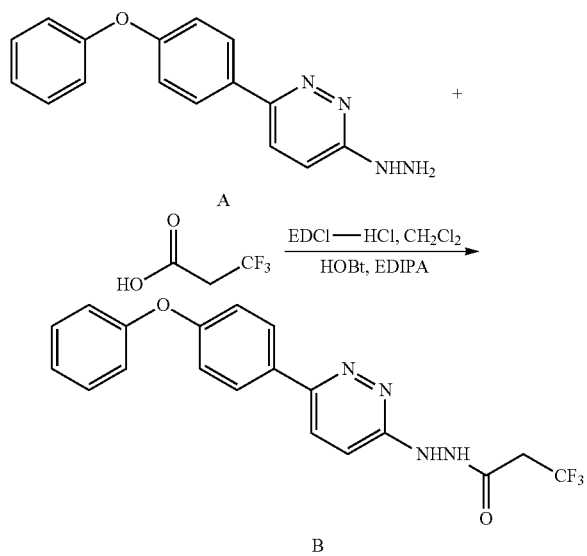

To a solution of 3,3,3-trifluoropropionic acid (2.07 mmole) in DCM (10 mL), was added EDCI HCl (3.02 mmole) and HOBt (2.07 mmole). The solution was stirred at RT for 0.5 hour followed by addition of 3-hydrazinyl-6-(4-phenoxyphenyl)pyridazine A, prepared as disclosed in Example 3, (2.07 mmole) in 30 mL of DCM and EDIPA ((7.24 mmole). The coupling reaction will also work with 1,3-dicyclohexylcarbodiimide and DCM as a solvent or EDCI HCl and methanol as a solvent. The resulting reaction mixture was stirred at RT overnight. The mixture was diluted with saturated aqueous NaHCO₃. The organic extract was washed with H₂O and dried over Na₂SO₄ and then evaporated in vacuo. The crude product was purified with prep TLC eluting with 5% methanol and dichloromethane mixture to give B.

Step 2. Preparation of 6-(4-phenoxyphenyl)-3-(2,2,2-trifluoroethyl)-[1,2,4]triazolo[4,3-b]pyridazine, a Compound of Formula I

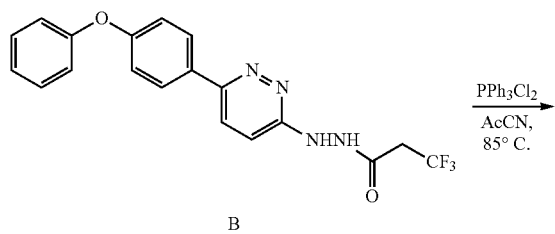

76

-continued

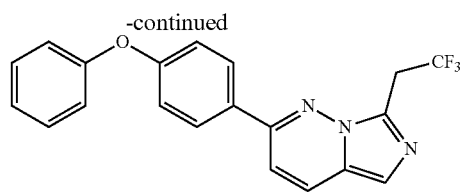

To a solution of B (0.67 mmole) in acetonitrile was added triphenylphosphine dichloride (4.02 mmole). The reaction mixture was heated at 85 C. overnight. The reaction mixture was evaporated in vacuo. The residue was diluted with DCM, washed with water and purified by preparative HPLC to give 6-(4-phenoxyphenyl)-3-(2,2,2-trifluoroethyl)-[1,2,4]triazolo[4,3-b]pyridazine.

MS m/z 371 (M⁺).

¹H-NMR (DMSO) 8.477-8.509 (d, 1H), 8.185-8.214 (d, 2H), 7.997-8.030 (d, 1H), 7.431-7.483 (t, 2H), 7.118-7.229 (m, 5H), 4.400-4.588 (m, 2H).

Optional Step 3. Addition of R¹ Moeity via Suzuki Coupling

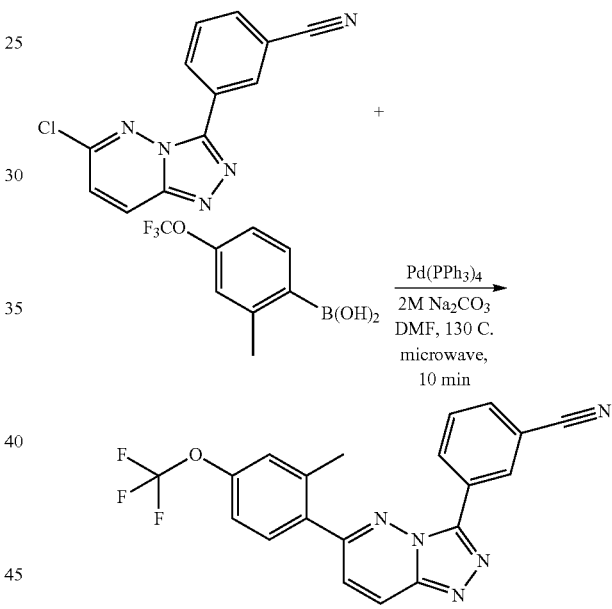

The compound 3-(6-(2-methyl-4-(trifluoromethoxy)phenyl)[1,2,4]triazolo[4,3-b]pyridazin-3-yl)benzonitrile was made using by reacting 3-(6-chloro-[1,2,4]triazolo[4,3-b]pyridazin-3-yl)benzonitrile, made using the methods disclosed in Example 3, with 2-methyl-4-(trifluoromethoxy)phenylboronic acid according the method disclosed in Example 2, Alternative Step 2.

B. Preparation of a Compound of Formula I Varying R¹

Similarly, following the procedures of Example 4A above, but substituting other hydrazinopyridazine for 3-hydrazinyl-6-(4-phenoxyphenyl)pyridazine or other acids for 3,3,3-trifluoropropionic acid, the following compound of Formula I were prepared:

3-cyclopropyl-6-(4-phenoxyphenyl)[1,2,4]triazolo[4,3-b] pyridazine,
  MS m/z 329.1 (M⁺);
3-(1-methyl-1H-pyrazol-4-yl)-6-(4-phenoxyphenyl)[1,2,4] triazolo[4,3-b]pyridazine,
  MS m/z 369.1 (M⁺);

3-[4-(methylsulfonyl)phenyl]-6-(4-phenoxyphenyl)[1,2,4] triazolo[4,3-b]pyridazine, MS m/z 443.1 (M+);

6-bromo-3-(1-methyl-1H-pyrazol-4-yl)-[1,2,4]triazolo[4,3-a]pyridine;

3-[6-(4-fluorophenyl) [1,2,4]triazolo[4,3-b]pyridazin-3-yl] benzonitrile,

MS m/z 316 (M+);

3-[6-(4-methoxyphenyl)[1,2,4]triazolo[4,3-b]pyridazin-3-yl]benzonitrile,

MS m/z 328.1 (M+);

4-[6-(4-methoxyphenyl)[1,2,4]triazolo[4,3-b]pyridazin-3-yl]benzonitrile,

MS m/z 328.1 (M+);

4-{6-[4-(trifluoromethoxy)phenyl][1,2,4]triazolo[4,3-b]pyridazin-3-yl}benzonitrile, MS m/z 382.0 (M+);

4-{6-[2-methyl-4-(trifluoromethoxy)phenyl][1,2,4]triazolo[4,3-b]pyridazin-3-yl}benzonitrile, MS m/z 396.1 (M+);

4-[6-(4-phenoxyphenyl)[1,2,4]triazolo[4,3-b]pyridazin-3-yl]benzonitrile,

MS m/z 390 (M+);

6-bromo-3-(4-(trifluoromethoxy)phenyl)-[1,2,4]triazolo[4,3-a]pyridine;

6-bromo-3-(4-(trifluoromethoxy)phenyl)[1,2,4]triazolo[4,3-b]pyridazine; and

2-[6-(4-phenoxyphenyl)[1,2,4]triazolo[4,3-b]pyridazin-3-yl]propan-2-ol,

MS m/z 347.1 (M+).

C. Preparation of Compounds of Formula I Varying $R^1$ and $R^a$

Similarly, following the procedure of Example 4A above, but substituting other hydrazinopyridazine for 3-hydrazinyl-6-(4-phenoxyphenyl)pyridazine or other acids for 3,3,3-trifluoropropionic acid, other compounds of Formula I may be prepared.

EXAMPLE 5

Preparation of a Compound of Formula I wherein $R^1$ is Substituted Phenyl, $W^1$ and $W^2$ are CH, $W^3$ is N, and $X^1$ is $CR^a$, and $X^2$ is N A. Preparation of a Compound of Formula I in which $R^1$ is 4-(pyridin-3-yloxy)phenyl)-3-(trifluoromethyl), Q is a Covalent Bond, $W^1$, $W^2$, and $W^3$ are CH, and $X^1$ is $CCH_2CF_3$, and $X^2$ is N

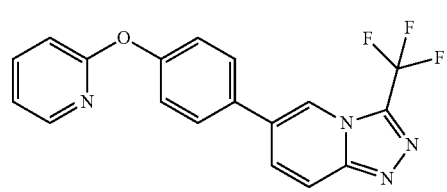 [SMILES: FC(F)(F)c1nnc2ccc(-c3ccc(Oc4ccccn4)cc3)cn12]

Step 1—Preparation of a Triazolopyridine Boronic Acid Intermediate

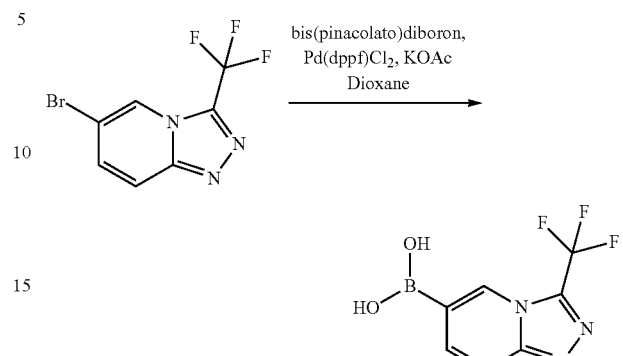

To a mixture of the aryl bromide, prepared as disclosed in Example 1 (10 g, 38 mmol), bis(pinacolato)diboron (14.3 g, 56 mmol), Pd(dppf)Cl$_2$ (1.1 g, 1.5 mmol), and KOAc (6.6 g, 68 mmol) is added degassed dioxane (90 mL). The reaction is heated to 75° C. for 4 hours and AcOH (684 mg, 114 mmol) and H$_2$O (30 mL) are added, stirred 10 minutes and cooled. The residue is partitioned between 2N NaOH and Et$_2$O, the layers are separated and the aqueous layer is washed an additional time with Et$_2$O. The aqueous layer is acidified with 1N HCl to pH=~2, and a precipitate is formed. The aqueous layer is filtered, and the solids are successively washed with CH$_3$CN/H$_2$O (1:1), CH$_3$CN, and Et$_2$O. The solids are dried and collected to yield the boronic acid.

Step 2—Preparation of a Compound of Formula I

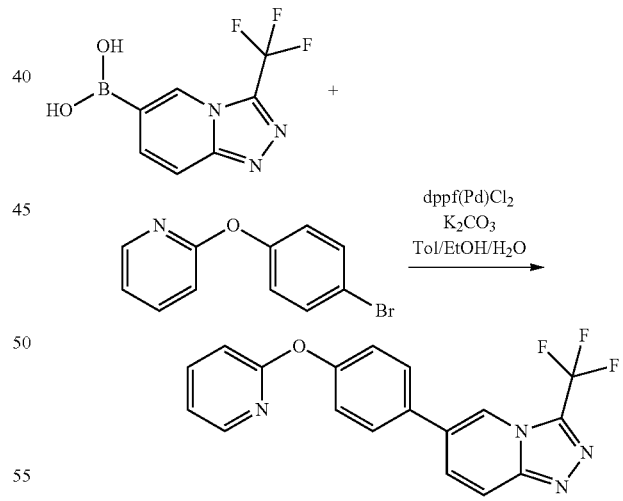

A suspension of 3-(trifluoromethyl)-[1,2,4]triazolo[4,3-a]pyridin-6-ylboronic acid (80 mg, 0.35 mmol), 2-(4-bromophenoxy)pyridine (79 mg, 0.32 mmol), dppf(Pd)Cl$_2$ (12 mg, 0.016 mmol), potassium carbonate (87 mg, 0.63 mmol) in degassed toluene (1 mL), degassed water (0.5 mL) and degassed ethanol (0.5 mL) was heated at 90° C. for 1 hour. The solvent was removed and the residue was purified by RP-HPLC to provide the product as a white powder.

357.1 (M+1).

Alternative Step 2—Preparation of a Compound of Formula I

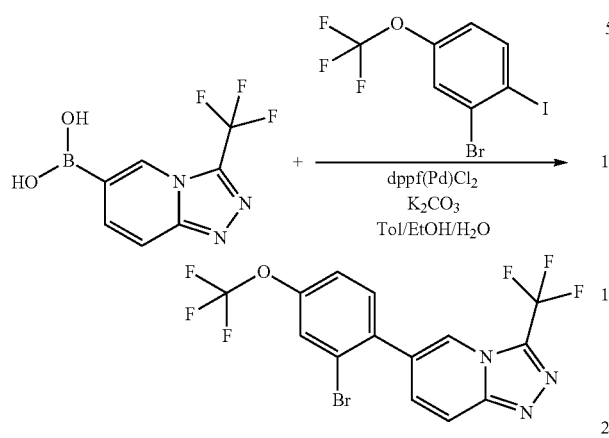

A suspension of the boronic acid (360 mg, 1.6 mmol), 2-bromo-1-iodo-4-(trifluoromethoxy)benzene (575 mg, 1.6 mmol), dppf(Pd)Cl$_2$ (57 mg, 0.078 mmol), potassium carbonate (433 mg, 3.1 mmol) in degassed toluene (4 mL), degassed water (2 mL) and degassed ethanol (2 mL) was heated at 45° C. for 3 hours. The layers were separated and the organics were concentrated and purified by column chromatography to provide the desired product.

426.0 (M+1).

$^1$H NMR (CDCl$_3$) d 8.23 (s, 1H), 7.99 (s, 1H), 7.64 (s, 1H), 7.30-7.53 (m, 3H).

Alternative Step 2—Preparation of a Compound of Formula I

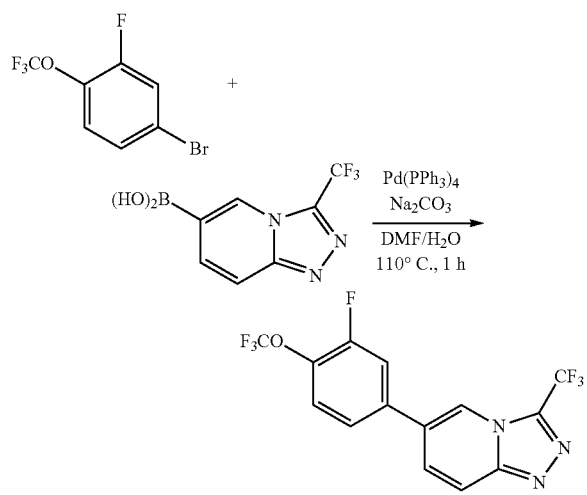

3-(trifluoromethyl)-[1,2,4]triazolo[4,3-a]pyridin-6-yl-boronic acid (56.2 mg, 0.217 mmol), 4-bromo-2-fluoro-1-(trifluoromethoxy)benzene (50.0 mg, 0.217 mmol, 1.0 equiv.) and Pd(PPh$_3$)$_4$ (12.6 mg, 0.0109 mmol, 0.05 equiv.) was placed in a 50 mL round bottomed flask under a nitrogen atmosphere. To the flask were added 2M-Na$_2$CO$_3$ (1.0 mL, 2.0 mmol) and DMF (4 mL) subsequently at ambient temperature. The mixture was heated at 110° C. for 1 hours. The mixture was filtered through Celite (3 g) and the Celite was washed with EtOAc (70 mL). The organic layer was washed with brine (30 mL) and dried with Na$_2$SO$_4$. The solvent was removed under a reduced pressure. Obtained crude mixture was purified by a column chromatography (SiO$_2$=25 g, EtOAc/hexane=1:3 to 1:1, Rf=0.3 with EtOAc/hexane=1:1) to give 6-(3-fluoro-4-(trifluoromethoxy)phenyl)-3-(trifluoromethyl)-[1,2,4]triazolo[4,3-a]pyridine as colorless crystals LCMS (EI: 70 eV) 366 (M$^+$+1)

$^1$H-NMR (300 MHz, CDCl$_3$): 7.43-7.66 (3H, m), 7.76 (1H, d, J=9.6 Hz), 8.13 (1H, d, J=9.6 Hz), 8.42 (1H, s).

B. Optional Secondary Modification of the R$^1$ Bromo Group

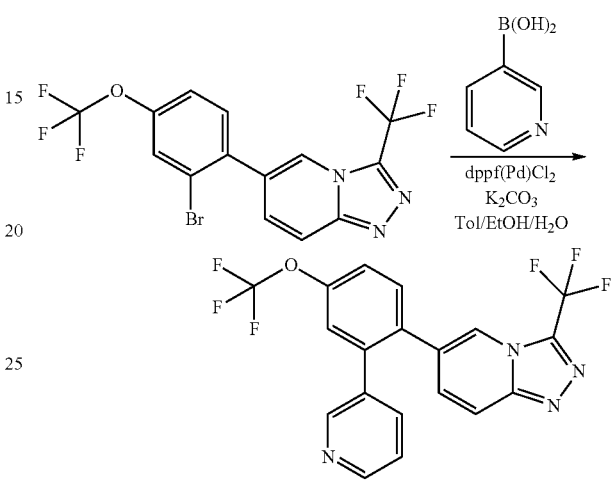

The compound, 6-(2-(pyridin-3-yl)-4-(trifluoromethoxy)phenyl)-3-(trifluoromethyl)-[1,2,4]triazolo[4,3-a]pyridine, was prepared using the methods disclosed in Example 1.

MS m/z 425.1 (M+1).

C. Preparation of a Compound of Formula I Varying R$^1$

Similarly, following the procedures of Example 5A or 5B above, but substituting other p aryl bromides or other brominated R$^1$ moieties, the following compounds of Formula I were prepared:

6-(2-(2-methoxypyrimidin-5-yl)-4-(trifluoromethoxy)phenyl)-3-(trifluoromethyl)-[1,2,4]triazolo[4,3-a]pyridine,
MS m/z 456.2 (M+1);

6-(3-chloro-4-(trifluoromethoxy)phenyl)-3-(trifluoromethyl)-[1,2,4]triazolo[4,3-a]pyridine,
LCMS (EI: 70 eV) 382 (M$^+$+1),
$^1$H-NMR (300 MHz, CDCl$_3$): 7.51 (1H, br s), 7.64-7.76 (2H, m), 8.12 (1H, d, J=9.6 Hz), 8.33 (1H, s);

5-(trifluoromethoxy)-8-(3-(trifluoromethyl)[1,2,4]triazolo[4,3-a]pyridin-6-yl)quinoline,
$^1$H-NMR (300 MHz, CDCl$_3$): 7.59 (1H, d, J=9.6 Hz), 7.63 (114, dd, J=8.4, 4.3 Hz), 7.83 (1H, d, J=8.4 Hz), 7.84 (1H, dd, J=8.4, 1.7 Hz), 8.00 (1H, d, J=9.6 Hz), 8.54 (1H, s), 8.59 (1H, d, J=8.4 Hz), 9.01 (1H, dd, 4.3, 1.7 Hz);

6-(2-fluoro-4-(trifluoromethoxy)phenyl)-3-(trifluoromethyl)-[1,2,4]triazolo[4,3-a]pyridine,
LCMS (EI: 70 eV) 366 (M$^+$+1),
$^1$H-NMR (300 MHz, CDCl$_3$): 7.17 (1H, d, J=10.8 Hz), 7.22 (1H, d, J=8.4 Hz), 7.55 (1H, J=8.4 Hz), 7.62 (1H, d, J=9.6 Hz), 8.01 (1, d, J=9.6 Hz), 8.36 (1H, s);

6-[4-(pyridin-4-yloxy)phenyl]-3-(trifluoromethyl)[1,2,4]triazolo[4,3-a]pyridine,
MS m/z 357.1 (M+1); and 6-[4-(cyclopropyloxy)phenyl]-3-(trifluoromethyl)[1,2,4]triazolo[4,3-a]pyridine,
MS m/z 320.1 (M+1).

D. Preparation of Compounds of Formula I Varying $R^1$

Similarly, following the procedure of Example 5A or 5B above, but substituting other aryl bromides or other brominated $R^1$ moieties, other compounds of Formula I may be prepared.

EXAMPLE 6

Alternative Preparation of a Compound of Formula I wherein $W^1$ and $W^2$ are CH, $W^3$ is N, and $X^1$ is $CR^a$, and $X^2$ is N A. Preparation of a Compound of Formula I in which $R^1$ is 4-trifluoromethoxyphenyl, Q is a Covalent Bond, $W^1$ and $W^2$ are CH, $W^3$ is N, and $X^1$ is $CCF_3$, and $X^2$ is N

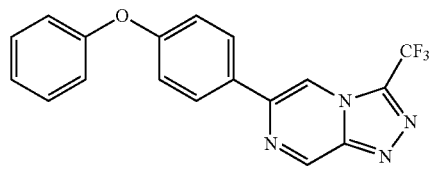 [SMILES: FC(F)(F)c1nnc2cnc(-c3ccc(Oc4ccccc4)cc3)cn12]

Step 1. Preparation of 6-chloro-3-(trifluoromethyl)[1,2,4]triazolo[4,3-b]pyridazine, a Compound of Formula (1)

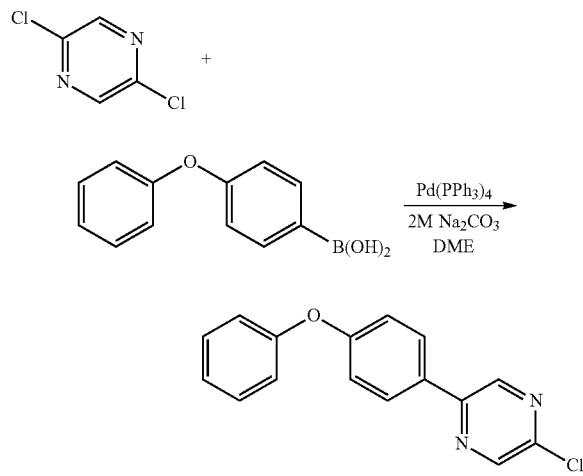

To a solution of 2,5-dichloropyrazine (2.91 mmole) in 1,2-dimethoxyethane (9 mL), was added 4-(phenoxyphenyl)lboronic acid (3.49 mmole) and tetrakis(triphenylphosphine)palladium (0.145 mmole) followed by 2M $Na_2CO_3$ (3mL). The resulting mixture was heated at 85 C for 2 hours. The reaction mixture was diluted with ethyl acetate and filtered through celite. The organic extract was dried over $Na_2SO_4$ and evaporated in vacuo. The crude product was purified by biotage chromatography and then with prep TLC eluting with 5% ethyl acetate and hexane mixture to give 2-chloro-5-(4-phenoxyphenyl)pyrazine.

Step 2. Preparation of 2-hydrazinyl-5-(4-phenoxyphenyl)pyrazine

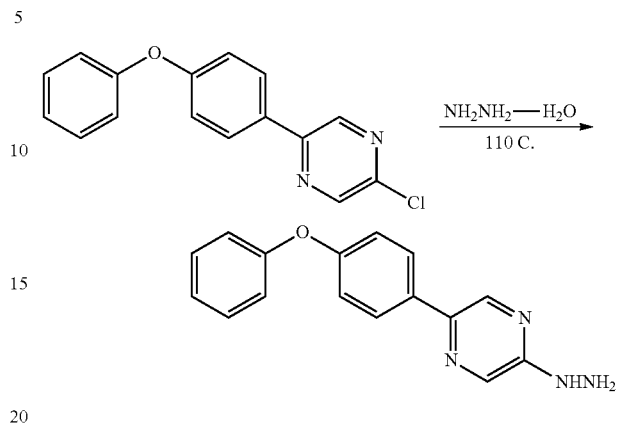

To a solution of 2-chloro-5-(4-phenoxyphenyl)pyrazine in 2 mL of ethanol was added hydrazine monohydrate (2 mL). The reaction mixture was heated at 110 C for 2 hours and evaporated in vacuo. The residue was dissolved in dichloromethane, washed with water, dried over $Na_2SO_4$, and evaporated in vacuo to afford 2-hydrazinyl-5-(4-phenoxyphenyl)pyrazine.

Step 3. Preparation of 6-(4-phenoxyphenyl)-3-(trifluoromethyl)[1,2,4]triazolo[4,3-a]pyrazine

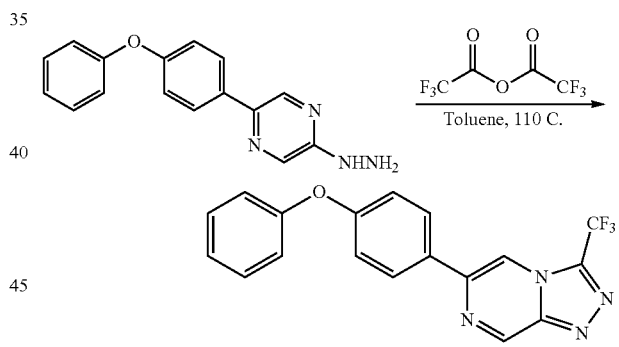

In a heavy-wall pressure tube, a suspension of 2-hydrazinyl-5-(4-phenoxyphenyl)pyrazine (0.827 mmole) and trifluoroacetic anhydride (0.993 mmole) in toluene (10 mL) was heated at 110 C for 2 hours. The reaction mixture evaporated in vacuo and purified by preparative HPLC to give 6-(4-phenoxyphenyl)-3-(trifluoromethyl)-[1,2,4]triazolo[4,3-a]pyrazine.

$^1$H-NMR (DMSO) 7.12 (t, 2H, J=8.0 Hz), 7.15 (d, 2H, J=8.0 Hz), 7.21 (t, 1H, J=8.0 Hz), 7.45 (t, 2H, J=8.0 Hz), 8.20 (d, 2H, J=8.0 Hz), 8.95 (s, 1H), 9.75 (s, 1H), (MS m/z 357.0 ($M^+$).

B. Preparation of a Compound of Formula I Varying $R^1$

Similarly, following the procedure of Example 6A above, but substituting other 4-(phenoxyphenyl)lboronic acid for 4-trifluoromethoxyphenylboronic acid, the following compound of Formula I was prepared:

6-(4-(trifluoromethoxy)phenyl)-3-(trifluoromethyl)-[1,2,4]triazolo[4,3-a]pyrazine C. Preparation of Compounds of Formula I Varying $R^1$ and $X^1$ Similarly, following the procedure of Example 6A above, but optionally substituting other boronic acids or pinacolate esters for 4-(phenoxyphenyl)lboronic acid and/or substituting other compounds of formula (1), either commercially obtained or prepared using different formula (1) precursors or different anhydrides, other compounds of Formula I may be prepared.

EXAMPLE 7

Preparation of a Compound of Formula I wherein $W^1$, $W^2$, and $W^3$ are CH, $X^1$ is $CR^a$, and $X^2$ is $CR^b$ A. Preparation of a Compound of Formula I in which $R^1$ is 4-trifluoromethylphenyl, is a Covalent Bond, $W^1$, $W^2$, and $W^3$ are CH, $X^1$ is $CCF_3$, and $X^2$ is CH

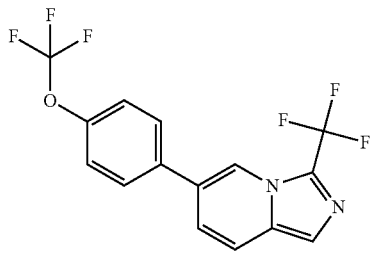 [SMILES: FC(F)(F)Oc1ccc(-c2ccc3cnc(C(F)(F)F)n3c2)cc1]

Step 1. Preparation of 6-bromo-3-(trifluoromethyl)imidazol[1,5-a]pyridine, a Compound of Formula (1)

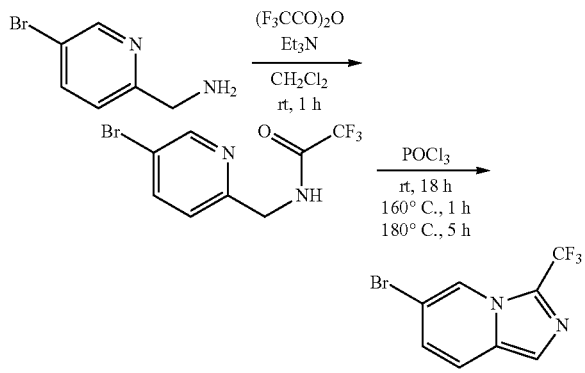

In a 50 mL round bottomed flask 5-bromo-2-aminomethylpyridine (113.8 mg, 0.608 mmol) was dissolve in $CH_2Cl_2$ (2 mL) at room temperature. Triethylamine (0.5 mL) and trifluoroacetic anhydride (TFAA, 300.0 mg, 1.428 mmol, 2.35 equiv.) were subsequently added. After stirring for 1 h at the same temperature, $POCl_3$ (1 mL) was added to the reaction mixture. The mixture was stirred at room temperature for 18 h, 160° C. for 1 h and then 180° C. for 5 h. The reaction mixture was poured into aqueous sat. $NaHCO_3$ solution (50 mL) under ice-water bath cooling. The mixture was extracted with EtOAc (30 mL×3). Combined organic layers were washed with brine (30 mL×2) and dried over $Na_2SO_4$. The solvent was removed a reduced pressure to give the crude material (brown oil, 141.4 mg). The crude product was purified by a silica gel column chromatography ($SiO_2$=25 g, EtOAc/hexane=1:3, Rf=0.4) to give the desired product, 6-bromo-3-(trifluoromethyl)imidazo[1,5-a]pyridine, a compound of formula (1).

Step 2. $R^1$ Coupling—Preparation of 3-ethyl-5-((6-(4-phenoxyphenyl)imidazo[1,2-a]pyridin-2-yl)methyl)-1,2,4-oxadiazole, a Compound of Formula I

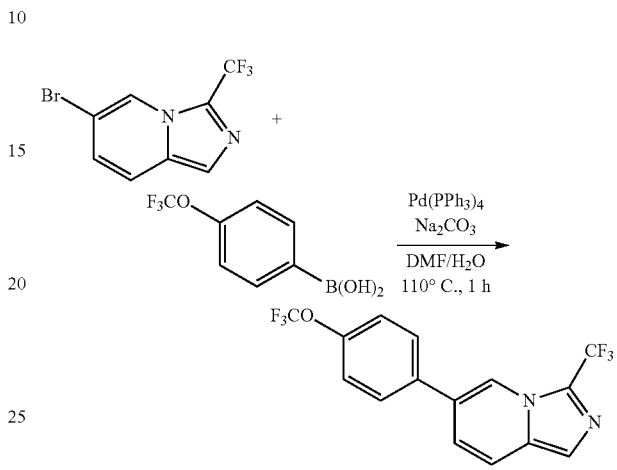

6-bromo-3-(trifluoromethyl)imidazo[1,5-a]pyridine, 4-trifluoromethylphenylboronic acid (127.7 mg, 0.620 mmol, 1.5 equiv.) and $Pd(PPh_3)_4$ (24.3 mg, 0.021 mmol, 0.05 equiv.) was placed in a 50 mL round bottomed flask under a nitrogen atmosphere. To the flask were added 2M-$Na_2CO_3$ (1.0 mL, 2.0 mmol, 4.8 equiv.) and DMF (4 mL) subsequently at ambient temperature. The mixture was heated at 110° C. for 2 hours. The mixture was filtered through Celite (3 g) and the Celite was washed with EtOAc (70 mL). The solvent was removed under a reduced pressure. Obtained crude mixture was purified by a column chromatography ($SiO_2$=25 g, EtOAc/hexane=1:3, Rf=0.35). The fractions containing the desired product were concentrated by rotary evaporator to give a contaminated material. The contaminated material was dissolved in $CH_2Cl_2$ (50 mL) and the solution was washed with aqueous 2N—NaOH (30 mL) to give the desired product as colorless crystals 6-(4-(trifluoromethoxy)phenyl)-3-(trifluoromethyl)imidazo[1,5-a]pyridine.

TLC: Rf 0.35 ($SiO_2$, EtOAc/hexane=1:3),

LCMS (EI: 70 eV) 347 ($M^+$), $^1$H-NMR (400 MHz, $CDCl_3$): 7.18 (1H, d, J=9.6 Hz), 7.36 (2H, d, J=8.0 Hz), 7.58 (1H, s), 7.60 (2H, d, J=8.0 Hz), 7.67 (1H, d, J=9.6 Hz), 8.25 (1H, s).

B. Alternative Preparation of a Compound of Formula I in which $R^1$ is Heteroaryl 6-bromo-3-(trifluoromethyl)imidazo[1,5-a]pyridine, prepared as disclosed in Example 1, (46.7 mg, 0.176 mmol), 4-trifluoromethylphenylboronic acid (107.8 mg, 0.264 mmol, 1.5 equiv.) and $Pd(PPh_3)_4$ (10.2 mg, 0.0088 mmol, 0.05 equiv.) was placed in a 50 mL round bottomed flask under a nitrogen atmosphere. To the flask were added DMF (4 mL) at ambient temperature. The mixture was heated at 110° C. for 1 hour. The mixture was filtered through Celite (3 g) and the Celite was washed with EtOAc (70 mL). The filtrate was washed with brine (30 mL) and dried with $Na_2SO_4$. The solvent was removed under a reduced pressure. Obtained crude mixture was purified by a column chromatography ($SiO_2$=25 g, EtOAc/hexane=1:3, Rf=0.37). The fractions containing the desired product were concentrated by rotary evaporator to give an organo-tin residue contaminated material. The contaminated material was suspended in hexane (5 mL) and the suspension was filtered to give the desired product, 2-(3-(trifluoromethyl)imidazo[1,5-a]pyridin-6-yl)benzo [d]oxazole, as colorless crystal.

C. Preparation of a Compound of Formula I Varying $R^1$

Similarly, following the procedures of Example 7A or 7B above, but substituting other boronic acids or pinacolate esters for 4-trifluoromethylphenyl boronic acid, the following compounds of Formula I were prepared:

6-(4-phenoxyphenyl)-3-(trifluoromethyl)imidazo[1,5-a]pyridine;

2-(3-(trifluoromethyl)imidazo[1,5-a]pyridin-6-yl)benzo[d]thiazole,
LCMS (EI: 70 eV) 320 ($M^+$+1);

2-(3-(trifluoromethyl)imidazo[1,5-a]pyridin-6-yl)benzo[d]oxazole,
$^1$H-NMR (300 MHz, $CDCl_3$): 7.36-7.50 (2H, m), 7.58-7.84 (5H, m), 7.58 (1H, s), 9.04 (1H, s);

2-(3-(trifluoromethyl)imidazo[1,5-a]pyridin-6-yl)thiazole,
LCMS (EI: 70 eV) 270 ($M^+$+1); and 2-(3-(trifluoromethyl)imidazo[1,5-a]pyridin-6-yl)oxazole,
LCMS (EI: 70 eV) 254 ($M^+$+1).

C. Preparation of Compounds of Formula I Varying $R^1$, $R^2$, and $R^3$

Similarly, following the procedure of Example 7A above, but optionally substituting other boronic acids or pinacolate esters for 4-trifluoromethoxyphenyl boronic acid and/or substituting other compounds of formula (1), either commercially obtained or prepared using different formula (1) precursors, other compounds of Formula I may be prepared.

EXAMPLE 8

Preparation of a Compound of Formula I wherein V is $CR^2$, $R^2$ is Methyl, $W^2$ and $W^3$ are CH, and $X^1$ and $X^2$ are N

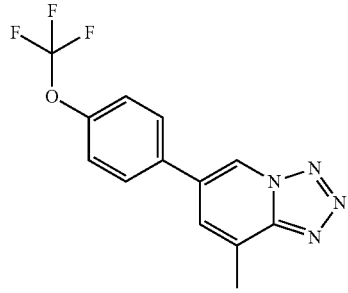 [SMILES: Cc1cc(-c2ccc(OC(F)(F)F)cc2)cn2nnnc12]

A. Preparation of a Compound of Formula I in which $W^1$ is $CR^2$, $R^2$ is Methyl, $W^2$ and $W^3$ are CH, and $X^1$ and $X^2$ are N Step 1. Preparation of 2-chloro-3-methyl-5-(4-(trifluoromethoxy)phenyl)pyridine, a Formula (1) Precursor Compound

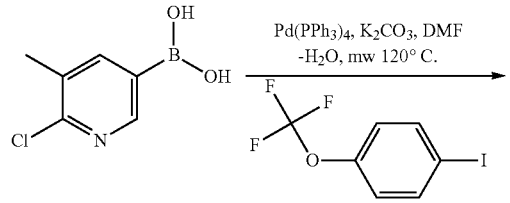

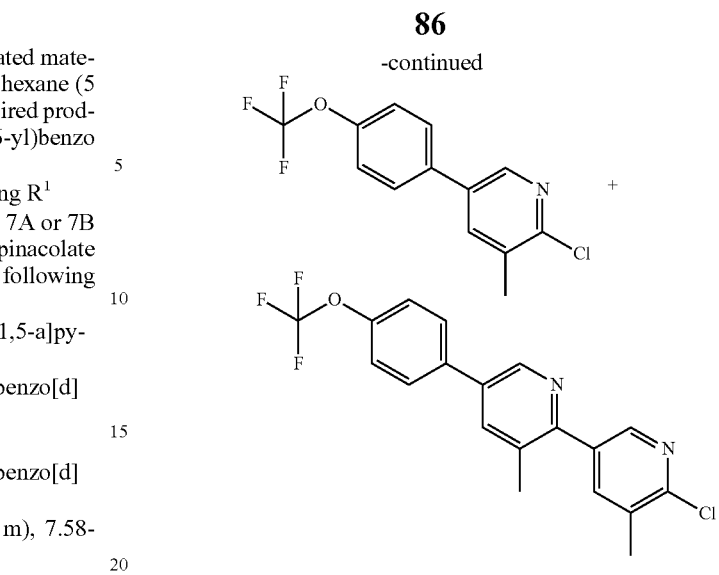

To a solution of 1-iodo-4-(trifluoromethoxy)benzene (288 mg, 1.0 mmol) and 6-chloro-5-methylpyridin-3-ylboronic acid (223 mg, 1.3 mmol) in DMF (2 mL) was added $K_2CO_3$ (552 mg, 4.0 mmol) and $H_2O$ (0.5 mL). The reaction mixture was stirred for 5 min under an atmosphere of dry $N_2$. $Pd(PPh_3)_4$ (10 mg, 0.009 mmol) was added, and the resulting mixture was subjected to irradiation at 120° C. for 10 min. Cooled, diluted with EtOAc (20 mL), filtered through a layer of celite, washed with 10% DMF in EtOAc (50 mL), transferred to a separation funnel, organic phase was washed with 2N $Na_2CO_3$ (20 mL, 4.00 mmol), $H_2O$ (20 mL), 30% aqueous $NH_4Cl$ (50 mL) and brine (50 mL), and dried and concentrated. The crude mixture was subjected to preparative HPLC with a gradient MeCN/$H_2O$ (5% to 98%) containing 0.1% TFA to afford 2-chloro-3-methyl-5-(4-(trifluoromethoxy)phenyl)pyridine,
MS m/z 288.0 (M+H), HPLC purity >97%.

Step 2. Preparation of 8-methyl-6-(4-(trifluoromethoxy)phenyl)tetrazolo[1,5-a]pyridine, a Compound of Formula I

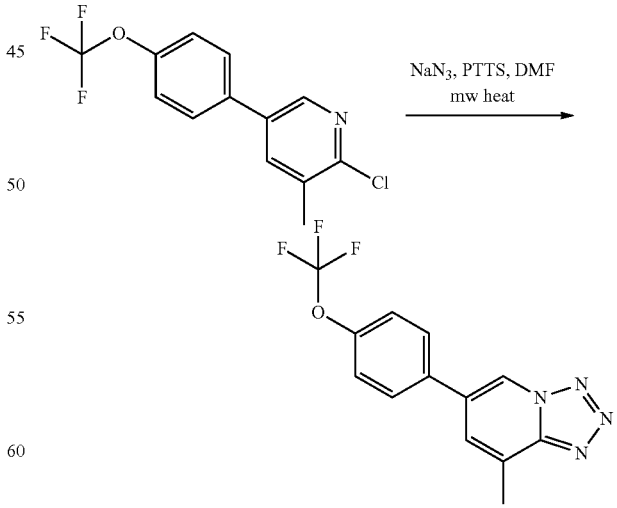

A mixture of 2-chloro-3-methyl-5-(4-(trifluoromethoxy)phenyl)pyridine prepared as described above (58 mg, 0.20 mmol), sodium azide (21 mg, 0.30 mmol), and pyridine 4-methylbenzenesulfonate (5 mg, 0.02 mmol) in anhydrous DMF (2.0 mL) was capped in a Biotage microwave reaction vial and subjected to irradiation at 160° C. for 30 min. Cooled, pressure released by opening the cap, additional sodium azide (65 mg, 1.00 mmol) and pyridine 4-methylbenzenesulfonate (52 mg, 0.20 mmol) were added, capped, and subjected to irradiation at 200° C. for 30 min. After cooling, the mixture was concentrated in vacuo, diluted with DMF (1.0 mL) and MeOH (2.0 mL), filtered, and subjected to preparative HPLC with a gradient MeCN/H$_2$O (5% to 98 containing 0.1% TFA to afford 8-methyl-6-(4-(trifluoromethoxy)phenyl)tetrazolo[1,5-a]pyridine MS m/z 295.0 (M+H), HPLC purity >97%.

$^1$H NMR (400 MHz; acetone-d$_6$) δ9.27 (d, J=0.8 Hz, 1H), 7.98 (m, 3H); 7.52 (d, J=8.2 Hz, 2H); 2.77 (s, 3H).

B. Preparation of a Compound of Formula I Varying R$^1$, W$^1$, and W$^2$

Similarly, following the procedures of Example 8A above, but substituting other precursors for 1-iodo-4-(trifluoromethoxy)benzene or other boronic acids for 6-chloro-5-methylpyridin-3-ylboronic acid, the following compounds of Formula I were prepared:

6-(4-phenoxyphenyl)tetrazolo[1,5-a]pyridine;

6-(4-(trifluoromethoxy)phenyl)tetrazolo[1,5-a]pyridine;

6-(4-(4-chlorophenoxy)phenyl)tetrazolo[1,5-a]pyridine;

6-(4-nitrophenyl)tetrazolo[1,5-a]pyridine;

6-(4-(4-fluoro-2-nitrophenoxy)phenyl)tetrazolo[1,5-a]pyridine;

N,N-dimethyl-6-(4-(trifluoromethoxy)phenyl)tetrazolo[1,5-a]pyridin-5-amine;

6-(4-(4-chlorophenoxy)phenyl)tetrazolo[1,5-b]pyridazine;

5-methyl-6-(6-methyl-5-(4-(trifluoromethoxy)phenyl)pyridin-2-yl)tetrazolo[1,5-a]pyridine;

6-(4-(4-chlorophenoxy)phenyl)tetrazolo[1,5-a]pyridin-5-amine;

6-(2-methoxy-5-(trifluoromethoxy)phenyl)tetrazolo[1,5-a]pyridine;

6-[6-(2,2,2-trifluoroethoxy)pyridin-3-yl]tetrazolo[1,5-a]pyridine;

5-methyl-6-(4-(trifluoromethoxy)phenyl)tetrazolo[1,5-a]pyridine; and 8-methyl-6-(3-methyl-5-(4-(trifluoromethoxy)phenyl)pyridin-2-yl)tetrazolo[1,5-a]pyridine.

C. Preparation of Compounds of Formula I Varying R$^1$, W$^1$, and W$^2$

Similarly, following the procedure of Example 8A above, but substituting other precursors for 1-iodo-4-(trifluoromethoxy)benzene or other boronic acids for 6-chloro-5-methylpyridin-3-ylboronic acid, other compounds of Formula I may be prepared.

EXAMPLE 9

Preparation of a Compound of Formula I where W$^1$, W$^2$, and W$^3$ are CH, X$^1$ is CR$^a$, and X$^2$ is N A. Preparation of a Compound of Formula I in which R$^1$ is 4-phenoxyphenyl, Q is a Covalent Bond, W$^1$ is N, W$^2$ and W$^3$ are CH, X$^1$ is Isopropyl, and X$^2$ is N

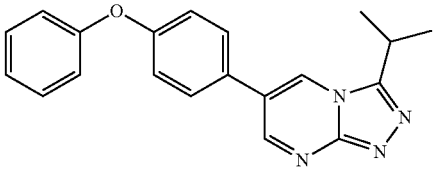 [SMILES: CC(C)c1nnc2ncc(-c3ccc(Oc4ccccc4)cc3)cn12]

Step 1. Preparation of 6-bromo-3-isopropyl-[1,2,4]triazolo[4,3-a]pyrimidine, a Compound of Formula (1)

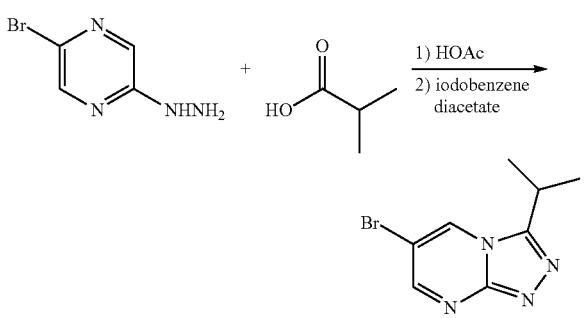

To a round bottom flask was added 5-bromo-2-hydrazinopyrimidine (2.65 mmole) in dichloromethane (40 mL). To this solution was added isobutyraldehyde (2.65 mmole) followed by 2 drops of acetic acid. The reaction mixture was stirred at room temperature for 2 hours after which was added iodobenzene diacetate (2.77 mmole). The resulting reaction mixture was stirred at RT for another 2 hours. The mixture was evaporated in vacuo and purified by preparative TLC eluting with 5% methanol and dichloromethane mixture to give 6-bromo-3-isopropyl-[1,2,4]triazolo[4,3-a]pyrimidine.

MS m/z 330.1 (M$^+$).

Step 2. 3-isopropyl-6-(4-phenoxyphenyl)-[1,2,4]triazolo[4,3-a]pyrimidine

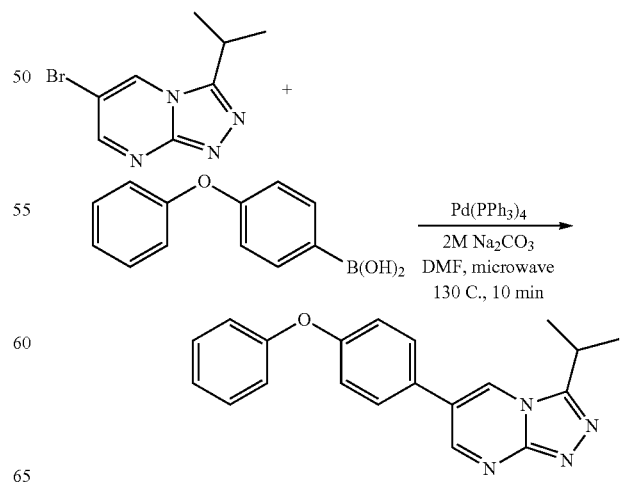

Formation of the final product was achieved using the same methods as those disclosed in Example 1A, Step 2.

MS m/z 330.1 (M+).

B. Preparation of Compounds of Formula I Varying R¹ and X¹

Similarly, following the procedure of Example 9A above, but optionally substituting other boronic acids or pinacolate esters for 4-trifluoromethoxyphenylboronic acid and/or substituting other compounds of formula (1), either commercially obtained or prepared using different formula (1) precursors or different anhydrides, other compounds of Formula I may be prepared.

EXAMPLE 10

Preparation of a Compound of Formula I

A. Preparation of a Compound of Formula I in which R¹ is 4-trifluoromethoxyphenyl, Q is a Covalent Bond, W¹, W² and W³ are CH, X¹ is 1,1-difluoro-2-hydroxyethyl, and X² is N

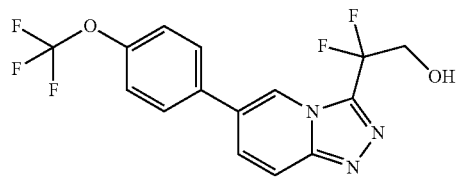 [SMILES: OCC(F)(F)c1nnc2ccc(-c3ccc(OC(F)(F)F)cc3)cn12]

Step 1. Preparation of Difluorohydroxymethyl Intermediate

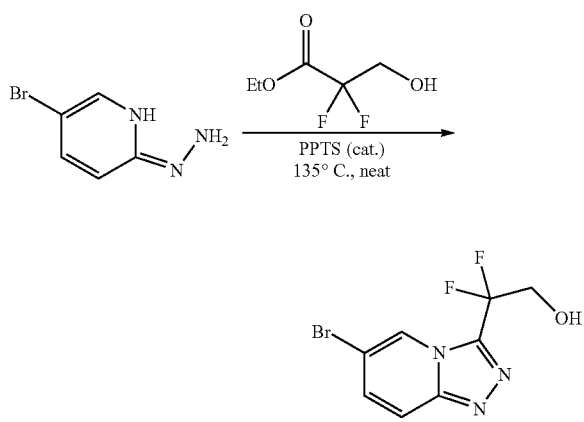

In a sealable flask, the hydrazide (3.84 g, 20.4 mmol), ethyl 2,2-difluoro-3-hydroxypropanoate (3.15 g, 20.4 mmol) and pyridinium p-toluenesulfonate (775 mg, 3.06 mmol) are combined and heated to 135° C. Caution: a significant amount of pressure is generated from the EtOH being evolved. The reaction is stirred for 6 hours and cooled. The resultant solid cake is suspended in EtOAc, homogenized with sonication, and filtered to provide the desired product, 2-(6-bromo-[1,2,4]triazolo[4,3-a]pyridin-3-yl)-2,2-difluoroethanol.

Step 2. Addition of the R¹ Moiety

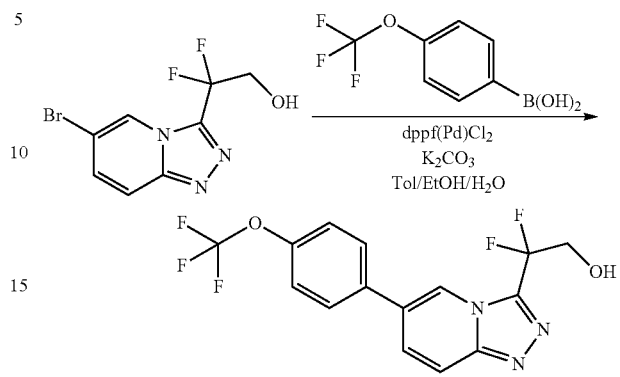

Formation of the final product was achieved using the same methods as those disclosed in Example 1A, Step 2, to give the final product, 2,2-difluoro-2-(6-(4-(trifluoromethoxy)phenyl)[1,2,4]triazolo[4,3-a]pyridin-3-yl)ethanol.

MS m/z 375.2 (M+1).

B. Optional Secondary Modification of the Rᵃ Alcohol Moiety

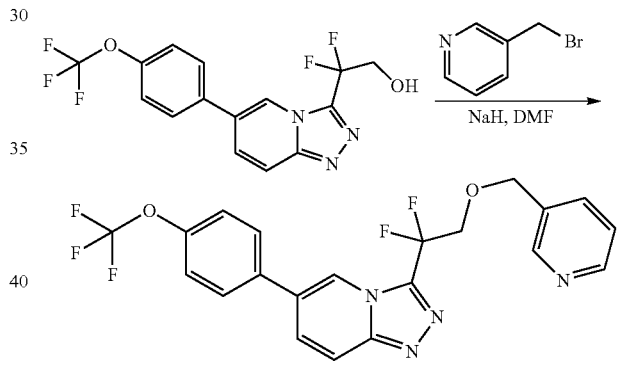

To a mixture of the alcohol (55 mg, 0.153 mmol), NaH (24 mg, 0.60 mmol, 60% dispersion in mineral oil), and 3-(bromomethyl)pyridine hydrobromide (58 mg, 0.23 mmol) is added DMF (1 mL). The reaction is stirred at room temperature for several hours and concentrated. The residue was purified by RP-HPLC to provide the product, 3-(1,1-difluoro-2-(pyridin-3-ylmethoxy)ethyl)-6-(4-(trifluoromethoxy)phenyl)[1,2,4]triazolo[4,3-a]pyridine, as a white powder.

451.1 (M+1).

C. Optional Secondary Modification of the Rᵃ Alcohol Moiety

Step 1

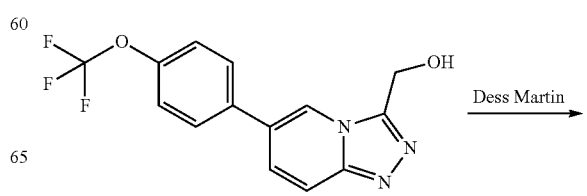

-continued

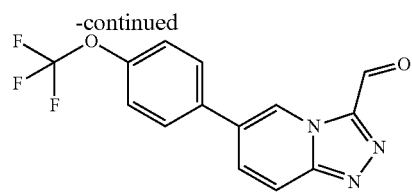

To a solution of the alcohol (400 mg, 1.24 mmol) in CH$_2$Cl$_2$ (60 mL) is added Dess Martin periodinane (610 mg, 1.42 mmol), and the reaction is stirred 1 hour. Na$_2$S$_2$O$_3$ (430 mg, 2.8 mmol) in NaHCO$_{3(aq)}$ is added and stirred 1 hour. The layers are separated and the aqueous layer is washed with CH$_2$Cl$_2$ (2×25 mL). the combined organic layers are dried over MgSO$_4$, filtered and concentrated to afford the product, 6-(4-(trifluoromethoxy)phenyl)-[1,2,4]triazolo[4,3-a]pyridine-3-carbaldehyde, as a white solid.

Step 2

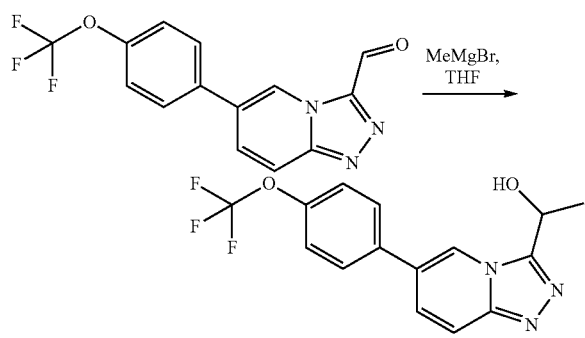

To a solution of the aldehyde (65 mg, 0.21 mmol) in THF (1 mL) at 0° C. is added methylmagnesium bromide (75 µL, 0.25 mmol, 3.0 M solution in THF). The reaction is stirred for 10 minutes, warmed to room temperature, and quenched by the addition of water. The mixture is diluted with EtOAc, the layers are separated, organics are concentrated and the residue is purified by column chromatography (Rf=0.55, EtOAc/ 10% MeOH) to afford the product, 1-(6-(4-(trifluoromethoxy)phenyl)-[1,2,4]triazolo[4,3-a]pyridin-3-yl) ethanol, as a white solid.

324.1 (M+1).

Alternative Step 2

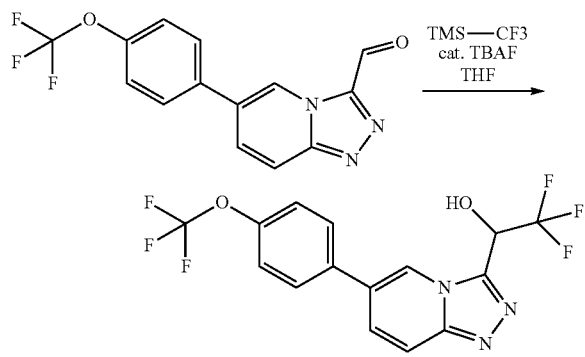

To a solution of the aldehyde (62 mg, 0.20 mmol) is added TMS-CF$_3$ (57 µL, 0.36 mmol) and the reaction is stirred for 1 hour. 1N HCl (2 mL) is added, stirred 1 hour and the reaction is diluted with Et$_2$O and water. The layers are separated, the organics are concentrated, and the residue was purified by RP-HPLC to provide the product, 2,2,2-trifluoro-1-(6-(4-(trifluoromethoxy)phenyl)-[1,2,4]triazolo[4,3-a]pyridin-3-yl) ethanol, as a white powder.

378.1 (M+1).

Alternative Step 2

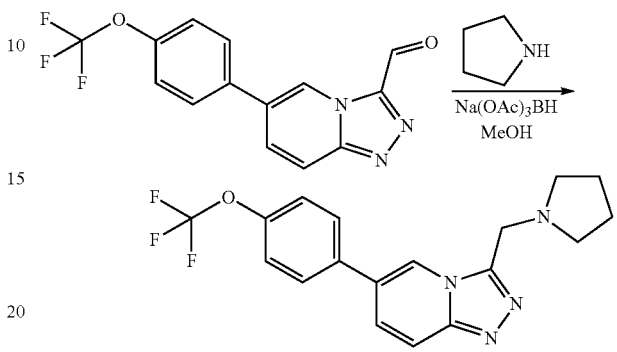

To a mixture of the aldehyde (70 mg, 0.23 mmol), pyrrolidine (38 µL, 0.46 mmol), and MeOH (1 mL) is added sodium triacetoxyborohydride (72 mg, 0.34 mmol) and the reaction is stirred overnight. The mixture is concentrated, and the residue was purified by RP-HPLC to provide the product, 3-(pyrrolidin-1-ylmethyl)-6-(4-(trifluoromethoxy)phenyl)-[1,2,4]triazolo[4,3-a]pyridine, as a white powder.

363.1 (M+1).

D. Optional Secondary Modification of the R$^a$ Alcohol Moiety

Step 1

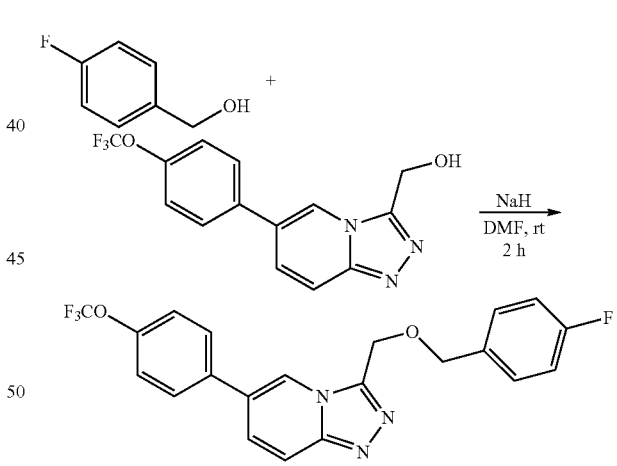

(6-(4-(trifluoromethoxy)phenyl)[1,2,4]triazolo[4,3-a]pyridin-3-yl)methanol (50.0 mg, 0.162 mmol) was dissolved in DMF (3 mL) in a 50 mL round bottomed flask. The solution was treated with NaH (60% in mineral oil, 9.7 mg, 0.243 mmol, 1.5 equiv.) at room temperature for 20 min. And then 4-fluorobenzyl bromide (61.2 mg, 0.324 mmol, 2.0 equiv.) was added to the reaction mixture. The mixture was stirred for 1 h at the same temperature. To the reaction mixture was added H$_2$O (30 mL) and the whole was extracted with EtOAc (30 mL×3). Combined organic layers were washed with brine (30 mL) and dried with Na$_2$SO$_4$. The solvent was removed under a reduced pressure. Obtained crude mixture was purified by a column chromatography (SiO$_2$=25 g, EtOAc/hexane=1:1 to EtOAc to 5% MeOH/EtOAc, Rf=0.2 with EtOAc) to give the desired product as a colorless oil.

LCMS (EI: 70 eV) 418 (M+1)

E. Optional Secondary Modification of the $R^a$ Alcohol Moiety to Provide and $R^a$ Amino Group Step 1

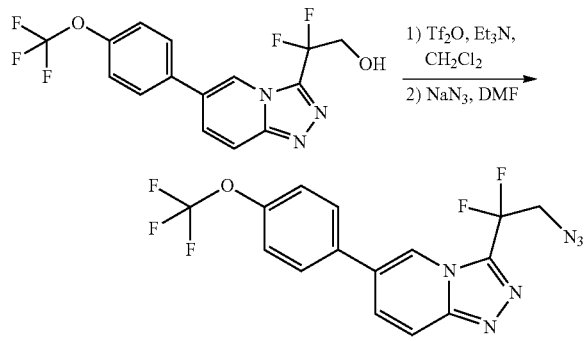

To a solution of the alcohol (240 mg, 0.68 mmol) and Et$_3$N (120 μL, 0.88 mmol) in CH$_2$Cl$_2$ (7 mL) is added Tf$_2$O (140 μL, 0.81 mmol), and the reaction is stirred at room temperature for 30 minutes. The mixture is concentrated, the residue is dissolved in DMF (2 mL), and NaN$_3$(176 mg, 2.7 mmol) is added. The reaction is stirred for 1 hour, concentrated, and the residue is purified by column chromatography (Rf=0.43, 1:1 Hexanes/EtOAc) to afford the product, 3-(2-azido-1,1-difluoroethyl)-6-(4-(trifluoromethoxy)phenyl)[1,2,4]triazolo[4,3-a]pyridine, as a brown solid.

Step 2

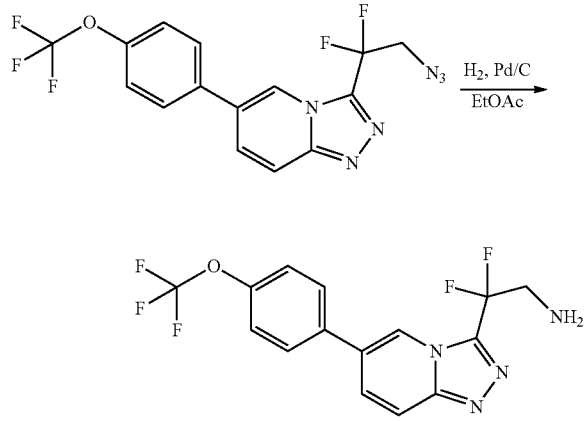

To the material isolated above (172 mg, 0.45 mmol) is added 10% Pd/C (22 mg, 50 mg/mmol), the flask is backfilled with N$_2$ and EtOAc (5 mL) is added. The reaction is purged with H$_2$ and stirred for 4 hours. The mixture is filtered through celite and the filtrate is concentrated under reduced pressure to the amine, 2,2-difluoro-2-(6-(4-(trifluoromethoxy)phenyl) [1,2,4]triazolo[4,3-a]pyridin-3-yl)ethanamine, as a brown solid.

359.2 (M+1).

Optional Step 3—Modification of the $R^a$ Amino Group

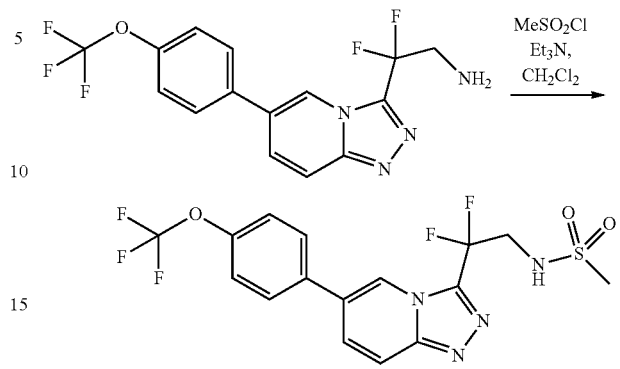

To a solution of the amine (34 mg, 0.095 mmol) in CH$_2$Cl$_2$ is added Et$_3$N (40 μL, 0.28 mmol) and MsCl (18 μL, 0.23 mmol), and the reaction is stirred 30 minutes. The mixture is concentrated, and the residue was purified by RP-HPLC to provide the product as a white powder.

437.0 (M+1).

Optional Step 3—Modification of the $R^a$ Amino Group

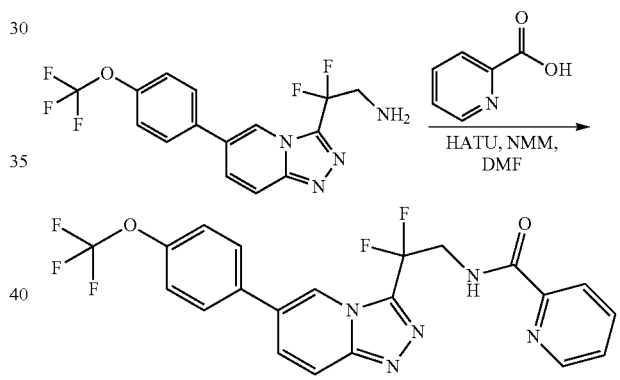

To a mixture of the amine (49 mg, 0.14 mmol), picolinic acid (19 mg, 0.15 mmol), HATU (63 mg, 0.16 mmol), and NMM (18 μL, 0.16 mmol) was added DMF (1 mL) and the reaction was stirred for 1 hr. The mixture was concentrated, CH$_3$CN and H$_2$O were added and the solids collected by filtration to provide the amide, N-(2,2-difluoro-2-{6-[4-(trifluoromethoxy)phenyl][1,2,4]triazolo[4,3-a]pyridin-3-yl}ethyl)pyridine-2-carboxamide, as a white solid. Alternatively, the product may be purified by RP-HPLC.

464.3 (M+1).

Optional Step 3—Modification of the $R^a$ Amino Group to Form a Urea Linkage

-continued

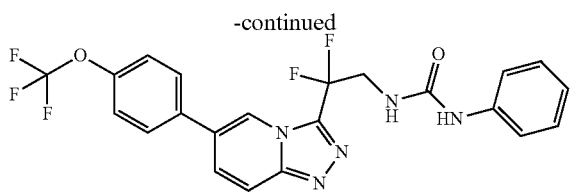

To solution of the amine (46 mg, 0.15 mmol) in CH$_2$Cl$_2$ (1 mL) is added phenyl isocyanate (18 µL, 0.16 mmol) and a precipitate is immediately fowled. The solids are collected by filtration to provide the urea, 1-(2,2-difluoro-2-{6-[4-(trifluoromethoxy)phenyl][1,2,4]triazolo[4,3-a]pyridin-3-yl}ethyl)-3-phenylurea, as a white solid. Alternatively, the product may be purified by RP-HPLC.

478.0 (M+1).

F. Preparation of Compounds of Formula I Varying R$^1$ and X$^1$

Similarly, following the procedures of Example 10A-10E above, but utilizing other precursors or secondary reactants, the following other compounds of Formula I were be prepared:

2-(6-(6-cyclopropylpyridin-3-yl)[1,2,4]triazolo[4,3-a]pyridin-3-yl)-2,2-difluoroethanol,
317.0 (M+1);

3-benzyl-6-(4-(trifluoromethoxy)phenyl)-[1,2,4]triazolo[4,3-a]pyridine,
370.2 (M+1),
$^1$H NMR (DMSO) d 8.73 (s, 1H), 7.83-7.87 (m, 3H), 7.71 (dd, J=1.2, 9.6 Hz, 1H), 7.52 (d, J=8.0 Hz, 2H), 7.28-7.36 (m, 4H), 7.21-7.25 (m, 1H), 4.64 (s, 2H);

(6-(4-(trifluoromethoxy)phenyl)[1,2,4]triazolo[4,3-a]pyridin-3-yl)methanol;

3-[(1-phenylethoxy)methyl]-6-[4-(trifluoromethoxy)phenyl][1,2,4]triazolo[4,3-a]pyridine
$^1$H-NMR (acetone) δ 8.54 (s, 1H), 7.71-7.85 (m, 4H), 7.52 (d, 2H), 7.27-7.41 (m, 5H), 5.03 (s, 2H), 4.67 (q, 1H), 2.80 (d, 3H);
MS m/z 414.1 (M+H)

3-{[difluoro(pyridin-3-yl)methoxy]methyl}-6-[4-(trifluoromethoxy)phenyl][1,2,4]triazolo[4,3-a]pyridine,
MS m/z 437.0 (M+H)

ethyl 2-(2,2-difluoro-2-(6-(4-(trifluoromethoxy)phenyl)-[1,2,4]triazolo[4,3-a]pyridin-3-yl)ethoxy)acetate;

2-(2,2-difluoro-2-{6-[4-(trifluoromethoxy)phenyl][1,2,4]triazolo[4,3-a]pyridin-3-yl}ethoxy)-N,N-dimethylethanamine,
431.2 (M+1).

N-(2,2-difluoro-2-{6-[4-(trifluoromethoxy)phenyl][1,2,4]triazolo[4,3-a]pyridin-3-yl}ethyl)benzamide,
463.0 (M+1).

3-[1-(pyridin-2-ylmethoxy)ethyl]-6-[4-(trifluoromethoxy)phenyl][1,2,4]triazolo[4,3-a]pyridine,
415.0 (M+1).

3-(difluoro(pyridin-2-ylmethoxy)methyl)-6-(4-(trifluoromethoxy)phenyl)-[1,2,4]triazolo[4,3-a]pyridine,
LCMS (EI: 70 eV) 451 (M$^+$+1).

ethyl 2-(difluoro(6-(4-(trifluoromethoxy)phenyl)[1,2,4]triazolo[4,3-a]pyridin-3-yl)methoxy)acetate,
LCMS (EI: 70 eV) 446 (M$^+$+1).

2-(difluoro(6-(4-(trifluoromethoxy)phenyl)[1,2,4]triazolo[4,3-a]pyridin-3-yl)methoxy)acetonitrile,
LCMS (EI: 70 eV) 399 (M$^+$+1).

6-(4-(trifluoromethoxy)phenyl)-3-((4-(trifluoromethyl)benzyloxy)methyl)-[1,2,4]triazolo[4,3-a]pyridine,
LCMS (EI: 70 eV) 468 (M$^+$+1).

3-((pyridin-2-ylmethoxy)methyl)-6-(4-(trifluoromethoxy)phenyl)-[1,2,4]triazolo[4,3-a]pyridine,
LCMS (EI: 70 eV) 401 (M$^+$+1).

3-[1-(pyridin-2-ylmethoxy)ethyl]-6-[4-(trifluoromethoxy)phenyl][1,2,4]triazolo[4,3-a]pyridine,
415.0 (M+1).

3-({[4-(trifluoromethoxy)benzyl]oxy}methyl)-6-[4-(trifluoromethoxy)phenyl][1,2,4]triazolo[4,3-a]pyridine,
484 (M$^+$+1).

3-{[(4-chlorobenzyl)oxy]methyl}-6-[4-(trifluoromethoxy)phenyl][1,2,4]triazolo[4,3-a]pyridine,
434 (M+1).

D. Preparation of Compounds of Formula I Varying R$^1$ and X$^1$

Similarly, following the procedures of Example 10A-10D above, but utilizing other precursors or secondary reactants, other compounds of Formula I may be prepared:

EXAMPLE 11

Preparation of a Compound of Formula I

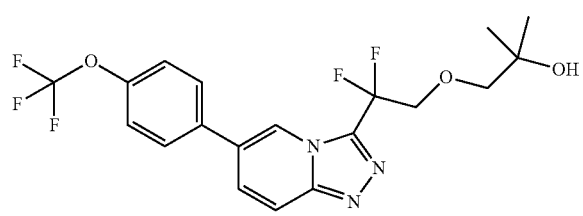 [SMILES: CC(C)(O)COCC(F)(F)c1nnc2ccc(-c3ccc(OC(F)(F)F)cc3)cn12]

A. Preparation of a Compound of Formula I

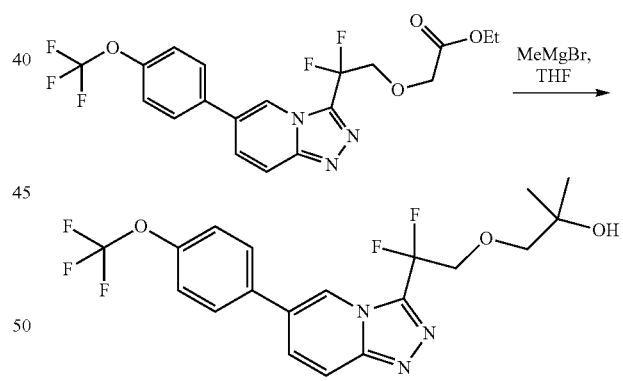

To a solution of the ester, prepared as disclosed in Example 10 (50 mg, 0.11 mmol) in THF (1 mL) at 0° C. is added methylmagnesium bromide (94 µL, 0.28 mmol, 3.0 M solution in THF). The reaction is stirred for 10 minutes, warmed to room temperature, and quenched by the addition of water. The mixture is diluted with EtOAc, the layers are separated, organics are concentrated and the residue was purified by RP-HPLC to provide the product, V, as a white powder.

MS m/z 432.1.1 (M+1).

B. Preparation of Other Compounds of Formula

Similarly, following the procedures of Example 11A above, but substituting other ester compounds, other compounds of Formula I may be prepared.

EXAMPLE 12

Preparation of a Compound of Formula I where $W^3$ is C—$R^4$

A. Preparation of a Compound of Formula I in which $R^4$ is Hydroxymethyl

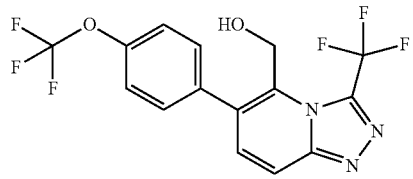 [SMILES: OCc1c(-c2ccc(OC(F)(F)F)cc2)ccc2nnc(C(F)(F)F)n12]

Step 1 Formation of the Hydroxymethyl Group.

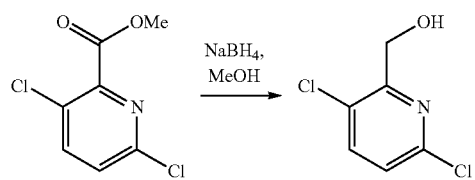 [SMILES: COC(=O)c1nc(Cl)ccc1Cl ; OCc1nc(Cl)ccc1Cl]

To a solution of the commercially available ester (2.1 g, 10 mmol) in MeOH (50 mL) at 0° C. was added NaBH$_4$ (570 mg, 0.15 mmol) portionwise over 30 minutes. The reaction was stirred an additional 30 minutes and quenched by the addition of water. The reaction was diluted with EtOAc (100 mL), and the organics were washed with NaHCO$_3$ and Brine. The organic layer was dried over MgSO$_4$, filtered and concentrated to provide the alcohol as a yellow oil.

Step 2.—Protection of the Hydroxy Group

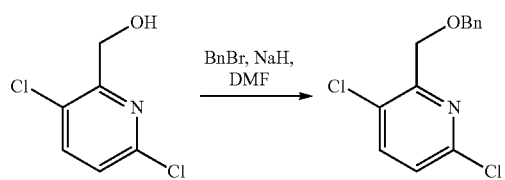 [SMILES: OCc1nc(Cl)ccc1Cl ; Clc1ccc(Cl)c(COCc2ccccc2)n1]

To a mixture of the alcohol prepared in Step 1 (775 mg, 434 mmol) and benzyl bromide (570 µL, 4.8 mmol) in DMF (8 mL) is added NaH (522 mg, 13 mmol, 60% dispersion in mineral oil). The reaction is stirred for 2 hrs and diluted with EtOAc (50 mL), washed with brine (2×), the organics are dried over MgSO$_4$, filtered and concentrated. The residue is purified by column chromatography (Rf=0.5, 5:1 Hexanes/EtOAc) to afford the product.

Step 3.—Addition of the Hydrazine Chain

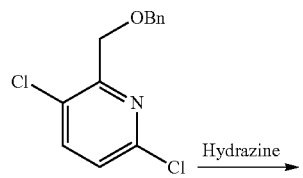

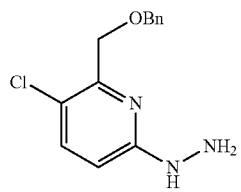

A sealable flask is charged with 2-(benzyloxymethyl)-3,6-dichloropyridine as prepared in Step 2 (950 mg, 3.5 mmol), hydrazine hydrate (1 mL) is added, and the reaction is heated to 120° C. overnight. After cooling the solids are collected by filtration to provide 2-(benzyloxymethyl)-3-chloro-6-hydrazinylpyridine.

Step 4.—Cyclization of the Core

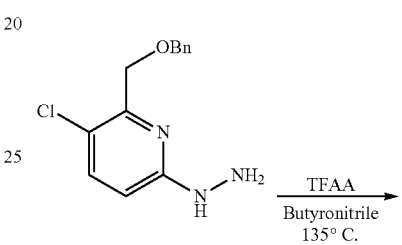

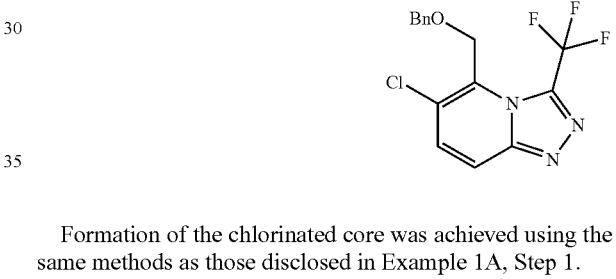

Formation of the chlorinated core was achieved using the same methods as those disclosed in Example 1A, Step 1.

Step 5.—Deprotection of the Hydroxy Group

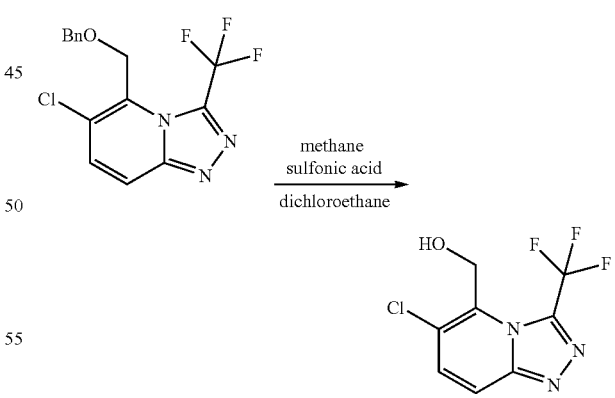

To a solution of 5-(benzyloxymethyl)-6-chloro-3-(trifluoromethyl)-[1,2,4]triazolo[4,3-a]pyridine, prepared as described in Step 4 (700 mg, 2.1 mmol) was added methanesulfonic acid (2 mL, 70% in water) and the reaction was heated to reflux overnight. The reaction was concentrated and the residue purified by flash chromatography to yield (6-chloro-3-(trifluoromethyl)[1,2,4]triazolo[4,3-a]pyridin-5-yl)methanol.

Step 6—Addition of the R[1] Moiety

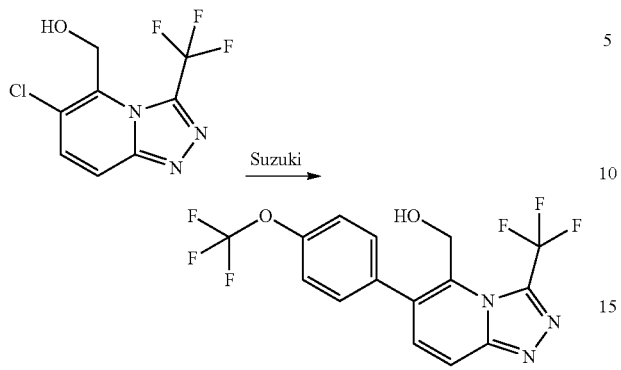

Formation of the final product was achieved using the same methods as those disclosed in Example 1A, Step 2.

MS m/z 378.1 (M+1)

Optional Step 7—Modification of the R[4] Hydroxy Group

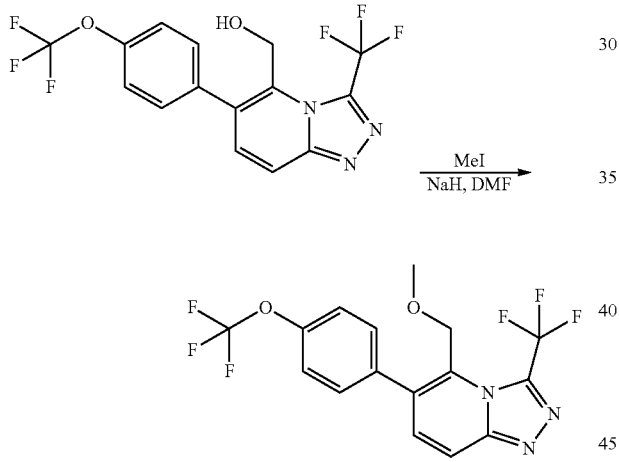

Formation of the final product, 5-(methoxymethyl)-6-[4-(trifluoromethoxy)phenyl]-3-(trifluoromethyl)[1,2,4]triazolo[4,3-a]pyridine, was achieved according to the methods disclosed in Example 10B.

MS m/z 392.2 (M+1).

B. Preparation of Compounds of Formula I Varying R[4]

Similarly, following the procedures of Example 12A above, but utilizing other precursors or secondary reactants, the following compound of Formula I was prepared:

({6-[4-(trifluoromethoxy)phenyl]-3-(trifluoromethyl)[1,2,4]triazolo[4,3-a]pyridin-5-yl}methoxy)acetonitrile, MS m/z 416.3 (M+1)

C. Preparation of Compounds of Formula I Varying R[1], R[4], and X[1]

Similarly, following the procedure of Example 12A above, but utilizing other precursors or secondary reactants, other compounds of Formula I may be prepared.

EXAMPLE 13

Preparation of a Compound of Formula I wherein R[1] is 2-(morpholinomethyl)-3-(trifluoromethoxy)phenyl, W[1], W[2] and W[3] are CH, and X[1] is CHCF$_3$, and X[2] is N

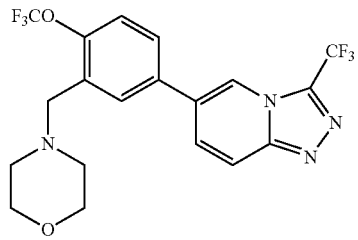

A. Preparation of a Compound of Formula I in which R[1] is 2-(morpholinomethyl)-3-(trifluoromethoxy)phenyl, W[1], W[2] and W[3] are CH, and X[1] is CHCF$_3$, and X[2] is N

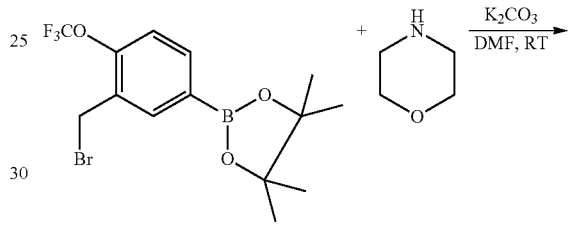

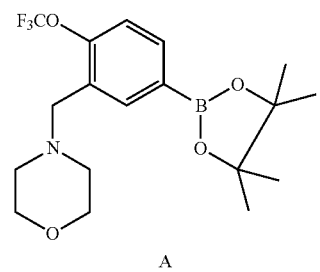

A

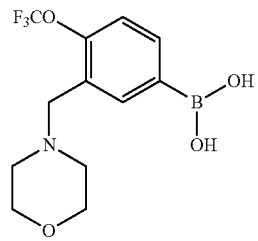

B

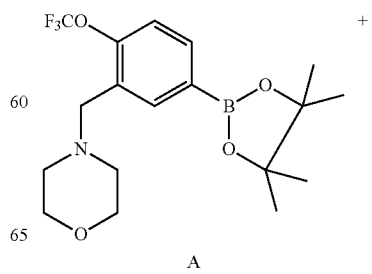

A

-continued

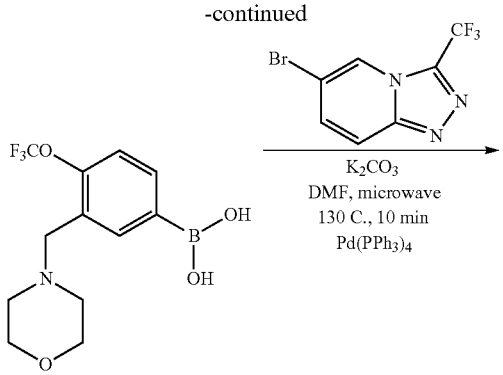

B

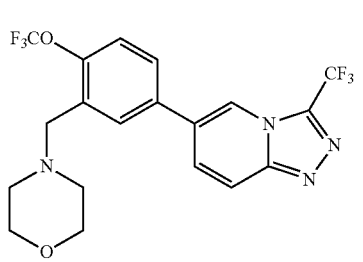 [SMILES: FC(F)(F)Oc1ccc(-c2ccc3nnc(C(F)(F)F)n3c2)cc1CN1CCOCC1]

To a round bottom flask was added 3-bromomethyl-4-trifluoromethoxyphenyl boronic acid pinacol ester (0.420 mmole) in DMF (3 mL). To this solution was added potassium carbonate (0.840 mmole) followed by morpholine (0.84 mmole). The suspension was stirred at room temperature for 4 hours after which the reaction mixture was transferred to a microwave reaction tube. To this mixture was added tetrakis (triphenylphosphine)palladium (0.021 mmole) and 1 mL of water followed by 6-bromo-3-(trifluoromethyl)[1,2,4]triazolo[4,3-b]pyridine (0.462 mmole). The resulting reaction mixture was heated in the microwave at 130 C for 10 min. The reaction mixture was diluted with ethyl acetate and filtered through celite. The filtrate was washed with water. The organic extract was dried over Na$_2$SO$_4$ and evaporated in vacuo. The crude residue was purified by preparative HPLC to afford 4-(2-(trifluoromethoxy)-5-(3-(trifluoromethyl)-[1,2,4]triazolo[4,3-a]pyridin-6-yl)benzyl)morpholine.

MS m/z 447.1 (M$^+$).

B. Preparation of a Compound of Formula I Varying R$^1$, W$^1$, and W$^2$

Similarly, following the procedures of Example 13A above, but substituting other precursors for 6-bromo-3-(trifluoromethyl)[1,2,4]triazolo[4,3-b]pyridine or other boronic acids for 3-bromomethyl-4-trifluoromethoxyphenyl boronic acid pinacol ester, the following compound of Formula I were prepared:

6-{3-[(4-methylpiperazin-1-yl)methyl]-4-(trifluoromethoxy)phenyl}-3-(trifluoromethyl)[1,2,4]triazolo[4,3-a]pyridine,
  MS m/z 460.1 (M$^+$); and
2-({2-(trifluoromethoxy)-5-[3-(trifluoromethyl)[1,2,4]triazolo[4,3-a]pyridin-6-yl]benzyl}amino)ethanol,
  MS m/z 421.1 (M$^+$).

C. Preparation of Compounds of Formula I Varying R$^1$

Similarly, following the procedure of Example 13A above, but substituting other precursors for 6-bromo-3-(trifluoromethyl)[1,2,4]triazolo[4,3-b]pyridine or other boronic acids for 3-bromomethyl-4-trifluoromethoxyphenyl boronic acid pinacol ester, other compounds of Formula I may be prepared.

EXAMPLE 14

Preparation of a Compound of Formula I wherein R$^2$ is Amino

A. Preparation of a Compound of Formula I in which R$^1$ is 4-trifluoromethylphenyl, W$^1$, W$^2$ and W$^3$ are CH, R$^2$ is NH$_2$, and X$^1$ is CHR$^a$, R$^a$ is Isopropyl, and X$^2$ is N Step 1—Reduction of the Nitro Group to Form an Amine

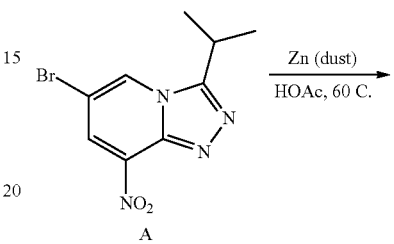

A

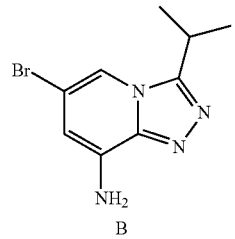

B

Compound B was prepared by heating A, 6-bromo-3-isopropyl-8-nitro-[1,2,4]triazolo[4,3-a]pyridine, prepared as described in Example 9A, Step 1, (0.777 mmole) in acetic acid (6 mL) in the presence of Zinc dust (3.89 mmole) at 60 C for 1 hour. The reaction mixture was then diluted with methanol and filtered to celite. The filtrate was concentrated down and the residue was then filtered through silica gel with first ethyl acetate and then with 1:4 mixture of methanol and dichloromethane. The filtrate was evaporated in vacuo to yield B, 6-bromo-3-isopropyl-[1,2,4]triazolo[4,3-a]pyridin-8-amine.

Step 2. Addition of the R$^1$ Moiety.

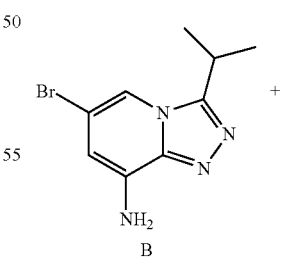

B

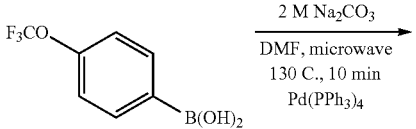

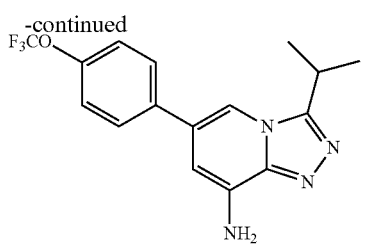

Formation of the final product was achieved using the same methods as those disclosed in Example 1A, Step 2, to give the final product, 3-isopropyl-6-(4-(trifluoromethoxy)phenyl)[1,2,4]triazolo[4,3-a]pyridin-8-amine.

MS m/z 337.1 (M+).

B. Optional Secondary Modification of the R² Amino Group

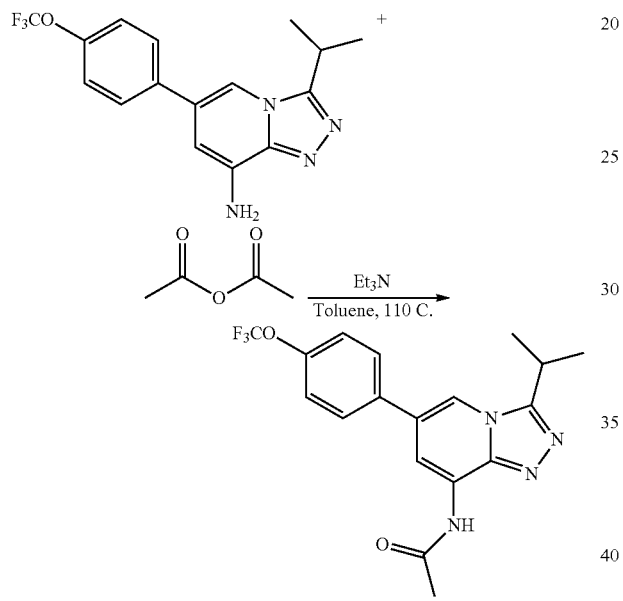

In a heavy-wall pressure tube was added 3-isopropyl-6-(4-(trifluoromethoxy)phenyl)[1,2,4]triazolo[4,3-a]pyridin-8-amine prepared in 9A in toluene. To this suspension was added the acetic anhydride (0.1 mL) followed my triethylamine (0.1 mL). The mixture was heated in a 110 C oil bath for 12 hours. The reaction mixture was evaporated in vacuo and purified by preparative HPLC to afford N-(3-isopropyl-6-(4-(trifluoromethoxy)phenyl)[1,2,4]triazolo[4,3-a]pyridin-8-yl)acetamide.

MS m/z 379.1 (M+).

C. Preparation of Compounds of Formula I Varying R¹, R², X¹, and X²

Similarly, following the procedure of Example 14A and B above, but substituting other nitro precursors for 6-bromo-3-isopropyl-8-nitro-[1,2,4]triazolo[4,3-a]pyridine, other boronic acids for 4-(trifluoromethoxy)phenylboronic acid, or other anhydrides for acetic anhydride, the following compounds of Formula I were prepared N-{3-methyl-6-[4-(trifluoromethoxy)phenyl][1,2,4]triazolo[4,3-a]pyridin-8-yl}propanamide,
    MS m/z 365 (M+);
3-methyl-6-[2-methyl-4-(trifluoromethoxy)phenyl][1,2,4]triazolo[4,3-a]pyridin-8-amine,
    MS m/z 323 (M+);
3-methyl-6-[4-(trifluoromethoxy)phenyl][1,2,4]triazolo[4,3-a]pyridin-8-amine,
    MS m/z 309 (M+);
3-phenyl-6-[4-(trifluoromethoxy)phenyl][1,2,4]triazolo[4,3-a]pyridin-8-amine.
    MS m/z 371.1 (M+); and
N-{3-methyl-6-[2-methyl-4-(trifluoromethoxy)phenyl][1,2,4]triazolo[4,3-a]pyridin-8-yl}acetamide,
    MS m/z 365 (M+).

D. Preparation of Compounds of Formula I Varying R¹, R², X¹, and X²

Similarly, following the procedure of Example 14A and B above, but substituting other nitro precursors for 6-bromo-3-isopropyl-8-nitro-[1,2,4]triazolo[4,3-a]pyridine, other boronic acids for 4-(trifluoromethoxy)phenylboronic acid, or other anhydrides for acetic anhydride, other compounds of Formula I may be prepared.

EXAMPLE 15

Preparation of a Compound of Formula I wherein $R^1$ is 3-(1,3,4-oxadiazol-2-yl)-4-(trifluoromethoxy)phenyl, $W^1$, $W^2$ and $W^3$ are CH, and $X^1$ is CHCF₃, and $X^2$ is N

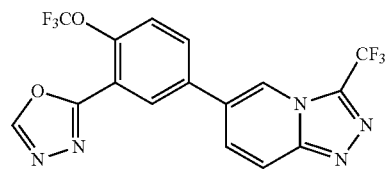 [SMILES: FC(F)(F)Oc1ccc(-c2ccc3nnc(C(F)(F)F)n3c2)cc1-c1nnco1]

A. Preparation of a Compound of Formula I in which $R^1$ is 3-(1,3,4-oxadiazol-2-yl)-4-(trifluoromethoxy)phenyl, $W^1$, $W^2$ and $W^3$ are CH, and $X^1$ is CHCF₃, and $X^2$ is N

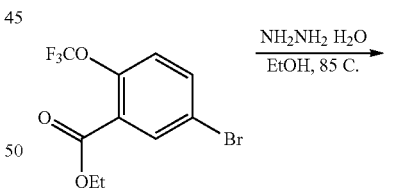

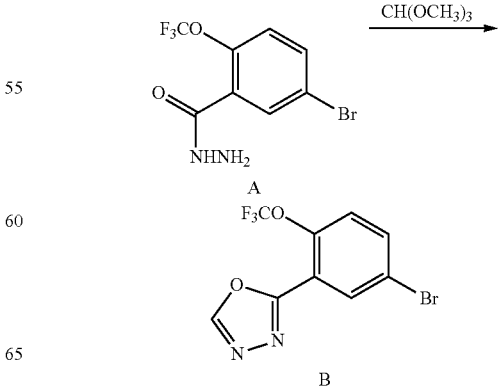

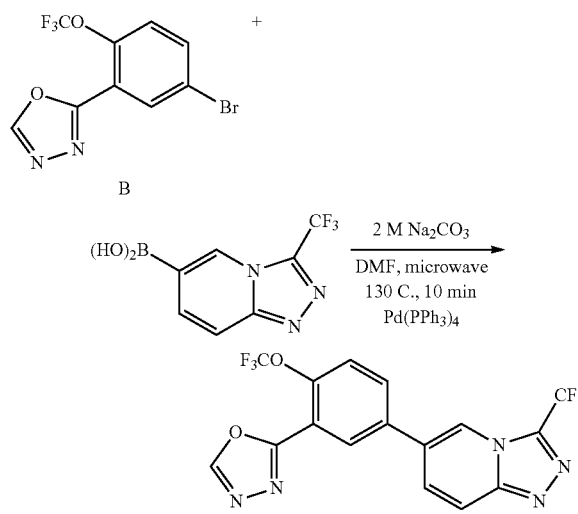

To a round bottom flask was added ethyl-5-bromo-2-(trifluoromethoxy)benzoate (0.638 mmole) in ethanol (10 mL). To this solution was added 1 mL of hydrazine monohydrate and the resulting mixture was refluxed overnight. The reaction mixture was evaporated in vacuo to give A. To A was added trimethylorthoformate in a heavy wall pressure tube. This resulting mixture was heated at 100 C for 18 hours. The reaction mixture was concentrated down and purified by preparative TLC to afford B which was coupled with 3-(trifluoromethyl)[1,2,4]triazolo[4,3-a]pyridin-6-ylboronic acid using methods disclosed above to give 2-(2-(trifluoromethoxy)-5-(3-(trifluoromethyl)-[1,2,4]triazolo[4,3-a]pyridin-6-yl)phenyl)-1,3,4-oxadiazole.

MS m/z 416.1 (M+).

B. Preparation of a Compound of Formula I Varying $R^1$, $W^1$, and $W^2$

Similarly, following the procedures of Example 15A above, but substituting other precursors for ethyl-5-bromo-2-(trifluoromethoxy)benzoate or other boronic acids for 3-(trifluoromethyl)[1,2,4]triazolo[4,3-a]pyridin-6-ylboronic acid, other compound of Formula I may be prepared.

EXAMPLE 16

Preparation of a Compound of Formula I wherein $R^1$ is 3-(methylcarbamoyl)-4-(trifluoromethoxy)phenyl, $W^1$, $W^2$ and $W^3$ are CH, and $X^1$ is CHCF$_3$, and $X^2$ is N

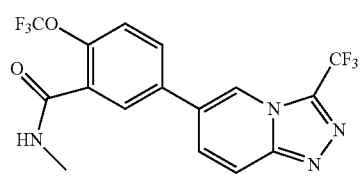 [SMILES: CNC(=O)c1cc(-c2ccc3nnc(C(F)(F)F)n3c2)ccc1OC(F)(F)F]

A. Preparation of a Compound of Formula I in which $R^1$ is 3-(methylcarbamoyl)-4-(trifluoromethoxy)phenyl, $W^1$, $W^2$ and $W^3$ are CH, and $X^1$ is CHCF$_3$, and $X^2$ is N

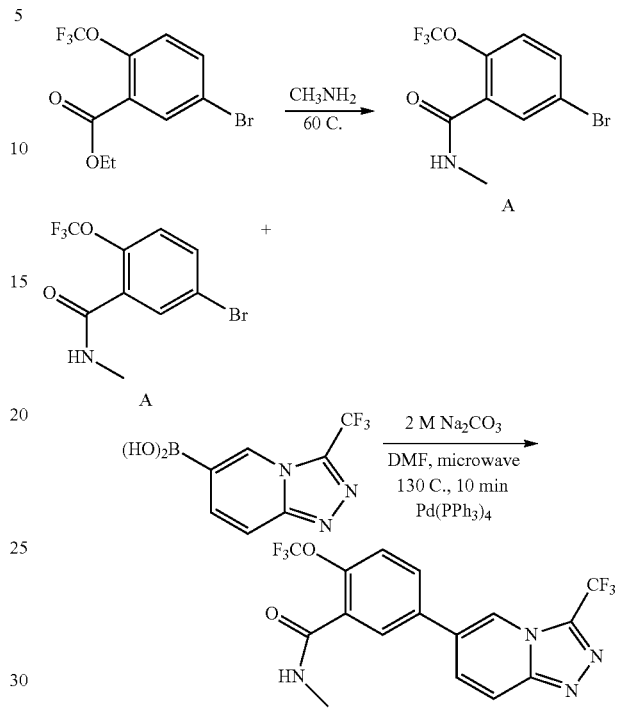

In a heavy-wall pressure tube was added ethyl-5-bromo-2-(trifluoromethoxy)benzoate (0.3 mL) and methylamine (1.5 mL). The mixture was heated at 60 C for 2 hours. The reaction mixture was concentrated to afford A which was coupled to with 3-(trifluoromethyl)[1,2,4]triazolo[4,3-a]pyridin-6-yl-boronic acid using methods disclosed above to give to give N-methyl-2-(trifluoromethoxy)-5-[3-(trifluoromethyl)[1,2,4]triazolo[4,3-a]pyridin-6-yl]benzamide.

MS m/z 405.1 (M+).

B. Preparation of a Compound of Formula I Varying $R^1$, $W^1$, and $W^2$

Similarly, following the procedures of Example 16A above, but substituting other precursors for ethyl-5-bromo-2-(trifluoromethoxy)benzoate or other boronic acids for 3-(trifluoromethyl)[1,2,4]triazolo[4,3-a]pyridin-6-ylboronic acid, other compounds of Formula I may be prepared.

EXAMPLE 17

Preparation of a Compound of Formula I wherein $R^1$ is Substituted with oxadiazol-5-yl

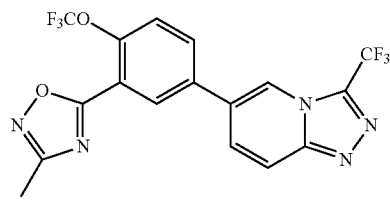 [SMILES: Cc1noc(-c2cc(-c3ccc4nnc(C(F)(F)F)n4c3)ccc2OC(F)(F)F)n1]

A. Preparation of a Compound of Formula I in which $R^1$ is 3-(3-methyl-1,2,4-oxadiazol-5-yl)-4-(trifluoromethoxy)phenyl, $W^1$, $W^2$ and $W^3$ are CH, and $X^1$ is CHCF$_3$, and $X^2$ is N Step 1—Formation of the Acid Precursor

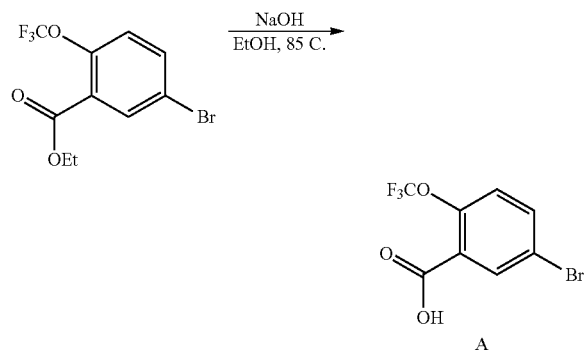

To a round bottom flask was added ethyl-5-bromo-2-(trifluoromethoxy)benzoate (1.59 mmole) and sodium hydroxide (3.99 mmole) in ethanol (12 mL). The reaction mixture was refluxed for 18 hours. The mixture was concentrated down and diluted with water and washed with dichloromethane. The aqueous layer was treated with 1N HCl to pH 4. The precipitate was filtered and air dried overnight to give A.

Step 2—Addition of the Ring Chain

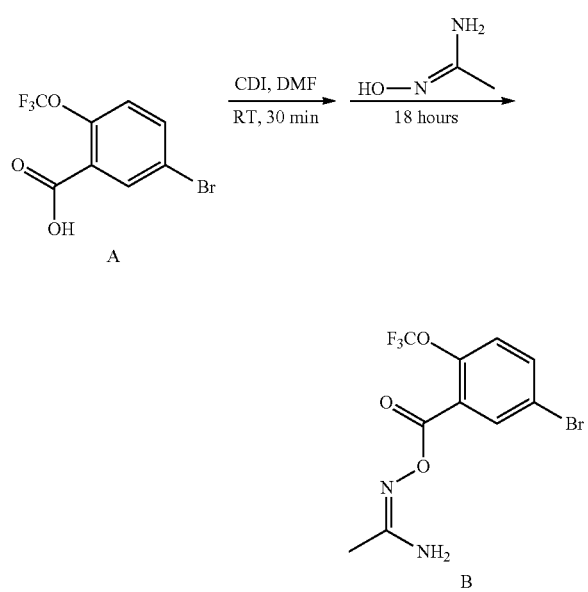

To a round bottom flask was added A (0.484) and 1,1-carbonyldiimidazole (CDT) (0.964 mmole) in DMF (3 mL). The mixture was stirred at room temperature for 30 min followed by the addition of the hydroxyacetimidamide. The resulting mixture was stirred at room temperature for another 18 hours. The reaction mixture was concentrated down and purified by preparative TLC to give B.

Step 3—Cyclization of the Oxadiazol Ring and Coupling to the Compound Core

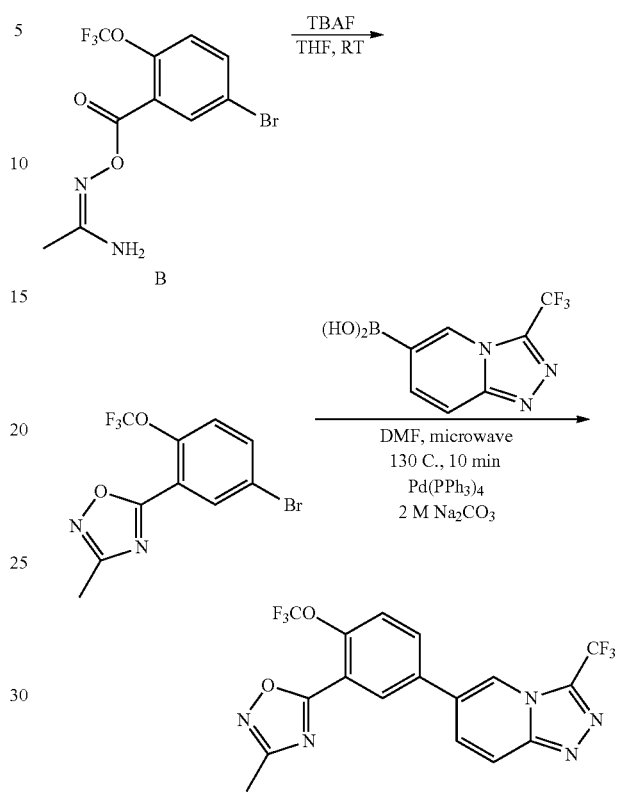

To a round bottom flask was added B (0.322 mmole), and tetrabutylammonium fluoride hydrate (0.645 mmol) in THF (3 mL). The reaction mixture was stirred at room temperature overnight. The reaction mixture was concentrated down and purified by preparative TLC to afford C which was then coupled with the desired boronic acid to give 6-[3-(3-methyl-1,2,4-oxadiazol-5-yl)-4-(trifluoromethoxy)phenyl]-3-(trifluoromethyl)[1,2,4]triazolo[4,3-a]pyridine.

MS m/z 430.1 (M$^+$).

B. Preparation of a Compound of Formula I Varying $R^1$, $W^1$, and $W^2$

Similarly, following the procedures of Example 17A above, but substituting other precursors for ethyl 5-bromo-2-(trifluoromethoxy)benzoate and 1,1-carbonyldiimidazole or other boronic acids for 3-(trifluoromethyl)[1,2,4]triazolo[4,3-a]pyridin-6-ylboronic acid, other compounds of Formula I may be prepared.

EXAMPLE 18

Preparation of a Compound of Formula I wherein $R^1$ is 4-(trifluoromethoxy)phenyl, $W^1$, $W^2$ and $W^3$ are CH, and $X^1$ is CH—$R^a$, $R^a$ is 2-fluorobenzyloxy)methyl and $X^2$ is N

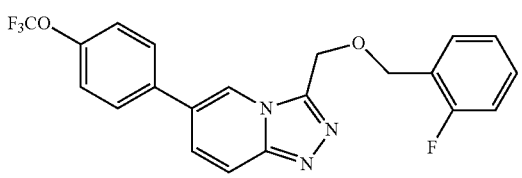 [SMILES: Fc1ccccc1COCc1nnc2ccc(-c3ccc(OC(F)(F)F)cc3)cn12]

A. Preparation of a Compound of Formula I

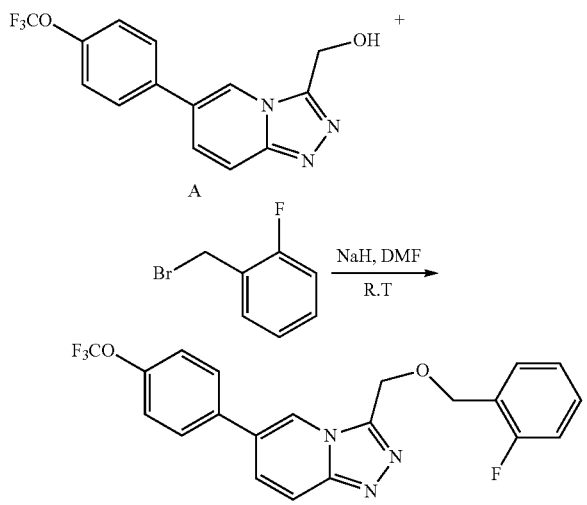

To a round bottom flask was added A, (6-(4-(trifluoromethoxy)phenyl)-[1,2,4]triazolo[4,3-a]pyridin-3-yl) methanol, prepared as disclosed in Example 10 (0.162 mmole) and 2-fluorobenzyl bromide (0.324 mmole) in DMF followed by sodium hydride. The reaction mixture was stirred at room temperature for 1 hour. The mixture was treated with 1N HCl. The precipitate, 3-{[(2-fluorobenzyl)oxy]methyl}-6-[4-(trifluoromethoxy)phenyl][1,2,4]triazolo[4,3-a]pyridine, was filtered and purified by prep HPLC.

MS m/z 418.1 (M+).

$^1$H-NMR (DMSO) 8.694 (s, 1H), 7.764-7.913 (m, 4H), 7.526-7.554 (d, 2H), 7.200-7.411 (m, 2H), 7.123-7.173 (m, 2H), 5.169 (s, 2H), 4.665 (s, 2H).

B. Preparation of a Compound of Formula I Varying $R^a$

Similarly, following the procedures of Example 18A above, but substituting other precursors for 2-fluorobenzyl bromide, the following compounds of Formula I were prepared:

3-(1,1-difluoro-2-(oxiran-2-ylmethoxy)ethyl)-6-(4-(trifluoromethoxy)phenyl)[1,2,4]triazolo[4,3-a]pyridine;

6-[4-(trifluoromethoxy)phenyl]-3-({[2-(trifluoromethyl)benzyl]oxy}methyl)[1,2,4]triazolo[4,3-a]pyridine,
MS m/z 468.1 (M+),
$^1$H-NMR (DMSO) 8.771 (s, 1H), 7.513-7.930 (m, 10H), 5.225 (s, 2H), 4.782 (s, 2H);

3-{[(2,4-difluorobenzyl)oxy]methyl}-6-[4-(trifluoromethoxy)phenyl][1,2,4]triazolo[4,3-a]pyridine,
MS m/z 436.1 (M+),
$^1$H-NMR (DMSO) 8.681 (s, 1H), 7.763-7.911 (m, 4H), 7.451-7.555 (m, 3H), 7.200-7.311 (t, 1H), 7.000-7.173 (t, 1H), 5.158 (s, 2H), 4.630 (s, 2H);

3-{[(2-fluorobenzyl)oxy]methyl}-6-[4-(trifluoromethoxy)phenyl][1,2,4]triazolo[4,3-a]pyridine,
MS m/z 469.1 (M+),
$^1$H-NMR (DMSO) 8.741 (s, 1H), 7.803-7.889 (m, 4H), 7.402-7.549 (m, 5H), 5.212 (s, 2H), 4.668 (s, 2H);

3-{[(2,4-dimethylbenzyl)oxy]methyl}-6-[4-(trifluoromethoxy)phenyl][1,2,4]triazolo[4,3-a]pyridine,
MS m/z 428.1 (M+),
$^1$H-NMR (DMSO) 8.657 (s, 1H), 7.827-7.883 (m, 4H), 7.519-7.546 (d, 2H), 7.119-7.911 (d, 1H), 6.856-7.000 (m, 1H), 5.113 (s, 2H), 4.546 (s, 2H), 2.162-2.208 (m, 6H);

3-{[(5-methylpyridin-2-yl)methoxy]methyl}-6-[4-(trifluoromethoxy)phenyl][1,2,4]triazolo[4,3-a]pyridine,
MS m/z 415.1 (M+);

3-[(benzyloxy)methyl]-6-[4-(trifluoromethoxy)phenyl][1,2,4]triazolo[4,3-a]pyridine,
400.1 (M+1);

3-[(cyclopropylmethoxy)methyl]-6-[4-(trifluoromethoxy)phenyl][1,2,4]triazolo[4,3-a]pyridine,
364.1 (M+1); and 3-[(2,2,2-trifluoroethoxy)methyl]-6-[4-(trifluoromethoxy)phenyl][1,2,4]triazolo[4,3-a]pyridine,
392.1 (M+1).

C. Preparation of Compounds of Formula I Varying $R^1$

Similarly, following the procedure of Example 18A above, but substituting other but substituting other precursors for 2-fluorobenzyl bromide or other alcohol substituted cores for (6-(4-(trifluoromethoxy)phenyl)[1,2,4]triazolo[4,3-a]pyridin-3-yl)methanol, other compounds of Formula. I may be prepared.

EXAMPLE 19

Preparation of a Compound of Formula I wherein $R^1$ is 4-(trifluoromethoxy)phenyl, $X^1$ is CH—$R^a$, $R^a$ is 1,1-difluoro-2-(oxiran-2-ylmethoxy)ethyl, $W^1$, $W^2$ and $W^3$ are CH, and $X^2$ is N

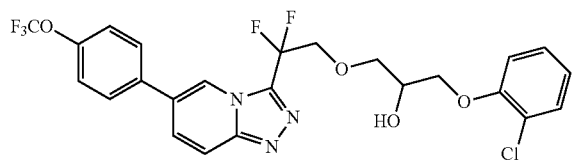 [SMILES: OC(COCC(F)(F)c1nnc2ccc(-c3ccc(OC(F)(F)F)cc3)cn12)COc1ccccc1Cl]

A. Preparation of a Compound of Formula I

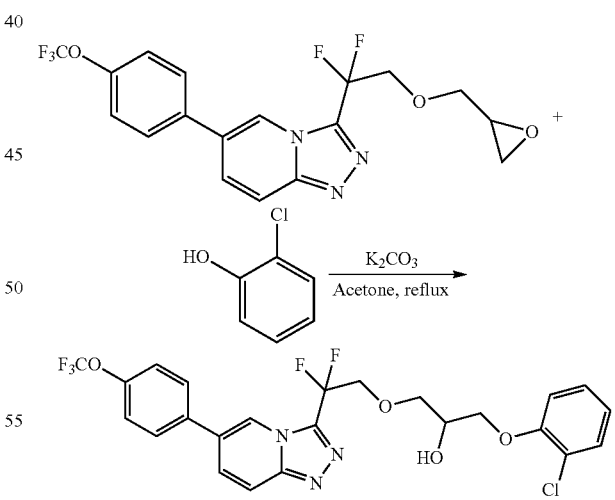

1 To a round bottom flask was added 3-(1,1-difluoro-2-(oxiran-2-ylmethoxy)ethyl)-6-(4-(trifluoromethoxy)phenyl)[1,2,4]triazolo[4,3-a]pyridine, prepared as described in Example 15, and 2-chlorophenol in acetone followed by potassium carbonate (sodium hydride in DMF at RT will also work). The reaction mixture was refluxed overnight. Potassium carbonate was filtered off. The filtrate was concentrated down and purified by prep TLC followed by prep HPLC to afford 1-(2-chlorophenoxy)-3-(2,2-difluoro-2-(6-(4-(trifluoromethoxy)phenyl)-[1,2,4]triazolo[4,3-a]pyridin-3-yl)ethoxy)propan-2-ol.

MS m/z 545.1 (M+).

B. Preparation of a Compound of Formula I Varying $R^a$

Similarly, following the procedures of Example 19A above, but substituting other hydroxyl substituted compounds for 2-chlorophenol, the following compound of Formula I was prepared:

1-(2,2-difluoro-2-{6-[4-(trifluoromethoxy)phenyl][1,2,4]triazolo[4,3-a]pyridin-3-yl}ethoxy)-3-(2,5-dimethylphenoxy)propan-2-ol, MS m/z 538.1 (M+).

C. Preparation of a Compound of Formula I Varying $R^1$, $W^3$, and $W^2$

Similarly, following the procedures of Example 19A above, but substituting o other hydroxyl substituted compounds for 2-chlorophenol or other oxiran-2-yl substituted compounds for 33-(1,1-difluoro-2-(oxiran-2-ylmethoxy)ethyl)-6-(4-(trifluoromethoxy)phenyl)[1,2,4]triazolo[4,3-a]pyridine, other compounds of Formula I may be prepared.

EXAMPLE 20

Preparation of a Compound of Formula I—Modification of an $R^1$ Hydroxy Group

A. Preparation of a Compound of Formula I

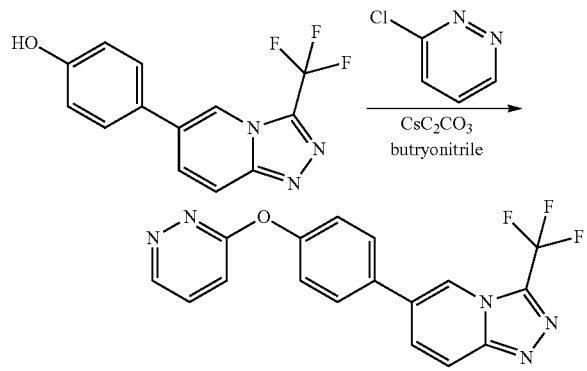

In a sealable flask, a suspension of the phenol, 4-(3-(trifluoromethyl)-[1,2,4]triazolo[4,3-a]pyridin-6-yl)phenol, prepared as described in Example 1 (47 mg, 0.17 mmol), heteroaryl chloride (39 mg, 0.34 mmol), Cs$_2$CO$_3$ (111 mg, 0.34 mmol), and butyronitrile (1 mL) is heated to 140° C. overnight. The reaction is concentrated and purified by RP-HPLC to afford the desired product, 6-(4-(pyridazin-3-yloxy)phenyl)-3-(trifluoromethyl)[1,2,4]triazolo[4,3-a]pyridine.

MS m/z 358.1 (M+1).

B. Alternative Preparation of a Compound of Formula I

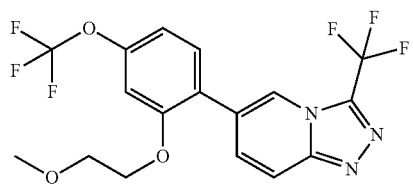

To a mixture of the phenol, prepared as described in Example 1 (40 mg, 0.11 mmol), NaH (8 mg, 0.33 mmol, 60% dispersion in mineral oil), and 1-bromo-2-methoxyethane (16μL, 0.17 mmol) is added DMF (1 mL). The reaction is stirred at room temperature for several hours and concentrated. The residue was purified by RP-HPLC to provide the product, 6-[2-(2-methoxyethoxy)-4-(trifluoromethoxy)phenyl]-3-(trifluoromethyl)[1,2,4]triazolo[4,3-a]pyridine, as a white powder MS m/z 422.4 (M+1).

C. Alternative Preparation of a Compound of Formula I

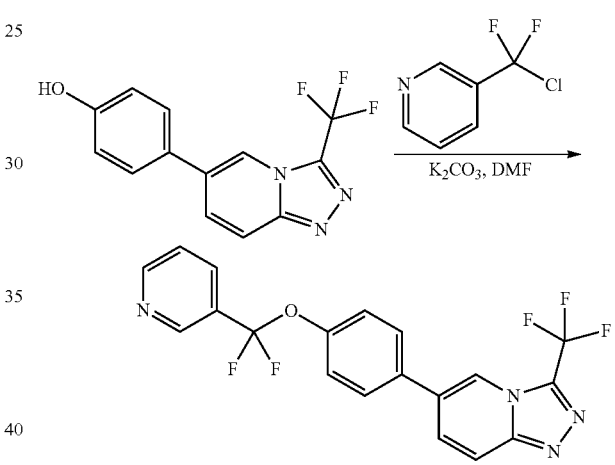

To a mixture of the phenol, prepared as described in Example 1, (50 mg, 0.18 mmol), K$_2$CO$_3$ (75 mg, 0.54 mmol), and 3-(chlorodifluoromethyl)pyridine (147 mg, 0.90 mmol) is added DMF (1 mL). The reaction is stirred at 100-140° C. overnight (for less reactive substrates the higher end of the temperature range is required). The reaction is diluted with EtOAC and water, the layers are separated and the organics are concentrated. The residue was purified by RP-HPLC to provide the product, 6-{4-[difluoro(pyridin-3-yl)methoxy]phenyl}-3-(trifluoromethyl)[1,2,4]triazolo[4,3-a]pyridine, as a white powder.

MS m/z 407.2 (M+1)

D. Preparation of a Compound of Formula I

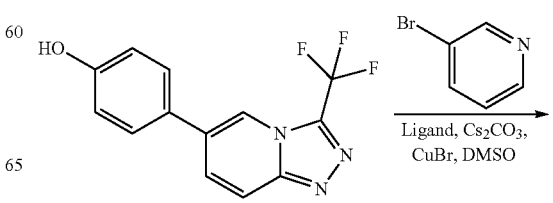

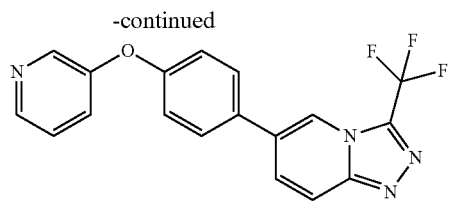

In a sealable flask, a suspension of the phenol, 4-(3-(trifluoromethyl)-[1,2,4]triazolo[4,3-a]pyridin-6-yl)phenol, prepared as described in Example 1 (47 mg, 0.17 mmol), aryl halide (46 mg, 0.29 mmol), Cs$_2$CO$_3$ (132 mg, 0.41 mmol), ethyl 2-oxocyclohexanecarboxylate (62 µL, 0.039 mmol), CuBr (2.8 mg, 0.019 mmol) and DMSO (1 mL) is heated to 100° C. overnight. The reaction is concentrated and purified by RP-HPLC to afford 20 mg of the desired product, 6-(4-(pyridin-3-yloxy)phenyl)-3-(trifluoromethyl)-[1,2,4]triazolo[4,3-a]pyridine.

357.1 (M+1).

D. Preparation of a Compound of Formula I Varying R$^1$

Similarly, following the procedures of Example 20A, B, C, or D above, but substituting other halide compounds or R$^1$ hydroxy compounds, the following compounds of Formula I were prepared:

6-(4-(pyrazin-2-yloxy)phenyl)-3-(trifluoromethyl)[1,2,4]triazolo[4,3-a]pyridine,
  MS m/z 358.1 (M+1);
{5-(trifluoromethoxy)-2-[3-(trifluoromethyl)[1,2,4]triazolo[4,3-a]pyridin-6-yl]phenoxy}acetonitrile,
  MS m/z 403.2 (M+1);
6-[6-(methylsulfanyl)pyridin-3-yl]-3-(trifluoromethyl)imidazo[1,5-a]pyridine,
  MS m/z 434.1 (M+1);
6-[2-ethoxy-4-(trifluoromethoxy)phenyl]-3-(trifluoromethyl)[1,2,4]triazolo[4,3-a]pyridine,
  MS m/z 392.3 (M+1),
  $^1$H NMR (CDCl$_3$) d 8.47 (s, 1H), 7.95 (d, J=7.6 Hz, 1H), 7.65 (d, J=8.0 Hz, 1H), 7.41 (d, J=8.4 Hz, 1H), 6.97 (d, J=7.2 Hz, 1H), 6.87 (s, 1H), 4.11 (q, J=6.8 Hz, 1H), 1.42 (t, J=6.8 Hz, 3H);
6-{4-[difluoro(phenyl)methoxy]phenyl}-3-(trifluoromethyl)[1,2,4]triazolo[4,3-a]pyridine,
  MS m/z 406.2 (M+1),
  $^1$H NMR (DMSO) 8.74 (s, 1H), 8.16 (dd, J=1.2, 10.0 Hz, 1H), 8.01 (dd, J=1.2, 9.6 Hz, 1H), 7.90 (t, J=4.8 Hz, 1H), 7.88 (t, J=4.8 Hz, 1H), 7.79-7.83 (m, 2H), 7.57-7.66 (m, 3H), 7.48 (t, J=8.4 Hz, 2H);
4-(difluoro{4-[3-(trifluoromethyl)[1,2,4]triazolo[4,3-a]pyridin-6-yl]phenoxy}methyl)benzonitrile,
  MS m/z 431.2 (M+1),
  $^1$H NMR (DMSO) 8.73 (s, 1H), 8.15 (d, J=9.6 Hz, 1H), 8.08 (d, J=8.4 Hz, 2H), 7.89-8.04 (m, 3H), 7.89 (d, J=8.4 Hz, 2H), 7.49 (d, J=8.4 Hz, 2H); and
6-[2-(propan-2-yloxy)-4-(trifluoromethoxy)phenyl]-3-(trifluoromethyl)[1,2,4]triazolo[4,3-a]pyridine
  MS m/z 406.1 (M+1),
  $^1$H NMR (CDCl$_3$) d 8.47 (s, 1H), 7.94 (s, 1H), 7.63 (s, 1H), 7.40 (d, J=8.4 Hz, 1H), 6.95 (d, J=7.6 Hz, 1H), 6.87 (s, 1H), 4.64 (sept, J=6.0 Hz, 1H), 1.35 (d, J=6.0 Hz, 6H).

F. Preparation of a Compound of Formula I Varying R$^1$, W$^1$, and W$^2$

Similarly, following the procedures of Example 20A, B, C, or D above, but substituting other halide compounds or other R$^1$ hydroxy compounds, other compounds of Formula I may be prepared.

EXAMPLE 21

Preparation of a Compound of Formula I—Modification of an R$^1$ Amino Group

A. Preparation of a Compound of Formula I

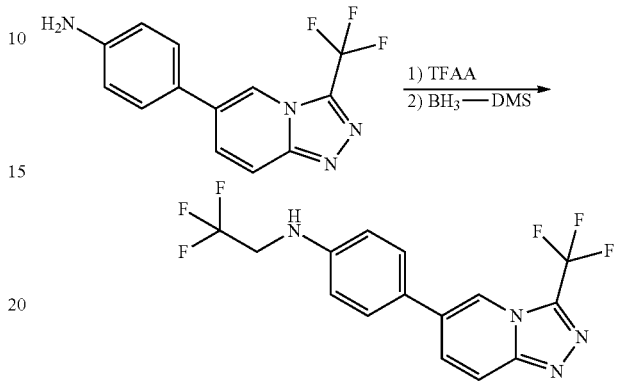

To a suspension of the aniline prepared in Example 1 (104 mg, 0.37 mmol) in CH$_2$Cl$_2$ (2 mL) is added trifluoroacetic anhydride (58 µL, 0.41 mmol) and the reaction is done immediately. CH$_2$Cl$_2$ (10 mL) is added and the solids are collected by filtration to yield 122 mg of solid. To a suspension of the collected solids c in THF (2 mL) is added a 10.1M solution of BH$_3$•dimethylsulfide (48 pt, 0.48 mmol). The reaction is heated to 90° C. for 90 minutes, an additional aliquot of borane solution (16 µL, 0.16 mmol) is added and stirred 30 minutes. The reaction is cooled, 1N HCl (1 mL) and MeOH (1 mL) are added and the reaction is heated to 60° C. for 15 minutes. The reaction is concentrated and the residue was purified by RP-HPLC to provide the product, N-(2,2,2-trifluoroethyl)-4-(3-(trifluoromethyl)[1,2,4]triazolo[4,3-a]pyridin-6-yl)aniline, as a white powder.

MS m/z 361.1 (M+1).

B. Preparation of a Compound of Formula I

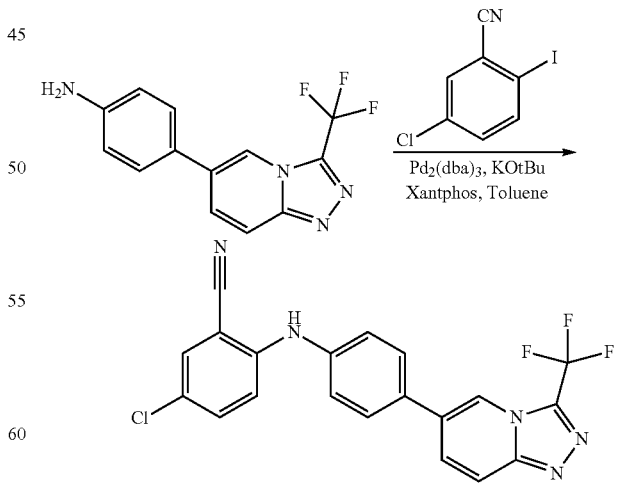

A mixture of the aniline prepared in Example 1 (50 mg, 0.18 mmol), 5-chloro-2-iodobenzonitrile (72 mg, 0.27 mmol), Pd$_2$(dba)$_3$ (8.2 mg, 0.0090 mmol), 4,5-Bis(diphenylphosphino)-9,9-dimethylxanthene (16 mg, 0.030 mmol), and KOtBu (28 mg, 0.25 mmol) in a sealable flask is charged with $N_2$, heated to 100° C. and stirred overnight. The reaction is concentrated and the residue was purified by RP-HPLC to provide the product, 5-chloro-2-({4-[3-(trifluoromethyl)[1,2,4]triazolo[4,3-a]pyridin-6-yl]phenyl}amino)benzonitrile, as a white powder.

MS m/z 414.2 (M+1).

C. Preparation of a Compound of Formula I

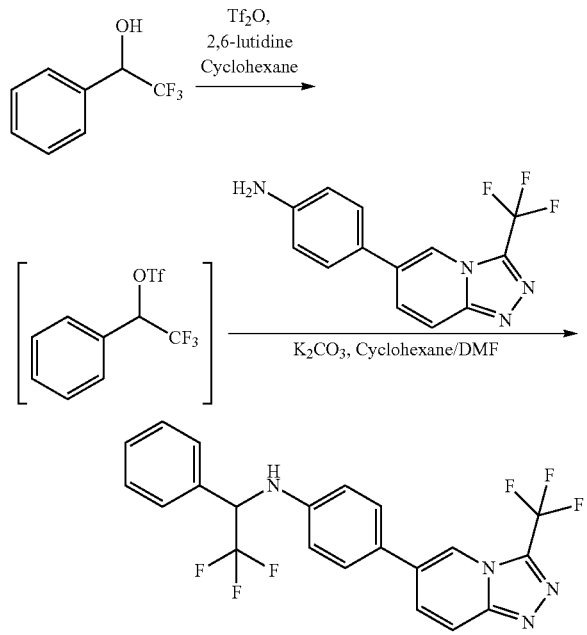

A solution of a-trifluoromethyl benzyl alcohol (73 μL, 0.54 mmol) and 2,6 lutidine (100 μL, 0.81 mmol) in cyclohexane (1 mL) was cooled to 0° C. and trifluoroacetic anhydride (140 μL, 0.78 mmol) was added. The mixture was stirred for 30 minutes, warmed to room temperature and water (5 mL) and cyclohexane (5 mL) were added. The layers were separated and the organic layer is washed with brine, dried over $MgSO_4$, filtered and concentrated. To a solution of the concentrated material in cyclohexane (1 mL) was added the aniline, 4-(3-(trifluoromethyl)[1,2,4]triazolo[4,3-a]pyridin-6-yl)aniline as prepared in Example 1 (90 mg, 0.33 mmol), $K_2CO_3$ (90 mg, 0.66 mmol), and DMF (1 mL). The reaction was stirred overnight, concentrated, and the residue was purified by RP-HPLC to provide the product, N-(2,2,2-trifluoro-1-phenyl-ethyl)-4-(3-(trifluoromethyl)-[1,2,4]triazolo[4,3-a]pyridin-6-yl)aniline, as a white powder 437.2 (M+1).

D. Preparation of a Compound of Formula I—Alkylation of the $R^1$ Amino Group

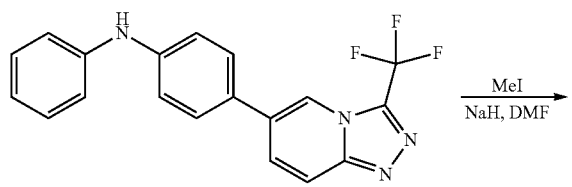

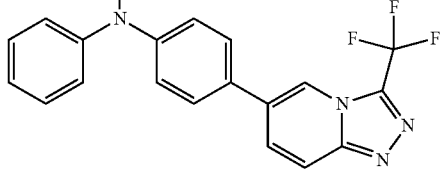

To a mixture of the aniline prepared in Example 1 (20 mg, 0.056 mmol), NaH (7 mg, 0.11 mmol, 60% dispersion in mineral oil), and iodomethane (11 μL, 0.11 mmol) is added DMF (0.5 mL). The reaction is stirred at room temperature for two hours and concentrated. The residue is purified by column chromatography (Rf=0.53, 1:1 Hexanes/EtOAc) to afford the product, N-methyl-N-phenyl-4-[3-(trifluoromethyl)[1,2,4]triazolo[4,3-a]pyridin-6-yl]aniline.

MS m/z 369.2 (M+1).

$^1$H NMR (DMSO) 8.57 (s, 1H), 8.11 (d, J=9.6 Hz, 1H), 798 (dd, J=1.6, 9.6 Hz, 1H), 7.68 (d, 8.8 Hz, 2H), 7.38 (t, J=7.6 Hz, 2H), 7.18 (d, J=8.0 Hz, 2H), 7.10 (t, J=7.6 Hz, 1H), 7.03 (d, J=8.8 Hz, 2H), 3.33 (s, 3H).

Alternate Alkylation of the $R^1$ Amino Group

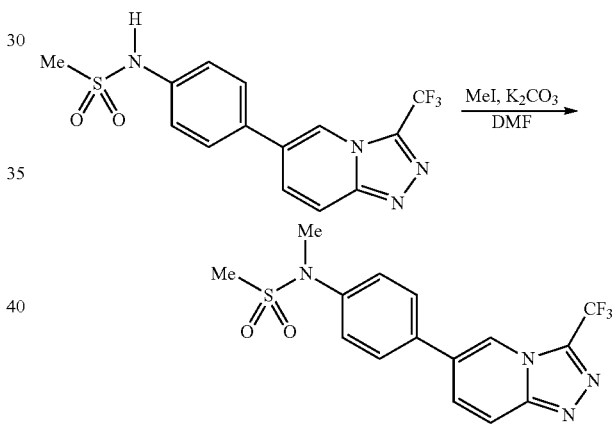

N-(4-(3-(trifluoromethyl)[1,2,4]triazolo[4,3-a]pyridin-6-yl)phenyl)methanesulfonamide (10 mg) was dissolved in DMF (1 mL) and heated with potassium carbonate (39 mg) and methyl iodide (40 mg) for 2 h at 85° C. The reaction mixture was filtered, concentrated, and purified by chromatography using 2% MeOH in methylene chloride as eluent. N-methyl-N-(4-(3-(trifluoromethyl)[1,2,4]triazolo[4,3-a]pyridin-6-yl)phenyl)methanesulfonamide was obtained as white solid.

$^1$H NMR (400 MHz, $CDCl_3$): δ 8.61 (s, 1H); 8.03 (d, 1H); 7.69 (d, 1H); 7.68 (d, 1H); 7.58 (m, 4H), 3.40 (s, 3H), 2.91 (s, 3H).

MS (ES+, m/z) 371.0 (base peak, M+H$^+$); 763.0 (2M+Na$^+$).

E. Preparation of a Compound of Formula I Varying $R^1$

Similarly, following the procedures of Example 21A, B, or C above, but substituting other halide or anhydride compounds or other $R^1$ amino compounds, the following other compounds of Formula I were prepared.

4-chloro-N-{4-[3-(trifluoromethyl)[1,2,4]triazolo[4,3-a]pyridin-6-yl]phenyl}aniline, MS m/z 389.2 (M+1); and 4-fluoro-N-{4-[3-(trifluoromethyl)[1,2,4]triazolo[4,3-a]pyridin-6-yl]phenyl}aniline, MS m/z 373.2 (M+1).

F. Preparation of a Compound of Formula I Varying $R^1$, $W^1$, and $W^2$

Similarly, following the procedures of Example 21A, B, or C above, but substituting other halide or anhydride compounds or other $R^1$ amino compounds, other compounds of Formula I may be prepared.

EXAMPLE 22

Preparation of a Compound of Formula I

A. Preparation of a Compound of Formula I in which $R^1$ is 4-trifluoromethoxyphenyl, Q is a Covalent Bond, $W^1$, $W^2$, and $W^3$ are CH, $X^1$ is $CCF_2Cl$, and $X^2$ is N Step 1. Preparation of 6-bromo-3-(chloro-difluoromethyl)-[1,2,4]triazolo[4,3-a]pyridine, a Compound of Formula (1)

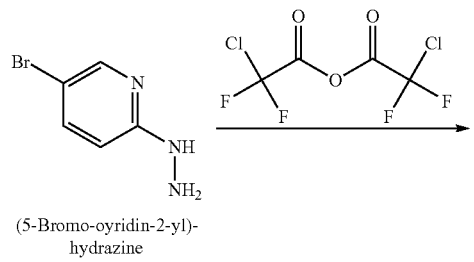

(5-Bromo-oyridin-2-yl)-hydrazine

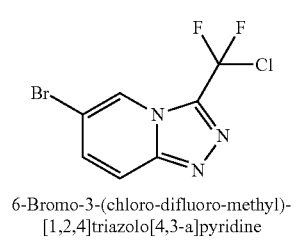

6-Bromo-3-(chloro-difluoro-methyl)-[1,2,4]triazolo[4,3-a]pyridine (5-Bromo-pyridin-2-yl)-hydrazine (5.0 g, 26.5 mmol) in chlorodifluoroacetic anhydride (11 mL) was heated in a microwave with careful monitoring of the pressure at 160° C. for 1 h. The reaction was cooled to room temperature before being carefully vented with a needle. The reaction was slowly added to a stirred saturated solution of sodium bicarbonate (250 mL), extracted with ethyl acetate and dried before being purified by flash chromatography (rf=0.5 in 1:1 hexanes/ethyl acetate) to give 6-bromo-3-(chloro-difluoro-methyl)[1,2,4]triazolo[4,3-a]pyridine as a pale yellow powder.

M+1=282/284.

Step 2. Preparation of 3-(chloro-difluoro-methyl)-6-(4-trifluoromethoxy-phenyl)-[1,2,4]triazolo[4,3-a]pyridine, a Compound of Formula I

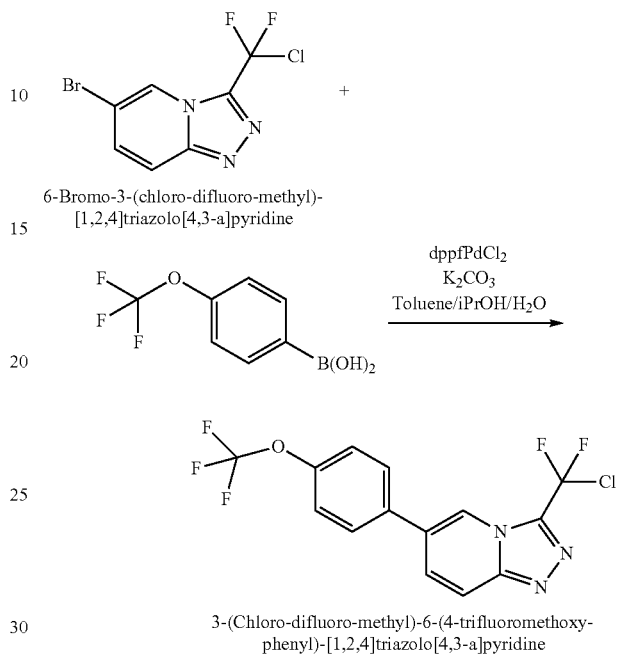

3-(Chloro-difluoro-methyl)-6-(4-trifluoromethoxy-phenyl)-[1,2,4]triazolo[4,3-a]pyridine 6-Bromo-3-(chloro-difluoro-methyl)-[1,2,4]triazolo[4,3-a]pyridine (2.76 g, 9.8 mmol), 4-trifluoromethoxyphenyl boronic acid (2.5 g, 12.1 mmol), dppfPdCl$_2$ (1,1'-bis(diphenylphosphino)ferrocene palladium dichloride) (350 mg, 0.5 mmol), and potassium carbonate (2.76 g, 20 mmol) were suspended in degassed toluene (20 mL), degassed isopropanol (10 mL) and degassed water (10 mL) under an atmosphere of nitrogen. The reaction mixture was heated at 70° C. for 1 hour before being cooled to room temperature. The aqueous phase was discarded and the organic phase was concentrated and purified by flash chromatography (rf=0.5 in 1:1 hexanes/ethyl acetate) to give 3-(chloro-difluoro-methyl)-6-(4-trifluoromethoxy-phenyl)[1,2,4]triazolo[4,3-a]pyridine as a pale orange powder.

M+1=364.

Optional Step 3. Preparation of 4-((difluoro(6-(4-(trifluoromethoxy)phenyl)-[1,2,4]triazolo[4,3-a]pyridin-3-yl)methoxy)methyl-2-phenyl-5-trifluoromethyl)oxazole, a Compound of Formula I

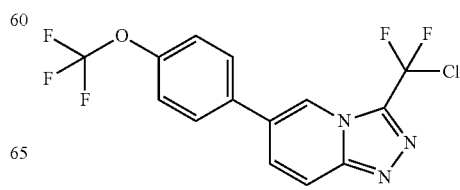

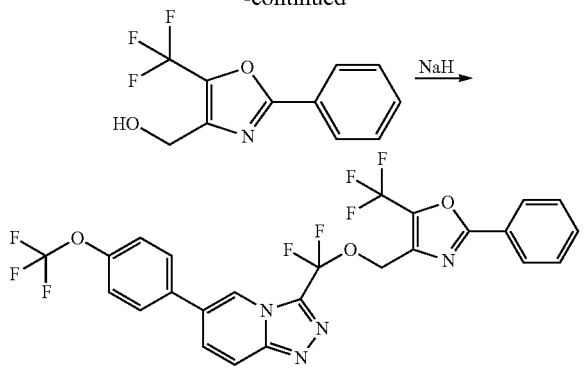

In a 5 mL microwave vial under a nitrogen atmosphere 3-(Chloro-difluoro-methyl)-6-(4-trifluoromethoxy-phenyl)-[1,2,4]triazolo[4,3-a]pyridine (100 mg, 0.275 mmol), (2-phenyl-5-(trifluoromethyl)oxazol-4-yl)methanol (107 mg, 0.440 mmol), and NaH (39 mg, 0.96 mmol) in DMF (3 ml) were combined and stirred for 10 minutes. The reaction mixture was quenched with 1M HCl and concentrated before being purified the product, 4-((difluoro(6-(4-(trifluoromethoxy)phenyl)-[1,2,4]triazolo[4,3-a]pyridin-3-yl)methoxy)methyl)-2-phenyl-5-(trifluoromethyl)oxazole, by prep-HPLC (HCl).
571.1 (M+1).

B. Preparation of Compounds of Formula I Varying $R^1$ and $R^a$

Similarly, following the procedure of Example 22A above, but substituting other alcohols for (2-phenyl-5-(trifluoromethyl)oxazol-4-yl)methanol or other boronic acids for 4-trifluoromethoxyphenyl boronic acid, the following compounds of Formula I were prepared:

3-[difluoro(methoxy)methyl]-6-[4-(trifluoromethoxy)phenyl][1,2,4]triazolo[4,3-a]pyridine
360.1 (M+1).
$^1$H NMR (DMSO) d 8.64 (s, 1H), 8.09 (dd, J=9.2, 1.2 Hz, 1H), 7.90 (m, 3H), 7.55 (d, J=8.0 Hz, 2H), 3.88 (s, 3H).
$^{19}$F NMR (DMSO) d −57.3 (s, 3F), −70.1 (s, 2F).

3-[difluoro(2-methoxyethoxy)methyl]-6-[4-(trifluoromethoxy)phenyl][1,2,4]triazolo[4,3-a]pyridine
404.1 (M+1).
$^1$H NMR (DMSO) d 8.69 (s, 1H), 8.10 (dd, J=9.6, 1.2 Hz, 1H), 7.94 (dd, J=8.0, 1.6 Hz, 1H), 7.87 (m, 2H), 7.56 (dd, J 8.8, 0.8 Hz, 2H), 4.34 (m, 2H), 3.67 (m, 2H), 3.27 (s, 3H).
$^{19}$F NMR (DMSO) d −57.3 (s, 3F), −67.6 (s, 2F).

3-{difluoro[(3-methyloxetan-3-yl)methoxy]methyl}-6-[4-(trifluoromethoxy)phenyl][1,2,4]triazolo[4,3-a]pyridine
430.1 (M+1).
$^1$H NMR (DMSO) d 8.68 (s, 1H), 8.11 (d, J=8.0 Hz, 1H), 7.95 (d, J=8.0 Hz, 1H), 7.86 (d, J=8.0 Hz, 2H), 7.54 (d, J=8.0 Hz, 2H), 4.53 (m, 2H), 4.35 (m, 4H), 1.27 (s, 3H).
$^{19}$F NMR (DMSO) d −57.2 (s, 3F), −66.7 (s, 2F).

3-{difluoro[2-(morpholin-4-yl)ethoxy]methyl}-6-[4-(trifluoromethoxy)phenyl][1,2,4]triazolo[4,3-a]pyridine
459.1 (M+1).
1H NMR (DMSO) d 10.45 (br, 1H), 8.74 (s, 1H), 8.12 (d, J=8.8 Hz, 1H), 7.92 (m, 3H), 7.55 (d, J=8.0 Hz, 2H), 4.67 (m, 2H), 3.95 (m, 2H), 3.10-3.80 (m, 8H).
$^{19}$F NMR (DMSO) d −57.3 (s, 3F), −69.0 (s, 2F).

3-{difluoro[(5-methyl-1,2,4-oxadiazol-3-yl)methoxy]methyl}-6-[4-(trifluoromethoxy)phenyl][1,2,4]triazolo[4,3-a]pyridine
442.1 (M+1).
$^1$H NMR (DMSO) d 8.90 (s, 1H), 8.11 (dd, J=9.6, 1.6 Hz, 1H), 7.96 (dd, J=9.6, 1.6 Hz, 1H), 7.91 (dd, J=6.8, 2.0 Hz, 2H), 7.57 (d, J=8.4 Hz, 2H), 5.52 (s, 2H), 2.57 (s, 3H).
$^{19}$F NMR (DMSO) d −57.3 (s, 3F), −68.9 (s, 2F).

3-[(benzyloxy)(difluoro)methyl]-6-[4-(trifluoromethoxy)phenyl][1,2,4]triazolo[4,3-a]pyridine
436.1 (M+1).
$^1$H NMR (DMSO) d 8.51 (s, 1H), 8.09 (dd, J=9.6, 1.2 Hz, 1H), 7.91 (dd, J=9.6, 1.2 Hz, 1H), 7.75 (m, 2H), 7.53 (m, 4H), 7.41 (m, 3H), 5.32 (s, 2H).
$^{19}$F NMR (DMSO) d −57.3 (s, 3F), −66.8 (s, 2F).

3-[difluoro(pyridin-4-ylmethoxy)methyl]-6-[4-(trifluoromethoxy)phenyl][1,2,4]triazolo[4,3-a]pyridine
437.1 (M+1).
$^1$H NMR (DMSO) d 8.63 (m, 3H), 8.11 (m, 1H), 7.93 (dd, J=9.6, 2.0 Hz, 1H), 7.83 (m, 2H), 7.53 (m, 4H), 5.41 (s, 2H).
$^{19}$F NMR (DMSO) d −57.3 (s, 3F), −67.4 (s, 2F).

2-(difluoro{6-[4-(trifluoromethoxy)phenyl][1,2,4]triazolo[4,3-a]pyridin-3-yl}methoxy)ethanol
390.1 (M+1).
$^1$H NMR (DMSO) d 8.83 (s, 1H), 8.09 (dd, J=9.6, 2.0 Hz, 1H), 7.93 (m, 3H), 7.52 (dd, J=8.8, 1.0 Hz, 2H), 5.14 (m, 1H), 4.24 (m, 2H), 3.75 (m, 2H).
$^{19}$F NMR (DMSO) d −57.2 (s, 3F), −67.4 (s, 2F).

1-(difluoro{6-[4-(trifluoromethoxy)phenyl][1,2,4]triazolo[4,3-a]pyridin-3-yl}methoxy)propan-2-ol
404.1 (M+1).
$^1$H NMR (DMSO) d 8.85 (s, 1H), 8.09 (dd, J=9.6, 1.2 Hz, 1H), 7.91 (m, 3H), 7.53 (dd, J=9.2, 1.2 Hz, 2H), 5.14 (d, J=4.4 Hz, 1H), 4.14 (m, 1H), 4.00 (m, 2H), 1.15 (d, J=6.0 Hz, 3H).
$^{19}$F NMR (DMSO) d −57.2 (s, 3F), −67.4 (s, 2F).

3-[difluoro(pyridin-3-ylmethoxy)methyl]-6-[4-(trifluoromethoxy)phenyl][1,2,4]triazolo[4,3-a]pyridine
437.1 (M+1).
$^1$H NMR (DMSO) d 8.80 (s, 1H), 8.65 (m, 1H), 8.59 (s, 1H), 8.13 (d, J=8.0 Hz, 1H), 8.09 (d, J=9.6 Hz, 1H), 7.93 (m, 1H), 7.81 (m, 2H), 7.59 (m, 1H), 7.54 (d, J=8.4 Hz, 2H), 5.43 (s, 2H).
$^{19}$F NMR (DMSO) d −57.3 (s, 3F), −67.3 (s, 2F).

3-{[(5-cyclopropyl-1,2,4-oxadiazol-3-yl)methoxy](difluoro)methyl}-6-[4-(trifluoromethoxy)phenyl][1,2,4]triazolo[4,3-a]pyridine
468.1 (M+1).
$^1$H NMR (DMSO) d 8.84 (s, 1H), 8.12 (dd, J=9.6, 1.6 Hz, 1H), 7.95 (dd, J=9.6, 1.6 Hz, 1H), 7.90 (m, 2H), 7.56 (d, J=8.0 Hz, 2H), 5.46 (s, 2H), 2.31 (m, 1H), 1.19 (m, 2H), 1.01 (m, 2H).
$^{19}$F NMR (DMSO) d −57.3 (s, 3F), −68.8 (s, 2F).

3-(difluoro{[5-(2-methylpropyl)-1,2,4-oxadiazol-3-yl]methoxy}methyl)-6-[4-(trifluoromethoxy)phenyl][1,2,4]triazolo[4,3-a]pyridine
484.1 (M+1).
$^1$H NMR (DMSO) d 8.90 (s, 1H), 8.11 (dd, J=9.6, 1.6 Hz, 1H), 7.96 (dd, J=9.6, 1.6 Hz, 1H), 7.91 (m, 2H), 7.56 (d, J=8.0 Hz, 2H), 5.54 (s, 2H), 2.79 (d, J=6.8 Hz, 2H), 2.01 (sept, J=6.8 Hz, 1H), 0.84 (d, J=6.8 Hz, 6H).
$^{19}$F NMR (DMSO) d −57.3 (s, 3F), −68.8 (s, 2F).

3-(difluoro{[5-(propan-2-yl)-1,2,4-oxadiazol-3-yl]methoxy}methyl)-6-[4-(trifluoromethoxy)phenyl][1,2,4]triazolo[4,3-a]pyridine
470.1 (M+1).
$^1$H NMR (DMSO) d 8.86 (s, 1H), 8.22 (dd, J=9.6, 1.6 Hz, 1H), 7.95 (dd, J=9.6, 1.6 Hz, 1H), 7.90 (m, 2H), 7.55 (d, J=8.0 Hz, 2H), 5.52 (s, 2H), 3.24 (sept, J=6.8 Hz, 1H), 1.22 (d, J=6.8 Hz, 6H).
$^{19}$F NMR (DMSO) d −57.3 (s, 3F), −68.8 (s, 2F).

3-[difluoro(pyridin-2-ylmethoxy)methyl]-6-[4-(trifluoromethoxy)phenyl][1,2,4]triazolo[4,3-a]pyridine
437.1 (M+1).

$^1$H NMR (DMSO) d 8.94 (s, 1H), 8.56 (m, 1H), 8.09 (dd, J=9.6, 1.6 Hz, 1H), 7.88 (m, 4H), 7.60 (m, 3H), 7.42 (m, 1H), 5.41 (s, 2H).

$^{19}$F NMR (DMSO) d −57.3 (s, 3F), −67.4 (s, 2F).

4-[(difluoro{6-[4-(trifluoromethoxy)phenyl][1,2,4]triazolo[4,3-a]pyridin-3-yl}methoxy)methyl]quinoline
487.1 (M+1).

$^1$H NMR (DMSO) d 8.92 (d, J=4.8 Hz, 1H), 8.44 (s, 1H), 8.24 (d, J=7.2 Hz, 1H), 8.07 (d, J=8.4 Hz, 2H), 7.87 (dd, J=9.6, 1.6 Hz, 1H), 7.77 (m, 1H), 7.64 (m, 4H), 7.47 (d, J=8.4 Hz, 2H), 5.88 (s, 2H).

$^{19}$F NMR (DMSO) d −57.3 (s, 3F), −67.6 (s, 2F).

3-[(cyclopropylmethoxy)(difluoro)methyl]-6-[4-(trifluoromethoxy)phenyl][1,2,4]triazolo[4,3-a]pyridine
400.1 (M+1).

$^1$H NMR (DMSO) d 8.66 (s, 1H), 8.10 (dd, J=9.6, 1.6 Hz, 1H), 7.94 (dd, J=9.6, 1.6 Hz, 1H), 7.88 (m, 2H), 7.55 (d, J=8.0 Hz, 2H), 4.09 (d, J=7.6 Hz, 2H), 1.27 (m, 1H), 0.60 (m, 2H), 0.38 (m, 2H).

$^{19}$F NMR (DMSO) d −57.3 (s, 3F), −66.7 (s, 2F).

3-{difluoro [(1-phenyl-1H-1,2,3-triazol-4-yl)methoxy]methyl}-6-[4-(trifluoromethoxy)phenyl][1,2,4]triazolo[4,3-a]pyridine
503.1 (M+1).

$^1$H NMR (DMSO) d 9.03 (s, 1H), 8.66 (s, 1H), 8.08 (dd, J=9.6, 1.2 Hz, 1H), 7.90 (m, 5H), 7.60 (m, 2H), 7.53 (m, 1H), 7.41 (d, J=8.0 Hz, 2H), 5.51 (s, 2H).

$^{19}$F NMR (DMSO) d −57.3 (s, 3F), −67.7 (s, 2F).

3-[difluoro(pyridazin-3-ylmethoxy)methyl]-6-[4-(trifluoromethoxy)phenyl][1,2,4]triazolo[4,3-a]pyridine
438.1 (M+1).

$^1$H NMR (DMSO) d 9.30 (m, 1H), 9.02 (s, 1H), 8.10 (dd, J=9.6, 1.2 Hz, 1H), 7.95 (m, 4H), 7.81 (m, 1H), 7.55 (dd, J=9.2, 0.8 Hz, 2H), 5.65 (s, 2H).

$^{19}$F NMR (DMSO) d −57.2 (s, 3F), −67.6 (s, 2F).

3-{difluoro[(1-methyl-5-phenyl-1H-pyrazol-3-yl)methoxy]methyl}-6-[4-(trifluoromethoxy)phenyl][1,2,4]triazolo[4,3-a]pyridine
516.1 (M+1).

$^1$H NMR (DMSO) d 8.62 (s, 1H), 8.07 (dd, J=9.6, 1.2 Hz, 1H), 7.91 (dd, J=9.6, 1.6 Hz, 1H), 7.80 (m, 2H), 7.48 (m, 5H), 7.38 (d, J=8.0 Hz, 2H), 6.58 (s, 1H), 5.25 (s, 2H), 3.74 (s, 3H).

$^{19}$F NMR (DMSO) d −57.3 (s, 3F), −67.3 (s, 2F).

3-{[(2,2-difluoro-1,3-benzodioxol-5-yl)methoxy](difluoro)methyl}-6-[4-(trifluoromethoxy)phenyl][1,2,4]triazolo[4,3-a]pyridine
516.1 (M+1).

$^1$H NMR (DMSO) d 8.52 (s, 1H), 8.08 (d, J=9.2 Hz, 1H), 7.91 (d, J=9.6 Hz, 1H), 7.78 (m, 2H), 7.66 (s, 1H), 7.51 (d, J=8.4 Hz, 2H), 7.45 (d, J=8.4 Hz, 1H), 7.39 (m, 1H), 5.32 (s, 2H).

$^{19}$F NMR (DMSO) d −49.7 (s, 2H), −57.3 (s, 3F), −66.9 (s, 2F).

3-{[(2,5-dimethyl-1,3-oxazol-4-yl)methoxy](difluoro)methyl}-6-[4-(trifluoromethoxy)phenyl][1,2,4]triazolo[4,3-a]pyridine
455.1 (M+1).

$^1$H NMR (DMSO) d 8.64 (s, 1H), 8.08 (dd, J=9.6, 1.2 Hz, 1H), 7.92 (dd, J=9.6, 1.6 Hz, 1H), 7.87 (m, 2H), 7.56 (d, J=8.0 Hz, 2H), 5.13 (s, 2H), 2.28 (s, 3H), 2.21 (s, 3H).

$^{19}$F NMR (DMSO) d −57.3 (s, 3F), −67.6 (s, 2F).

3-{difluoro[(5-methyl-2-phenyl-1,3-oxazol-4-yl)methoxy]methyl}-6-[4-(trifluoromethoxy)phenyl][1,2,4]triazolo[4,3-a]pyridine
517.1 (M+1).

$^1$H NMR (DMSO) d 8.57 (s, 1H), 8.06 (dd, J=9.6, 1.2 Hz, 1H), 7.85 (m, 3H), 7.72 (m, 2H), 7.48 (m, 3H), 7.23 (d, J=8.0 Hz, 2H), 5.26 (s, 2H), 2.43 (s, 3H).

$^{19}$F NMR (DMSO) d −57.2 (s, 3F), −67.4 (s, 2F).

3-{difluoro[1-(pyridin-2-yl)ethoxy]methyl}-6-[4-(trifluoromethoxy)phenyl][1,2,4]triazolo[4,3-a]pyridine
451.1 (M+1).

$^1$H NMR (DMSO) d 8.82 (s, 1H), 8.50 (d, J=4.8 Hz, 1H), 8.07 (d, J=9.6 Hz, 1H), 7.92 (dd, J=10.0, 1.6 Hz, 1H), 7.85 (m, 3H), 7.59 (m, 3H), 7.36 (m, 1H), 5.85 (q, J=6.4 Hz, 1H), 1.68 (d, J=6.4 Hz, 3H).

$^{19}$F NMR (DMSO) d −57.3 (s, 3F), −63.5 (d, J=155 Hz, 1F), −68.1 (d, J=155 Hz, 1F).

3-{[1-(4-chlorophenyl)ethoxy](difluoro)methyl}-6-[4-(trifluoromethoxy)phenyl][1,2,4]triazolo[4,3-a]pyridine
484.1 (M+1).

$^1$H NMR (DMSO) d 8.19 (s, 1H), 8.06 (dd, J=9.2, 1.2 Hz, 1H), 7.90 (dd, J=9.2, 1.2 Hz, 1H), 7.71 (an, 2H), 7.53 (m, 4H), 7.40 (m, 2H), 5.80 (q, J=6.8 Hz, 1H), 1.67 (d, J=6.8 Hz, 3H).

$^{19}$F NMR (DMSO) d −57.2 (s, 3F), −65.1 (d, J=155 Hz, 1F), −66.6 (d, J=155 Hz, 1F).

3-[difluoro(pyrimidin-2-ylmethoxy)methyl]-6-[4-(trifluoromethoxy)phenyl][1,2,4]triazolo[4,3-a]pyridine
438.1 (M+1).

$^1$H NMR (DMSO) d 9.43 (s, 1H), 8.83 (d, J=5.2 Hz, 2), 8.11 (dd, J=9.2, 1.2 Hz, 1H), 7.96 (dd, J=9.6, 1.6 Hz, 1H), 7.92 (m, 3H), 7.63 (d, J=8.0 Hz, 1H), 7.56 (t, J=5.2 Hz, 1H), 5.52 (s, 2H).

$^{19}$F NMR (DMSO) d −57.3 (s, 3F), −67.7 (s, 2F).

3-{[(5-cyclobutyl-1,2,4-oxadiazol-3-yl)methoxy](difluoro)methyl}-6-[4-(trifluoromethoxy)phenyl][1,2,4]triazolo[4,3-a]pyridine
482.1 (M+1).

$^1$H NMR (DMSO) d 8.87 (s, 1H), 8.11 (dd, J=9.6, 1.2 Hz, 1H), 7.95 (dd, J=9.6, 1.6 Hz, 1H), 7.90 (m, 2H), 7.56 (d, J=8.0 Hz, 2H), 5.52 (s, 2H), 3.81 (quint, J=8.0 Hz, 1H), 2.30 (m, 4H), 2.04 (m, 1H), 1.87 (m, 1H).

$^{19}$F NMR (DMSO) d −57.3 (s, 3F), −68.8 (s, 2F).

3-[(difluoro{6-[4-(trifluoromethoxy)phenyl][1,2,4]triazolo[4,3-a]pyridin-3-yl}methoxy)methyl]benzonitrile
461.1 (M+1).

$^1$H NMR (DMSO) d 8.59 (s, 1H), 8.09 (m, 2H), 7.90 (m, 3H), 7.80 (d, J=8.8 Hz, 2H), 7.63 (t, J=8.0 Hz, 1H), 7.54 (d, J=8.0 Hz, 2H), 5.38 (s, 2H).

$^{19}$F NMR (DMSO) d −57.3 (s, 3F), −67.2 (s, 2F).

3-[(cyclopropylmethoxy)(difluoro)methyl]-6-[6-(trifluoromethyl)pyridin-3-yl][1,2,4]triazolo[4,3-a]pyridine
385.1 (M+1).

$^1$H NMR (DMSO) d 9.16 (d, J=2.4 Hz, 1H), 8.87 (s, 1H), 8.48 (dd, J=8.0, 2.4 Hz, 1H), 8.17 (dd, 9.6, 1.2 Hz, 1H), 8.09 (d, J=8.4 Hz, 1H), 8.02 (dd, J=9.6, 1.6 Hz, 1H), 4.10 (d, J=7.2 Hz, 2H), 1.28 (m, 1H), 0.59 (m, 2H), 0.40 (m, 2H).

$^{19}$F NMR (DMSO) d −66.7 (s, 2F), −66.9 (s, 3F).

5-[(difluoro{6-[4-(trifluoromethoxy)phenyl][1,2,4]triazolo[4,3-a]pyridin-3-yl}methoxy)methyl]quinoline
487.1 (M+1).

$^1$H NMR (DMSO) d 8.90 (d, J=4.0 Hz, 1H), 8.68 (d, J=8.4 Hz, 1H), 8.28 (s, 1H), 8.05 (m, 2H), 7.83 (d, J=9.6 Hz, 1H), 7.76 (m, 2H), 7.57 (dd, J=8.4, 4.4 Hz, 1H), 7.48 (m, 4H), 5.83 (s, 2H).

$^{19}$F NMR (DMSO) d −57.3 (s, 3F), −67.1 (s, 2F).

3-[1-(difluoro{6-[4-(trifluoromethoxy)phenyl][1,2,4]triazolo[4,3-a]pyridin-3-yl}methoxy)ethyl]quinoline
501.1 (M+1).

$^1$H NMR (DMSO) d 9.04 (d, J=2.4 Hz, 1H), 8.48 (d, J=1.6 Hz, 1H), 8.23 (s, 1H), 8.01 (m, 2H), 7.95 (m, 1H), 7.80 (m,

2H), 7.62 (m, 3H), 7.34 (dd, J=9.2, 1.0 Hz, 2H), 6.06 (q, J=6.8 Hz, 1H), 1.84 (d, J=6.8 Hz, 3H).
 $^{19}$F NMR (DMSO) d −57.2 (s, 3F), −65.2 (d, J=157 Hz, 1F), −66.6 (d, J=157 Hz, 1F).
3-{[2-(2,6-dimethylphenoxy)ethoxy](difluoro)methyl}-6-[4-(trifluoromethoxy)phenyl][1,2,4]triazolo[4,3-a]pyridine
494.1 (M+1).
 $^1$H NMR (DMSO) d 8.82 (s, 1H), 8.11 (d, J=9.6 Hz, 1H), 7.94 (d, J=9.6, 1.6 Hz, 1H), 7.77 (d, J=8.8 Hz, 2H), 7.23 (d, J=8.0 Hz, 2H), 6.92 (m, 3H), 4.55 (m, 2H), 4.12 (m, 2H), 2.10 (s, 6H).
 $^{19}$F NMR (DMSO) d −57.3 (s, 3F), −67.7 (s, 2F).
3-{difluoro[(1-phenyl-1H-pyrazol-4-yl)methoxy]methyl}-6-[4-(trifluoromethoxy)phenyl][1,2,4]triazolo[4,3-a]pyridine
502.1 (M+1).
 $^1$H NMR (DMSO) d 8.74 (s, 1H), 8.51 (s, 1H), 8.06 (d, J=9.6 Hz, 1H), 7.89 (m, 2H), 7.81 (d, J=8.4 Hz, 2H), 7.73 (d, J=8.4 Hz, 2H), 7.50 (m, 2H), 7.34 (m, 3H), 5.31 (s, 2H).
 $^{19}$F NMR (DMSO) d −57.3 (s, 3F), −67.0 (s, 2F).
3-[difluoro({2-[4-(trifluoromethyl)phenyl]-1,3-oxazol-4-yl}methoxy)methyl]-6-[4-(trifluoromethoxy)phenyl][1,2,4]triazolo[4,3-a]pyridine
571.1 (M+1).
 $^1$H NMR (DMSO) d 8.58 (s, 1H), 8.46 (s, 1H), 8.09 (m, 4H), 7.88 (m, 4H), 7.70 (d, J=8.0 Hz, 2H), 7.21 (d, J=8.0 Hz, 2H), 5.33 (s, 2H).
 $^{19}$F NMR (DMSO) d −57.5 (s, 3F), 62.3 (s, 3F), −67.5 (s, 2F).
4-[(difluoro{6-[4-(trifluoromethoxy)phenyl][1,2,4]triazolo[4,3-a]pyridin-3-yl}methoxy)methyl]-2-methyl quinoline
501.1 (M+1).
 $^1$H NMR (DMSO) d 8.59 (s, 1H), 8.35 (d, J=8.0 Hz, 1H), 8.28 (d, J=8.0 Hz, 1H), 8.07 (d, J=9.6 Hz, 1H), 7.98 (m, 1H), 7.90 (m, 2H), 7.80 (m, 1H), 7.71 (d, J=8.0 Hz, 2H), 7.47 (d, J=8.0 Hz, 2H), 6.03 (s, 2H), 1.73 (s, 3H).
 $^{19}$F NMR (DMSO) d −57.3 (s, 3F), −67.8 (s, 2F).
6-[difluoro{6-[4-(trifluoromethoxy)phenyl][1,2,4]triazolo[4,3-a]pyridin-3-yl}methoxy)methyl]quinoxaline
488.1 (M+1).
 $^1$H NMR (DMSO) d 8.98 (s, 2H), 8.60 (s, 1H), 8.26 (d, J=1.6 Hz, 1H), 8.15 (d, J=8.4 Hz, 1H), 8.07 (dd, J=9.6, 1.2 Hz, 1H), 8.01 (dd, J=9.6, 1.6 Hz, 1H), 7.90 (dd, 9.6, 1.6 Hz, 1H), 7.76 (m, 2H), 7.45 (d, J=8.0 Hz, 2H), 5.61 (s, 2H).
 $^{19}$F NMR (DMSO) d −57.3 (s, 3F), −67.0 (s, 2F).
3-[(but-2-yn-1-yloxy)(difluoro)methyl]-6-[4-(trifluoromethoxy)phenyl][1,2,4]triazolo[4,3-a]pyridine
398.1 (M+1).
 $^1$H NMR (DMSO) d 8.63 (s, 1H), 8.10 (d, J=9.6 Hz, 1H), 7.93 (dd, J=9.6, 1.6 Hz, 1H), 7.88 (m, 2H), 7.56 (d, J=8.0 Hz, 2H), 4.94 (q, J=2.4 Hz, 2H), 1.79 (t, J=2.4 Hz, 3H).
 $^{19}$F NMR (DMSO) d −57.3 (s, 3F), −68.6 (s, 2F).
3-{[(2,2-difluorocyclopropyl)methoxy](difluoro)methyl}-6-[4-(trifluoromethoxy)phenyl][1,2,4]triazolo[4,3-a]pyridine
436.1 (M+1).
 $^1$H NMR (DMSO) d 8.64 (s, 1H), 8.10 (d, J=9.2 Hz, 1H), 7.94 (d, J=9.6 Hz, 1H), 7.88 (d, J=8.8 Hz, 2H), 7.54 (d, J=8.0 Hz, 2H), 4.43 (m, 1H), 4.23 (m, 1H), 2.31 (m, 1H), 1.77 (m, 1H), 1.62 (m, 1H). d −57.3 (s, 3F), −68.0 (m, 2F), 128.7 (m, 1F), 142.6 (m, 1F).
3-{difluoro[(3-phenylprop-2-yn-1-yl)oxy]methyl}-6-[4-(trifluoromethoxy)phenyl][1,2,4]triazolo[4,3-a]pyridine
460.1 (M+1).
 $^1$H NMR (DMSO) d 8.67 (s, 1H), 8.09 (d, J=8.8 Hz, 1H), 7.91 (dd, J=9.6, 1.6 Hz, 1H), 7.84 (m, 2H), 7.40 (m, 7H), 5.26 (s, 2H). d −57.3 (s, 3F), −68.5 (m, 2F).
3-{difluoro[(1-methyl-1H-benzimidazol-2-yl)methoxy]methyl}-6-[4-(trifluoromethoxy)phenyl][1,2,4]triazolo[4,3-a]pyridine
490.1 (M+1).
3-{[(1-benzyl-1H-1,2,3-triazol-4-yl)methoxy](difluoro)methyl}-6-[4-(trifluoromethoxy)phenyl][1,2,4]triazolo[4,3-a]pyridine
517.1 (M+1).
3-{difluoro[(5-phenyl-1,2-oxazol-3-yl)methoxy]methyl}-6-[4-(trifluoromethoxy)phenyl][1,2,4]triazolo[4,3-a]pyridine
503.1 (M+1).
 $^1$H NMR (DMSO) d 8.78 (s, 1H), 8.01 (d, J=9.2 Hz, 1H), 7.90 (m, 5H), 7.55 (m, 3H), 7.38 (d, J=8.4 Hz, 2H), 7.39 (s, 1H), 5.52 (s, 2H).
 $^{19}$F NMR (DMSO) d −57.3 (s, 3F), −68.1 (s, 2F).
3-{difluoro[(2-phenyl-1,3-oxazol-4-yl)methoxy]methyl}-6-[4-(trifluoromethoxy)phenyl][1,2,4]triazolo[4,3-a]pyridine
503.1 (M+1).
3-{difluoro[(5-methyl-2-phenyl-2H-1,2,3-triazol-4-yl)methoxy]methyl}-6-[4-(trifluoromethoxy)phenyl][1,2,4]triazolo[4,3-a]pyridine
517.1 (M+1).
3-[{[1-(4-chlorophenyl)-5-methyl-1H-pyrazol-3-yl]methoxy}(difluoro)methyl]-6-[4-(trifluoromethoxy)phenyl][1,2,4]triazolo[4,3-a]pyridine
550.1 (M+1).
3-[(3,3-diphenylpropoxy)(difluoro)methyl]-6-[4-(trifluoromethoxy)phenyl][1,2,4]triazolo[4,3-a]pyridine
540.1 (M+1).
3-(difluoro{[3-(pyrimidin-2-yl)benzyl]oxy}methyl)-6-[4-(trifluoromethoxy)phenyl][1,2,4]triazolo[4,3-a]pyridine
514.1 (M+1).
3-(difluoro{[3-(pyridin-3-yl)benzyl]oxy}methyl)-6-[4-(trifluoromethoxy)phenyl][1,2,4]triazolo[4,3-a]pyridine
513.1 (M+1).
3-{difluoro[(1-methyl-1H-indazol-3-yl)methoxy]methyl}-6-[4-(trifluoromethoxy)phenyl][1,2,4]triazolo[4,3-a]pyridine
490.1 (M+1).
 $^1$H NMR (DMSO) d 8.45 (s, 1H), 8.05 (d, J=8.8 Hz, 1H), 7.87 (m, 2H), 7.63 (m, 3H), 7.47 (d, J=8.4 Hz, 2H), 7.41 (t, J=8.8 Hz, 1H), 7.14 (t, J=8.0 Hz, 1H), 5.65 (s, 2H), 3.96 (s, 3H).
 $^{19}$F NMR (DMSO-d$_6$) d −57.3 (s, 3F), −67.3 (s, 2F).
3-(difluoro{[2-(1H-1,2,4-triazol-1-yl)benzyl]oxy}methyl)-6-[4-(trifluoromethoxy)phenyl][1,2,4]triazolo[4,3-a]pyridine
503.1 (M+1).
3-(difluoro{[2-(2-methyl-1H-imidazol-1-yl)benzyl]oxy}methyl)-6-[4-(trifluoromethoxy)phenyl][1,2,4]triazolo[4,3-a]pyridine
516.1 (M+1).
3-(difluoro{[2-phenyl-5-(trifluoromethyl)-1,3-oxazol-4-yl]methoxy}methyl)-6-[4-(trifluoromethoxy)phenyl][1,2,4]triazolo[4,3-a]pyridine
571.1 (M+1).
3-(difluoro{[6-(1H-pyrazol-1-yl)pyridin-3-yl]methoxy}methyl)-6-[4-(trifluoromethoxy)phenyl][1,2,4]triazolo[4,3-a]pyridine
503.1 (M+1).

6-cyclopropyl-2'-[(difluoro{6-[4-(trifluoromethoxy)phenyl][1,2,4]triazolo[4,3-a]pyridin-3-yl}methoxy)methyl]-3,4'-bipyridine 554.1 (M+1).

3-[{[3-(4-cyclopropyl-1H-imidazol-1-yl)benzyl]oxy}(difluoro)methyl]-6-[4-(trifluoromethoxy)phenyl][1,2,4]triazolo[4,3-a]pyridine 521.1 (M+1).

3-(difluoro{[2-(piperidin-1-yl)pyridin-4-yl]methoxy}methyl)-6-[4-(trifluoromethoxy)phenyl][1,2,4]triazolo[4,3-a]pyridine 520.1 (M+1).

3-{[(2,2-dimethyl-2,3-dihydro-1-benzofuran-7-yl)methoxy](difluoro)methyl}-6-[4-(trifluoromethoxy)phenyl][1,2,4]triazolo[4,3-a]pyridine 506.1 (M+1).

3-{[2-(2,6-difluorophenyl)ethoxy](difluoro)methyl}-6-[4-(trifluoromethoxy)phenyl][1,2,4]triazolo[4,3-a]pyridine 486.1 (M+1).

3-{difluoro[(5-phenyl-1,2,4-oxadiazol-3-yl)methoxy]methyl}-6-[4-(trifluoromethoxy)phenyl][1,2,4]triazolo[4,3-a]pyridine 504.1 (M+1).

$^1$H NMR (DMSO) d 8.87 (s, 1H), 8.11 (dd, J=9.6, 1.2 Hz, 1H), 8.04 (m, 2H), 7.94 (dd, J=9.6, 1.6 Hz, 1H), 7.86 (m, 2H), 7.72 (m, 1H), 7.60 (m, 2H), 7.41 (d, J=8.0 Hz, 2H), 5.63 (s, 2H).

$^{19}$F NMR (DMSO) d −57.2 (s, 3F), −68.6 (s, 2F).

3-[{[2-(6-cyclopropylpyridin-3-yl)benzyl]oxy}(difluoro)methyl]-6-[4-(trifluoromethoxy)phenyl][1,2,4]triazolo[4,3-a]pyridine 553.1 (M+1).

3-(difluoro(3-(2-methoxyphenylthio)-2-methylpropoxy)methyl)-6-(4-(trifluoromethoxy)phenyl)-[1,2,4]triazolo[4,3-a]pyridine:

LCMS (EI: 70 eV) 540 (M$^+$+1)

3-(difluoro(2-(4-(4-methoxyphenyl)piperazin-1-yl)ethoxy)methyl)-6-(4-(trifluoromethoxy)phenyl)[1,2,4]triazolo[4,3-a]pyridine:

LCMS (EI: 70 eV) 564 (M$^+$+1)

3-(((3-cyclopropyl-1-methyl-1H-pyrazol-5-yl)methoxy)difluoromethyl)-6-(4-(trifluoromethoxy)phenyl)[1,2,4]triazolo[4,3-a]pyridine:

LCMS (EI: 70 eV) 480 (M$^+$+1)

C. Preparation of Compounds of Formula I Varying R$^1$ and X$^1$

Similarly, following the procedure of Example 22A above, but optionally substituting other boronic acids or pinacolate esters for 4-trifluoromethoxyphenylboronic acid and/or substituting other alcohols for (2-phenyl-5-(trifluoromethyl)oxazol-4-yl)methanol, other compounds of Formula I may be prepared.

EXAMPLE 23

Preparation of a Compound of Formula I

A. Preparation of a Compound of Formula I in which R$^1$ is 4-trifluoromethoxyphenyl, Q is a Covalent Bond, W$^1$, W$^2$, and W$^3$ are CH, X$^1$ is CCF$_2$Cl, and X$^2$ is N Step 1. Addition of the R$^a$ Group and Ring Chain

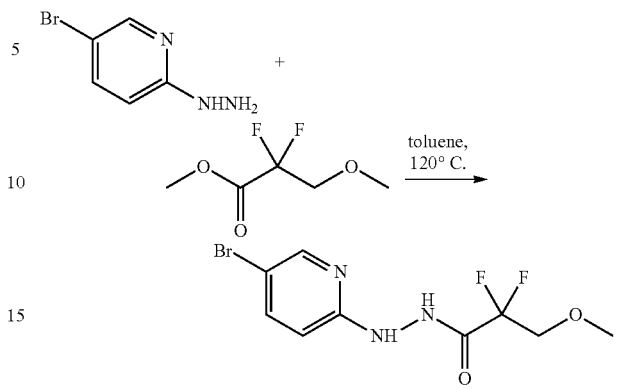

(5-bromo-2-hydrazinylpyridine (1.83 g, 9.73 mmol) and methyl 2,2-difluoro-3-methoxypropanoate (1.00 g, 6.49 mmol) were refluxed in toluene (35 mL) overnight. The reaction mixture was concentrated and purified by chromatography (EtOAc:hexanes=1:4) to give N'-(5-bromopyridin-2-yl)-2,2-difluoro-3-methoxypropanehydrazide.

Step 2. Cyclization

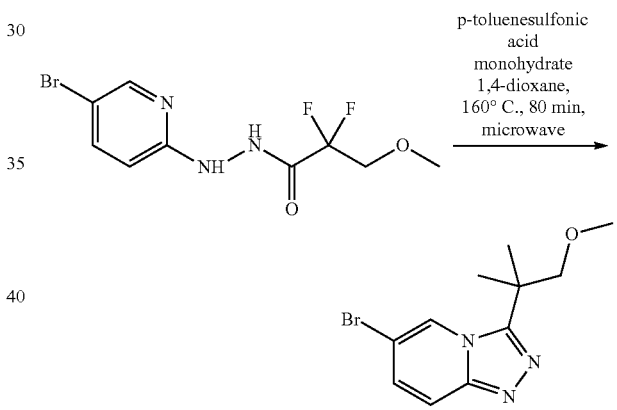

N'-(5-bromopyridin-2-yl)-2,2-difluoro-3-methoxypropanehydrazide (0.25 g, 0.81 mmol) and p-toluenesulfonic acid monohydrate (0.12 g, 0.65 mmol) in 1,4-dioxane (3.5 mL) were put onto microwave at 160° C. for 80 min. The reaction mixture was diluted with EtOAc and washed sequentially with NaHCO$_3$ aqueous solution and brine. The organic layer was dried over Na$_2$SO$_4$. Evaporation of the solvent and purification by HPLC gave 6-bromo-3-(1,1-difluoro-2-methoxyethyl)[1,2,4]triazolo[4,3-a]pyridine.

Optional Step 3. Formation of a "Q" Alenkynylene Linker and Addition of the R$^1$ Group

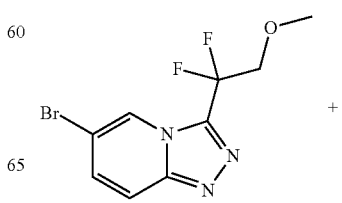

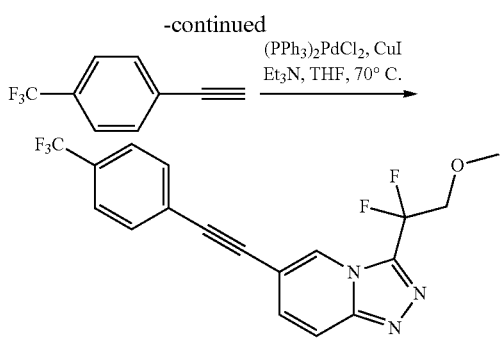

To a stirred solution of 6-bromo-3-(1,1-difluoro-2-methoxyethyl)[1,2,4]triazolo[4,3-a]pyridine (46 mg, 0.16 mmol) in THF (5 mL) was added catalytical amount of dichlorobis(triphenylphosphine)palladium(II) (11 mg) and copper(I) iodide (3 mg), followed by 1-ethynyl-4-(trifluoromethyl)benzene (41 mg, 0.24 mmol). The resulting mixture was flushed with $N_2$ and $Et_3N$ (2 mL) was added. The reaction mixture was stirred at 70° C. overnight and purified by prep-TLC (EtOAc:hexanes=2:3) followed by HPLC to give 3-(1,1-difluoro-2-methoxyethyl)-6-((4-(trifluoromethyl)phenyl)ethynyl)-[1,2,4]triazolo[4,3-a]pyridine.

MS m/z 382.0 (M+H)

$^1$H-NMR (acetone) δ 8.81 (s, 1H), 7.94 (dd, 1H), 7.83 (dd, 4H), 7.65 (dd, 1H), 4.36 (t, 2H), 3.52 (s, 3H);

B. Preparation of Compounds of Formula I Varying $R^1$ and $R^a$

Similarly, following the procedure of Example 23A above, but substituting other precursors for methyl 2,2-difluoro-3-methoxypropanoate or other alkynyl $R^1$ compounds for 1-ethynyl-4-(trifluoromethyl)benzene, the following compounds of Formula I were prepared:

3-(trifluoromethyl)-6-{[4-(trifluoromethyl)phenyl]ethynyl}[1,2,4]triazolo[4,3-a]pyridine,
MS m/z 356.0 (M+H);

3-(1,1-difluoro-2-methoxyethyl)-6-[4-(trifluoromethoxy)phenyl][1,2,4]triazolo[4,3-a]pyridine,
MS m/z 374.0 (M+H);

6-[4-(4-chlorophenoxy)phenyl]-3-(1,1-difluoro-2-methoxyethyl)[1,2,4]triazolo[4,3-a]pyridine
MS m/z 416.0 (M+H)

3-(1,1-difluoro-2-methoxyethyl)-6-[4-(4-fluorophenoxy)phenyl][1,2,4]triazolo[4,3-a]pyridine
MS m/z 400.0 (M+H)

3-(1,1-difluoro-2-methoxyethyl)-6-[6-(2,2,2-trifluoroethoxy)pyridin-3-yl][1,2,4]triazolo[4,3-a]pyridine
MS m/z 389.0 (M+H)

3-(1,1-difluoro-2-methoxyethyl)-6-[3-methyl-4-(trifluoromethoxy)phenyl][1,2,4]triazolo[4,3-a]pyridine
MS m/z 388.0 (M+H)

3-(1,1-difluoro-2-methoxyethyl)-6-[2-methyl-4-(trifluoromethoxy)phenyl][1,2,4]triazolo[4,3-a]pyridine
MS m/z 388.0 (M+H)

3-(1,1-difluoro-2-methoxyethyl)-6-[3-fluoro-4-(trifluoromethoxy)phenyl][1,2,4]triazolo[4,3-a]pyridine
MS m/z 392.0 (M+H)

3-(1,1-difluoro-2-methoxyethyl)-6-(3,5-difluoro-4-phenoxyphenyl)[1,2,4]triazolo[4,3-a]pyridine
MS m/z 418.0 (M+H)

3-(1,1-difluoro-2-methoxyethyl)-6-(phenylethynyl)[1,2,4]triazolo[4,3-a]pyridine,
MS m/z 314.1 (M+H); and 2,2-difluoro-2-(6-{[4-(trifluoromethyl)phenyl]ethynyl}[1,2,4]triazolo[4,3-a]pyridin-3-yl)ethanol,
MS m/z 368.0 (M+H).

C. Preparation of Compounds of Formula I Varying $R^1$ and $R^a$

Similarly, following the procedure of Example 23A above, but substituting other precursors for methyl 2,2-difluoro-3-methoxypropanoate or other alkynyl. $R^1$ compounds for 1-ethynyl-4-(trifluoromethyl)benzene, other compounds of Formula I may be prepared:

EXAMPLE 24

Preparation of a Compound of Formula I wherein $X^2$ is C—$R^b$

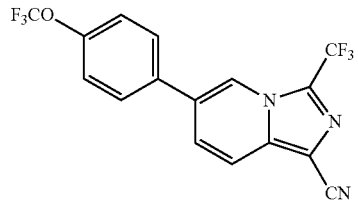 [SMILES: N#Cc1nc(C(F)(F)F)n2cc(-c3ccc(OC(F)(F)F)cc3)ccc12]

A. Preparation of a Compound of Formula I wherein $X^2$ is C—$R^b$

Step 1—Formation of the Halide Intermediate

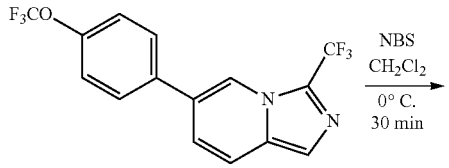

6-(4-(trifluoromethoxy)phenyl)-3-(trifluoromethyl)imidazo[1,5-a]pyridine (1.2001 g, 3.466 mmol) was dissolved in $CH_2Cl_2$ (20 mL) in a 250 mL round bottomed flask. The solution was treated with NBS (925.4 mg, 5.199 mmol, 1.5 equiv.) at 0° C. for 30 min. And then the solvent was removed by rota-vap to give a crude mixture. Obtained crude mixture was purified by a column chromatography (SiO2=80 g, EtOAc/hexane=1:7 Rf=0.5) to give 1-bromo-6-(4-(trifluoromethoxy)phenyl)-3-(trifluoromethyl)imidazo[1,5-a]pyridine as a colorless oil.

Step 2—Addition of the $R^b$ Moiety

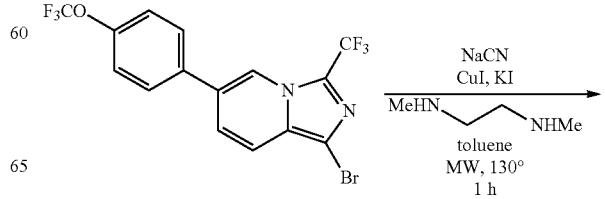

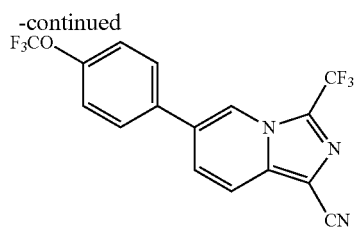

1-bromo-6-(4-(trifluoromethoxy)phenyl)-3-(trifluoromethyl)imidazo[1,5-a]pyridine (50.0 mg, 0.118 mmol), NaCN (7.0 mg, 0.142 mmol, 1.2 equiv.), CuI (2.2 mg, 0.0118 mmol, 0.1 equiv.) and KI (3.9 mg, 0.0236 mmol, 0.2 equiv.) were successively placed in a 5 mL Samith vial. To the vial was added a solution of N,N'-dimethylethylenediamine (10.4 mg, 0.118 mmol, 1.0 equiv.) in toluene (5 mL). The suspension was heated by the microwave reactor (Biotage, Personal Chemistry) at 130° C. for 60 min. The suspension was filtered through Celite (3 g) using EtOAc (70 mL). The solvent was removed from the filtrate under a reduced pressure to give a crude mixture. The crude mixture was purified by a preparative TLC ($SiO_2$=1 plate, EtOAc/hexane=1:7 Rf=0.1) to give 6-(4-(trifluoromethoxy)phenyl)-3-(trifluoromethyl)imidazo[1,5-a]pyridine-1-carbonitrile as colorless crystals.

LCMS (EI: 70 eV) 372 ($M^+$+1), $^1$H-NMR (300 MHz, $CDCl_3$): 7.40 (2H, d, J=8.4 Hz), 7.57 (1H, d, J=9.6 Hz), 7.61 (2H, d, J=8.4 Hz), 7.93 (1H, d, J=9.6 Hz), 8.35 (1H, s).

Alternative Step 2—Addition of the $R^b$ Moiety via Lithiation

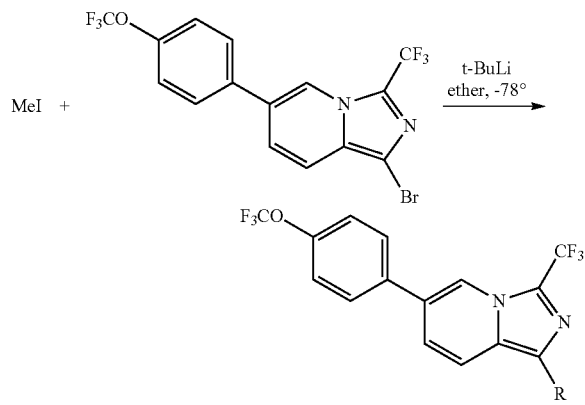

1-bromo-6-(4-(trifluoromethoxy)phenyl)-3-(trifluoromethyl)imidazo[1,5-a]pyridine (50.0 mg, 0.118 mmol) was dissolved in ether (2 mL) in a 50 mL round bottomed flask under a nitrogen atmosphere. The solution was cooled down to −78° C. and treated with t-BuLi (1.7 M pentane solution, 0.15 mL, 0.255 mmol, 2.2 equiv.) for 5 min. To the mixture was added a solution of MeI (65.8 mg, 0.464 mmol, 4.0 equiv.) in ether (1 mL). The reaction was allowed to warm up to room temperature for 30 min. To the mixture was added $H_2O$ (30 mL) and the whole was extracted with EtOAc (30 mL×3). Combined organic layers were washed with brine (30 mL) and dried with $Na_2SO_4$. The solvent was removed under a reduced pressure to give a crude mixture. The crude mixture was purified by a preparative TLC ($SiO_2$=1 plate, ether/hexane=1:3 Rf=0.4) to give 1-methyl-6-(4-(trifluoromethoxy)phenyl)-3-(trifluoromethyl)imidazo[1,5-a]pyridine as light yellow crystals.

LCMS (EI: 70 eV) 361 ($M^+$+1)

Alternative Step 2—Addition of an $R^b$ Alkoxycarbonyl Moiety

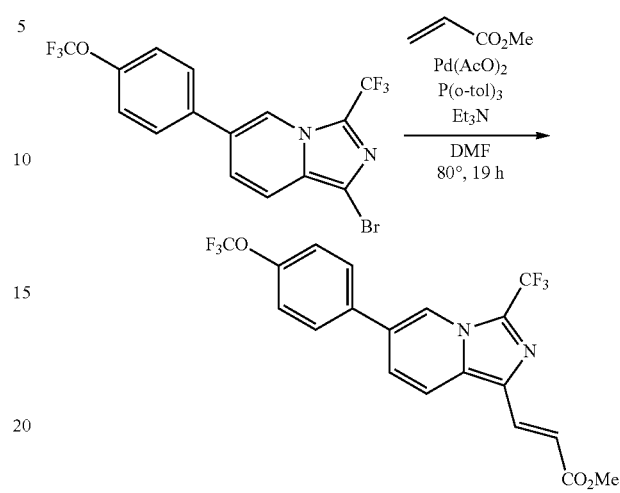

1-bromo-6-(4-(trifluoromethoxy)phenyl)-3-(trifluoromethyl)imidazo[1,5-a]pyridine (50.0 mg, 0.118 mmol), $Pd(AcO)_2$ (2.6 mg, 0.0118 mmol, 0.1 equiv.) and $P(o-tol)_3$ (14.4 mg, 0.0472 mmol, 0.4 equiv.) were placed in a 50 mL round bottomed flask under a nitrogen atmosphere. To the flask were added DMF (1 mL), a solution of $Et_3N$ (30.0 mg, 0.295 mmol, 2.5 equiv.) in DMF (1 mL) and a solution of methyl acrylate (50.8 mg, 0.59 mmol, 5.0 equiv.) were successively added. The mixture was heated at 80° C. for 19 h. And then, the solvent was removed from the reaction mixture to give a crude mixture. The crude mixture was purified by a column chromatography ($SiO_2$=25 g, EtOAc/hexane=1:7 to 1:3, Rf=0.1 with EtOAc/hexane=1:7) to give (E)-methyl 3-(6-(4-(trifluoromethoxy)phenyl)-3-(trifluoromethyl)imidazo[1,5-a]pyridin-1-yl)acrylate as light yellow crystals.

LCMS (EI: 70 eV) 431 ($M^+$+1).

Optional Step 3—Saturation of an $R^b$ Alkoxycarbonylalkenyl Moiety

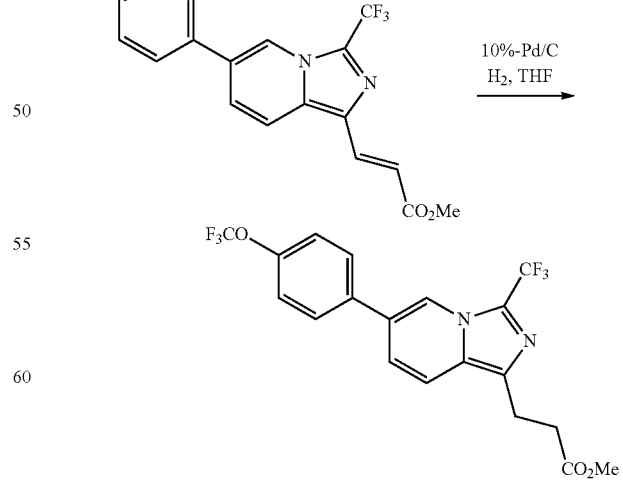

E)-methyl 3-(6-(4-(trifluoromethoxy)phenyl)-3-(trifluoromethyl)imidazo[1,5-a]pyridin-1-yl)acrylate (25.6 mg, 0.0595 mmol) and 10% Pd/C (25.6 mg) were placed in a 100 mL round bottomed flask under a nitrogen atmosphere. To the flask was added THF (5 mL). And then nitrogen was replaced with hydrogen. The reaction mixture was stirred at room temperature. After 17 h (57% conv.), the Pd catalyst was removed by a filtration using Celite (3 g). The reaction was started over using Pd/C (25.6 mg) under a hydrogen atmosphere at 45° C. After 4 h (100% conv.), the Pd catalyst was removed in a similar fashion. The solvent was removed from the filtrate under a reduced pressure to give a crude mixture. The crude mixture was purified by a column chromatography (SiO$_2$ 25 g, EtOAc/hexane=1:7 to 1:3, Rf=0.4 with EtOAc/hexane=1:3) to give 3-(6-(4-(trifluoromethoxy)phenyl)-3-(trifluoromethyl)imidazo[1,5-a]pyridin-1-yl)propanoate as colorless crystals.

LCMS (EI: 70 eV) 433 (M$^+$+1)

B. Preparation of Compounds of Formula I Varying R$^b$

Similarly, following the procedure of Example 24A above, but substituting other electrophiles for MeI for, the following compound of Formula I was prepared:

6-(4-(trifluoromethoxy)phenyl)-3-(trifluoromethyl)imidazo [1,5-a]pyridin-1-yl)methanol:

LCMS (EI: 70 eV) 377 (M$^+$+1).

C. Preparation of Compounds of Formula I Varying R$^b$

Similarly, following the procedure of Example 24A above, but substituting other electrophiles for MeI or other R$^b$ unsubstituted cores for 6-(4-(trifluoromethoxy)phenyl)-3-(trifluoromethyl)imidazo[1,5-a]pyridine, other compound of Formula I may be prepared:

EXAMPLE 25

Preparation of a Compound of Formula I via Addition of R$^a$ to Core

A. Preparation of a Compound of Formula I in which R$^1$ is 4-trifluoromethoxyphenyl, Q is a Covalent Bond, W$^1$, W$^2$, and W$^3$ are CH, X$^1$ is O-(4-Py), and X$^2$ and X$^3$ are N

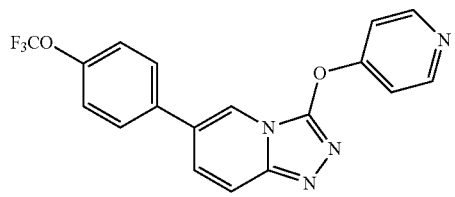 [SMILES: FC(F)(F)Oc1ccc(-c2ccc3nnc(Oc4ccncc4)n3c2)cc1]

Step 1. Preparation of 3-chloro-6-(4-(trifluoromethoxy)phenyl)-[1,2,4]triazolo[4,3-a]pyridine (1)

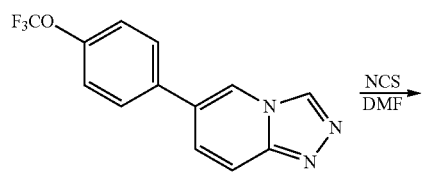

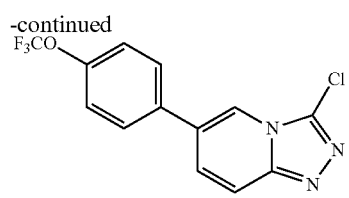

6-(4-(trifluoromethoxy)phenyl)-[1,2,4]triazolo[4,3-a]pyridine (0.6 g) was placed in a 50 mL round-bottom flask and dissolved in 10 mL of DMF. NCS was added (0.43 g) and the reaction mixture was heated to 50° C. for 1 h, diluted with EtOAc (100 mL), washed 3 times with water, brine, dried over Na$_2$SO$_4$, and concentrated to afford an orange solid containing 3-chloro-6-(4-(trifluoromethoxy)phenyl)[1,2,4]triazolo[4,3-a]pyridine and a trace of succinimide (<5% wt.).

$^1$H NMR (400 MHz, CDCl$_3$): δ 8.11 (t, 1H); 7.62 (dd, 1H); 7.62 (d, 2H), 7.57 (dd, 1H), 7.38 (d, 2H).

Step 2. Preparation of 3-(pyridin-4-yloxy)-6-(4-(trifluoromethoxy)phenyl)-[1,2,4]triazolo[4,3-a]pyridine via S$_N$Ar Reaction

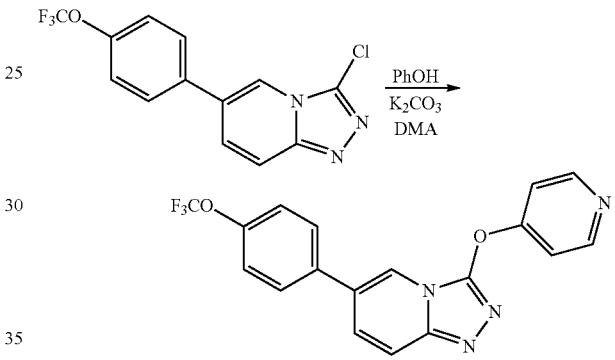

In a 15 mL round-bottom flask 3-chloro-6-(4-(trifluoromethoxy)phenyl)-[1,2,4]triazolo[4,3-a]pyridine (100 mg), 4-hydroxypyridine (60 mg), and potassium carbonate (88 mg) were suspended in DMA (3 mL). The reaction mixture stirred at 150° C. for 6 h, concentrated, the residue subjected to gradient chromatography (MeOH/dichloromethane) to produce 3-(pyridin-4-yloxy)-6-(4-(trifluoromethoxy)phenyl)-[1,2,4]triazolo[4,3-a]pyridine as amber oil (28 mg, 24%).

$^1$H NMR (400 MHz, CDCl$_3$): δ 7.99 (s, 1H); 7.88 (d. J=9.6 Hz, 1H); 7.63-7.53 (m, 5H); 7.30 (d, J=8.0 Hz, 2H); 6.59 (d, J=7.2 Hz, 2H).

MS (ES+, m/z) 373.0 (base peak, M+H$^+$); 767.1 (2M+Na$^+$).

Alternative Step 2. Preparation of 3-(pyridin-4-yloxy)-6-(4-(trifluoromethoxy phenyl)-[1,2,4]triazolo[4,3-a]pyridine via Ullmann Coupling

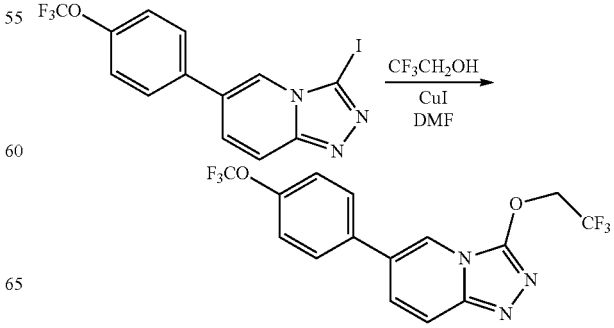

In a 15 mL round-bottom flask, NaH (60% wt., 40 mg) was added to a solution of trifluoroethanol (0.072 mL) in DMF (3 mL). After 10 minutes, 3-iodo-6-(4-(trifluoromethoxy)phenyl)[1,2,4]triazolo[4,3-c]pyridine, prepared according to the method disclosed in Step 1, (100 mg) and CuI (48 mg) were added. The reaction mixture stirred at 90° C. for 4 h, concentrated, the residue subjected to gradient chromatography (ethyl acetate/hexanes). The resulting mixture was subjected to hydrogenolysis (cyclohexene/Pd on carbon, 10%, in EtOAc) and re-subjected to chromatography using first 3% MeOH in dichloromethane, and then 1:1 EtOAc/hexanes to produce 3-(pyridin-4-yloxy)-6-(4-(trifluoromethoxy)phenyl)[1,2,4]triazolo[4,3-a]pyridine as amber oil (3.4 mg, 3.6%).

$^1$H NMR (400 MHz, CDCl$_3$): δ 8.02 (s, 1H); 7.82 (d, 1H); 7.63-7.53 (m, 3H); 7.39 (d, 2H).

$^{19}$F NMR (377 MHz, CDCl$_3$): δ −58.39 (s, 1F); −74.48 (t, 1F).

MS (ES+, m/z) 378.0 (base peak, M+H$^+$); 777.1 (2M+Na$^+$).

B. Preparation of Compounds of Formula I Varying R$^1$, X$^1$, and X$^2$

Similarly, following the procedure Example 25A above for S$_N$Ar or Ullmann reactions above, but optionally substituting other O-, N-, or S-nucleophiles for 4-hydroxypyridine and/or substituting N-bromosucinimide or N-iodosuccinimide for N-chlorosuccinimide and utilizing the corresponding 3-bromo-6-(4-(trifluoromethoxy)phenyl)-[1,2,4]triazolo[4,3-a]pyridine or 3-iodo-6-(4-(trifluoromethoxy)phenyl)-[1,2,4]triazolo[4,3-a]pyridine, the following compounds of Formula I were prepared:

3-(phenylsulfanyl)-6-[4-(trifluoromethoxy)phenyl][1,2,4]triazolo[4,3-a]pyridine

MS (ESI+) 388.0 (base peak, M+H$^+$); 797.1 (2M+Na$^+$);

N,N-dimethyl-6-[4-(trifluoromethoxy)phenyl][1,2,4]triazolo[4,3-a]pyridin-3-amine, MS (ESI+) 323.0 (base peak, M+H$^+$); 667.1 (2M+Na$^+$);

3-phenoxy-6-[4-(trifluoromethoxy)phenyl][1,2,4]triazolo[4,3-a]pyridine,

MS (ESI+) 365.0 (base peak, M+H$^+$); 751.1 (2M+Na$^+$);

6-[4-(trifluoromethoxy)phenyl]-3-[3-(trifluoromethyl)phenoxy][1,2,4]triazolo[4,3-a]pyridine, MS (ESI+) 440.0 (base peak, M+H$^+$);

3-(4,4-difluoropiperidin-1-yl)-6-[4-(trifluoromethoxy)phenyl][1,2,4]triazolo[4,3-a]pyridine, MS (ESI+) 399.2 (base peak, M+H$^+$); and 3-(2-methylphenoxy)-6-[4-(trifluoromethoxy)phenyl][1,2,4]triazolo[4,3-a]pyridine, MS (ESI+) 386.1 (base peak, M+H$^+$); 793.1 (2M+Na$^+$).

C. Preparation of Compounds of Formula I Varying R$^1$, X$^1$, and X$^2$

Similarly, following the procedure Example 25A above for S$_5$Ar or Ullmann reactions above, but optionally substituting other O-, N-, or S-nucleophiles for 4-hydroxypyridine and/or substituting N-bromosucinimide or N-iodosuccinimide for N-chlorosuccinimide and utilizing the corresponding 3-bromo-6-(4-(trifluoromethoxy)phenyl)-[1,2,4]triazolo[4,3-a]pyridine or 3-iodo-6-(4-(trifluoromethoxy)phenyl)[1,2,4]triazolo[4,3-a]pyridine, other compounds of Formula I may be prepared:

EXAMPLE 26

Preparation of a Compound of Formula I—Modification of an R$^1$ Methy Ester Group A. Preparation of a Compound of Formula I

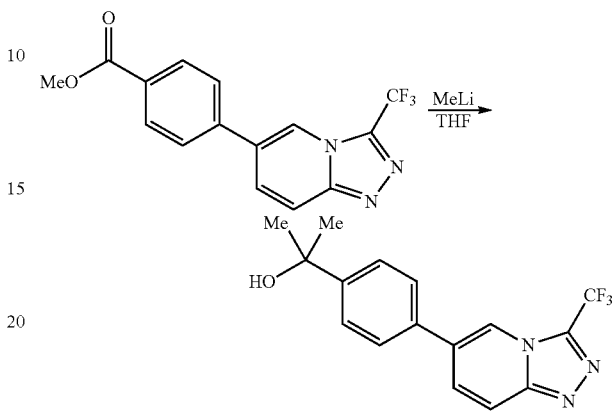

Methyl 4-(3-(trifluoromethyl)[1,2,4]triazolo[4,3-a]pyridin-6-yl)benzoate (33 mg) was dissolved in THF (1 mL) and cooled to −78° C. Methyllithium (1.6 M in ether) was added as one portion. Quenched with 1 mL of water to which 2 drops of 1N HCl were added. Extracted with EtOAc and purified by chromatography using 1:1 hexanes/ethyl acetate as eluent. Isolated 11 mg of 2-(4-(3-(trifluoromethyl)[1,2,4]triazolo[4,3-a]pyridin-6-yl)phenyl)propan-2-ol (33%).

$^1$H NMR (400 MHz, CDCl$_3$): δ 8.32 (s, 1H); 7.99 (d, J=9.6 Hz, 1H); 7.73 (dd, J=10.8, 1.5 Hz, 1H); 7.66 (d, J=8.4 Hz, 2H); 7.55 (d, J=8.4, 2H); 1.91 (s, 1H); 1.65 (s, 6H).

MS (ES+, m/z) 322.1 (base peak, M+H$^+$); 665.1 (2M+Na$^+$).

Optional Secondary Modification of Hydroxy Group

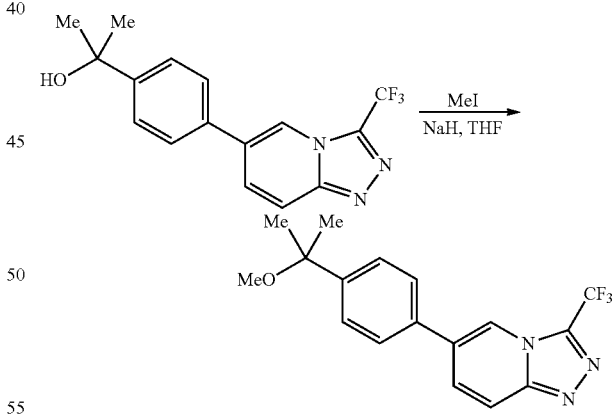

In a 10-mL cone-shaped flask equipped with a magnetic stir bar 2-(4-(3-(trifluoromethyl)[1,2,4]triazolo[4,3-a]pyridin-6-yl)phenyl)propan-2-ol (28 mg) was dissolved in dry THF (1 mL) and NaH (60% suspension in mineral oil, 20 eq.) and MeI (50 eq.) were added. The reaction mixture was stirred overnight at room temperature. Extracted with water and EtOAc, organic layer dried over MgSO$_4$, concentrated, and purified by chromatography (3% MeOH in methylene chloride). The desired 6-(4-(2-methoxypropan-2-yl)phenyl)-3-(trifluoromethyl)[1,2,4]triazolo[4,3-a]pyridine was isolated.

$^1$H NMR (400 MHz, CDCl$_3$): δ 8.27 (s, 1H); 7.95 (d, 1H); 7.70 (d, 1H); 7.53 (br s, 4H); 3.09 (s, 3H); 1.54 (s, 6H).

MS (ES+, m/z) 336.1 (base peak, M+H$^+$); 358.1 (M+Na$^+$); 693.1 (2M+Na$^+$).

B. Preparation of a Compound of Formula I

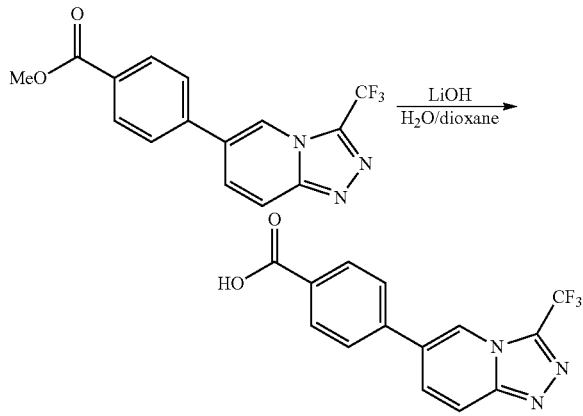

Step 1

Methyl 4-(3-(trifluoromethyl)-[1,2,4]triazolo[4,3-a]pyridin-6-yl)benzoate (12 mg) was dissolved in dioxane (1.5 mL). Lithium hydroxide (1 M in water, 0.5 mL) was added as one portion. After 24 h, quenched with 1N HCl. Extracted with dichloromethane, dried with MgSO$_4$, and concentrated. Isolated 11 mg of 4-(3-(trifluoromethyl)[1,2,4]triazolo[4,3-a]pyridin-6-yl)benzoic acid (~100%).

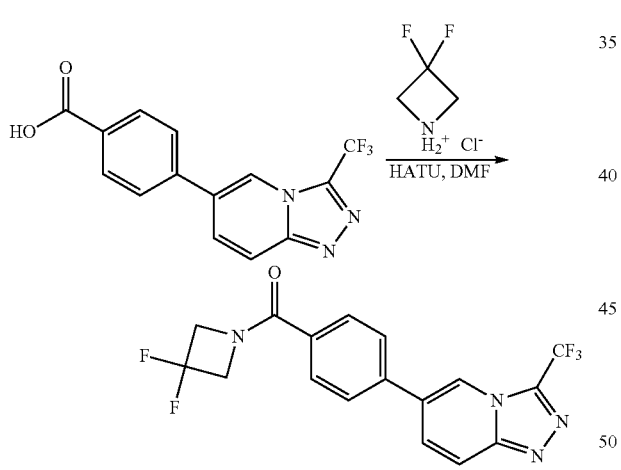

Step 2

4-(3-(trifluoromethyl)-[1,2,4]triazolo[4,3-a]pyridin-6-yl)benzoic acid (52 mg) was dissolved in DMF (2 mL). 3,3-difluoroazetidine hydrochloride (26 mg), diisopropylethylamine (35 μL) and HATU (93 mg) were added sequentially. After 24 h, added additional amounts of Diisopropylethylamine (105 μL) and HATU (279 mg). When the reaction was mostly complete, quenched with ethyl acetate/water, washed with 0.1N HCl, and concentrated NaHCO$_3$. Purified on prep-TLC plate using 5% MeOH/dichloromethane. Isolated 37 mg of (3,3-difluoroazetidin-1-yl)(4-(3-(trifluoromethyl)-[1,2,4]triazolo[4,3-a]pyridin-6-yl)phenyl)methanone (57%).

$^1$H NMR (400 MHz, CDCl$_3$): δ 8.35 (s, 1H); 8.01 (d, J=9.2 Hz, 1H); 7.80 (d, J=8.4 Hz, 2H); 7.71 (dd, J=9.2, 1.2 Hz, 1H); 7.66 (d, J=8.4 Hz, 2H); 4.57 (t, J=11.8 Hz).

$^{19}$F NMR (377 MHz, CDCl$_3$): δ −63 (s, 3F); −100 (quintet, 2F).

MS (ES+, m/z) 383.2 (base peak, M+H$^+$).

C. Preparation of Compounds of Formula I Varying R$^1$

Similarly, following the above procedure, but optionally substituting 3,3-difluoroazetidine hydrochloride for 4,4-difluoropyrimidine hydrochloride, the following compound of Formula I was prepared (4,4-difluoropiperidin-1-yl)(4-(3-(trifluoromethyl))[1,2,4]triazolo[4,3-a]pyridin-6-yl)phenyl)methanone, $^{19}$F NMR: −63.49 (s, 3F); −98.47 (m, 2F).

D. Preparation of Compounds of Formula I Varying R$^1$, X$^1$, and X$^2$

Similarly, following the procedure Example 26A or B above, but optionally substituting other benzoates for Methyl 4-(3-(trifluoromethyl)-[1,2,4]triazolo[4,3-a]pyridin-6-yl) benzoate or compounds for methyllithium, lithium hydroxide, or 4,4-difluoropyrimidine hydrochloride, other compounds of Formula I may be prepared:

EXAMPLE 27

Preparation of a Compound of Formula I—Modification of an R$^1$ Methy EsterEthanone Group A. Preparation of a Compound of Formula I

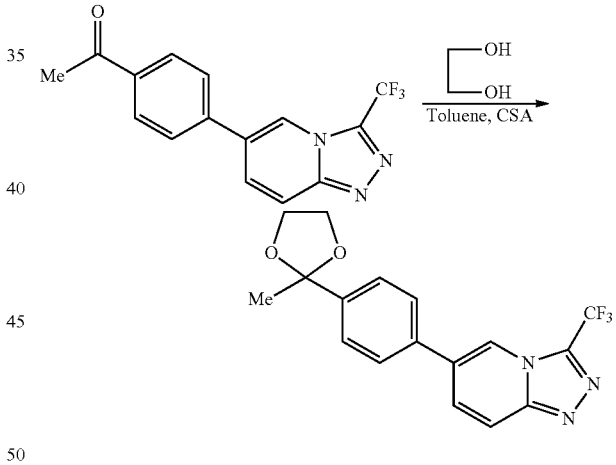

In a 50-mL round-bottom flask equipped with a magnetic stir bar 1-(4-(3-(trifluoromethyl)-[1,2,4]thiazolo[4,3-a]pyridin-6-yl)phenyl)ethanone (50 mg) was dissolved in dry toluene (1 mL), ethylene glycol (0.1 mL) and camphorsulfonic acid (a few crystals) were added. The reaction mixture was stirred overnight at reflux temperature. Extracted with concentrated NaHCO$_3$ and EtOAc, organic layer dried over MgSO$_4$, concentrated, and purified by chromatography (1:1 hexanes/EtOAc). The desired 6-(4-(2-methyl-1,3-dioxolan-2-yl)phenyl)-3-(trifluoromethyl)-[1,2,4]triazolo[4,3-a]pyridine was isolated.

$^1$H NMR (400 MHz, CDCl$_3$): δ 8.38 (s, 1H); 8.02 (d, 1H); 7.75 (d, 1H); 7.70 (d, 2H); 7.57 (d, 2H); 4.12 (t, 2H); 3.83 (t, 2H).

MS (ES+, m/z) 350.0 (base peak, M+H$^+$); 721.1 (2M+Na$^+$).

B. Preparation of a Compound of Formula I

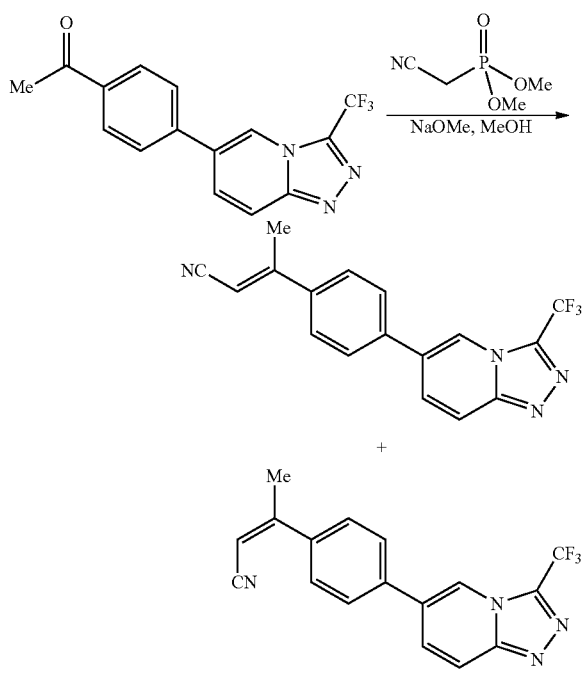

In a 50-mL round-bottom flask equipped with a magnetic stir bar ethyl cyanomethylphosphonate (73 mg) was mixed with NaOMe (0.1 mL, 25 wt. % in MeOH) in 4 mL of MeOH and stirred for 15 min at room temperature. To that mixture, 1-(4-(3-(trifluoromethyl)[1,2,4]triazolo[4,3-a]pyridin-6-yl)phenyl)ethanone (104 mg) was added as a solution in MeOH (1 mL) and dry THF (3 mL). The reaction mixture was stirred overnight at reflux temperature. Extracted with water and dichloromethane, organic layer dried over $MgSO_4$, concentrated, and mixture separated by reverse-phase chromatography (C(18), ACN/water).

(Z)-3-(4-(3-(trifluoromethyl)[1,2,4]triazolo[4,3-a]pyridin-6-yl)phenyl)but-2-enenitrile was isolated and was found to be ~100% pure.

$^1$H NMR (400 MHz, $CDCl_3$): δ 8.35 (s, 1H); 8.03 (d, J=9.6 Hz, 1H); 7.75 (d, J=8.4 Hz, 1H); 7.64 (s, 4H); 5.72 (s, 1H); 2.54 (s, 3H).

MS (ES+, m/z) 329.0 (base peak, M+H$^+$); 351.0 (M+Na$^+$); 679.1 (2M+Na$^+$).

(E)-3-(4-(3-(trifluoromethyl)[1,2,4]triazolo[4,3-a]pyridin-6-yl)phenyl)but-2-enenitrile was isolated as a 5:1 mixture with (Z)-3-(4-(3-(trifluoromethyl)-[1,2,4]triazolo[4,3-a]pyridin-6-yl)phenyl)but-2-enenitrile.

$^1$H NMR (400 MHz, $CDCl_3$): δ 8.35 (s, 1H); 8.03 (d, J=9.6 Hz, 1H); 7.75-7.70 (m, 3H); 7.64 (d, J=8.8 Hz, 2H); 5.49 (s, 1H); 2.34 (s, 3H).

MS (ES+, m/z) 329.0 (base peak, M+H$^+$); 351.0 (M+Na$^+$); 679.1 (2M+Na$^+$).

C. Preparation of Compounds of Formula I Varying $R^1$, $X^1$, and $X^2$

Similarly, following the procedure Example 27A or B above, but optionally substituting other ethanones for 1-(4-(3-(trifluoromethyl)[1,2,4]triazolo[4,3-a]pyridin-6-yl)phenyl)ethanone or other compounds for ethylene glycol or ethyl cyanomethylphosphonate, other compounds of Formula I may be prepared:

EXAMPLE 28

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

EXAMPLE 29

A tablet Formula (I)s prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 30

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

EXAMPLE 31

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 32

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 33

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 34

A subcutaneous formulation may be prepared as follows:

| Ingredient | Quantity |
| --- | --- |
| Active Ingredient | 5.0 mg |
| Corn Oil | 1.0 mL |

EXAMPLE 35

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

EXAMPLE 36

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 37

Sustained Release Composition

| Ingredient | Weight Range % |
| --- | --- |
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 38

Activity testing is conducted in the Examples below using methods described herein and those well known in the art.
Sodium Current Screening Assays:

The late sodium current (Late INa) and peak sodium current (Peak INa) assays are performed on an automated electrophysiology platform, PatchXpress 7000A (MDS Analytical Technologies, Sunnyvale, Calif.), which uses the whole cell patch clamp technique to measure currents through the cell membrane of up to 16 cells at a time. The assay uses an HEK293 (human embryonic kidney) cell line heterologously expressing the wild-type human cardiac sodium channel, hNa$_v$1.5, purchased from Millipore (Billerica, Mass.). No beta subunits were coexpressed with the Na channel alpha subunit. Cells are maintained with standard tissue culture procedures and stable channel expression is maintained with 400 μg/ml Geneticin in the culture medium. Cells isolated for use on PatchXpress are incubated for 5 minutes in Versene 1× and then for 2 minutes in 0.0125% Trypsin-EDTA (both at 37° C.) to ensure that 80-90% of the cells are single and not part of a cell cluster. Experiments are carried out at 24-27° C.

For both the Late INa and Peak INa assays, series resistance compensation is set to 50% and whole-cell compensation is performed automatically. Currents are low-pass filtered at 10 kHz and digitized at 31.25 kHz. Currents through open sodium channels are automatically recorded and stored in the DataXpress2 database (MDS Analytical Technologies, Sunnyvale, Calif.). Analysis is performed using DataXpress2 analysis software and data are compiled in Excel.

Compound stocks are routinely made in glass vials to 10 mM in dimethyl sulfoxide (DMSO). In some cases, when compounds are not soluble in DMSO, they are made in 100% ethanol. Stocks are sonicated as necessary. The extracellular solution for screening Late INa is composed of: 140 mM NaCl, 4 mM KCl, 1.8 mM CaCl$_2$, 0.75 mM MgCl$_2$, and 5 mM HEPES with pH adjusted to 7.4 using NaOH. The extracellular solution for screening Peak INa is composed of: 20 mM NaCl, 120 mM N-methyl-D glucamine, 4 mM KCl, 1.8 mM CaCl$_2$, 0.75 mM MgCl$_2$, and 5 mM HEPES with pH adjusted to 7.4 using HCl. The intracellular solution used to perfuse the inside of the cells for both the Late INa and Peak INa assays contains: 120 mM CsF, 20 mM CsCl, 5 mM EGTA, 5 mM HEPES and pH adjusted to 7.4 with CsOH. Compounds are diluted in extracellular solution to 10 μM in glass vials and then transferred to glass well plates before robotic addition to the cells. The 0Na extracellular solution used at the end of each experiment for the Late INa and Peak INa assays to measure baseline current contains: 140 mM N-methyl-D-glucamine; 4 mM KCl; 1.8 mM CaCl$_2$; 0.75 mM MgCl$_2$; 5 mM HEPES and pH was adjusted to 7.4 with HCl.

Late INa Screening Assay:

For the Late INa assay, sodium channels are activated every 10 seconds (0.1 Hz) by depolarizing the cell membrane to −20 mV for 250 milliseconds (ms) from a holding potential of −120 mV. In response to a −20 mV voltage step, typical Na$_v$1.5 sodium currents activate rapidly to a peak negative current and then inactivate nearly completely within 3-4 ins.

All compounds are tested to determine their activity in blocking the late sodium current. Late INa current is generated by adding 10 μM Tefluthrin (pyrethroid) to the extracellular solution while recording Na currents For some experiments, 50 nM ATX II (sea anemone toxin), another late INa activator, was used to generate the late component. Both activators generate late components that are large enough that block of the late component by compounds can be measured easily. For the purposes of the screening, late INa is defined as the mean current between 225 ms and 250 ms after stepping to −20 mV to activate Na channels. After establishing the whole cell recording configuration, late INa activators are added to each well 4 times over a 16-17 minute period so that the late component of the Na current reaches a stable value. Compounds are then added (typically at 10 μM), in the presence of late INa activator, with 3 additions over the course of 7 or 8 minutes. Measurements are made typically at the end of exposure to the third compound addition. Measurements are made at the end of exposure to the third compound addition and values are normalized to the current level when all Na$^+$ is removed from the extracellular solution after two additions of 0Na-ECF. Results are reported as percent block of late INa
Peak INa Screening Assay:

Compounds were also evaluated for their effect in several other assays, including their effect on Peak INa. After screening compounds against late INa, selected compounds are evaluated for their effect in several other assays, including their effect on peak INa. One goal of this program is to avoid significant block of peak INa. Since the peak INa in our cells can be very large, introducing artifacts in the recording, the concentration of Na$^+$ in the bath is reduced to 20 mM and a nonpermeant cation is added to compensate for the Na$^+$ that was removed to maintain the osmolarity and ionic strength of the solution (see solution details above). All measurements are normalized to the current level when all Na$^+$ is removed from the extracellular solution, after two additions of 0Na-ECF.

In some cases we measured the effect of compound on peak INa using data from the late INa assay. But often peak currents were too large to make this possible, requiring that we perform a separate assay to evaluate the effect on peak INa. For the original peak INa assay, we activate the channel every 10 seconds by depolarizing the cell membrane to −20 mV for 250 ms from a holding potential of −120 mV. After establishing the whole cell recording configuration, the recorded currents are allowed to stabilize for 6-7 minutes. Compound is added at 10 μM with three additions over an 8-9 minute period. Analysis of peak INa generally requires correction for rundown before determining the % block of peak current by the tested compound.

A new Peak INa screening assay was developed to allow assessment of the effect of compounds on peak INa at both low and high stimulation frequencies. The goal is to find compounds that are highly selective for block of late INa but do not block peak INa. A low stimulation frequency of 0.1 Hz is used to determine the effect of compound when the channel spends most of the time in the resting (closed) state and provides information about Tonic Block (TB). A higher stimulation frequency (3 Hz) is used to measure block of the channel when it spends more time in the activated and inactivated states, and provides a measure of Use-Dependent Block (UDB). The −100 mV holding potential and the 3 Hz stimulation frequency were chosen so that our benchmark compound would have a small but detectable effect under experimental conditions, allowing for direct comparison of new compounds with the benchmark.

For the new peak INa assay, Na$^+$ channels are activated by depolarizing the cell membrane to 0 mV for 20 ms from a holding potential of −100 mV. After establishing the whole cell recording configuration, channels are stimulated to open with low frequency stimulation (0.1 Hz) for 7 minutes so that we can monitor the recording and assess the extent to which the recording has stabilized. After this stabilization period the stimulation frequency is increased to 3 Hz for 2 minutes, and then returned to 0.1 Hz. Since 3 Hz stimulation causes a small decrease in the peak current even in the absence of compound, we use this internal control for each cell, when no compound is present, to correct the results from 3 Hz stimulation when compound is present. Following 3 Hz stimulation under control conditions, the cell is allowed to recover for 200 seconds before compound is added. Compound (10 µM) is added 3 times at 60 second intervals, while stimulating the channels to open at 0.1 Hz to monitor the progression of block. After the 3$^{rd}$ compound addition, a 320 second wait period is imposed to allow for equilibration before the second period of 3 Hz stimulation begins. TB is measured before the second period of 3 Hz stimulation. Both TB and UDB are analyzed by incorporating rundown correction for the peak INa and UDB is calculated by compensating for the small use-dependent effect of the stimulation protocol on peak INa in the absence of compound.

hERG Screening Assay:

Compounds were screened to test their activity in blocking the hERG potassium channel. The hERG channel is heterologously expressed in a CHO (Chinese Hamster Ovary) cell line. Cells are maintained with standard tissue culture procedures and stable channel expression is maintained with 500 µg/ml G418 in the culture medium. Cells are harvested for testing on the PatchXpress automated patch clamp with Accumax (Innovative Cell Technologies, San Diego, Calif.) to isolate single cells.

The following solutions are used for electrophysiological recordings. The external solution contains: 2 mM CaCl$_2$; 2 mM MgCl$_2$; 4 mM KCl; 150 mM NaCl; 10 mM Glucose; 10 mM HEPES (pH 7.4 with 1M NaOH, osmolarity). The internal solution contains: 140 mM KCl, 10 mM MgCl$_2$, 6 mM EGTA, 5 mM HEPES, 5 mM ATP (pH adjusted to 7.25 with KOH).

hERG channels are activated when the voltage is stepped to +20 mV from the −80 mV holding potential. During a 5 second step at +20 mV, the channels activate and then largely inactivate, so the currents are relatively small. Upon returning to −50 mV from +20 mV, hERG currents transiently become much larger as inactivation is rapidly removed and then the channel closes. The first step to −50 mV for 300 ms is used as a baseline for measuring the peak amplitude during the step to −50 mV after channel activation. The peak current at −50 mV is measured both under control conditions and after addition of compound.

All compounds are prepared as 10 mM DMSO stocks in glass vials. Stock solutions are mixed by vigorous vortexing and sonication for about 2 minutes at room temperature. For testing, compounds are diluted in glass vials using an intermediate dilution step in pure DMSO and then further diluted to working concentrations in external solution. Dilutions are prepared no longer than 20 minutes before use.

After achieving the whole-cell configuration, cells are monitored for 90 seconds to assess stability and washed with external solution for 66 seconds. The voltage protocol described above is then applied to the cells every 12 seconds and throughout the whole procedure. Only cells with stable recording parameters and meeting specified health criteria are allowed to enter the compound addition procedure.

External solution containing 0.1% DMSO (vehicle) is applied to the cells first to establish the control peak current amplitude. After allowing the current to stabilize for 3 to 5 minutes, 1 µM and then 10 µM test compounds are applied. Each compound concentration is added 4 times and cells are kept in test solution until the effect of the compound reaches steady state or for a maximum of 12 minutes. After addition of test compound, a positive control (1 µM Cisapride) is added and must block >95% of the current for the experiment to be considered valid. Washout in the external solution compartment is performed until the recovery of the current reaches steady state. Data are analyzed using DataXpress, Clampfit (Molecular Devices, Inc., Sunnyvale) and Origin 7 (Originlab Corp.)

L-type Calcium Channel Activity Well-Plate Assay:

Cell Culture: IMR-32 (human neuroblastoma) cells were obtained from The American Type Culture Collection. The cells were maintained in MEM supplemented with 10% fetal bovine serum, 2 mM of L-glutamine, 100 IU/ml of penicillin, 50 mg/ml of streptomycin, 1% of sodium pyruvate, 1% of sodium bicarbonate and 1% of non-essential amino acid. The cells were cultured at 37° C. in a humidified 5% CO2/95% air incubator. Culture medium was changed every two days and cells were recultivated when they reached 70-80% confluent.

Assay: IMR-32 cells were seeded on a Microtest 96-well Assay Plate (BD FALCON™) at a density of 200,000 cells/well in 200 µl culture medium for overnight. The culture medium was removed, and replaced by 120 µl Ca-4 dye (MDS Analytical Technologies, Sunnyvale, Calif.) in HBSS (1× Hank's Balanced Salt solution plus 20 mM HEPES, pH 7.4) containing 2 mM probenecid. Cells were then incubated for 1 hour at 37° in incubator. Testing compounds were diluted from 5-50 µM in HBSS, and 40 µl were added in cells before assay. L-type calcium channel activities (Max-Min) were measured after addition of 40 µl of 1 µM (−)Bay K 8644 plus 50 mM KCl (final concentration) using FlexStation (Molecular Devices) immediately after addition of testing compounds. The inhibition of L-type calcium channel activity by compounds was then calculated.

Compounds were tested and found to be effective using the described assay methods at a concentration of 1 µM and 10 µM in the late INa and Peak INa assays, and at 1 µM and 10 µM for the hERG and L-type calcium channel assays. The assay results demonstrated that the compounds tested showed activity as modulators of late sodium current, for example by inhibiting (or reducing) the late sodium current.

Compounds were tested using the described assay methods. Data are obtained obtained by testing the listed compounds at 10 µM and 1 µM concentrations in the late INa assay, and at 1 µM and 10 µM for the hERG and L-type calcium channel assays. Data are shown in Table 1 below for those compounds that inhibit Late Ina by at least 10% at the 10 µM concentration.

TABLE 1

Late INa Assay results

| Example No. | Name | LateINa__1 uM | LateINa__10 uM |
|---|---|---|---|
| BHN-1. | 7-methyl-6-(4-(trifluoromethoxy)phenyl)-3-(trifluoromethyl)-[1,2,4]triazolo[4,3-a]pyridine | 49 | 67.5 |
| BHN-2. | 6-(3-(trifluoromethoxy)phenyl)-3-(trifluoromethyl)-[1,2,4]triazolo[4,3-a]pyridine | | 52.9 |
| BHN-3. | 3-(trifluoromethyl)-6-[4-(trifluoromethyl)phenyl][1,2,4]triazolo[4,3-a]pyridine | 60 | 76.8 |
| BHN-4. | 6-(2,4-dichlorophenyl)-3-(trifluoromethyl)[1,2,4]triazolo[4,3-a]pyridine | | 53.5 |
| BHN-5. | 6-[4-(trifluoromethoxy)phenyl]-3-(trifluoromethyl)imidazo[1,5-a]pyridine | 50.3 | 81.3 |
| BHN-6. | 6-[4-(difluoromethoxy)phenyl]-3-(trifluoromethyl)[1,2,4]triazolo[4,3-a]pyridine | | 54 |
| BHN-7. | 6-(4-phenoxyphenyl)-3-(trifluoromethyl)imidazo[1,5-a]pyridine | | 55.4 |
| BHN-8. | 6-[4-(trifluoromethoxy)phenyl]-3-(trifluoromethyl)[1,2,4]triazolo[4,3-b]pyridazine | 36 | 78.8 |
| BHN-9. | 6-(3-phenoxyphenyl)-3-(trifluoromethyl)[1,2,4]triazolo[4,3-a]pyridine | 29.6 | 75.7 |
| BHN-10. | 6-[4-chloro-3-(trifluoromethyl)phenyl]-3-(trifluoromethyl)[1,2,4]triazolo[4,3-a]pyridine | | 51.2 |
| BHN-11. | 6-(4-phenoxyphenyl)-3-(trifluoromethyl)[1,2,4]triazolo[4,3-b]pyridazine | | 44.7 |
| BHN-12. | 3-(difluoromethyl)-6-[4-(trifluoromethoxy)phenyl][1,2,4]triazolo[4,3-b]pyridazine | 39.6 | 79.7 |
| BHN-13. | 3-(difluoromethyl)-6-(4-phenoxyphenyl)[1,2,4]triazolo[4,3-b]pyridazine | 44.8 | 87.1 |
| BHN-14. | 6-(4-chloro-3-fluorophenyl)-3-(trifluoromethyl)[1,2,4]triazolo[4,3-a]pyridine | | 28.3 |
| BHN-15. | 6-[4-(trifluoromethoxy)phenyl]-3-(trifluoromethyl)[1,2,4]triazolo[4,3-a]pyrazine | | 52.5 |
| BHN-16. | 6-(4-phenoxyphenyl)-3-(trifluoromethyl)[1,2,4]triazolo[4,3-a]pyrazine | | 54.3 |
| BHN-17. | 7-methyl-6-[3-(trifluoromethoxy)phenyl]-3-(trifluoromethyl)[1,2,4]triazolo[4,3-a]pyridine | | 25.3 |
| BHN-18. | 3-(difluoromethyl)-6-(4-phenoxyphenyl)[1,2,4]triazolo[4,3-a]pyrazine | | 54.6 |
| BHN-19. | {6-[4-(trifluoromethoxy)phenyl][1,2,4]triazolo[4,3-a]pyridin-3-yl}acetic acid | | 35.4 |
| BHN-20. | 3-(difluoromethyl)-6-[4-(trifluoromethoxy)phenyl][1,2,4]triazolo[4,3-a]pyridine | 46.6 | 72.9 |
| BHN-21. | 3-phenyl-6-[4-(trifluoromethoxy)phenyl][1,2,4]triazolo[4,3-a]pyridine | 65.1861 | 86.5 |
| BHN-22. | 6-(4-phenoxyphenyl)[1,2,4]triazolo[4,3-b]pyridazine | | 58.9946 |
| BHN-23. | 3-(difluoromethyl)-6-[4-(trifluoromethoxy)phenyl][1,2,4]triazolo[4,3-a]pyrazine | 53.5406 | 74.6757 |
| BHN-24. | 6-(4-tert-butylphenyl)-3-(trifluoromethyl)[1,2,4]triazolo[4,3-a]pyridine | 67.723 | 89.4833 |
| BHN-25. | 6-[4-(trifluoromethoxy)phenyl][1,2,4]triazolo[4,3-b]pyridazine | | 38.9637 |
| BHN-26. | 6-[2-methyl-4-(trifluoromethoxy)phenyl]-3-(trifluoromethyl)[1,2,4]triazolo[4,3-b]pyridazine | 64.4143 | 75.3492 |
| BHN-27. | 3-(trifluoromethyl)-6-[4-(trimethylsilyl)phenyl][1,2,4]triazolo[4,3-a]pyridine | 71.9653 | 84.8865 |
| BHN-28. | 6-[4-(2,2,2-trifluoroethoxy)phenyl]-3-(trifluoromethyl)imidazo[1,5-a]pyridine | 46.1443 | 78.3068 |
| BHN-29. | 6-(4-methoxyphenyl)-3-(trifluoromethyl)[1,2,4]triazolo[4,3-a]pyridine | 20.888 | 62.8222 |
| BHN-30. | 6-(4-methoxyphenyl)-3-(trifluoromethyl)imidazo[1,5-a]pyridine | 24.5771 | 77.2627 |
| BHN-31. | 6-(4-phenoxyphenyl)-3-(2,2,2-trifluoroethyl)[1,2,4]triazolo[4,3-b]pyridazine | 57.5195 | 82.5547 |
| BHN-32. | 6-(4-phenoxyphenyl)-3-(propan-2-yl)[1,2,4]triazolo[4,3-b]pyridazine | 63.4332 | 83.3609 |
| BHN-33. | 6-[2-methyl-4-(trifluoromethoxy)phenyl]-3-(propan-2-yl)[1,2,4]triazolo[4,3-b]pyridazine | 59.2146 | 75.9223 |
| BHN-34. | 1-phenyl-6-[4-(trifluoromethoxy)phenyl]-3-(trifluoromethyl)imidazo[1,5-a]pyridine | | 33.3917 |
| BHN-35. | 3-tert-butyl-6-(4-phenoxyphenyl)[1,2,4]triazolo[4,3-b]pyridazine | | 68.5617 |
| BHN-36. | 3-tert-butyl-6-[4-(2,2,2-trifluoroethoxy)phenyl][1,2,4]triazolo[4,3-b]pyridazine | | 64.5106 |
| BHN-37. | 6-[4-(2,2,2-trifluoroethoxy)phenyl]-3-(trifluoromethyl)[1,2,4]triazolo[4,3-a]pyridine | 41.7903 | 59.7614 |
| BHN-38. | 3-ethyl-6-(4-phenoxyphenyl)[1,2,4]triazolo[4,3-b]pyridazine | 54.508 | 79.348 |

TABLE 1-continued

Late INa Assay results

| Example No. | Name | LateINa_1 uM | LateINa_10 uM |
|---|---|---|---|
| BHN-39. | 3-cyclopropyl-6-(4-phenoxyphenyl)[1,2,4]triazolo[4,3-b]pyridazine | 44.4142 | 74.2699 |
| BHN-40. | 4-[6-(4-phenoxyphenyl)[1,2,4]triazolo[4,3-b]pyridazin-3-yl]benzonitrile | | 38.2354 |
| BHN-41. | 4-{6-[2-methyl-4-(trifluoromethoxy)phenyl][1,2,4]triazolo[4,3-b]pyridazin-3-yl}benzonitrile | | 59.1461 |
| BHN-42. | 4-{6-[4-(trifluoromethoxy)phenyl][1,2,4]triazolo[4,3-b]pyridazin-3-yl}benzonitrile | | 43.8433 |
| BHN-43. | 3-(1-methyl-1H-pyrazol-4-yl)-6-(4-phenoxyphenyl)[1,2,4]triazolo[4,3-b]pyridazine | | 25.2135 |
| BHN-44. | 4-[6-(4-methoxyphenyl)[1,2,4]triazolo[4,3-b]pyridazin-3-yl]benzonitrile | | 15.0257 |
| BHN-45. | 3-[6-(4-methoxyphenyl)[1,2,4]triazolo[4,3-b]pyridazin-3-yl]benzonitrile | | 36.2623 |
| BHN-46. | methyl 4-[3-(trifluoromethyl)[1,2,4]triazolo[4,3-a]pyridin-6-yl]benzoate | | 53.9313 |
| BHN-47. | 3-[4-(methylsulfonyl)phenyl]-6-(4-phenoxyphenyl)[1,2,4]triazolo[4,3-b]pyridazine | | 50.7485 |
| BHN-48. | 2-{4-[3-(trifluoromethyl)[1,2,4]triazolo[4,3-a]pyridin-6-yl]phenyl}propan-2-ol | | 18.8946 |
| BHN-49. | 3-{6-[6-(morpholin-4-yl)pyridin-3-yl][1,2,4]triazolo[4,3-b]pyridazin-3-yl}benzonitrile | | |
| BHN-50. | 6-(4-phenoxyphenyl)-3-[4-(2H-tetrazol-5-yl)phenyl][1,2,4]triazolo[4,3-b]pyridazine | | 31.0469 |
| BHN-51. | 3-[6-(4-fluorophenyl)[1,2,4]triazolo[4,3-b]pyridazin-3-yl]benzonitrile | | 40.5409 |
| BHN-52. | 3-phenyl-6-[4-(trifluoromethoxy)phenyl][1,2,4]triazolo[4,3-a]pyridin-8-amine | | 44.8746 |
| BHN-53. | 4-[3-(trifluoromethyl)[1,2,4]triazolo[4,3-a]pyridin-6-yl]benzonitrile | | 25.1019 |
| BHN-54. | 6-[2-(1H-tetrazol-5-yl)phenyl]-3-(trifluoromethyl)[1,2,4]triazolo[4,3-a]pyridine | | |
| BHN-55. | 3,6-bis[4-(trifluoromethoxy)phenyl][1,2,4]triazolo[4,3-a]pyridine | 89.1394 | 90.7299 |
| BHN-56. | 3-(propan-2-yl)-6-[4-(trifluoromethoxy)phenyl][1,2,4]triazolo[4,3-a]pyridine | | 48.512 |
| BHN-57. | 6-(biphenyl-4-yl)-3-(trifluoromethyl)[1,2,4]triazolo[4,3-a]pyridine | 45.8426 | 39.4525 |
| BHN-58. | methyl (2E)-3-{6-[4-(trifluoromethoxy)phenyl]-3-(trifluoromethyl)imidazo[1,5-a]pyridin-1-yl}prop-2-enoate | | 27.6455 |
| BHN-59. | 6-(1-methyl-1H-indazol-5-yl)-3-(trifluoromethyl)[1,2,4]triazolo[4,3-a]pyridine | | 39.8471 |
| BHN-60. | 2-[6-(4-phenoxyphenyl)[1,2,4]triazolo[4,3-b]pyridazin-3-yl]propan-2-ol | | 48.5826 |
| BHN-61. | 6-[4-(1H-1,2,4-triazol-1-yl)phenyl]-3-(trifluoromethyl)[1,2,4]triazolo[4,3-a]pyridine | | 23.4548 |
| BHN-62. | methyl 6-[4-(trifluoromethoxy)phenyl][1,2,4]triazolo[4,3-a]pyridine-3-carboxylate | | |
| BHN-63. | N-methyl-6-[4-(trifluoromethoxy)phenyl][1,2,4]triazolo[4,3-a]pyridine-3-carboxamide | | |
| BHN-64. | 6-[4-(4-fluorophenoxy)phenyl]-3-(trifluoromethyl)[1,2,4]triazolo[4,3-a]pyridine | 38.1971 | 69.6326 |
| BHN-65. | 6-[4-(4-chlorophenoxy)phenyl]-3-(trifluoromethyl)[1,2,4]triazolo[4,3-a]pyridine | 55.5803 | 85.7214 |
| BHN-66. | 2-methyl-2-{4-[3-(trifluoromethyl)[1,2,4]triazolo[4,3-a]pyridin-6-yl]phenyl}propanenitrile | 33.1801 | 70.6838 |
| BHN-67. | 6-[3-methyl-4-(trifluoromethoxy)phenyl]-3-(trifluoromethyl)[1,2,4]triazolo[4,3-a]pyridine | 71.8028 | 80.6821 |
| BHN-68. | 6-[4-(propan-2-ylsulfonyl)phenyl]-3-(trifluoromethyl)[1,2,4]triazolo[4,3-a]pyridine | | 21.9692 |
| BHN-69. | 3-methyl-6-[4-(trifluoromethoxy)phenyl][1,2,4]triazolo[4,3-a]pyridin-8-amine | | 32.102 |
| BHN-70. | 3-methyl-6-[2-methyl-4-(trifluoromethoxy)phenyl][1,2,4]triazolo[4,3-a]pyridin-8-amine | | 40.385 |
| BHN-71. | 6-[4-(5-methyl-1,3,4-oxadiazol-2-yl)phenyl]-3-(trifluoromethyl)[1,2,4]triazolo[4,3-a]pyridine | | 20.5184 |
| BHN-72. | 6-[3-(morpholin-4-ylmethyl)-4-(trifluoromethoxy)phenyl]-3-(trifluoromethyl)[1,2,4]triazolo[4,3-a]pyridine | | 26.735 |

TABLE 1-continued

Late INa Assay results

| Example No. | Name | LateINa__1 uM | LateINa__10 uM |
|---|---|---|---|
| BHN-73. | 4-{6-[4-(trifluoromethoxy)phenyl][1,2,4]triazolo[4,3-a]pyridin-3-yl}benzenesulfonamide | | 17.4588 |
| BHN-74. | 3-(1,1-difluoro-2-methoxyethyl)-6-[4-(trifluoromethoxy)phenyl][1,2,4]triazolo[4,3-a]pyridine | 46.9061 | 67.0321 |
| BHN-75. | N-(4-{6-[4-(trifluoromethoxy)phenyl][1,2,4]triazolo[4,3-a]pyridin-3-yl}phenyl)methanesulfonamide | | 30.0736 |
| BHN-76. | N-{3-methyl-6-[2-methyl-4-(trifluoromethoxy)phenyl][1,2,4]triazolo[4,3-a]pyridin-8-yl}acetamide | | 31.8678 |
| BHN-77. | 6-(4-ethoxyphenyl)-3-(trifluoromethyl)[1,2,4]triazolo[4,3-a]pyridine | | 56.8121 |
| BHN-78. | 6-(4-tert-butoxyphenyl)-3-(trifluoromethyl)[1,2,4]triazolo[4,3-a]pyridine | | 49.8074 |
| BHN-79. | 4-{6-[4-(trifluoromethoxy)phenyl][1,2,4]triazolo[4,3-a]pyridin-3-yl}benzamide | | 19.2748 |
| BHN-80. | diethyl 3,3'-[1,2,4]triazolo[4,3-a]pyridine-3,6-diyldibenzoate | | 58.9887 |
| BHN-81. | 6-{3-[(4-methylpiperazin-1-yl)methyl]-4-(trifluoromethoxy)phenyl}-3-(trifluoromethyl)[1,2,4]triazolo[4,3-a]pyridine | | 30.3438 |
| BHN-82. | 3-(1-methyl-1H-pyrazol-4-yl)-6-[4-(trifluoromethoxy)phenyl][1,2,4]triazolo[4,3-a]pyridine | | 38.8602 |
| BHN-83. | N,N-dimethyl-1-{2-(trifluoromethoxy)-5-[3-(trifluoromethyl)[1,2,4]triazolo[4,3-a]pyridin-6-yl]phenyl}methanamine | | 29.7759 |
| BHN-84. | 2-({2-(trifluoromethoxy)-5-[3-(trifluoromethyl)[1,2,4]triazolo[4,3-a]pyridin-6-yl]benzyl}amino)ethanol | | |
| BHN-85. | N-{3-methyl-6-[4-(trifluoromethoxy)phenyl][1,2,4]triazolo[4,3-a]pyridin-8-yl}propanamide | | 20.5208 |
| BHN-86. | ethyl 4-{6-[4-(trifluoromethoxy)phenyl][1,2,4]triazolo[4,3-a]pyridin-3-yl}benzoate | 82.7225 | 86.8539 |
| BHN-87. | ethyl 3-{6-[4-(trifluoromethoxy)phenyl][1,2,4]triazolo[4,3-a]pyridin-3-yl}benzoate | 38.949 | 72.2054 |
| BHN-88. | 6-(6-cyclopropylpyridin-3-yl)-3-(trifluoromethyl)[1,2,4]triazolo[4,3-a]pyridine | | 35.9522 |
| BHN-89. | 6-(2-cyclopropylpyrimidin-5-yl)-3-(trifluoromethyl)[1,2,4]triazolo[4,3-a]pyridine | | 20.4645 |
| BHN-90. | 6-(4-cyclopropylphenyl)-3-(trifluoromethyl)[1,2,4]triazolo[4,3-a]pyridine | 63.3768 | 74.8949 |
| BHN-91. | 3-(trifluoromethyl)-6-[6-(trifluoromethyl)pyridin-3-yl][1,2,4]triazolo[4,3-a]pyridine | | 46.7392 |
| BHN-92. | 6-[6-(2,2,2-trifluoroethoxy)pyridin-3-yl]-3-(trifluoromethyl)[1,2,4]triazolo[4,3-a]pyridine | 63.5039 | 76.3047 |
| BHN-93. | N-(2-{6-[4-(trifluoromethoxy)phenyl][1,2,4]triazolo[4,3-a]pyridin-3-yl}phenyl)methanesulfonamide | | 20.9754 |
| BHN-94. | 6-[4-(pyrazin-2-yloxy)phenyl]-3-(trifluoromethyl)[1,2,4]triazolo[4,3-a]pyridine | | 27.4516 |
| BHN-95. | N-({6-[4-(trifluoromethoxy)phenyl][1,2,4]triazolo[4,3-a]pyridin-3-yl}methyl)methanesulfonamide | | |
| BHN-96. | 6-(5-cyclopropyl-1,3,4-thiadiazol-2-yl)-3-(trifluoromethyl)[1,2,4]triazolo[4,3-a]pyridine | 20.2987 | |
| BHN-97. | 6-(4-phenoxyphenyl)tetrazolo[1,5-a]pyridine | 73.2015 | |
| BHN-98. | 6-[4-(trifluoromethoxy)phenyl]tetrazolo[1,5-a]pyridine | 54.0834 | |
| BHN-99. | N-methyl-3-{6-[4-(trifluoromethoxy)phenyl][1,2,4]triazolo[4,3-a]pyridin-3-yl}benzamide | 19.5847 | |
| BHN-100. | 6-[4-(pyridin-3-yloxy)phenyl]-3-(trifluoromethyl)[1,2,4]triazolo[4,3-a]pyridine | 27.6277 | |
| BHN-101. | 6-[6-(methylsulfanyl)pyridin-3-yl]-3-(trifluoromethyl)imidazo[1,5-a]pyridine | 32.3221 | |
| BHN-102. | 6-[4-(cyclopropyloxy)phenyl]-3-(trifluoromethyl)[1,2,4]triazolo[4,3-a]pyridine | 45.5067 | |
| BHN-103. | 8-methyl-6-[4-(trifluoromethoxy)phenyl]-3-(trifluoromethyl)[1,2,4]triazolo[4,3-a]pyridine | 40.7323 | |
| BHN-104. | 7-methoxy-6-[4-(trifluoromethoxy)phenyl]-3-(trifluoromethyl)[1,2,4]triazolo[4,3-a]pyridine | 31.6916 | |
| BHN-105. | 6-[2-methoxy-4-(trifluoromethyl)phenyl]-3-(trifluoromethyl)[1,2,4]triazolo[4,3-a]pyridine | 49.3177 | |
| BHN-106. | 6-(naphthalen-2-yl)-3-(trifluoromethyl)[1,2,4]triazolo[4,3-a]pyridine | 38.2035 | |
| BHN-107. | 3-(trifluoromethyl)-6-(3,4,5-trimethoxyphenyl)[1,2,4]triazolo[4,3-a]pyridine | 16.5096 | |

TABLE 1-continued

Late INa Assay results

| Example No. | Name | LateINa_1 uM | LateINa_10 uM |
|---|---|---|---|
| BHN-108. | 8-(trifluoromethoxy)-5-[3-(trifluoromethyl)[1,2,4]triazolo[4,3-a]pyridin-6-yl)quinoline | 45.7361 | 63.0914 |
| BHN-109. | 6-(3,5-difluoro-4-phenoxyphenyl)-3-(trifluoromethyl)[1,2,4]triazolo[4,3-a]pyridine | 61.8009 | |
| BHN-110. | 6-[4-(4-fluoro-2-nitrophenoxy)phenyl]-3-(trifluoromethyl)[1,2,4]triazolo[4,3-a]pyridine | 18.2387 | |
| BHN-111. | 2,2-difluoro-2-[6-(4-phenoxyphenyl)[1,2,4]triazolo[4,3-a]pyridin-3-yl]ethanol | 28.9842 | |
| BHN-112. | 6-[4-(2-fluorophenoxy)phenyl]-3-(trifluoromethyl)[1,2,4]triazolo[4,3-a]pyridine | 32.8537 | |
| BHN-113. | 6-[4-(pyridin-4-yloxy)phenyl]-3-(trifluoromethyl)[1,2,4]triazolo[4,3-a]pyridine | 20.132 | |
| BHN-114. | N-phenyl-4-[3-(trifluoromethyl)[1,2,4]triazolo[4,3-a]pyridin-6-yl]aniline | 37.3626 | |
| BHN-115. | N-(2,2,2-trifluoroethyl)-4-[3-(trifluoromethyl)[1,2,4]triazolo[4,3-a]pyridin-6-yl]aniline | 18.9269 | |
| BHN-116. | N-[5-(trifluoromethoxy)-2-{3-[4-(trifluoromethoxy)phenyl][1,2,4]triazolo[4,3-a]pyridin-6-yl}phenyl]acetamide | 16.4416 | |
| BHN-117. | 6-[4-(trifluoromethoxy)phenyl]-3-(trifluoromethyl)imidazo[1,5-a]pyridine-1-carbonitrile | 66.3166 | |
| BHN-118. | 3,6-bis[4-(trifluoromethoxy)phenyl][1,2,4]triazolo[4,3-b]pyridazine | 46.2911 | |
| BHN-119. | 6-[4-(phenylsulfanyl)phenyl]-3-(trifluoromethyl)[1,2,4]triazolo[4,3-a]pyridine | 70.4905 | |
| BHN-120. | 6-(naphthalen-1-yl)-3-(trifluoromethyl)[1,2,4]triazolo[4,3-a]pyridine | 20.3841 | |
| BHN-121. | 3-(trifluoromethyl)-6-[6-(trifluoromethyl)pyridazin-3-yl][1,2,4]triazolo[4,3-a]pyridine | 21.9422 | |
| BHN-122. | 3-(trifluoromethyl)-6-[2-(trifluoromethyl)pyrimidin-5-yl][1,2,4]triazolo[4,3-a]pyridine | 31.8383 | |
| BHN-123. | 4-[3-(trifluoromethyl)[1,2,4]triazolo[4,3-a]pyridin-6-yl]-N-(2,2,2-trifluoro-1-phenylethyl)aniline | 23.357 | |
| BHN-124. | 6-[2-bromo-4-(trifluoromethoxy)phenyl]-3-(trifluoromethyl)[1,2,4]triazolo[4,3-a]pyridine | 81.9921 | |
| BHN-125. | {6-[4-(trifluoromethoxy)phenyl]-3-(trifluoromethyl)imidazo[1,5-a]pyridin-1-yl}methanol | 33.8728 | |
| BHN-126. | 3-(difluoromethyl)-8-methoxy-6-[4-(trifluoromethoxy)phenyl][1,2,4]triazolo[4,3-a]pyridine | 26.8698 | |
| BHN-127. | 3-[(benzyloxy)methyl]-6-[4-(trifluoromethoxy)phenyl][1,2,4]triazolo[4,3-a]pyridine | 93.196 | |
| BHN-128. | 3-[(cyclopropylmethoxy)methyl]-6-[4-(trifluoromethoxy)phenyl][1,2,4]triazolo[4,3-a]pyridine | 65.6436 | |
| BHN-129. | 3-[(2,2,2-trifluoroethoxy)methyl]-6-[4-(trifluoromethoxy)phenyl][1,2,4]triazolo[4,3-a]pyridine | 48.3508 | |
| BHN-130. | {6-[4-(trifluoromethoxy)phenyl][1,2,4]triazolo[4,3-a]pyridin-3-yl}methanol | 21.9314 | |
| BHN-131. | 6-[2-(2-methoxypyrimidin-5-yl)-4-(trifluoromethoxy)phenyl]-3-(trifluoromethyl)[1,2,4]triazolo[4,3-a]pyridine | 18.5361 | |
| BHN-132. | 6-[2-(pyridin-3-yl)-4-(trifluoromethoxy)phenyl]-3-(trifluoromethyl)[1,2,4]triazolo[4,3-a]pyridine | 29.4015 | |
| BHN-133. | 1-melhyl-6-[4-(trifluoromethoxy)phenyl]-3-(trifluoromethyl)imidazo[1,5-a]pyridine | 42.4689 | |
| BHN-134. | 2-(trifluoromethoxy)-5-[3-(trifluoromethyl)[1,2,4]triazolo[4,3-a]pyridin-6-yl]aniline | 27.754 | |
| BHN-135. | 1-{4-[3-(trifluoromethyl)[1,2,4]triazolo[4,3-a]pyridin-6-yl]phenyl}cyclopentanecarbonitrile | 49.1989 | |
| BHN-136. | 3-(1,1-difluoro-2-methoxyethyl)-6-(4-phenoxyphenyl)[3,2,4]triazolo[4,3-a]pyridine | 44.9887 | |
| BHN-137. | 6-[4-(4-chlorophenoxy)phenyl]-3-(1,1-difluoro-2-methoxyethyl)[1,2,4]triazolo[4,3-a]pyridine | 48.1809 | |
| BHN-138. | 3-(1,1-difluoro-2-methoxyethyl)-6-[4-(4-fluorophenoxy)phenyl][1,2,4]triazolo[4,3-a]pyridine | 42.777 | |
| BHN-139. | 3-[1,1-difluoro-2-(pyridin-3-ylmethoxy)ethyl]-6-[4-(trifluoromethoxy)phenyl][1,2,4]triazolo[4,3-a]pyridine | 15.3935 | |
| BHN-140. | 3-[difluoro(methoxy)methyl]-6-[4-(trifluoromethoxy)phenyl][1,2,4]triazolo[4,3-a]pyridine | 53.2223 | |
| BHN-141. | 3-[difluoro(2-methoxyethoxy)methyl]-6-[4-(trifluoromethoxy)phenyl][1,2,4]triazolo[4,3-a]pyridine | 32.4632 | |
| BHN-142. | 3-{difluoro[(3-methyloxetan-3-yl)methoxy]methyl}-6-[4-(trifluoromethoxy)phenyl][1,2,4]triazolo[4,3-a]pyridine | 38.7883 | |
| BHN-143. | 3-phenoxy-6-[4-(trifluoromethoxy)phenyl][1,2,4]triazolo[4,3-a]pyridine | 81.4091 | |

TABLE 1-continued

Late INa Assay results

| Example No. | Name | LateINa_1 uM | LateINa_10 uM |
|---|---|---|---|
| BHN-144. | 3-(1,1-difluoro-2-methoxyethyl)-6-[6-(2,2,2-trifluoroethoxy)pyridin-3-yl][1,2,4]triazolo[4,3-a]pyridine | 36.3798 | |
| BHN-145. | 6-[2-fluoro-4-(trifluoromethoxy)phenyl]-3-(trifluoromethyl)[1,2,4]triazolo[4,3-a]pyridine | 55.3219 | |
| BHN-146. | 6-[3-fluoro-4-(trifluoromethoxy)phenyl]-3-(trifluoromethyl)[1,2,4]triazolo[4,3-a]pyridine | 58.2431 | |
| BHN-147. | 3-{difluoro[(5-methyl-1,2,4-oxadiazol-3-yl)methoxy]methyl}-6-[4-(trifluoromethoxy)phenyl][1,2,4]triazolo{4,3-a]pyridine | 29.0541 | |
| BHN-148. | 3-[(benzyloxy)(difluoro)methyl]-6-[4-(trifluoromethoxy)phenyl][1,2,4]triazolo[4,3-a]pyridine | 71.6539 | |
| BHN-149. | 3-[difluoro(pyridin-4-ylmethoxy)methyl]-6-[4-(trifluoromethoxy)phenyl][1,2,4]triazolo[4,3-a]pyridine | 34.0139 | |
| BHN-150. | 2-(2,2-difluoro-2-{6-[4-(trifluoromethoxy)phenyl][1,2,4]triazolo[4,3-a]pyridin-3-yl}ethoxy)-N,N-dimethylethanamine | 15.6231 | |
| BHN-151. | 6-[4-(cyclopropylmethoxy)phenyl]-3-(trifluoromethyl)[1,2,4]triazolo[4,3-a]pyridine | 43.0922 | |
| BHN-152. | 6-[2-methoxy-4-(trifluoromethoxy)phenyl]-3-(trifluoromethyl)[1,2,4]triazolo[4,3-a]pyridine | 71.7552 | |
| BHN-153. | 6-[3-(1,3,4-oxadiazol-2-yl)-4-(trifluoromethoxy)phenyl]-3-(trifluoromethyl)[1,2,4]triazolo[4,3-a]pyridine | 17.1762 | |
| BHN-154. | 1-(4-(3-(trifluoromethyl)-[1,2,4]triazolo[4,3-a]pyridin-6-yl)phenyl)ethanone | 19.2153 | |
| BHN-155. | 2,2,2-trifluoro-1-{6-[4-(trifluoromethoxy)phenyl][1,2,4]triazolo[4,3-a]pyridin-3-yl}ethanol | 16.193 | |
| BHN-156. | (2,2-difluoro-2-{6-[4-(trifluoromethoxy)phenyl][1,2,4]triazolo[4,3-a]pyridin-3-yl}ethoxy)acetonitrile | 22.3286 | |
| BHN-157. | 2-(difluoro{6-[4-(trifluoromethoxy)phenyl][1,2,4]triazolo[4,3-a]pyridin-3-yl}methoxy)ethanol | 18.2775 | |
| BHN-158. | 1-(difluoro{6-[4-(trifluorotmethoxy)phenyl][1,2,4]triazolo[4,3-a]pyridin-3-yl}methoxy)propan-2-ol | 32.8836 | |
| BHN-159. | 3-{6-[2-methyl-4-(trifluoromethoxy)phenyl][1,2,4]triazolo[4,3-b]pyridazin-3-yl}benzonitrile | | |
| BHN-160. | 3-(2-chloro-1,1-difluoroethyl)-6-[4-(trifluoromethoxy)phenyl][1,2,4]triazolo[4,3-a]pyridine | 61.9972 | |
| BHN-161. | 5-(trifluoromethoxy)-8-[3-(trifluoromethyl)[1,2,4]triazolo[4,3-a]pyridin-6-yl]quinoline | 49.498 | |
| BHN-162. | 6-[4-(2-methyl-1,3-dioxolan-2-yl)phenyl]-3-(trifluoromethyl)[1,2,4]triazolo[4,3-a]pyridine | 29.9168 | |
| BHN-163. | 6-(phenylethynyl)-3-(trifluoromethyl)[1,2,4]triazolo[4,3-a]pyridine | 57.2895 | |
| BHN-164. | 6-[3-chloro-4-(trifluoromethoxy)phenyl]-3-(trifluoromethyl)[1,2,4]triazolo[4,3-a]pyridine | 50.7435 | |
| BHN-165. | 1,1-difluoro-1-{6-[4-(trifluoromethoxy)phenyl][1,2,4]triazolo[4,3-a]pyridin-3-yl}propan-2-ol | 28.0578 | |
| BHN-166. | 1-cyclopropyl-2,2-difluoro-2-{6-[4-(trifluoromethoxy)phenyl][1,2,4]triazolo[4,3-a]pyridin-3-yl}ethanol | 29.4783 | |
| BHN-167. | ethyl (2,2-difluoro-2-{6-[4-(trifluoromethoxy)phenyl][1,2,4]triazolo[4,3-a]pyridin-3-yl}ethoxy)acetate | 45.8073 | |
| BHN-168. | N,N-dimethyl-6-[4-(trifluoromethoxy)phenyl][1,2,4]triazolo[4,3-a]pyridin-3-amine | 36.0758 | |
| BHN-169. | (2E)-3-{4-[3-(trifluoromethyl)[1,2,4]triazolo[4,3-a]pyridin-6-yl]phenyl}but-2-enenitrile | 30.5402 | |
| BHN-170. | 3-(phenylsulfanyl)-6-[4-(trifluoromethoxy)phenyl][1,2,4]triazolo[4,3-a]pyridine | 66.193 | |
| BHN-171. | 3-(cyclopropylethynyl)-6-[4-(trifluoromethoxy)phenyl][1,2,4]triazolo[4,3-a]pyridine | 49.2574 | |
| BHN-172. | 3-[1,1-difluoro-2-(pyridin-2-y)methoxy)ethyl]-6-[4-(trifluoromethoxy)phenyl][1,2,4]triazolo[4,3-a]pyridine | 30.6872 | |
| BHN-173. | 2-methyl-4-{6-[4-(trifluoromethoxy)phenyl][1,2,4]triazolo[4,3-a]pyridin-3-yl}but-3-yn-2-ol | 30.761 | |

TABLE 1-continued

Late INa Assay results

| Example No. | Name | LateINa__1 uM | LateINa__10 uM |
|---|---|---|---|
| BHN-174. | N-methyl-2-(trifluoromethoxy)-5-[3-(trifluoromethyl)[1,2,4]triazolo[4,3-a]pyridin-6-yl]benzamide | 16.021 | |
| BHN-175. | N-(2,2-difluoro-2-{6-[4-(trifluoromethoxy)phenyl][1,2,4]triazolo[4,3-a]pyridin-3-yl}ethyl)methanesulfonamide | 16.3147 | |
| BHN-176. | 1,1-difluoro-2-methyl-1-{6-[4-(trifluoromethoxy)phenyl][1,2,4]triazolo[4,3-a]pyridin-3-yl}propan-2-ol | 15.2148 | |
| BHN-177. | 3-(trifluoromethyl)-6-{[4-(trifluoromethyl)phenyl]ethynyl}[1,2,4]triazolo[4,3-a]pyridine | 23.6006 | |
| BHN-178. | 6-[2-(2-methoxyethoxy)-4-(trifluoromethoxy)phenyl]-3-(trifluoromethyl)[1,2,4]triazolo[4,3-a]pyridine | 28.5149 | |
| BHN-179. | 6-[6-(2,2,2-trifluoroethoxy)pyridin-3-yl]-3-(trifluoromethyl)imidazo[1,5-a]pyridine | 49.6909 | |
| BHN-180. | 6-[6-(cyclopropyloxy)pyridin-3-yl]-3-(trifluoromethyl)[1,2,4]triazolo[4,3-a]pyridine | 21.0867 | |
| BHN-181. | {5-(trifluoromethoxy)-2-[3-(trifluoromethyl)[1,2,4]triazolo[4,3-a]pyridin-6-yl]phenoxy}acetonitrile | 18.745 | |
| BHN-182. | 6-[3-(3-methyl-1,2,4-oxadiazol-5-yl)-4-(trifluoromethoxy)phenyl]-3-(trifluoromethyl)[1,2,4]triazolo[4,3-a]pyridine | 18.9433 | |
| BHN-183. | 6-(1,3-oxazol-2-yl)-3-(trifluoromethyl)imidazo[1,5-a]pyridine | 19.4806 | |
| BHN-184. | N-(2,2-difluoro-2-{6-[4-(trifluoromethoxy)phenyl][1,2,4]triazolo[4,3-a]pyridin-3-yl}ethyl)pyridine-2-carboxamide | 29.83 | |
| BHN-185. | 3-methoxy-6-[4-(trifluoromethoxy)phenyl][1,2,4]triazolo[4,3-a]pyridine | 29.11 | |
| BHN-186. | 3-(2,2,2-trifluoroethoxy)-6-[4-(trifluoromethoxy)phenyl][1,2,4]triazolo[4,3-a]pyridine | 45.1555 | |
| BHN-187. | 6-[6-(2,2,2-trifluoroethoxy)pyridazin-3-yl]-3-(trifluoromethyl)[1,2,4]triazolo[4,3-a]pyridine | 15.2091 | |
| BHN-188. | 3-(1,1-difluoro-2-methoxyethyl)-6-[3-methyl-4-(trifluoromethoxy)phenyl][1,2,4]triazolo[4,3-a]pyridine | 41.2582 | |
| BHN-189. | 6-[4-(trifluoromethoxy)-3-(trifluoromethyl)phenyl]-3-(trifluoromethyl)[1,2,4]triazolo[4,3-a]pyridine | 56.8752 | |
| BHN-190. | 3-{2-[(3,4-difluorobenzyl)oxy]-1,1-difluoroethyl}-6-[4-(trifluoromethoxy)phenyl][1,2,4]triazolo[4,3-a]pyridine | 24.3379 | |
| BHN-191. | 6-(1,3-thiazol-2-yl)-3-(trifluoromethyl)imidazo[1,5-a]pyridine | 19.7625 | |
| BHN-192. | 3-(1,1-difluoro-2-methoxyethyl)-6-(phenylethynyl)[1,2,4]triazolo[4,3-a]pyridine | 31.0201 | |
| BHN-193. | 3-{difluoro[(5-methyl-1,2-oxazol-3-yl)methoxy]methyl}-6-[4-(trifluoromethoxy)phenyl][1,2,4]triazolo[4,3-a]pyridine | 54.7255 | |
| BHN-194. | 6-phenyl-3-(trifluoromethyl)imidazo[1,5-a]pyridine | 22.1586 | |
| BHN-195. | 1-{4-[3-(trifluoromethyl)[1,2,4]triazolo[4,3-a]pyridin-6-yl]phenyl}cyclopropanecarbonitrile | 47.3307 | |
| BHN-196. | 2-[3-(trifluoromethyl)imidazo[1,5-a]pyridin-6-yl]-1,3-benzoxazole | 26.84 | |
| BHN-197. | 3-(difluoro{6-[4-(trifluoromethoxy)phenyl][1,2,4]triazolo[4,3-a]pyridin-3-yl}methyl)pentan-3-ol | 25.3533 | |
| BHN-198. | 2,2-difluoro-2-(6-{[4-(trifluoromethyl)phenyl]ethynyl}[1,2,4]triazolo[4,3-a]pyridin-3-yl)ethanol | 17.4232 | |
| BHN-199. | 6-[2,4-bis(trifluoromethyl)phenyl]-3-(trifluoromethyl)[1,2,4]triazolo[4,3-a]pyridine | 20.5936 | |
| BHN-200. | 3-(1,1-difluoro-2-methoxyethyl)-6-[2-methyl-4-(trifluoromethoxy)phenyl][1,2,4]triazolo[4,3-a]pyridine | 40.8285 | |
| BHN-201. | 6-(3,5-difluoro-4-phenoxyphenyl)-3-(propan-2-yl)[1,2,4]triazolo[4,3-b]pyridazine | 29.6644 | |
| BHN-202. | 5-methyl-6-[4-(trifluoromethoxy)phenyl]-3-(trifluoromethyl)[1,2,4]triazolo[4,3-a]pyridine | 74.1576 | |
| BHN-203. | 3-(propan-2-yl)-6-[6-(2,2,2-trifluoroethoxy)pyridin-3-yl][1,2,4]triazolo[4,3-b]pyridazine | 19.2583 | |
| BHN-204. | 3-[difluoro(pyridin-3-ylmethoxy)methyl]-6-[4-(trifluoromethoxy)phenyl][1,2,4]triazolo[4,3-a]pyridine | 43.8565 | |
| BHN-205. | 1-(2,2-difluoro-2-{6-[4-(trifluoromethoxy)phenyl][1,2,4]triazolo[4,3-a]pyridin-3-yl}ethoxy)-2-methylpropan-2-ol | 25.1679 | |

TABLE 1-continued

Late INa Assay results

| Example No. | Name | LateINa_1 uM | LateINa_10 uM |
|---|---|---|---|
| BHN-206. | 3-{[(5-cyclopropyl-1,2,4-oxadiazol-3-yl)methoxy](difluoro)methyl}-6-[4-{trifluoromethoxy)phenyl][1,2,4]triazolo[4,3-a]pyridine | 44.7461 | |
| BHN-207. | 3-(difluoro{5-(2-methylpropyl)-1,2,4-oxadiazol-3-yl]methoxy}methyl)-6-[4-[trifluoromethoxy)phenyl][1,2,4]triazolo[4,3-a]pyridine | 60.2606 | |
| BHN-208. | 3-(difluoro{5-(propan-2-yl)-1,2,4-oxadiazol-3-yl]methoxy}methyl)-6-[4-(trifluoromethoxy)phenyl][1,2,4]triazolo[4,3-a]pyridine | 70.5329 | |
| BHN-209. | 6-[3-fluoro-4-(trifluoromethoxy)phenyl]-3-(trifluoromethyl)[1,2,4]triazolo[4,3-b]pyridazine | 60.9978 | |
| BHN-210. | 6-(3,5-difluoro-4-phenoxyphenyl)-3-(trifluoromethyl)[1,2,4]triazolo[4,3-b]pyridazine | 33.773 | |
| BHN-211. | 3-[difluoro(pyridin-2-ylmethoxy)methyl-6-[4-{trifluoromethoxy)phenyl][1,2,4]triazolo[4,3-a]pyridine | 57.4166 | |
| BHN-212. | 4-[(difluoro{6-[4-(trifluoromethoxy)phenyl][1,2,4]triazolo[4,3-a]pyridin-3-yl}methoxy)methyl]quinoline | 59.6452 | |
| BHN-213. | 2-[3-(trifluoromethyl)imidazo[1,5-a]pyridin-6-yl]-1,3-benzothiazole | 23.9625 | |
| BHN-214. | 3-[(cyclopropylmethoxy)(difluoro)methyl]-6-[4-(trifluoromethoxy)phenyl][1,2,4]triazolo[4,3-a]pyridine | 80.8168 | |
| BHN-215. | 3-{difluoro[(1-phenyl-1H-1,2,3-triazol-4-yl)methoxy]methyl}-6-[4-(trifluoromethoxy)phenyl][1,2,4]triazolo[4,3-a]pyridine | 36.4338 | |
| BHN-216. | 3-[difluoro(pyridazin-3-ylmethoxy)methyl]-6-[4-(trifluoromethoxy)phenyl][1,2,4]triazolo[4,3-a]pyridine | 26.1001 | |
| BHN-217. | 3-{difluoro[3-(4-fluorophenyl)ethoxy]methyl}-6-[4-(trifluoromethoxy)phenyl][1,2,4]triazolo[4,3-a]pyridine | 16.834 | |
| BHN-218. | 6-[4-(4-chlorophenoxy)phenyl]tetrazolo[1,5-a]pyridine | 35.9854 | |
| BHN-219. | 6-[6-(2,2,2-trifluoroethoxy)pyridin-3-yl]tetrazolo[1,5-a]pyridine | 36.8658 | |
| BHN-220. | 6-[4-(2-methoxypropan-2-yl)phenyl]-3-(trifluoromethyl)[1,2,4]triazolo[4,3-a]pyridine | 58.508 | |
| BHN-221. | 6-[6-(2,2,2-trifluoroethoxy)pyridin-3-yl]-3-(trifluoromethyl)[1,2,4]triazolo[4,3-b]pyridazine | 55.0196 | |
| BHN-222. | 6-[2-ethoxy-4-(trifluoromethoxy)phenyl]-3-(trifluoromethyl)[1,2,4]triazolo[4,3-a]pyridine | 65.3354 | |
| BHN-223. | 6-[2-(propan-2-yloxy)-4-(trifluoromethoxy)phenyl]-3-(trifluoromethyl)[1,2,4]triazolo[4,3-a]pyridine | 54.5146 | |
| BHN-224. | 3-{difluoro[(1-methyl-5-phenyl-1H-pyrazol-3-yl)methoxy]methyl}-6-[4-(trifluoromethoxy)phenyl][1,2,4]triazolo[4,3-a]pyridine | 24.1854 | |
| BHN-225. | 3-{[(2,2-difluoro-1,3-benzodioxol-5-yl)methoxy](difluoro)methyl}-6-[4-(trifluoromethoxy)phenyl][1,2,4]triazolo[4,3-a]pyridine | 63.0442 | |
| BHN-226. | 6-[4-(trifluoromethoxy)phenyl]-3-({[4-(trifluoromethyl)benzyl]oxy}methyl)[1,2,4]triazolo[4,3-a]pyridine | 59.326 | |
| BHN-227. | 3-{[(4-fluorobenzyl)oxy]methyl}-6-[4-(trifluoromethoxy)phenyl][1,2,4]triazolo[4,3-a]pyridine | 79.7579 | |
| BHN-228. | 3-{[(2,5-dimethyl-1,3-oxazol-4-yl)methoxy](difluoro)methyl}-6-[4-(trifluoromethoxy)phenyl][1,2,4]triazolo[4,3-a]pyridine | 73.0091 | |
| BHN-229. | 3-{difluoro[(5-methyl-2-phenyl-1,3-oxazol-4-yl)methoxy]methyl}-6-[4-(trifluoromethoxy)phenyl][1,2,4]triazolo[4,3-a]pyridine | 72.1636 | |
| BHN-230. | 3-{difluoro[1-(pyridin-2-yl)ethoxy]methyl}-6-[4-(trifluoromethoxy)phenyl][1,2,4]triazolo[4,3-a]pyridine | 42.2926 | |
| BHN-231. | 3-{[1-(4-chlorophenyl)ethoxy](difluoro)methyl}-6-[4-(trifluoromethoxy)phenyl][1,2,4]triazolo[4,3-a]pyridine | 62.9341 | |
| BHN-232. | 3-(1,1-difluoro-2-methoxyethyl)-6-[3-fluoro-4-(trifluoromethoxy)phenyl][1,2,4]triazolo[4,3-a]pyridine | 45.3007 | |
| BHN-233. | 3-(1,1-difluoro-2-methoxyethyl)-6-(3,5-difluoro-4-phenoxyphenyl)[1,2,4]triazolo[4,3-a]pyridine | 31.397 | |
| BHN-234. | 3-(1,1-difluoro-2-methoxyethyl)-6-{[4-(trifluoromethyl)phenyl]ethynyl}[1,2,4]triazolo[4,3-a]pyridine | 57.8164 | |
| BHN-235. | 3-(2-{[3-(4-chlorophenyl)-1,2-oxazol-5-yl]methoxy}-1,1-difluoroethyl)-6-[4-(trifluoromethoxy)phenyl][1,2,4]triazolo[4,3-a]pyridine | 41.5423 | |
| BHN-236. | 6-[4-(4-chlorophenoxy)phenyl]-3-(trifluoromethyl)[1,2,4]triazolo[4,3-b]pyridazine | 39.9596 | |
| BHN-237. | 3-(difluoromethyl)-6-[6-(2,2,2-trifluoroethoxy)pyridin-3-yl][1,2,4]triazolo[4,3-b]pyridazine | 44.7068 | |

TABLE 1-continued

Late INa Assay results

| Example No. | Name | LateINa_1 uM | LateINa_10 uM |
|---|---|---|---|
| BHN-238. | 3-{[(2-fluorobenzyl)oxy]methyl}-6-[4-(trifluoromethoxy)phenyl][1,2,4]triazolo[4,3-a]pyridine | 80.6183 | |
| BHN-239. | 6-[4-(trifluoromethoxy)phenyl]-3-({[2-(trifluoromethyl)benzyl]oxy}methyl)[1,2,4]triazolo[4,3-a]pyridine | 65.115 | |
| BHN-240. | 3-{[(2,4-difluorobenzyl)oxy]methyl}-6-[4-(trifluoromethoxy)phenyl][1,2,4]triazolo[4,3-a]pyridine | 83.3836 | |
| BHN-241. | 3-{[(4-chlorobenzyl)oxy]methyl}-6-[4-(trifluoromethoxy)phenyl][1,2,4]triazolo[4,3-a]pyridine | 82.2111 | |
| BHN-242. | 3-({[4-(trifluoromethoxy)benzyl]oxy}methyl)-6-[4-(trifluoromethoxy)phenyl][1,2,4]triazolo[4,3-a]pyridine | 72.2094 | |
| BHN-243. | N-(2,2-difluoro-2-{6-[4-(trifluoromethoxy)phenyl][1,2,4]triazolo[4,3-a]pyridin-3-yl}ethyl)benzamide | 20.9902 | |
| BHN-244. | 3-[(pyridin-2-ylmethoxy)methyl]-6-[4-(trifluoromethoxy)phenyl][1,2,4]triazolo[4,3-a]pyridine | 17.5037 | |
| BHN-245. | 3-[difluoro(pyrimidin-2-ylmethoxy)methyl]-6-[4-(trifluoromethoxy)phenyl][1,2,4]triazolo[4,3-a]pyridine | 38.7693 | |
| BHN-246. | 3-[(1-phenylethoxy)methyl]-6-[4-(trifluoromethoxy)phenyl][1,2,4]triazolo[4,3-a]pyridine | 85.8171 | |
| BHN-247. | 3-{[1-(2,4-dichlorophenyl)ethoxy](difluoro)methyl}-6-[4-(trifluoromethoxy)phenyl][1,2,4]triazolo[4,3-a]pyridine | 74.1378 | |
| BHN-248. | 1-[(difluoro-{6-[4-(trifluoromethoxy)phenyl][1,2,4]triazolo[4,3-a]pyridin-3-yl}methoxy)methyl]cyclobutanol | 50.2191 | |
| BHN-249. | 3-{1-[difluoro(pyridin-3-yl)methoxy]ethyl}-6-[4-(trifluoromethoxy)phenyl][1,2,4]triazolo[4,3-a]pyridine | 22.7039 | |
| BHN-250. | 3-{[(2,4-dichlorobenzyl)oxy]methyl}-6-[4-(trifluoromethoxy)phenyl][1,2,4]triazolo[4,3-a]pyridine | 79.0732 | |
| BHN-251. | 3-{[(2,4-dimethylbenzyl)oxy]methyl}-6-[4-(trifluoromethoxy)phenyl][1,2,4]triazolo[4,3-a]pyridine | 75.7567 | |
| BHN-252. | 3-{[(5-methylpyridin-2-yl)methoxy]methyl}-6-[4-(trifluoromethoxy)phenyl][1,2,4]triazolo[4,3-a]pyridine | 20.6482 | |
| BHN-253. | 3-(difluoromethyl)-6-[3-fluoro-4-(trifluoromethoxy)phenyl][1,2,4]triazolo[4,3-b]pyridazine | 39.3884 | |
| BHN-254. | 4-{4-[3-(trifluoromethyl)[1,2,4]triazolo[4,3-a]pyridin-6-yl]phenyl}tetrahydro-2H-pyran-4-carbonitrile | 24.5777 | |
| BHN-255. | 3-[1-(pyridin-2-ylmethoxy)ethyl]-6-[4-(trifluoromethoxy)phenyl][1,2,4]triazolo[4,3-a]pyridine | 22.7999 | |
| BHN-256. | tert-butyl (2S)-2-[(difluoro{6-[4-(trifluoromethoxy)phenyl][1,2,4]triazolo[4,3-a]pyridin-3-yl}methoxy)methyl]pyrrolidine-1-carboxylate | 62.5676 | |
| BHN-257. | 3-{[difluoro(pyridin-3-yl)methoxy]methyl}-6-[4-(trifluoromethoxy)phenyl][1,2,4]triazolo[4,3-a]pyridine | 46.2206 | |
| BHN-258. | 6-[4-(trifluoromethoxy)phenyl]-3-[3-(trifluoromethyl)phenoxy][1,2,4]triazolo[4,3-a]pyridine | 80.1084 | |
| BHN-259. | 3-{[(5-cyclobutyl-1,2,4-oxadiazol-3-yl)methoxy](difluoro)methyl}-6-[4-(trifluoromethoxy)phenyl][1,2,4]triazolo[4,3-a]pyridine | 71.5761 | |
| BHN-260. | 3-(4,4-difluoropiperidin-1-yl)-6-[4-(trifluoromethoxy)phenyl][1,2,4]triazolo[4,3-a]pyridine | 38.4527 | |
| BHN-261. | 3-[(difluoro{6-[4-(trifluoromethoxy)phenyl][1,2,4]triazolo[4,3-a]pyridin-3-yl}methoxy)methyl]benzonitrile | 56.8413 | |
| BHN-262. | 3-(difluoro{3-[(2-methoxyphenyl)sulfanyl]-2-methylpropoxy}methyl)-6-[4-(trifluoromethoxy)phenyl][1,2,4]triazolo[4,3-a]pyridine | 47.7989 | |
| BHN-263. | 1-(2,2-difluoro-2-{6-[4-(trifluoromethoxy)phenyl][1,2,4]triazolo[4,3-a]pyridin-3-yl}ethyl)-3-phenylurea | 22.5529 | |
| BHN-264. | 3-(difluoro{2-[4-(4-methoxyphenyl)piperazin-1-yl]ethoxy}methyl)-6-[4-(trifluoromethoxy)phenyl][1,2,4]triazolo[4,3-a]pyridine | 54.3394 | |
| BHN-265. | 6-[4-(trifluoromethoxy)phenyl][1,2,4]triazolo[4,3-a]pyridine-3-carboxamide | 15.3022 | |
| BHN-266. | 3-{[(3-cyclopropyl-1-methyl-1H-pyrazol-5-yl)methoxy](difluoro)methyl}-6-[4-(trifluoromethoxy)phenyl][1,2,4]triazolo[4,3-a]pyridine | 50.2004 | |
| BHN-267. | 1-(2-chlorophenoxy)-3-(2,2-difluoro-2-{6-[4-(trifluoromethoxy)phenyl][1,2,4]triazolo[4,3-a]pyridin-3-yl}-ethoxy)propan-2-ol | 26.5068 | |
| BHN-268. | 8-methyl-6-[4-(trifluoromethoxy)phenyl]tetrazolo[1,5-a]pyridine | 43.151 | |

TABLE 1-continued

Late INa Assay results

| Example No. | Name | LateINa_1 uM | LateINa_10 uM |
|---|---|---|---|
| BHN-269. | 5-methyl-6-[4-(trifluoromethoxy)phenyl]tetrazolo[1,5-a]pyridine | 44.6912 | |
| BHN-270. | 6-[4-(4-chlorophenoxy)phenyl]tetrazolo[1,5-b]pyridazine | 21.7058 | |
| BHN-271. | 6-{4-[difluoro(pyridin-3-yl)methoxy]phenyl}-3-(trifluoromethyl)[1,2,4]triazolo[4,3-a]pyridine | 19.8602 | |
| BHN-272. | 6-{4-[difluoro(phenyl)methoxy]phenyl}-3-(trifluoromethyl)[1,2,4]triazolo[4,3-a]pyridine | 64.8954 | |
| BHN-273. | 3-(2-methylphenoxy)-6-[4-(trifluoromethoxy)phenyl][1,2,4]triazolo[4,3-a]pyridine | 68.6671 | |
| BHN-274. | 1-(2,2-difluoro-2-{6-[4-(trifluoromethoxy)phenyl][1,2,4]triazolo[4,3-a]pyridin-3-yl}ethoxy)-3-(2,5-dimethylphenoxy)propan-2-ol | 38.8563 | |
| BHN-275. | 3-[(cyclopropylmethoxy)(difluoro)methyl]-6-[6-(trifluoromethyl)pyridin-3-yl][1,2,4]triazolo[4,3-a]pyridine | 28.6093 | |
| BHN-276. | 5-chloro-2-({4-[3-(trifluoromethyl)[1,2,4]triazolo[4,3-a]pyridin-6-yl]phenyl}amino)benzonitrile | 16.248 | |
| BHN-277. | 5-(methoxymethyl)-6-[4-(trifluoromethoxy)phenyl]-3-(trifluoromethyl)[1,2,4]triazolo[4,3-a]pyridine | 38.0075 | |
| BHN-278. | N-methyl-N-phenyl-4-[3-(trifluoromethyl)[1,2,4]triazolo[4,3-a]pyridin-6-yl]aniline | 54.2033 | |
| BHN-279. | ({6-[4-(trifluoromethoxy)phenyl]-3-(trifluoromethyl)[1,2,4 triazolo[4,3-a]pyridin-5-yl}methoxy)acetonitrile | 19.1346 | |
| BHN-280. | 4-(difluoro{4-[3-(trifluoromethyl)[1,2,4]triazolo[4,3-a]pyridin-6-yl]phenoxy}methyl)benzonitrile | 63.6981 | |
| BHN-281. | 5-[(difluoro{6-[4-(trifluoromethoxy)phenyl][1,2,4]triazolo[4,3-a]pyridin-3-yl}methoxy)methyl]quinoline | 53.9362 | |
| BHN-282. | 3-[1-(difluoro{6-[4-(trifluoromethoxy)phenyl][1,2,4]triazolo[4,3-a]pyridin-3-yl}methoxy)ethyl]quinoline | 62.7413 | |
| BHN-283. | 4-chloro-N-{4-[3-(trifluoromethyl)[1,2,4]triazolo[4,3-a]pyridin-6-yl]phenyl}aniline | 27.1761 | |
| BHN-284. | 4-fluoro-N-{4-[3-(trifluoromethyl)[1,2,4]triazolo[4,3-a]pyridin-6-yl]phenyl}aniline | 31.3958 | |
| BHN-285. | 3-{[2-(2,6-dimethylphenoxy)ethoxy](difluoro)methyl}-6-[4-(trifluoromethoxy)phenyl][1,2,4]triazolo[4,3-a]pyridine | 68.0043 | |
| BHN-286. | 6-[4-(pentafluoro-lambda~6~-sulfanyl)phenyl]-3-(trifluoromethyl)[1,2,4]triazolo[4,3-a]pyridine | 56.4045 | |
| BHN-287. | 3-{difluoro[(1-phenyl-1H-pyrazol-4-yl)methoxy]methyl}-6-[4-(trifluoromethoxy)phenyl][1,2,4]triazolo[4,3-a]pyridine | 47.119 | |
| BHN-288. | 3-[difluoro({2-[4-(trifluoromethyl)phenyl]-1,3-oxazol-4-yl}methoxy)methyl]-6-[4-(trifluoromethoxy)phenyl][1,2,4]triazolo[4,3-a]pyridine | 39.2489 | |
| BHN-289. | 4-[(difluoro{6-[4-(trifluoromethoxy)phenyl][1,2,4]triazolo[4,3-a]pyridin-3-yl}methoxy)methyl]-2-methylquinoline | 47.9164 | |
| BHN-290. | 4-[(difluoro{6-[4-(trifluoromethoxy)phenyl][1,2,4]triazolo[4,3-a]pyridin-3-yl}methoxy)methyl]-2-(trifluoromethyl)quinoline | 34.6127 | |
| BHN-291. | 6-[(difluoro{6-[4-(trifluoromethoxy)phenyl][1,2,4]triazolo[4,3-a]pyridin-3-yl}methoxy)methyl]quinoxaline | 47.0299 | |
| BHN-292. | 6-(2-chloro-4-nitrophenyl)-3-(trifluoromethyl)[1,2,4]triazolo[4,3-a]pyridine | 25.9657 | |
| BHN-293. | 3-[(but-2-yn-1-yloxy)(difluoro)methyl]-6-[4-(trifluoromethoxy)phenyl][1,2,4]triazolo[4,3-a]pyridine | 80.6107 | |
| BHN-294. | 3-{[(2,2-difluorocyclopropyl)methoxy](difluoro)methyl}-6-[4-(trifluoromethoxy)phenyl][1,2,4]triazolo[4,3-a]pyridine | 77.5676 | |
| BHN-295. | 3-{difluoro[(3-phenylprop-2-yn-1-yl)oxy]methyl}-6-[4-(trifluoromethoxy)phenyl][1,2,4]triazolo[4,3-a]pyridine | 87.7093 | |
| BHN-296. | 3-{difluoro[(1-methyl-1H-benzimidazol-2-yl)methoxy]methyl}-6-[4-(trifluoromethoxy)phenyl][1,2,4]triazolo[4,3-a]pyridine | 40.1113 | |
| BHN-297. | 3-{[(1-benzyl-1H-1,2,3-triazol-4-yl)methoxy](difluoro)methyl}-6-[4-(trifluoromethoxy)phenyl][1,2,4]triazolo[4,3-a]pyridine | 63.3909 | |
| BHN-298. | 3-{difluoro[(5-phenyl-1,2-oxazol-3-yl)methoxy]methyl}-6-[4-(trifluoromethoxy)phenyl][1,2,4]triazolo[4,3-a]pyridine | 70.3125 | |

TABLE 1-continued

Late INa Assay results

| Example No. | Name | LateINa_1 uM | LateINa_10 uM |
|---|---|---|---|
| BHN-299. | 3-{difluoro[(2-phenyl-1,3-oxazol-4-yl)methoxy]methyl}-6-[4-(trifluoromethoxy)phenyl][1,2,4]triazolo[4,3-a]pyridine | 51.1075 | |
| BHN-300. | 3-{difluoro[(5-methyl-2-phenyl-2H-1,2,3-triazol-4-yl)methoxy]methyl}-6-[4-(trifluoromethoxy)phenyl][1,2,4]triazolo[4,3-a]pyridine | 62.965 | |
| BHN-301. | 3-{difluoro[(1-methyl-1H-pyrazol-3-yl)methoxy]methyl}-6-[4-(trifluoromethoxy)phenyl][1,2,4]triazolo[4,3-a]pyridine | 29.8716 | |
| BHN-302. | 3-[{[1-(4-chlorophenyl)-5-methyl-1H-pyrazol-3-yl]methoxy}(difluoro)methyl]-6-[4-(trifluoromethoxy)phenyl][1,2,4]triazolo[4,3-a]pyridine | 52.8348 | |
| BHN-303. | 3-[(3,3-diphenylpropoxy)(difluoro)methyl]-6-[4-(trifluoromethoxy)phenyl][1,2,4]triazolo[4,3-a]pyridine | 51.0168 | |
| BHN-304. | 3-phenoxy-6-{[4-(trifluoromethyl)phenyl]ethynyl}[1,2,4]triazolo[4,3-a]pyridine | 28.2018 | |
| BHN-305. | 3-(difluoro{[3-(pyrimidin-2-yl)benzyl]oxy}methyl)-6-[4-(trifluoromethoxy)phenyl][1,2,4]triazolo[4,3-a]pyridine | 59.565 | |
| BHN-306. | 3-(difluoro{[3-(pyridin-3-yl)benzyl]oxy}methyl)-6-[4-(trifluoromethoxy)phenyl][1,2,4]triazolo[4,3-a]pyridine | 49.7279 | |
| BHN-307. | 3-{difluoro[(1-methyl-1H-indazol-3-yl)methoxy]methyl}-6-[4-(trifluoromethoxy)phenyl][1,2,4]triazolo[4,3-a]pyridine | 68.4897 | |
| BHN-308. | 3-[chloro(difluoro)methyl]-6-[4-(trifluoromethoxy)phenyl][1,2,4]triazolo[4,3-a]pyridine | 71.237 | |
| BHN-309. | 3-(1,1-difluoro-2-methoxyethyl)-6-{[4-(trifluoromethoxy)phenyl]ethynyl}[1,2,4]triazolo[4,3-a]pyridine | 25.1867 | |
| BHN-310. | 3-(1,1-difluoro-2-methoxyethyl)-6-[(4-fluorophenyl)ethynyl][1,2,4]triazolo[4,3-a]pyridine | 21.69 | |
| BHN-311. | 3-(difluoro{[2-(1H-1,2,4-triazol-1-yl)benzyl]oxy}methyl)-6-[4-(trifluoromethoxy)phenyl][1,2,4]triazolo[4,3-a]pyridine | 47.274 | |
| BHN-312. | 3-(difluoro{[2-(2-methyl-1H-imidazol-1-yl)benzyl]oxy}methyl)-6-[4-(trifluoromethoxy)phenyl][1,2,4]triazolo[4,3-a]pyridine | 51.3863 | |
| BHN-313. | 3-(difluoro{[2-phenyl-5-(trifluoromethyl)-1,3-oxazol-4-yl]methoxy}methyl)-6-[4-(trifluoromethoxy)phenyl][1,2,4]triazolo[4,3-a]pyridine | 49.9572 | |
| BHN-314. | 3-(difluoro{[1-phenyl-3-(trifluoromethyl)-1H-pyrazol-4-yl]methoxy}methyl)-6-[4-(trifluoromethoxy)phenyl][1,2,4]triazolo[4,3-a]pyridine | 24.1634 | |
| BHN-315. | 3-(difluoro{[6-(1H-pyrazol-1-yl)pyridin-3-yl]methoxy}methyl)-6-[4-(trifluoromethoxy)phenyl][1,2,4]triazolo[4,3-a]pyridine | 55.8573 | |
| BHN-316. | 6-cyclopropyl-2'-[(difluoro{6-[4-(trifluoromethoxy)phenyl][1,2,4]triazolo[4,3-a]pyridin-3-yl}methoxy)methyl]-3,4'-bipyridine | 59.01 | |
| BHN-317. | 3-[{[3-(4-cyclopropyl-1H-imidazol-1-yl)benzyl]oxy}(difluoro)methyl]-6-[4-(trifluoromethoxy)phenyl][1,2,4]triazolo{4,3-a]pyridine | 46.44 | |
| BHN-318. | 3-(difluoro{[5-(4-fluorophenyl)-1,2-oxazol-3-yl]methoxy}methyl)-6-[4-(trifluoromethoxy)phenyl][1,2,4]triazolo[4,3-a]pyridine | 28.92 | |
| BHN-319. | 3-{difluoro[(5-phenyl-1,2-oxazol-3-yl)methoxy]methyl}-6-[6-(trifluoromethyl)pyridin-3-yl][1,2,4]triazolo[4,3-a]pyridine | 30.50 | |
| BHN-320. | 3-(difluoro{[2-(piperidin-1-yl)pyridin-4-yl]methoxy}methyl)-6-[4-(trifluoromethoxy)phenyl][1,2,4]triazolo[4,3-a]pyridine | 76.34 | |
| BHN-321. | 3-{[(2,2-dimethyl-2,3-dihydro-l-benzofuran-7-yl)methoxy](difluoro)methyl}-6-[4-(trifluoromethoxy)phenyl][1,2,4]triazolo[4,3-a]pyridine | 65.59 | |
| BHN-322. | 3-{[2-(2,6-difluorophenyl)ethoxy](difluoro)methyl}-6-[4-(trifluoromethoxy)phenyl][1,2,4]triazolo[4,3-a]pyridine | 72.48 | |
| BHN-323. | 3-{difluoro[(5-phenyl-1,2,4-oxadiazol-3-yl)methoxy]methyl}-6-[4-(trifluoromethoxy)phenyl][1,2,4]triazolo[4,3-a]pyridine | 73.00 | |
| BHN-324. | 3-{difluoro[(5-phenyl-1,2-oxazol-3-yl)methoxy]methyl}-6-[6-(2,2,2-trifluoroethoxy)pyridin-3-yl][1,2,4]triazolo[4,3-a]pyridine | 46.33 | |
| BHN-325. | 3-[{[2-(6-cyclopropylpyridin-3-yl)benzyl]oxy}(difluoro)methyl]-6-[4-(trifluoromethoxy)phenyl][1,2,4]triazolo[4,3-a]pyridine | 68.33 | |

TABLE 1-continued

Late INa Assay results

| Example No. | Name | LateINa_1 uM | LateINa_10 uM |
|---|---|---|---|
| BHN-326. | 3-[{[5-(2-chlorophenyl)-1,2-oxazol-3-yl]methoxy}(difluoro)methyl]-6-[4-(trifluoromethoxy)phenyl][1,2,4]triazolo[4,3-a]pyridine | 52.39 | |
| BHN-327. | 3-(difluoro{[2-(pyridin-3-yl)benzyl]oxy}methyl)-6-[4-(trifluoromethoxy)phenyl][1,2,4]triazolo[4,3-a]pyridine | 54.20 | |
| BHN-328. | 3-(difluoro{[2-(1H-pyrazol-1-yl)benzyl]oxy}methyl)-6-[4-(trifluoromethoxy)phenyl][1,2,4]triazolo[4,3-a]pyridine | 70.86 | |
| BHN-329. | 6-[4-(trifluoromethoxy)phenyl][1,2,4]triazolo[4,3-a]pyridine | | 38.7 |
| BHN-330. | 3-methyl-6-[4-(trifluoromethoxy)phenyl][1,2,4]triazolo[4,3-a]pyridine | | 57.2 |
| BHN-331. | N-ethyl-6-[4-(trifluoromethoxy)phenyl][1,2,4]triazolo[4,3-a]pyridin-3-amine | | 38.2 |
| BHN-332. | 6-(4-phenoxyphenyl)-3-(trifluoromethyl)[1,2,4]triazolo[4,3-a]pyridine | | 83.5 |
| BHN-333. | 3-methyl-6-(4-phenoxyphenyl)[1,2,4]triazolo[4,3-a]pyridine | | 61.6 |
| BHN-334. | N-ethyl-6-(4-phenoxyphenyl)[1,2,4]triazolo[4,3-a]pyridin-3-amine | | 40.6 |
| BHN-335. | 6-[4-(trifluoromethoxy)phenyl]-3-(trifluoromethyl)[1,2,4]triazolo[4,3-a]pyridine | | 87.7 |
| BHN-336. | 7-methyl-6-[4-(trifluoromethoxy)phenyl]-3-(trifluoromethyl)[1,2,4]triazolo[4,3-a]pyridine | | 67.5 |
| BHN-337. | 6-[3-(trifluoromethoxy)phenyl]-3-(trifluoromethyl)[1,2,4]triazolo[4,3-a]pyridine | | 52.9 |
| BHN-338. | 3-(trifluoromethyl)-6-[4-(trifluoromethyl)phenyl][1,2,4]triazolo[4,3-a]pyridine | | 76.8 |
| BHN-339. | 6-(2,4-dichlorophenyl)-3-(trifluoromethyl)[1,2,4]triazolo[4,3-a]pyridine | | 53.5 |
| BHN-340. | 6-[4-(difluoromethoxy)phenyl]-3-(trifluoromethyl)[1,2,4]triazolo[4,3-a]pyridine | | 54 |
| BHN-341. | 6-(3-phenoxyphenyl)-3-(trifluoromethyl)[1,2,4]triazolo[4,3-a]pyridine | | 75.7 |
| BHN-342. | 6-[4-chloro-3-(trifluoromethyl)phenyl]-3-(trifluoromethyl)[1,2,4]triazolo[4,3-a]pyridine | | 51.2 |
| BHN-343. | 6-(4-chloro-3-fluorophenyl)-3-(trifluoromethyl)[1,2,4]triazolo[4,3-a]pyridine | | 28.3 |
| BHN-344. | 6-[4-(trifluoromethoxy)phenyl]-3-(trifluoromethyl)imidazo[1,5-a]pyridine | | 81.3 |
| BHN-345. | 6-(4-phenoxyphenyl)-3-(trifluoromethyl)imidazo[1,5-a]pyridine | | 55.4 |
| BHN-346. | 6-[4-(trifluoromethoxy)phenyl][1,2,4]triazolo[1,5-a]pyridine | | 75.1 |
| BHN-347. | 6-(3-phenoxyphenyl)[1,2,4]triazolo[1,5-a]pyridine | | 73.6 |
| BHN-348. | 2-methyl-6-(3-phenoxyphenyl)[1,2,4]triazolo[1,5-a]pyridine | | 65.7 |
| BHN-349. | 8-methyl-6-(4-phenoxyphenyl)[1,2,4]triazolo[1,5-a]pyridine | | 65.1 |
| BHN-350. | 5-methyl-6-[4-(trifluoromethyl)phenyl][1,2,4]triazolo[1,5-a]pyridine | | 44.5 |
| BHN-351. | 6-[4-(trifluoromethoxy)phenyl]-3-(trifluoromethyl)[1,2,4]triazolo[4,3-b]pyridazine | | 78.8 |
| BHN-352. | 6-(4-phenoxyphenyl)-3-(trifluoromethyl)[1,2,4]triazolo[4,3-b]pyridazine | | 44.7 |
| BHN-353. | 3-(difluoromethyl)-6-[4-(trifluoromethoxy)phenyl][1,2,4]triazolo[4,3-b]pyridazine | | 79.7 |
| BHN-354. | 3-(difluoromethyl)-6-(4-phenoxyphenyl)[1,2,4]triazolo[4,3-b]pyridazine | | 87.1 |
| BHN-355. | 6-(4-phenoxyphenyl)-3-(trifluoromethyl)[1,2,4]triazolo[4,3-a]pyrazine | | 54.3 |

The assay results shown in the above Table 1 establish that compounds tested showed activity as modulators of late sodium current, for example by inhibiting (or reducing) the late sodium current.

In some embodiments the effects of a compound of Formula I are specific for the late sodium current and show little or no activity with respect to one or more other ion channels. Thus, in some embodiments, a compound having an activity of reducing late sodium current will also exhibit little or no activity with regard to the peak sodium current. In particular embodiments, a compound having an activity of reducing late sodium current will also exhibit little or no activity with regard to the hERG potassium channel. In some embodiments, a compound having an activity of reducing late sodium current will also exhibit little or no activity with regard to the L-type calcium channel. For example, a given compound may provide a 30% (or greater, e.g. more than 40%, more than 50%, more than 60%, more than 70%, more than 80%) reduction in late sodium current in the assay described herein, and the same compound may exhibit little or no activity for one or more of the peak sodium current, the hERG potassium channel, and the L-type calcium channel. In this regard, a compound having "little" effect will typically show less then a 30% reduction (e.g. less than a 20% reduction, less than a 15% reduction, less than a 10% reduction) in the given activity (e.g. Peak INa, hERG, L-type calcium), when measured using the assay described herein. In this regard, "no" effect means that any activity measured will differ from the control by less than the standard error of the measurement. The assays conducted to measure activities in this regard should be performed as described above, with the compound at a concentration of 10 µM (or at the upper limit of solubility, if less).

L-type Ca2+ Channel Assay—ChanTest

Selected compounds were screened for block of the cardiac L-type $Ca^{2+}$ channel (hCav1.2, encoded by the human CACNA1C gene and coexpressed with the beta 2 subunit, encoded by the human CACNB2 gene, and alpha2delta1, encoded by the CACNA2D1 gene). The $Ca^{2+}$ channel is heterologously expressed in a CHO (Chinese Hamster Ovary) cell line. Cells are maintained following standard tissue culture procedures and stable channel expression is maintained with appropriate selection antibiotics in the culture medium. Cells are harvested for testing on the PatchXpress automated patch clamp (Model 7000A, Molecular Devices, Sunnyvale, Calif.) by washing twice with Hank's Balanced Salt Solution, treating the cells with trypsin, and re-suspending cells in culture medium ($4\text{-}6\times10^6$ cells in 20 mL). Cells in suspension are allowed to recover for 10 minutes in a tissue culture incubator set at 37° C. in a humidified 95% air, 5% $CO_2$ atmosphere.

The following solutions are used for electrophysiological recordings. The external solution contains (mM): 137 NaCl, 4 KCl, 1.8 CaCl2, 1 MgCl2, 10 Glucose, 10 HEPES (pH 7.4 with NaOH). The internal solution contains (mM): 130 Cs Aspartate, 5 MgCl2, 5 EGTA, 4 ATP, 0.1 GTP, 10 HEPES, (pH adjusted to 7.2 with N-methyl-D-glucamine).

Vehicle is applied to naïve cells (n≥2, where n=the number cells), for a 5-10 minute exposure interval. Each solution exchange is performed in quadruplicate. At the end of each experiment, a saturating concentration of nifedipine (10 µM) is added to block hCav1.2 current. Leak current is digitally subtracted from the total membrane current record.

Test compound stock solutions are prepared by addition of dimethyl sulfoxide (DMSO) and stored frozen. Each test compound DMSO stock is sonicated (Model 2510/5510, Branson Ultrasonics, Danbury, Conn.), at ambient room temperature for at least 20 minutes to facilitate dissolution. Test compound concentrations are prepared fresh daily by diluting stock solutions into the standard extracellular physiological saline solution (see above). The maximum percent of DMSO added with compound is 0.1%. All test compound and control solutions are placed in a glass-lined 96-well compound plate before loading on PatchXpress.

One or two concentrations (1, 10 µM) of each test compound is applied at five (5) minute intervals via disposable polyethylene micropipette tips to naïve cells (n≥2, where n=the number cells/concentration). Each test compound concentration is added to the cell in quadruplicate. Total duration of exposure to each test compound concentration is 5 minutes.

Onset and steady state block of hCav1.2 (α1C/β2/α2 δ) channels is measured using a stimulus voltage pattern consisting of a depolarizing test pulse (duration, 200 ms; amplitude, 10 mV) at 10 s intervals from a −80 mV holding potential. Peak current is measured during a step to 10 mV.

EXAMPLE 39

$Na_v1.7$ Screening Assay:

Evidence supports a role for the tetrodotoxin-sensitive $Na_v1.7$ in the pathogenesis of pain. In this assay, whole-cell patch-clamp techniques were used to determine the effects of compounds of Formula (I) on human Nav1.7 (hNav1.7+β1 subunits) channels expressed in HEK293 cells. The $Na_v1.7$ cell line was prepared by stably transfecting HEK293 cells with human $Na_v1.7$ cc unit and (β1 subunit. HEK293 cells stably expressing hu$Na_v1.7$ were analysed by patch clamp techniques and were found to have $Na^+$ currents between −400 and −1800 pA (no currents were recorded in untransfected cells). The $Na^+$ current in these cells was blocked by tetrodotoxin (TTX) with an $IC_{50}$ value of 10-74 nmol/L. Similar results were obtained by use of membrane potential-sensitive dyes.

Stock solutions of compounds of Formula I ("test compounds") were prepared in DMSO at a concentration of 40 mmol/L just prior to use. Each test compound was tested in duplicate at 100 µM, then a 1 in 4 serial dilution to yield 8 concentrations for testing. TTX was used as a control inhibitor of $Na_v1.7$ current.

The effect of test compounds to reduce $Na_v1.7$ $Na^+$ current was measured using a fluorescent dye-based membrane potential assay kit (#R8123) from Molecular Devices (California, USA). Briefly, cells were seeded into poly-D-lysine pre-coated black-wall, clear-bottom 96-well Biocoat plates in 100 µl growth media 24 h prior to assay. On the day of the assay the membrane potential dye was prepared and pre-warmed with Hepes-HBSS solution to 37° C. To each well, 100 µl dye was added and incubated at 37° C. for 60 min. Veratridine was added to each well to achieve a final concentration of 50 µmol/L. Test compound was then added to each well in the desired concentration, and fluorescence was recorded. For each test compound data set, an $IC_{50}$ value was calculated based on the assay points generated.

In particular embodiments, a compound will exhibit a high selectivity for the late sodium current modulatory activity as compared to the activity in one or more other ion channels. The selectivity of a compound may be determined by determining the percentage reduction in late sodium current due to the compound, as measured by the assay described above. The percentage reduction in one other ion channel activity, such as the hERG potassium channel or L-type calcium channel, due to the compound is determined as described above. The selectivity is determined by taking the ratio of (percentage reduction in late sodium current) to (percentage reduction in one other ion channel activity). The assays conducted to measure activities in this regard should be performed as described above, with the compound at a concentration of 10 µM (or at the upper limit of solubility, if less). In particular embodiments, the selectivity of a compound of the invention will be at least 5:1, e.g. at least 6:1, at least 7:1, at least 8:1, at least 9:1, at least 10:1, at least 12:1, at least 15:1, at least 20:1, or at least 25:1, when comparing the percentage reduction in late sodium current versus percentage reduction of one of the peak sodium current, the hERG potassium channel current, or the L-type calcium channel.

EXAMPLE 40

Material and Methods
Expression of Human $Na_v1.1$ cDNA

All wild-type (WT) and mutant constructs have been studied previously by our laboratory (Kahlig, 2008; Lossin, 2002; Rhodes, 2004) and cDNA expression was performed as previously described (Kahlig, 2008). Briefly, expression of $Na_v1.1$ was achieved by transient transfection using Qiagen Superfect reagent (5.5 mg of DNA was transfected at a plasmid mass ratio of 10:1:1 for $a_1:\beta_1:\beta_2$). The human $\beta_1$ and $\beta_2$ cDNAs were cloned into plasmids containing the marker genes DsRed (DsRed-IRES2-h$\beta_1$) or EGFP (EGFP-IRES2-h$\beta_2$) along with an internal ribosome entry site (IRES). Unless otherwise noted, all reagents were purchased from Sigma-Aldrich (St Louis, Mo., U.S.A.).

Electrophysiology

Whole-cell voltage-clamp recordings are used to measure the biophysical properties of WT and mutant $Na_v1.1$ channels, as described previously (Kahlig, 2008). Briefly, the pipette solution consisted of (in mM) 110 CsF, 10 NaF, 20 CsCl, 2 EGTA, 10 HEPES, with a pH of 7.35 and osmolarity of 300 mOsmol/kg. The bath (control) solution contained in (mM): 145 NaCl, 4 KCl, 1.8 $CaCl_2$, 1 $MgCl_2$, 10 dextrose, 10 HEPES, with a pH of 7.35 and osmolarity of 310 mOsmol/kg. Cells are allowed to stabilize for 10 min after establishment of the whole-cell configuration before current was measured. Series resistance is compensated 90% to assure that the command potential is reached within microseconds with a voltage error <2 mV. Leak currents are subtracted by using an online P/4 procedure and all currents are low-pass Bessel filtered at 5 kHz and digitized at 50 kHz. For clarity, representative ramp currents are low pass filtered off-line at 50 Hz.

Specific voltage-clamp protocols assessing channel activation, fast inactivation and availability during repetitive stimulation are used as depicted as figure insets. Whole-cell conductance wisas calculated from the peak current amplitude by $G_{Na}=I_{Na}/(V-E_{Na})$ and normalized to the maximum conductance between −80 and +20 mV. Conductance-voltage and steady-state channel availability curves are fit with Boltzmann functions to determine the voltage for half-maximal activation/inactivation ($V_{1/2}$) and a slope factor (k). Time-dependent entry into and recovery from inactivation are evaluated by fitting the peak current recovery with the two exponential function, $I/I_{max}=A_f \times [1-\exp(-t/\tau_f)]+A_s \times [1-\exp(-t/\tau_s)]$, where $\tau_f$ and $\tau_s$ denote time constants (fast and slow components, respectively), $A_f$ and $A_s$ represent the fast and slow fractional amplitudes.

For use-dependent studies, cells are stimulated with depolarizing pulse trains (−10 mV, 5 ms, 300 pulses, 10 Hz) from a holding potential of 120 mV. Currents are then normalized to the peak current recorded in response to the first pulse in each frequency train. For tonic block studies, peak and persistent current are evaluated in response to a 200 ms depolarization to −10 mV (0.2 Hz) following digital subtraction of currents recorded in the presence and absence of 0.5 µM tetrodotoxin (TTX). Persistent current is calculated during the final 10 ms of the 200 ms step. Data analysis is performed using Clampfit 9.2 (Axon Instruments, Union City, Calif., U.S.A), Excel 2002 (Microsoft, Seattle, Wash., U.S.A.), and OriginPro 7.0 (OriginLab, Northampton, Mass., U.S.A) software. Results are presented as mean±SEM. Unless otherwise noted, statistical comparisons are made using one-way ANOVA followed by a Tukey post-hoc test in reference to WT-$Na_v1.1$.

In vitro Pharmacology

A stock solution of 20 mM ranolazine (Gilead, Foster City, Calif.) is prepared in 0.1 M HCl. A fresh dilution of the compound of Formula IA or IB in the bath solution is prepared every experimental day and the pH was readjusted to 7.35. Direct application of the perfusion solution to the clamped cell is achieved using the Perfusion Pencil system (Automate, Berkeley, Calif.). Direct cell perfusion is driven by gravity at a flow rate of 350 µL/min using a 250 micron tip. This system sequesters the clamped cell within a perfusion stream and enables complete solution exchange within 1 second. The clamped cell is perfused continuously starting immediately after establishing the whole-cell configuration. Control currents are measured during control solution perfusion.

Solutions containing the compounds of the invention are perfused for three minutes prior to current recordings to allow equilibrium (tonic) drug block. Tonic block of peak and persistent currents are measured from this steady-state condition. Three sequential current traces are averaged to obtain a mean current for each recording condition (control, ranolazine and TTX). The mean current traces are utilized for offline subtraction and analysis. Use-dependent block of peak current is measured during pulse number 300 of the pulse train, (−10 mV, 5 ms, 300 pulses, 10 Hz) from a holding potential of −120 mV. Two sequential pulse train stimulations are averaged to obtain mean current traces for each recording condition, which are then used for offline subtraction and analysis. Block of ramp current is assessed by voltage ramps to +20 mV from a holding potential of −120 mV at a rate of 20 mV/s stimulated every 30 s. To minimize time-dependent current drift, only one trace recorded during control, compound of the invention, or TTX superfusion is analyzed. TTX was applied in the presence of ranolazine. Concentration inhibition curves are fit with the Hill equation: $I/I_{max}=1/[1+10^{\wedge}(\log IC_{50}-I)*k]$, where $IC_{50}$ is the concentration that produces half inhibition and k is the Hillslope factor.

In vivo Pharmacology

Jugular vein cannulated male Sprague Dawley rats (250-350 g, Charles River Laboratories, Hollister, Calif.) are used to study brain penetration of the compounds of the invention in vivo. Animal use is approved by the Institutional Animal Care and Use Committee, Gilead Sciences. Three rats per group are infused intravenously with the compound of the invention in saline at 85.5 µg/kg/min. After 1, 2.5 or 5 h animals are sacrificed for plasma and brain collection, and concentrations of the compound of the invention are measured by liquid chromatography coupled with tandem mass spectrometry (LC-MS/MS). Brain tissue is homogenated in 1% 2N HCl acidified 5% sodium fluoride (final homogenate was diluted 3-fold). Plasma and brain homogenate samples (50 µl) are precipitated along with deuterated D3-ranolazine as an internal standard, vortexed and centrifuged. The supernatant (50 µL) is transferred and diluted with water (450 µl) prior to injection (10 µl). High performance liquid chromatography wisas performed using a Shimadzu LC-10AD liquid chromatograph and a Luna C18(2), 3 µm, 20×2.0 min column with a mobile phase consisting of water containing 0.1% formic acid (solution A) and acetonitrile (solution B) carried out under isocratic conditions (75% solution A, 25% solution B; flow rate 0.300 ml/min). Mass spectrometric analyses are performed using an API3000 mass spectrometer (Applied Biosystems, Foster City, Calif.) operating in positive ion mode with MRM transition 428.1>98. Brain-to-plasma ranolazine ratios were calculated for each sample as ng ranolazine/g brain divided by ng ranolazine/ml plasma.

Results

Using the above methods it can be demonstrated that the compound of the invention have the ability to inhibit WT-$Na_v1.1$ and a panel of $Na_v1.1$ mutant channels associated with the epilepsy and migraine syndromes GEFS+, SMEI and FHM3 demonstrating the ability of the compounds of the invention to preferentially block the abnormal increased persistent current carried by these mutant channels. The ability of the compounds of the invention to cross the blood brain barrier may also be established using the above methods.

EXAMPLE 41

Material and Methods

Expression of Human $Na_v1.2$ cDNA

Wild-type (WT) cDNA stably transfected in Chinese hamster ovary (CHO) cells is used to record Na+ currents. Unless otherwise noted, all reagents are purchased from Sigma-Aldrich (St Louis, Mo., U.S.A.).

Electrophysiology

Whole-cell voltage-clamp recordings are used to measure the biophysical properties of WT. Briefly, the pipette solution consists of (in mM) 110 CsF, 10 NaF, 20 CsCl, 2 EGTA, 10 HEPES, with a pH of 7.35 and osmolarity of 300 mOsmol/kg. The bath (control) solution contains in (mM): 145 NaCl, 4 KCl, 1.8 CaCl2, 1 MgCl2, 10 dextrose, 10 HEPES, with a pH of 7.35 and osmolarity of 310 mOsmol/kg. Cells are allowed to stabilize for 10 min after establishment of the whole-cell configuration before current is measured. Series resistance is compensated 90% to assure that the command potential is reached within microseconds with a voltage error <2 mV. Leak currents are subtracted by using an online P/4 procedure and all currents are low-pass Bessel filtered at 5 kHz and digitized at 50 kHz.

For clarity, representative ramp currents are low pass filtered off-line at 50 Hz. Specific voltage-clamp protocols assessing channel activation, fast inactivation and availability during repetitive stimulation are used. Results are presented as mean±SEM, and unless otherwise noted, statistical comparisons are made using one-way ANOVA.

Tonic block of peak current is measured. The mean current traces are utilized for offline subtraction and analysis. Use-dependent block of peak current is measured during pulse number 300 of a pulse train (−10 mV, 5 ms, 300 pulses) at frequencies between 10 and 135 Hz from a holding potential of 120 mV. Two sequential pulse train stimulations are averaged to obtain mean current traces for each recording condition, which are then used for offline subtraction and analysis.

Specific voltage-clamp protocols assessing channel activation, fast inactivation and availability during repetitive stimulation are used. Whole-cell conductance is calculated from the peak current amplitude by $G_{Na}=I_{Na}/(V-E_{Na})$ and normalized to the maximum conductance between 80 and +20 mV. Conductance-voltage and steady-state channel availability curves are fit with Boltzmann functions to determine the voltage for half-maximal activation/inactivation ($V_{1/2}$) and a slope factor (k). Time-dependent entry into and recovery from inactivation are evaluated by fitting the peak current recovery with the two exponential function, $I/I_{max}=A_f \times [1-\exp(t/\tau_f)] + A_s \times [1-\exp(-t/\tau_s)]$, where $\tau_f$ and $\tau_s$ denote time constants (fast and slow components, respectively), $A_f$ and $A_s$ represent the fast and slow fractional amplitudes.

For use-dependent studies, cells are stimulated with depolarizing pulse trains (−10 mV, 5 ms, 300 pulses, 10 Hz) from a holding potential of −120 mV. Currents are then normalized to the peak current recorded in response to the first pulse in each frequency train. For tonic block studies, peak and persistent current are evaluated in response to a 200 ms depolarization to −10 mV (0.2 Hz) following digital subtraction of currents recorded in the presence and absence of 0.5 µM tetrodotoxin (TTX). Persistent current is calculated during the final 10 ms of the 200 ms step. Data analysis is performed using Clampfit 9.2 (Axon Instruments, Union City, Calif., U.S.A), Excel 2002 (Microsoft, Seattle, Wash., U.S.A.), and OriginPro 7.0 (OriginLab, Northampton, Mass., U.S.A) software. Results are presented as mean±SEM. Unless otherwise noted, statistical comparisons are made using one-way ANOVA followed by a Tukey post-hoc test in reference to WT-$Na_v1.2$.

In vitro Pharmacology

Stock solutions of 20 mM of the compounds of the invention (Gilead, Foster City, Calif.) are prepared in 0.1 M HCl. Fresh dilutions of the compound of the inventions in the bath solution are prepared every experimental day and the pH is readjusted to 7.35. Direct application of the perfusion solutions to the clamped cells is achieved using the Perfusion Pencil system (Automate, Berkeley, Calif.). Direct cell perfusion is driven by gravity at a flow rate of 350 µL/min using a 250 micron tip. This system sequesters the clamped cell within a perfusion stream and enables complete solution exchange within 1 second. The clamped cell is perfused continuously starting immediately after establishing the whole-cell configuration. Control currents are measured during control solution perfusion.

Ranolazine containing solutions are perfused for three minutes prior to current recordings to allow equilibrium (tonic) drug block. Tonic block of peak and persistent currents are measured from this steady-state condition. Three sequential current traces are averaged to obtain a mean current for each recording condition (control, compounds of the invention, and TTX). The mean current traces are utilized for offline subtraction and analysis. Use-dependent block of peak current is measured during pulse number 300 of the pulse train, (−10 mV, 5 ms, 300 pulses, 10 Hz) from a holding potential of −120 mV. Two sequential pulse train stimulations are averaged to obtain mean current traces for each recording condition, which are then used for offline subtraction and analysis. Block of ramp current is assessed by voltage ramps to +20 mV from a holding potential of −120 mV at a rate of 20 mV/s stimulated every 30 s. To minimize time-dependent current drift, only one trace recorded during control, compound of the invention, or TTX superfusion is analyzed. TTX is applied in the presence of the compound of the invention. Concentration inhibition curves are fit with the Hill equation: $I/I_{max}=1/[1+10^{\wedge}(\log IC_{50}-I)*k]$, where $IC_{50}$ is the concentration that produces half inhibition and k is the Hill slope factor.

Results

It is thus demonstrated that the compounds of the invention have the ability to inhibit WT-$Na_v1.2$ demonstrating the ability of the compounds of the invention to preferentially block an abnormal increased persistent current carried by this channel.

What is claimed is:

1. A compound selected from the group consisting of:
   6-[4-(trifluoromethoxy)phenyl]-3-(trifluoromethyl)[1,2,4]triazolo[4,3-b]pyridazine;
   6-(4-phenoxyphenyl)-3-(trifluoromethyl)[1,2,4]triazolo[4,3-b]pyridazine;
   3-(difluoromethyl)-6-[4-(trifluoromethoxy)phenyl][1,2,4]triazolo[4,3-b]pyridazine;
   3-(difluoromethyl)-6-(4-phenoxyphenyl)[1,2,4]triazolo[4,3-b]pyridazine;
   6-(4-phenoxyphenyl)[1,2,4]triazolo[4,3-b]pyridazine;
   6-[4-(trifluoromethoxy)phenyl][1,2,4]triazolo[4,3-b]pyridazine;
   6-[2-methyl-4-(trifluoromethoxy)phenyl]-3-(trifluoromethyl)[1,2,4]triazolo[4,3-b]pyridazine;
   6-(4-phenoxyphenyl)-3-(2,2,2-trifluoroethyl)[1,2,4]triazolo[4,3-b]pyridazine;
   6-(4-phenoxyphenyl)-3-(propan-2-yl)[1,2,4]triazolo[4,3-b]pyridazine;
   6-[2-methyl-4-(trifluoromethoxy)phenyl]-3-(propan-2-yl)[1,2,4]triazolo[4,3-b]pyridazine;

3-tert-butyl-6-(4-phenoxyphenyl)[1,2,4]triazolo[4,3-b] pyridazine;
3-tert-butyl-6-[4-(2,2,2-trifluoroethoxy)phenyl][1,2,4] triazolo[4,3-b]pyridazine;
3-ethyl-6-(4-phenoxyphenyl)[1,2,4]triazolo[4,3-b]pyridazine;
3-cyclopropyl-6-(4-phenoxyphenyl)[1,2,4]triazolo[4,3-b] pyridazine;
4-[6-(4-phenoxyphenyl)[1,2,4]triazolo[4,3-b]pyridazin-3-yl]benzonitrile;
4-{6-[2-methyl-4-(trifluoromethoxy)phenyl][1,2,4]triazolo[4,3-b]pyridazin-3-yl}benzonitrile;
4-{6-[4-(trifluoromethoxy)phenyl][1,2,4]triazolo[4,3-b] pyridazin-3-yl}benzonitrile;
3-(1-methyl-1H-pyrazol-4-yl)-6-(4-phenoxyphenyl)[1,2,4]triazolo[4,3-b]pyridazine;
4-[6-(4-methoxyphenyl)[1,2,4]triazolo[4,3-b]pyridazin-3-yl]benzonitrile;
3-[6-(4-methoxyphenyl)[1,2,4]triazolo[4,3-b]pyridazin-3-yl]benzonitrile;
3-[4-(methylsulfonyl)phenyl]-6-(4-phenoxyphenyl)[1,2,4]triazolo[4,3-b]pyridazine;
3-{6-[6-(morpholin-4-yl)pyridin-3-yl][1,2,4]triazolo[4,3-b]pyridazin-3-yl}benzonitrile,
6-(4-phenoxyphenyl)-3-[4-(2H-tetrazol-5-yl)phenyl][1,2,4]triazolo[4,3-b]pyridazine;
3-[6-(4-fluorophenyl)[1,2,4]triazolo[4,3-b]pyridazin-3-yl]benzonitrile;
2-[6-(4-phenoxyphenyl)[1,2,4]triazolo[4,3-b]pyridazin-3-yl]propan-2-ol;
3,6-bis[4-(trifluoromethoxy)phenyl][1,2,4]triazolo[4,3-b] pyridazine;
3-{6-[2-methyl-4-(trifluoromethoxy)phenyl][1,2,4]triazolo[4,3-b]pyridazin-3-yl}benzonitrile;
6-(3,5-difluoro-4-phenoxyphenyl)-3-(propan-2-yl)[1,2,4] triazolo[4,3-b]pyridazine;
3-(propan-2-yl)-6-[6-(2,2,2-trifluoroethoxy)pyridin-3-yl][1,2,4]triazolo[4,3-b]pyridazine;
6-[3-fluoro-4-(trifluoromethoxy)phenyl]-3-(trifluoromethyl)[1,2,4]triazolo[4,3-b]pyridazine;
6-(3,5-difluoro-4-phenoxyphenyl)-3-(trifluoromethyl)[1,2,4]triazolo[4,3-b]pyridazine;
6-[6-(2,2,2-trifluoroethoxy)pyridin-3-yl]-3-(trifluoromethyl)[1,2,4]triazolo[4,3-b]pyridazine;
6-[4-(4-chlorophenoxy)phenyl]-3-(trifluoromethyl)[1,2,4]triazolo[4,3-b]pyridazine;
3-(difluoromethyl)-6-[6-(2,2,2-trifluoroethoxy)pyridin-3-yl][1,2,4]triazolo[4,3-b]pyridazine; and
3-(difluoromethyl)-6-[3-fluoro-4-(trifluoromethoxy)phenyl][1,2,4]triazolo[4,3-b]pyridazine.

2. A pharmaceutical composition comprising a pharmaceutically acceptable excipient and a therapeutically effective amount of the compound of claim 1 or a pharmaceutically acceptable salt thereof.

\* \* \* \* \*